US012569355B2

(12) United States Patent
Cook

(10) Patent No.: US 12,569,355 B2
(45) Date of Patent: Mar. 10, 2026

(54) SYSTEMS AND METHODS FOR TOTAL ANKLE ARTHROPLASTY

(71) Applicant: WRIGHT MEDICAL TECHNOLOGY, INC., Memphis, TN (US)

(72) Inventor: Daniel August Cook, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 25 days.

(21) Appl. No.: 18/815,932

(22) Filed: Aug. 27, 2024

(65) Prior Publication Data

US 2025/0073046 A1    Mar. 6, 2025

Related U.S. Application Data

(60) Provisional application No. 63/633,538, filed on Apr. 12, 2024, provisional application No. 63/625,970, filed on Jan. 27, 2024, provisional application No. 63/599,607, filed on Nov. 16, 2023, provisional application No. 63/536,061, filed on Aug. 31, 2023.

(51) Int. Cl.
*A61F 2/46* (2006.01)
*A61F 2/42* (2006.01)

(52) U.S. Cl.
CPC .......... *A61F 2/4606* (2013.01); *A61F 2/4202* (2013.01); *A61F 2002/4205* (2013.01); *A61F 2002/4207* (2013.01)

(58) Field of Classification Search
CPC ........ A61F 2/46; A61F 2/4603; A61F 2/4606; A61F 2002/4207; A61F 2002/4622; A61F 2002/4627; A61F 2002/4628; A61B 17/025; A61B 17/0206; A61B 2017/0256
See application file for complete search history.

(56) References Cited

U.S. PATENT DOCUMENTS

| | | | |
|---|---|---|---|
| 3,314,420 A | 4/1967 | Smith et al. | |
| 3,605,123 A | 9/1971 | Hahn | |
| 3,708,883 A | 1/1973 | Flander | |
| 3,798,679 A | 3/1974 | Ewald | |
| 3,808,606 A | 5/1974 | Tronzo | |
| 3,843,975 A | 10/1974 | Tronzo | |
| 3,855,638 A | 12/1974 | Pilliar | |
| 3,938,198 A | 2/1976 | Kahn et al. | |
| 3,987,499 A | 10/1976 | Scharbach et al. | |
| 4,052,753 A | 10/1977 | Dedo | |

(Continued)

FOREIGN PATENT DOCUMENTS

| | | |
|---|---|---|
| AU | 2014239584 B2 | 11/2017 |
| AU | 2019261830 | 11/2021 |

(Continued)

OTHER PUBLICATIONS

Andersson, et al., "Macintosh Arthroplasty In Rheumatoid Arthritis," Acta. Orthrop. Scand., 1974, pp. 245-259, 45(2).

(Continued)

*Primary Examiner* — Anu Ramana
(74) *Attorney, Agent, or Firm* — DUANE MORRIS LLP

(57) ABSTRACT
Disclosed are new and improved instruments, systems, and methods that relate to the field of orthopedic surgical instruments.

10 Claims, 92 Drawing Sheets

500

(56)                References Cited

U.S. PATENT DOCUMENTS

| 4,055,862 | A |   | 11/1977 | Farling |
| 4,085,466 | A |   | 4/1978 | Goodfellow et al. |
| 4,098,626 | A |   | 7/1978 | Graham et al. |
| 4,203,444 | A |   | 5/1980 | Bonnell et al. |
| 4,213,816 | A |   | 7/1980 | Morris |
| 4,340,978 | A |   | 7/1982 | Buechel et al. |
| 4,368,040 | A |   | 1/1983 | Weissman |
| 4,436,684 | A |   | 3/1984 | White |
| 4,501,266 | A |   | 2/1985 | McDaniel |
| 4,502,161 | A |   | 3/1985 | Wall |
| 4,578,806 | A |   | 3/1986 | Grass et al. |
| 4,586,496 | A |   | 5/1986 | Keller |
| 4,594,380 | A |   | 6/1986 | Chapin et al. |
| 4,601,290 | A |   | 7/1986 | Effron et al. |
| 4,609,551 | A |   | 9/1986 | Caplan et al. |
| 4,627,853 | A |   | 12/1986 | Campbell et al. |
| 4,703,751 | A |   | 11/1987 | Pohl |
| 4,704,686 | A |   | 11/1987 | Aldinger |
| 4,715,860 | A |   | 12/1987 | Amstutz et al. |
| 4,721,104 | A |   | 1/1988 | Kaufman et al. |
| 4,759,350 | A |   | 7/1988 | Dunn et al. |
| 4,769,040 | A |   | 9/1988 | Wevers |
| 4,841,975 | A |   | 6/1989 | Woolson |
| 4,846,835 | A |   | 7/1989 | Grande |
| 4,865,607 | A |   | 9/1989 | Witzel et al. |
| 4,878,917 | A |   | 11/1989 | Rybicki et al. |
| 4,880,429 | A |   | 11/1989 | Stone |
| 4,936,862 | A |   | 6/1990 | Walker et al. |
| 4,979,949 | A |   | 12/1990 | Matsen, III et al. |
| 5,002,547 | A |   | 3/1991 | Poggie |
| 5,041,138 | A |   | 8/1991 | Vacanti et al. |
| 5,059,216 | A |   | 10/1991 | Winters |
| 5,067,964 | A |   | 11/1991 | Richmond et al. |
| 5,122,144 | A |   | 6/1992 | Bert et al. |
| 5,129,908 | A |   | 7/1992 | Petersen |
| 5,133,759 | A |   | 7/1992 | Turner |
| 5,154,717 | A |   | 10/1992 | Matsen, III et al. |
| 5,162,430 | A |   | 11/1992 | Rhee et al. |
| 5,171,322 | A |   | 12/1992 | Kenny |
| 5,197,985 | A |   | 3/1993 | Caplan et al. |
| 5,206,023 | A |   | 4/1993 | Hunziker |
| 5,222,973 | A | * | 6/1993 | Sharpe .................. A61B 17/29 |
|   |   |   |   | 294/99.2 |
| 5,226,914 | A |   | 7/1993 | Caplan et al. |
| 5,234,433 | A |   | 8/1993 | Bert et al. |
| 5,250,050 | A |   | 10/1993 | Poggie et al. |
| 5,258,032 | A |   | 11/1993 | Bertin |
| 5,270,300 | A |   | 12/1993 | Hunziker |
| 5,288,797 | A |   | 2/1994 | Khalil et al. |
| 5,303,148 | A |   | 4/1994 | Mattson et al. |
| 5,306,311 | A |   | 4/1994 | Stone et al. |
| 5,314,482 | A |   | 5/1994 | Goodfellow et al. |
| 5,344,459 | A |   | 9/1994 | Swartz |
| 5,360,446 | A |   | 11/1994 | Kennedy |
| 5,365,996 | A |   | 11/1994 | Crook |
| 5,368,858 | A |   | 11/1994 | Hunziker |
| 5,370,692 | A |   | 12/1994 | Fink et al. |
| 5,380,332 | A |   | 1/1995 | Ferrante |
| 5,387,216 | A |   | 2/1995 | Thornhill et al. |
| 5,454,816 | A |   | 10/1995 | Ashby |
| 5,462,550 | A |   | 10/1995 | Dietz et al. |
| 5,468,787 | A |   | 11/1995 | Braden et al. |
| 5,474,559 | A |   | 12/1995 | Bertin et al. |
| 5,476,479 | A | * | 12/1995 | Green ................ A61B 17/2909 |
|   |   |   |   | 606/205 |
| 5,478,739 | A |   | 12/1995 | Slivka et al. |
| 5,486,180 | A |   | 1/1996 | Dietz et al. |
| 5,501,687 | A |   | 3/1996 | Willert et al. |
| 5,503,162 | A |   | 4/1996 | Athanasiou et al. |
| 5,520,695 | A |   | 5/1996 | Luckman |
| 5,523,843 | A |   | 6/1996 | Yamane et al. |
| 5,540,696 | A |   | 7/1996 | Booth, Jr. et al. |
| 5,542,947 | A |   | 8/1996 | Treacy |
| 5,554,190 | A |   | 9/1996 | Draenert |
| 5,556,432 | A |   | 9/1996 | Kubein-Meesenburg et al. |
| 5,571,205 | A |   | 11/1996 | James |
| 5,575,793 | A |   | 11/1996 | Carls et al. |
| 5,578,037 | A |   | 11/1996 | Sanders et al. |
| 5,593,450 | A |   | 1/1997 | Scott et al. |
| 5,597,379 | A |   | 1/1997 | Haines et al. |
| 5,601,563 | A |   | 2/1997 | Burke et al. |
| 5,613,970 | A |   | 3/1997 | Houston et al. |
| 5,616,146 | A |   | 4/1997 | Murray |
| 5,620,458 | A | * | 4/1997 | Green ............ A61B 17/320016 |
|   |   |   |   | 604/104 |
| 5,630,820 | A |   | 5/1997 | Todd |
| 5,632,745 | A |   | 5/1997 | Schwartz |
| 5,645,604 | A |   | 7/1997 | Schneider et al. |
| 5,649,929 | A |   | 7/1997 | Callaway |
| 5,658,290 | A |   | 8/1997 | Techeira |
| 5,671,741 | A |   | 9/1997 | Lang et al. |
| 5,682,886 | A |   | 11/1997 | Delp et al. |
| 5,683,466 | A |   | 11/1997 | Vitale |
| 5,684,562 | A |   | 11/1997 | Fujieda |
| 5,688,282 | A |   | 11/1997 | Baron et al. |
| 5,728,162 | A |   | 3/1998 | Eckhoff |
| 5,735,277 | A |   | 4/1998 | Schuster |
| 5,749,874 | A |   | 5/1998 | Schwartz |
| 5,749,876 | A |   | 5/1998 | Duvillier et al. |
| 5,755,732 | A | * | 5/1998 | Green ............ A61B 17/320016 |
|   |   |   |   | 30/2 |
| 5,765,561 | A |   | 6/1998 | Chen et al. |
| 5,766,259 | A |   | 6/1998 | Sammarco |
| 5,768,134 | A |   | 6/1998 | Swaelens et al. |
| 5,769,899 | A |   | 6/1998 | Schwartz et al. |
| 5,782,842 | A |   | 7/1998 | Kloess et al. |
| 5,786,217 | A |   | 7/1998 | Tuba et al. |
| 5,798,924 | A |   | 8/1998 | Eufinger et al. |
| 5,800,438 | A |   | 9/1998 | Tuke et al. |
| 5,824,083 | A |   | 10/1998 | Draenert |
| 5,827,289 | A |   | 10/1998 | Reiley et al. |
| 5,830,216 | A |   | 11/1998 | Insall et al. |
| 5,835,619 | A |   | 11/1998 | Morimoto et al. |
| 5,842,477 | A |   | 12/1998 | Naughton et al. |
| 5,847,804 | A |   | 12/1998 | Sarver et al. |
| 5,853,746 | A |   | 12/1998 | Hunziker |
| 5,860,981 | A |   | 1/1999 | Bertin et al. |
| 5,871,018 | A |   | 2/1999 | Delp et al. |
| 5,871,542 | A |   | 2/1999 | Goodfellow et al. |
| 5,871,546 | A |   | 2/1999 | Colleran et al. |
| 5,879,390 | A |   | 3/1999 | Kubein-Meesenburg et al. |
| 5,880,976 | A |   | 3/1999 | DiGioia, III et al. |
| 5,885,296 | A |   | 3/1999 | Masini |
| 5,885,297 | A |   | 3/1999 | Matsen, III |
| 5,885,298 | A |   | 3/1999 | Herrington et al. |
| 5,897,559 | A |   | 4/1999 | Masini |
| 5,899,859 | A |   | 5/1999 | Votruba et al. |
| 5,900,245 | A |   | 5/1999 | Sawhney et al. |
| 5,906,934 | A |   | 5/1999 | Grande et al. |
| 5,910,143 | A |   | 6/1999 | Cripe et al. |
| 5,911,723 | A |   | 6/1999 | Ashby et al. |
| 5,916,220 | A |   | 6/1999 | Masini |
| 5,916,268 | A |   | 6/1999 | Schoellner et al. |
| 5,939,323 | A |   | 8/1999 | Valentini et al. |
| 5,951,475 | A |   | 9/1999 | Gueziec et al. |
| 5,961,523 | A |   | 10/1999 | Masini |
| 5,968,051 | A |   | 10/1999 | Luckman et al. |
| 5,972,385 | A |   | 10/1999 | Liu et al. |
| 5,995,738 | A |   | 11/1999 | DiGioia, III et al. |
| 6,001,895 | A |   | 12/1999 | Harvey et al. |
| 6,002,859 | A |   | 12/1999 | DiGioia, III et al. |
| 6,006,126 | A |   | 12/1999 | Cosman |
| 6,007,537 | A |   | 12/1999 | Burkinshaw et al. |
| 6,010,509 | A |   | 1/2000 | Delgado et al. |
| 6,013,081 | A |   | 1/2000 | Burkinshaw et al. |
| 6,013,103 | A |   | 1/2000 | Kaufman et al. |
| 6,046,379 | A |   | 4/2000 | Stone et al. |
| 6,056,754 | A |   | 5/2000 | Haines et al. |
| 6,056,756 | A |   | 5/2000 | Eng et al. |
| 6,057,927 | A |   | 5/2000 | Levesque et al. |
| 6,077,270 | A |   | 6/2000 | Katz |
| 6,082,364 | A |   | 7/2000 | Balian et al. |
| 6,090,144 | A |   | 7/2000 | Letot et al. |
| 6,093,204 | A |   | 7/2000 | Stone |

(56)　　　　References Cited

U.S. PATENT DOCUMENTS

| | | |
|---|---|---|
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,409,767 B1 | 6/2002 | Perice et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,746,454 B2 | 6/2004 | Winterbottom et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,153,326 B1 | 12/2006 | Metzger |
| 7,184,814 B2 | 2/2007 | Lang et al. |
| 7,201,762 B2 | 4/2007 | Green, Jr. et al. |
| 7,217,276 B2 | 5/2007 | Henderson et al. |
| 7,239,908 B1 | 7/2007 | Alexander et al. |
| 7,245,697 B2 | 7/2007 | Lang |
| 7,250,055 B1 | 7/2007 | Vanderwalle |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,246 B2 | 5/2009 | Reiley et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,850,608 B2 * | 12/2010 | Hamada ............ A61B 17/0206 |
| | | 600/233 |
| 7,881,768 B2 | 2/2011 | Lang et al. |
| 7,887,482 B2 * | 2/2011 | Hamada ............ A61B 17/3439 |
| | | 600/233 |
| 7,914,533 B2 | 3/2011 | Nelson et al. |
| 7,935,054 B2 * | 5/2011 | Hamada ................ A61B 17/02 |
| | | 600/233 |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,592 B2 | 2/2012 | Burdulis, Jr. et al. |
| RE43,282 E | 3/2012 | Alexander et al. |
| 8,430,879 B2 | 4/2013 | Stoneburner et al. |
| 8,475,463 B2 | 7/2013 | Lian |
| 8,496,663 B2 | 7/2013 | White et al. |
| 8,535,319 B2 | 9/2013 | Ball |
| 8,579,980 B2 | 11/2013 | Delurio et al. |
| 8,636,657 B2 * | 1/2014 | Hamada ............ A61B 17/0218 |
| | | 600/233 |
| 8,636,744 B2 | 1/2014 | Tochigi et al. |
| 8,715,362 B2 | 5/2014 | Reiley et al. |
| 8,808,297 B2 | 8/2014 | Stemniski |
| 8,808,303 B2 | 8/2014 | Stemniski |
| 9,005,255 B2 | 4/2015 | Lewis et al. |
| 9,017,334 B2 | 4/2015 | Carroll et al. |
| 9,125,674 B2 | 9/2015 | White et al. |
| 9,128,627 B1 | 9/2015 | Bachu et al. |
| 9,220,543 B2 * | 12/2015 | Walker .............. A61B 17/3423 |
| 9,259,250 B2 | 2/2016 | Saravia et al. |
| 9,265,511 B2 | 2/2016 | White et al. |
| 9,402,640 B2 | 8/2016 | Stemniski et al. |
| 9,408,717 B2 | 8/2016 | Perrow |
| 9,480,490 B2 | 11/2016 | Metzger et al. |
| 9,672,607 B2 | 6/2017 | Demri et al. |
| 10,105,168 B2 | 10/2018 | Blau |
| 10,130,430 B2 | 11/2018 | Kao et al. |
| 10,390,842 B2 | 8/2019 | Sander |
| 10,413,308 B2 | 9/2019 | Stemniski et al. |
| 10,433,911 B2 | 10/2019 | Wang et al. |
| 10,456,179 B2 | 10/2019 | Luna et al. |
| 10,667,867 B2 | 6/2020 | Ashish et al. |
| 10,835,265 B2 | 11/2020 | White et al. |
| 10,835,266 B2 | 11/2020 | White et al. |

(56) References Cited

U.S. PATENT DOCUMENTS

| | | |
|---|---|---|
| 11,134,964 B2 | 10/2021 | Free et al. |
| 11,147,627 B2 | 10/2021 | Gangwar et al. |
| 11,172,945 B1 | 11/2021 | Lian |
| 11,246,610 B2 | 2/2022 | Lee et al. |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geisllich et al. |
| 2002/0029038 A1 | 3/2002 | Haines |
| 2002/0045940 A1 | 4/2002 | Giannelli et al. |
| 2002/0059049 A1 | 5/2002 | Bradbury et al. |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Asculai et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2003/0236526 A1 | 12/2003 | Van Hoeck et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193268 A1 | 9/2004 | Hazebrouck et al. |
| 2004/0193280 A1 | 9/2004 | Webster et al. |
| 2004/0199166 A1 | 10/2004 | Schmieding et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0187555 A1 | 8/2005 | Biedermann et al. |
| 2005/0192588 A1 | 9/2005 | Garcia |
| 2005/0216305 A1 | 9/2005 | Funderud |
| 2005/0234461 A1 | 10/2005 | Burdulis et al. |
| 2005/0267584 A1 | 12/2005 | Burdulis et al. |
| 2005/0288792 A1 | 12/2005 | Landes et al. |
| 2006/0052795 A1 | 3/2006 | Burdulis et al. |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0129808 A1 | 6/2007 | Justin et al. |
| 2007/0150065 A1 | 6/2007 | Angibaud |
| 2007/0162025 A1 | 7/2007 | Tornier et al. |
| 2007/0198022 A1 | 8/2007 | Lang et al. |
| 2007/0203430 A1 | 8/2007 | Lang et al. |
| 2007/0203455 A1 | 8/2007 | Tremaglio et al. |
| 2007/0233128 A1 | 10/2007 | Schmieding et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Delfosse et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195109 A1 | 8/2008 | Hunter et al. |
| 2008/0195216 A1 | 8/2008 | Lang |
| 2008/0219412 A1 | 9/2008 | Lang |
| 2008/0243127 A1 | 10/2008 | Lang |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2008/0288079 A1 | 11/2008 | Leibel |
| 2008/0306605 A1 | 12/2008 | Hasselman |
| 2009/0024131 A1 | 1/2009 | Metzger et al. |
| 2009/0043310 A1 | 2/2009 | Rasmussen |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0149964 A1 | 6/2009 | May et al. |
| 2009/0198244 A1 | 8/2009 | Leibl |
| 2009/0204115 A1 | 8/2009 | Dees et al. |
| 2009/0222014 A1 | 9/2009 | Bojarski et al. |
| 2009/0307893 A1 | 12/2009 | Bojarski et al. |
| 2010/0057133 A1 | 3/2010 | Simon |
| 2010/0076441 A1 | 3/2010 | May et al. |
| 2010/0160917 A1 | 6/2010 | Fitz et al. |
| 2010/0262150 A1 | 10/2010 | Lian |
| 2010/0274251 A1 | 10/2010 | Ranft |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2010/0318088 A1 | 12/2010 | Warne et al. |
| 2010/0331847 A1 | 12/2010 | Wilkinson et al. |
| 2011/0066193 A1 | 3/2011 | Lang et al. |
| 2011/0071581 A1 | 3/2011 | Lang et al. |
| 2011/0137422 A1 | 6/2011 | Wilkes |
| 2011/0213368 A1 | 9/2011 | Fitz et al. |

(56) References Cited

U.S. PATENT DOCUMENTS

| | | |
|---|---|---|
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0010719 A1 | 1/2012 | Reiley |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0083892 A1 | 4/2012 | Kehres et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2013/0261628 A1 | 10/2013 | Burley et al. |
| 2014/0020690 A1 | 1/2014 | Triplett |
| 2014/0243836 A1 | 8/2014 | Bake et al. |
| 2014/0270065 A1 | 9/2014 | Aram et al. |
| 2014/0275955 A1 | 9/2014 | Crawford et al. |
| 2014/0276853 A1 | 9/2014 | Long et al. |
| 2014/0277538 A1 | 9/2014 | Sander |
| 2015/0320567 A1 | 11/2015 | Terrill et al. |
| 2016/0022283 A1 | 1/2016 | Wallace et al. |
| 2016/0051369 A1 | 2/2016 | Sander |
| 2016/0262903 A1 | 9/2016 | West |
| 2017/0079798 A1 | 3/2017 | Forsell |
| 2017/0112509 A9 | 4/2017 | Lancianese et al. |
| 2017/0224383 A1 | 8/2017 | Wong |
| 2018/0055648 A1 | 3/2018 | Dhillon et al. |
| 2018/0303490 A1 | 10/2018 | Loring et al. |
| 2019/0070012 A1 | 3/2019 | Leemrijse et al. |
| 2019/0209080 A1 | 7/2019 | Gullotti et al. |
| 2019/0365394 A1 | 12/2019 | Abt et al. |
| 2020/0008959 A1 | 1/2020 | Oh et al. |
| 2020/0015867 A1 | 1/2020 | Luna et al. |
| 2020/0113712 A1 | 4/2020 | Luna et al. |
| 2020/0237519 A1 | 7/2020 | Ball et al. |
| 2020/0330238 A1 | 10/2020 | Calamel et al. |
| 2020/0337850 A1 | 10/2020 | Reiley |
| 2021/0282790 A1 | 9/2021 | Sellman et al. |
| 2021/0378753 A1 | 12/2021 | Christen et al. |
| 2022/0022894 A1 | 1/2022 | Allard et al. |
| 2022/0280307 A1 | 9/2022 | Haddad et al. |
| 2022/0316504 A1 | 10/2022 | Kubacki |

FOREIGN PATENT DOCUMENTS

| | | |
|---|---|---|
| CN | 1662186 | 8/2005 |
| CN | 101111197 | 1/2008 |
| DE | 2306552 | 8/1974 |
| DE | 3516743 | 11/1986 |
| DE | 44 34 539 | 4/1996 |
| DE | 19501069 | 7/1996 |
| DE | 10123517 C1 | 11/2002 |
| DE | 20303498 | 8/2003 |
| DE | 202008017199 | 3/2009 |
| DE | 202008017200 | 3/2009 |
| EP | 0377901 | 10/1989 |
| EP | 0385930 | 9/1990 |
| EP | 0528080 | 2/1993 |
| EP | 0530804 | 10/1993 |
| EP | 0626156 | 11/1994 |
| EP | 0512529 | 7/1995 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 1623686 | 2/2006 |
| EP | 2124832 | 12/2009 |
| EP | 2742877 | 8/2014 |
| EP | 3878383 | 9/2021 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2000093435 | 4/2000 |
| JP | 2002-102236 | 4/2002 |
| JP | 2008-537689 | 9/2008 |
| JP | 2009515610 | 4/2009 |
| WO | WO 87/02882 | 5/1987 |
| WO | WO 90/009769 | 9/1990 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |

(56) References Cited

FOREIGN PATENT DOCUMENTS

| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009143374 | 11/2009 |
| WO | WO2009158522 | 12/2009 |
| WO | WO 2010/099142 | 9/2010 |
| WO | WO 2010/120346 | 10/2010 |
| WO | WO 2010/121147 | 10/2010 |
| WO | WO2010135156 | 11/2010 |
| WO | WO 2011/110374 | 9/2011 |
| WO | WO2012121726 | 9/2012 |
| WO | WO2014020561 | 2/2014 |
| WO | WO2019022769 | 1/2019 |
| WO | WO2019009891 | 4/2019 |
| WO | WO2019091537 | 5/2019 |
| WO | WO2019213122 | 11/2019 |
| WO | WO 2020123295 | 6/2020 |
| WO | WO 2020124047 | 6/2020 |
| WO | WO 2020124052 | 6/2020 |
| WO | WO 2020242542 | 12/2020 |
| WO | WO 20200239909 | 12/2020 |
| WO | 2021174346 A1 | 9/2021 |
| WO | WO 2022015877 | 1/2022 |
| WO | WO 2022094052 | 5/2022 |

OTHER PUBLICATIONS

Anonymous: "Angle bracket (fastener)—Wikipedia", May 22, 2021, 1 page.
Anonymous: "Light Tube—Wikipedia", Mar. 4, 2021, 11 pages.
Anonymous: Newtonian Telescope—Wikipedia, May 23, 2021, 6 pages.
Argenson, et al., "Is There a Place for Patellofemoral Arthroplasty?, "Clinical Orthopaedics and Related Research No. 321, 1995, pp. 162-167.
Birnbaum, et al., "Computer-Assisted Orthopedic Surgery with Individual Templates and Comparison to Conventional Operation Method," Spine, Feb. 2001, pp. 365-369, vol. 26, No. 4.
Chelule, et al., "Computer Aided Design of Personalized Jigs in Total Knee Replacement," 3rd Annual Meeting of CAOS Int'l Proc., Jun. 18-21, 2003, pp. 58-59, Spain.
Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.
DePuy Synthes, "Flexible Reamers for Intramedullary Nails" Surgical Technique, 22 pages, 2017.
De Winter, et al., "The Richards Type II Patellofemoral Arthroplasty," Acta Orthop Scand, 2001, pp. 487-490, 72(5).
Delp, et al., "A Graphics-Based Software System to Develop and Analyze Models of Musculoskeletal Structures," Comput. Biol. Med., 1995, pp. 21-34, vol. 25, No. 1.

Farrar, et al., "Computed Tomography Scan Scout Film for Measurement of Femoral Axis in Knee Arthroplasty," J. Arthroplasty, 1999, pp. 1030-1031, vol. 14, No. 8.
Final Official Action for U.S. Appl. No. 13/465,547, dated Feb. 26, 2014.
First Office Action for Japanese Patent Appln. No. 2011-552091, dated Oct. 25, 2013.
Froemel, et al., "Computer Assisted Template Based Navigation for Total Knee Replacement," Documents presented at CAOS on Jun. 17, 2001, 4 pages.
Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Kim, et al., "Measurement of Femoral Neck Anteversion in 3D. Part 1: 3D Imaging Method," Med. and Biol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam et al.. "VarusNalgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).
Mahaisavariya, et al., "Morphological Study of the Proximal Femur: a New Method of Geometrical Assessment Using 3-Dimensional Reverse Engineering", Medical Engineering & Physics 24 (2002) pp. 617-622.
Marler, et al., "Soft-Tissue Augmentation with Injectable Alginate and Synegeneic Fibroblasts," Plastic & Reconstructive Surgery, May 2000 pp. 2049-2058, 105(6).
PCT/US2010/025143, International Preliminary Report on Patentability and Written Opinion, Sep. 9, 2011.
Portheine, et al., "Potentials of CT-based Planning and Template-based Procedure in Hip and Knee Surgery," Orth. Prac., 2000, pp. 786-791, vol. 36, English Translation with Certification.
Radermacher, "Computer Assisted Matching of Planning and Execution in Orthopedic Surgery," Slide Presentation, Nov. 29, 1993, 22 pages.
Radermacher, "Template Based Navigation- An Efficient Technique for Hip and Knee Surgery," CAOS First Asian Meet, Mar. 27-28, 2004, pp. 45-50, India.
Radermacher, et al., "Computer-Assisted Planning and Operation in Orthopedics," Orth. Prac. 36th Year, Dec. 2000, pp. 731-737, English Translation with Certification.
Rau, et al., "Small and Neat," Medical Tech. Int'l, 1993-94, pp. 65, 67 and 69.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: a Practical Approach," 1999, Title page and Table of Contents pages Only, ISBN 007058219, McGraw-Hill.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-Ray Structure Determination: A Practical Guide," 1989, Title page and Table of Contents pages Only, ISBN 0471607118, John Wiley & Sons.
Stryker Trauma GmbH, "Bixcut Reamer System" Osteosynthesis, 8 sheets, 2009.

(56)  References Cited

OTHER PUBLICATIONS

Synthes, "SynReam, The Synthes Reaming System" Surgical Technique, 22 pages, 2005.

Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.

Testi, et al., "Border Tracing Algorithm Implementation for the Femoral Geometry Reconstruction," Camp. Meth. and Programs in Biomed., 2001, pp. 175-182, vol. 65.

Vandeberg, et al., "Assessment of Knee Cartilage in Cadavers with Dual-Detector Spiral CT Arthrography and MR Imaging," Radiology, Feb. 2002, pp. 430-435, 222(2).

Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).

Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.

Yusof, et al., "Preparation and Characterization of Chitin Beads as a Wound Dressing Precursor," J. Biomedical Materials Research Part A, Oct. 2000, pp. 59-68, 54(1).

Examination Report issued in connection with corresponding Indian Patent Application No. 2004/KOLNP/2013, Nov. 27, 2018, 7 pages.

First Office Action issued in connection with corresponding Chinese Patent Application No. 201610973637.8, Nov. 28, 2018, 6 pages.

First Examination Repot issued in connection with corresponding Australian Patent Application No. 2018204063, Jul. 10, 2019, 2 pages.

Second Examination Report issued in connection with corresponding Australian Patent Application No. 2019261830, May 4, 2021, 9 pages.

First Examination Repot issued in connection with corresponding Australian Patent Application No. 201926183, Dec. 21, 2020, 4 pages.

International Search Report and Written Opinion issued in connection with International Patent Application No. PCT/US2022/070130, May 13, 2022, 17 pages.

Extended European Search Report issued in connection with European Patent Application No. 22172072, filed May 4, 2023, 25 pages.

Extended European Search Report issued in connection with European Patent Application No. 23172825.4, Dec. 1, 2023, 17 pages.

Extended European Search Report issued in connection with European Patent Application No. 23180097.0, Jan. 25, 2024, 9 pages.

Extended European Search Report issued in connection with European Patent Application No. 23185897.8, Feb. 1, 2024, 11 pages.

Extended European Search Report issued in connection with European Patent Application No. 23187086.6, Feb. 14, 2024, 8 pages.

Extended European Search Report issued in connection with corresponding European Patent Application No. 24197318.9, Jan. 29, 2025, 8 pages.

* cited by examiner

1000

1200

1100

2200

2206            2207

Posterior ⟷ Anterior

2230

2220

2205

2100

SECTION A - A

2700

2701

2703    2704

2713

2700

2701    2710

2702    2706

SECTION B - B

2733

2733

900G (Cross-Section view (A))

(Cross-Section view (B))

(Cross-Section view (C))

(Cross-Section view (D))

(Cross-Section view (E))

(Cross-Section view (F))

(Locked Position)

(First Plunge Position)

(Second Plunge Position)

3004

3004t

3010

SECTION B - B

3022

3300

3200

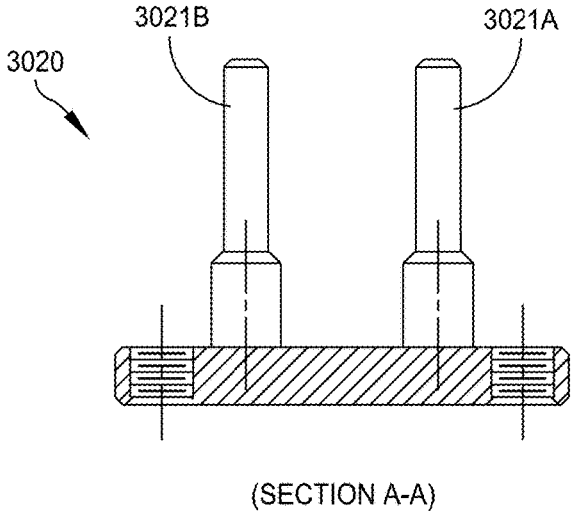
(SECTION A-A)
FIG. 45J-B
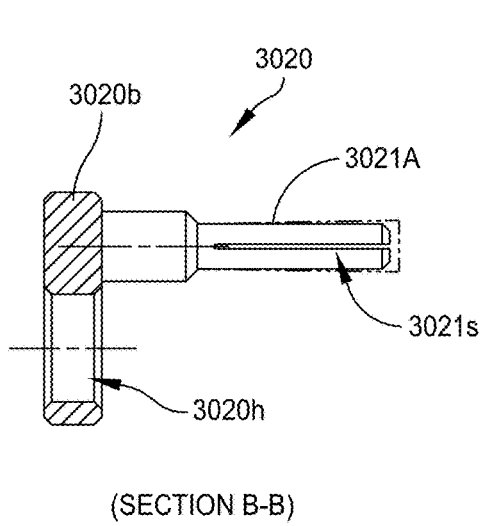
(SECTION B-B)
FIG. 45J-C
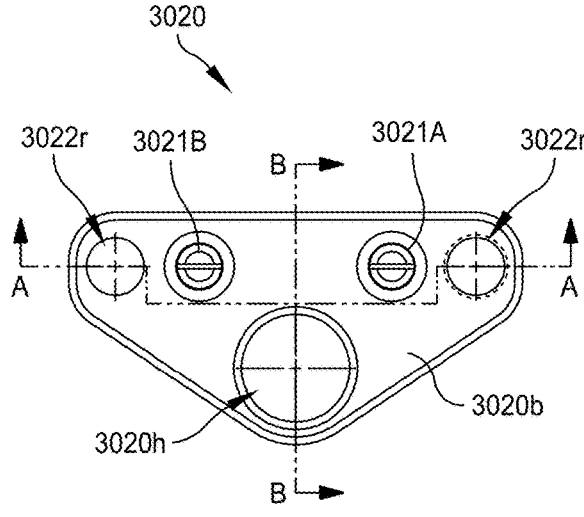
FIG. 45J-A

SECTION C - C

SECTION B - B

SECTION A - A

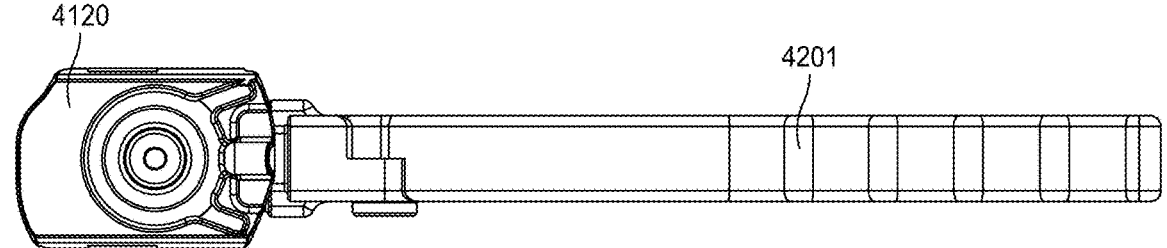
FIG. 54C
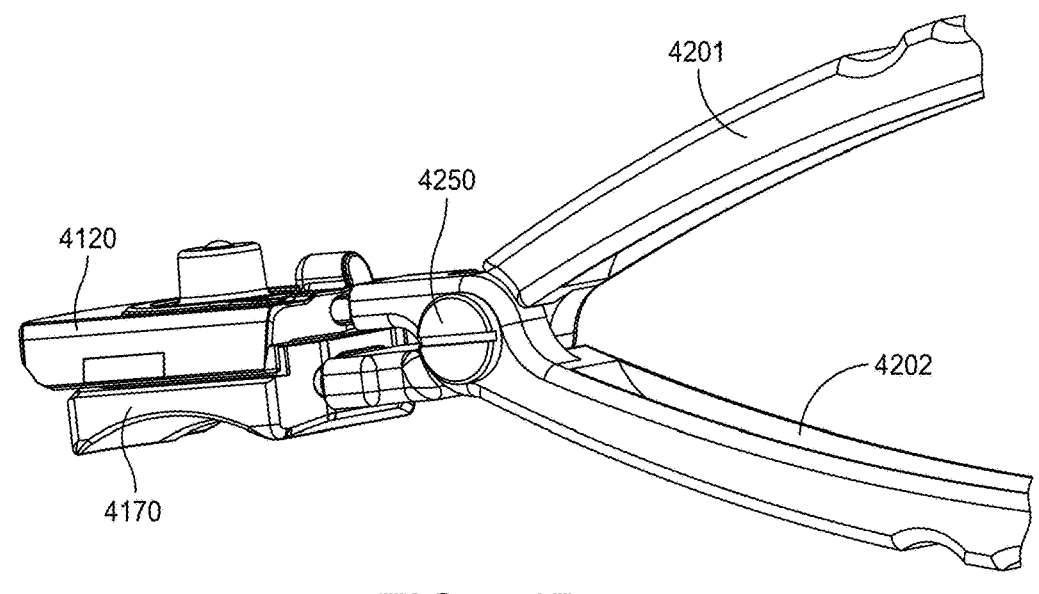
FIG. 54D
FIG. 54E

SECTION B - B

SECTION A - A

SECTION D - D

SECTION C - C

SYSTEMS AND METHODS FOR TOTAL ANKLE ARTHROPLASTY

CROSS-REFERENCE TO RELATED APPLICATIONS

This application claims priority under 35 U.S.C. § 119(e) to U.S. Provisional Applications No. 63/536,061, filed on Aug. 31, 2023, No. 63/599,607, filed on Nov. 16, 2023, No. 63/625,970, filed on Jan. 27, 2024, and No. 63/633,538, filed on Apr. 12, 2024, the entire contents of which are incorporated herein by reference.

FIELD OF DISCLOSURE

The disclosed instruments, systems, and methods relate to the field of orthopedic surgical instruments.

BACKGROUND

A variety of talar dome implants are used in ankle joint prosthetic procedures. These may include flat cut, chamfered, and stemmed talar dome implants. A surgeon may select the appropriate type of talar dome implant during the procedure based on each patient's unique joint space. However, current technology does not provide a uniform, simple, and reliable tool that a surgeon can use to securely hold, insert and remove each type of talar dome implant. Flat cut talar dome implants are typically inserted with a threaded rod. Whereas chamfered talar dome implants are inserted by hand, which can be unstable and difficult to do during the procedure. Therefore, a reliable and versatile system or instrument for talar dome implant insertion and removal is desired.

During ankle joint prosthetic procedures, surgeons may insert a talar dome trial into the joint space to determine the correct size talar dome implant to use in the procedure and to install pins in the talus in order to prepare the talar surface. The surgeon would subsequently insert the talar dome implant. Current trial holder tools, however, do not provide sufficient stability for inserting the talar dome trial into the joint space and can allow the talar dome trial to fall off of the trial holder during the procedure. Current trial holders feature a key shaped head that is inserted into a key hole in the talar dome trial and then twisted to attach the trial holder to the talar dome trial. However, if the trial holder moves within the keyhole, it can detach from the talar dome trial and allow the talar dome trial to fall off. Thus, a secure kit or instrument for talar dome trial insertion and removal is desired.

Once a surgeon has inserted a talar dome implant into the joint space during an ankle joint prosthetic procedure, the surgeon would typically use a talar dome impactor to secure the talar dome implant to drilled holes in the talus.

Many total ankle replacement prosthesis systems include an assembly of a tibia tray and a bearing component. Generally, tibia tray is first installed on to the distal end of the patient's tibia that has been prepared to receive the tibia tray. Then the bearing component is removably engaged to the bottom or distal surface of the tibia tray by a sliding mechanism.

Generally, to install a tibia tray to the prepared distal end of the tibia in the ankle joint space, a holder, an insertion instrument, an impaction instrument, or a remover instrument may be attached to the tibia tray for handling the tibia tray. Many currently available ankle prosthesis systems utilize a threaded connection to attach these instruments to a tibia tray. To achieve such connection, the tibia tray is provided with one or more threaded hole(s) that threadedly receive a threaded male component of an insertion/impaction instrument.

Making such threaded connection are time consuming because it takes some time to fiddle with the threaded components to get the threads properly aligned and to get the threading going. Thus, an instrument and tibia tray system that utilizes an improved connection scheme or configuration is desired.

SUMMARY

[Concept 1]

A surgical clamp is provided which comprises a first arm having a distal end and a proximal end; a second arm having a distal end and a proximal end, wherein the two distal ends together form a grasping end of the surgical clamp; and an attachment mechanism pivotally connecting the first arm and the second arm at a point between their respective distal and proximal ends, wherein the attachment mechanism comprises a body defining a pivot axis for the pivotal connection; and wherein the distal end of the first arm comprises a first protrusion configured to engage a corresponding first recess in a talar dome implant, wherein the distal end of the second arm comprises a second protrusion configured to engage a corresponding second recess in the talar dome implant, and wherein the grasping end of the surgical clamp securely holds the talar dome implant by the engagement of the first and second protrusions with the respective first and second recesses in the talar dome implant when the grasping end is closed around the talar dome implant.

Also provided is an implant system comprising: a surgical clamp that comprises: a first arm having a distal end and a proximal end; a second arm having a distal end and a proximal end, wherein the two distal ends form a grasping end of the surgical clamp; an attachment mechanism pivotally connecting the first arm and the second arm at a point between their respective distal and proximal ends, wherein the attachment mechanism comprises a body defining a pivot axis for the pivotal connection; wherein the distal end of the first arm comprises a first protrusion, wherein the distal end of the second arm comprises a second protrusion; and a talar dome implant comprising a first recess and a second recess, wherein the first protrusion is configured to engage the first recess, and the second protrusion is configured to engage the second recess; and wherein the grasping end of the surgical clamp securely holds the talar dome implant by the engagement of the first and second protrusions with the respective first and second recesses in the talar dome implant when the grasping end is closed around the talar dome implant.

[Concept 2]

Also provided is a holder apparatus comprising: a tubular sleeve housing having a proximal end and a distal end and having an internal bore extending from the proximal end to the distal end of the tubular sleeve housing; and a stem received in the bore of the tubular sleeve housing and extending a distance distally out of the tubular sleeve housing, wherein the stem's longitudinal axis defines the holder apparatus' longitudinal axis; wherein the stem comprises a first arm provided at the distal end of the stem and protruding orthogonal to the stem's longitudinal axis, wherein the first arm is spaced apart from the distal end of the tubular sleeve housing; wherein the tubular sleeve housing comprises a second arm provided at the distal end of the tubular sleeve housing, wherein the second arm extends distally from the distal end of the tubular sleeve housing adjacent to the stem and protruding orthogonal to the stem's longitudinal axis; and wherein the tubular sleeve housing and the stem are configured to rotate about the longitudinal axis of the stem with respect to each other so that the first and second arms can move from a first configuration in which the first arm and the second arm are radially aligned to a second configuration in which the first arm and the second arm are radially offset.

[Concepts 3 and 4]

Also provided is an ankle joint replacement system comprising: a tibia tray comprising: a first end configured to receive the instrument for holding the tibia tray; a second end; a top surface configured for engaging a distal end of a tibia bone; a bottom surface configured for engaging a bearing component; and two orthogonally oriented blind slots that intersect each other, each of the blind slots having a width and comprises an opening at one end and a blind end at a second end; and an instrument for holding the tibia tray, the instrument comprising: an elongated handle having a proximal end and a distal end; a forked clip portion provided at the distal end, wherein the forked clip portion comprises: two opposing arms each having a distal end and a proximal end, wherein the proximal ends of the two opposing arms are joined to the distal end of the elongated handle and extends distally further from the distal end of the elongated handle to their distal ends; wherein first of the two blind slots in the tibia tray opens to the first end of the tibia tray and second of the two blind slots opens to the bottom surface of the tibia tray, and the second blind slot is wider than the first blind slot, whereby the second blind slot forms a cavity at the blind end of the first blind slot, wherein the cavity is wider than the width of the first blind slot, thus forming two pockets located at each side of the blind end of the first blind slot, wherein the pockets are separated by a distance that is equal to the width of the first blind slot, whereby the distal ends of the two opposing arms of the forked clip portion are configured to engage the two pockets at the blind end of the first blind slot and hold the tibia tray when the forked clip portion is fully inserted into the first blind slot.

[Concept 4]

Also provided is a tibia tray for an ankle joint replacement system, the tibia tray comprising: a first end configured to receive the instrument for holding the tibia tray; a second end; a top surface configured for engaging a distal end of a tibia bone; a bottom surface configured for engaging a bearing component; and two orthogonally oriented blind slots that intersect each other, each of the blind slots having a width and comprises an opening at one end and a blind end at a second end; wherein first of the two blind slots in the tibia tray opens to the first end of the tibia tray and second of the two blind slots opens to the bottom surface of the tibia tray, and the second blind slot is wider than the first blind slot, whereby the second blind slot forms a cavity at the blind end of the first blind slot, wherein the cavity is wider than the width of the first blind slot, thus forming two pockets located at each side of the blind end of the first blind slot, wherein the pockets are separated by a distance that is equal to the width of the first blind slot, and the two pockets enable the tibia tray to removably engage an instrument that is configured to hold the tibia tray.

[Concept 5]

A holder apparatus comprising: an impactor having a proximal end and a distal end, wherein the impactor's longitudinal axis defines the holder apparatus' longitudinal axis, and wherein the impactor comprises: an impactor tip at the distal end;

wherein the holder apparatus further comprises: a first knob, wherein the first knob is configured to rotate about the longitudinal axis; a second knob, wherein the second knob is configured to rotate about the longitudinal axis; and a grasping assembly slidingly coupled to the impactor and configured to securely grasp a talar dome implant and capable of pulling the talar dome implant up against the impactor tip, wherein the grasping assembly comprises: a first arm having a proximal end and a distal end; a second arm having a proximal end and a distal end, wherein the distal end of the first arm and the distal end of the second arm form a grasping end of the grasping assembly, and wherein the first arm and the second arm are arranged in opposing positions about the longitudinal axis; a first scissor joint arrangement connecting the first arm to a first collar and a second collar; and a second scissor joint arrangement connecting the second arm to the first collar and the second collar, wherein the first knob is coupled to the first collar and configured to draw the first and second arms toward each other by rotating the first knob in one direction which, in turn, collapses the two scissor joint arrangements by sliding the first collar distally along the longitudinal axis, and the first knob is configured to draw the first and second arms away from each other by rotating the first knob in an opposite direction which, in turn, expands the two scissor joint arrangements by sliding the first collar proximally along the longitudinal axis, wherein the second knob is coupled to the second collar and configured to slide the second collar proximally which in turn slides the grasping assembly proximally along the longitudinal axis.

[Concept 6]

Disclosed herein is a system for establishing an intramedullary path, for example, at the distal end of a tibia in an ankle joint. The system comprise a cartridge and a clip; where the cartridge is sized and configured to be positioned in a resected ankle joint space of a patient, and the cartridge having an anterior side, a posterior side, a medial side, a lateral side, a superior side, and an inferior side corresponding to the anatomical directions when positioned in the resected joint space. The cartridge comprises: a body that defines a cartridge cavity and includes: a front surface that defines a first aperture that extends into the cartridge cavity from the anterior side in anterior-posterior direction and defining an anterior opening for receiving a reamer tip and the clip; a second aperture provided on the inferior side providing access to the cartridge cavity and sized and configured to pass a reamer shaft therethrough; and a third aperture provided on the superior side providing access to the cartridge cavity and sized and configured to pass a reamer tip therethrough. The clip comprises a top surface, a bottom surface, handle end, and a tool engaging end that comprises a space to receive and hold the reamer tip. The clip and the cartridge are configured to co-operate with each other to position the clip in a predefined relationship with respect to the cartridge as the clip is advanced into the cartridge cavity through the first aperture while the clip is holding the reamer tip. The reamer tip is positioned at a predetermined location within the cartridge cavity that allows the reamer tip to be aligned for receiving the reamer shaft that is passed through the second aperture.

[Concept 7]

Also provided is a C-bracket instrument for aligning ankle joint implant trials and implants. The C-bracket can also guide the reaming tool for establishing an intramedullary path, for example, at the distal end of a tibia in an ankle joint so that the tibia can receive the tibia tray component of an ankle prosthesis.

[Concept 8]

Also disclosed is a talar dome implant holder that clips on to a talar dome and protects the articular surface of the talar dome during positioning of the talar dome implant on to a resected talar bone. The talar dome implant holder comprises: a body sized and configured to couple to a talar dome implant to protect the talar dome implant's articular surface. The body comprises: a concave surface and a convex surface opposite from the concave surface; a first arm; and a second arm. The concave surface is contoured to substantially conform to the articular surface of the talar dome implant. The body includes an insertion end and a handle end, where the handle end is configured and arranged to receive a handle. The first arm extends medially from the body, and is configured to partially wrap around a first edge of the talar dome implant. The second arm extends laterally from the body, opposite the first arm, and is configured to partially wrap around a second edge of the talar dome implant.

[Concept 9]

Disclosed herein is a guiding instrument for adjusting a bone-cutting guide's position and/or angular orientation with respect to a bone, the guiding instrument comprises a primary element that is configured to be affixed to the bone and establish a reference point on the bone; a secondary element that is configured to hold the bone-cutting guide; and an intermediary assembly that connects the primary element and the secondary element, wherein the intermediary assembly comprises: a first part; a second part; and a third part; wherein: the first part is configured for adjusting position of the bone-cutting guide, along a first axis, with respect to the primary element; the second part is configured for adjusting position of the bone-cutting guide, along a second axis that is orthogonal to the first axis, with respect to the primary element; the third part is configured to cooperate with the second part for adjusting angular orientation of the bone-cutting guide along a first arc about a third axis that is orthogonal to both the first and second axes (varus/valgus angle); and the third part is also configured to cooperate with the secondary element for adjusting angular orientation of the bone-cutting guide about a fourth axis that is parallel with the first axis (flexion/extension angle).

[Concept 10]

An improved polymer insert implant inserter for inserting a polymer insert implant into a tibia tray mounted at the distal end of a tibia is also disclosed.

[Concept 11]

Also disclosed is a distractor for ankle joint space that is configured to distract the angle joint and keep the foot in neutral position to aid implantation of a stem construct version of a tibia tray.

[Concept 12]

Also disclosed is an ankle joint implant system that comprises: a tibia tray that includes: a first surface configured to engage a tibia bone; and a second surface configured to engage an articulating component; and an instrument configured to engage and hold the tibia tray by a first part of the instrument abutting against a second end of the tibia tray and a second part of the instrument hooking onto a first end of the tibia tray. The second part of the instrument is configured to pull on the second end of the tibia tray to apply a tension force on the tibia tray and securely hold the tibia tray.

[Concept 13a]

Also disclosed is a clamping hand tool for compressing a polymer articulating insert together with a tibia tray to form a snap-fit engagement between the tibia tray and the polymer insert. The clamping hand tool comprises: a first arm having a first end and a second end; and a second arm having a first end and a second end. The first arm and the second arm are pivotally connected at a point between their respective first and second ends. The second end of the first arm comprises one or more projections and each of the projections is configured to engage a corresponding recess among one or more recesses in a tibia tray, where the second end of the second arm comprises one or more projections. Each of the projections is configured to engage a corresponding recess among one or more recesses in an articulating insert that is configured to engage the tibia tray and form a snap-fitting engagement.

[Concept 13b]

Also disclosed is a distracting instrument to be used for dis-engaging the polymer articulating insert from the tibia tray so they can be separated.

[Concept 14a]

Also disclosed is a hole cutting saw comprising: a cylindrical wall body having a base portion at one end thereof and a plurality of cutting teeth at an opposite end of the cylindrical wall body, wherein the cylindrical wall body defining a main cavity that is open at the end with the cutting teeth and a closed at the end of the base portion, the closed end forming a cavity wall; and a driver bit positioned at a geometric center of the cavity wall and extending longitudinally from the cavity wall, wherein the driver bit is configured for engaging a bottom end of a modular tibia stem component.

[Concept 14b]

In some embodiments of the hole cutting saw, the cavity wall and the driver bit are configured so that the driver bit floats on an elastic member that urges the driver bit toward the end with the cutting teeth.

BRIEF DESCRIPTION OF THE DRAWINGS

FIGS. 45G-45I shows detailed views of the polymer insert holder portion of the polymer insert implant inserter engaging a polymer insert implant.

FIGS. 45J-A, 45J-B, and 45J-C show three different views of the polymer insert holder portion of the polymer insert implant inserter.

FIGS. 54C-54E are detailed views of the clamping instrument engaging an assembly of tibia tray and a corresponding articulating insert.

FIG. 54F is a side view of the

DETAILED DESCRIPTION

Figure 1:
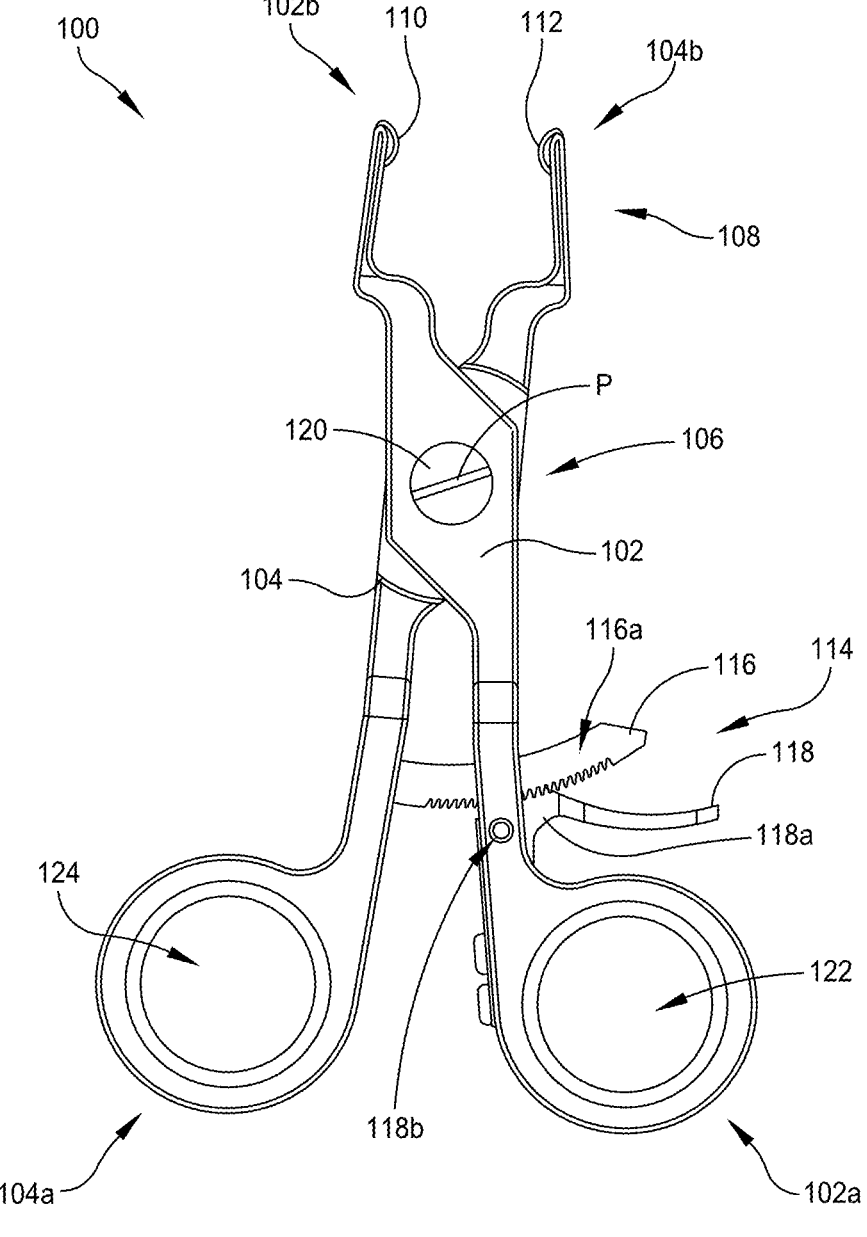
FIG. 1 shows a surgical clamp for holding a talar dome implant according to an embodiment of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

The disclosed devices and systems may be used in a wide variety of surgical methods and procedures. The disclosed devices and systems advantageously enable orthopedic surgical procedures (e.g., ankle joint prosthetic procedures). For example, the disclosed devices and systems enable talar dome trial insertion and removal in order to prepare for a talar dome implant insertion procedure. Further, the disclosed devices and systems enable talar dome implant insertion and removal.

[Concept 1]

FIG. 1 illustrates one example of a surgical clamp 100 according to some embodiments. The surgical clamp 100 may be used by a surgeon to insert a talar dome implant into or remove a talar dome implant from a joint space during an ankle joint prosthetic procedure. The talar dome implant may be a talar dome component of an ankle joint prosthesis. The surgical clamp 100 comprises a first arm 102, a second arm 104, and an attachment mechanism 106 that pivotally connects the first arm 102 and the second arm 104. The first arm 102 has a proximal end 102a and a distal end 102b. The second arm 104 has a proximal end 104a and a distal end 104b. The distal end 102b and the distal end 104b form a grasping end 108 of the surgical clamp 100. The attachment mechanism 106 pivotally connects the first arm 102 and the second arm 104 at a point between the distal end 102b and the proximal end 102a and between the distal end 104b and the proximal end 104a so that the first arm and the second arm form a scissor-like configuration where opening and closing the proximal ends 102a, 104a of the first arm and second arm opens and closes the respective distal ends 102b, 104b at the grasping end 108 of the surgical clamp 100. The attachment mechanism 106 comprises a body defining a pivot axis P for the hinged connection for the first arm 102 and the second arm 104. In some embodiments, the attachment mechanism 106 can be a hinge pin 120.

Figure 2A:
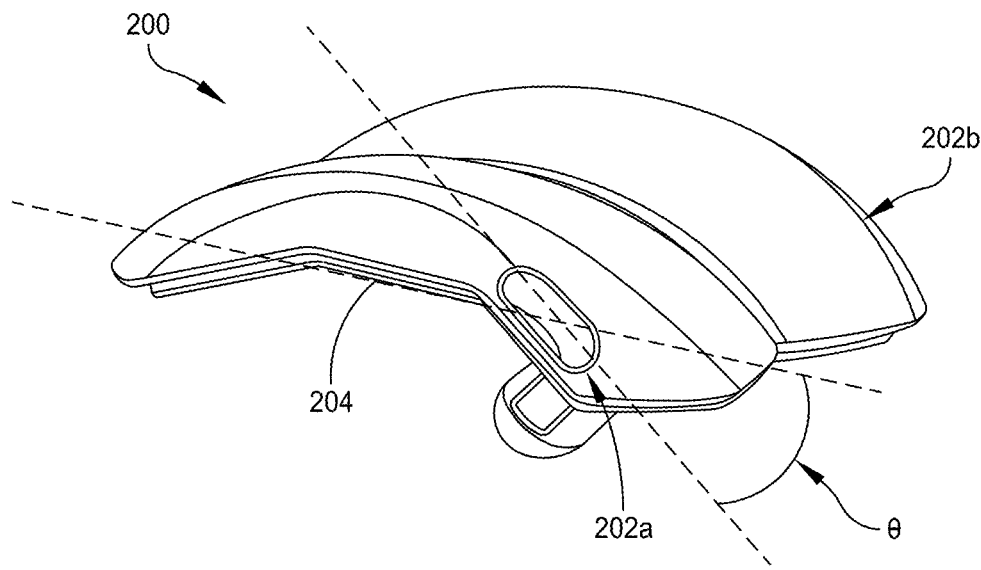
FIG. 2A shows a talar dome implant according to an embodiment of the present disclosure.
Figure 2B:
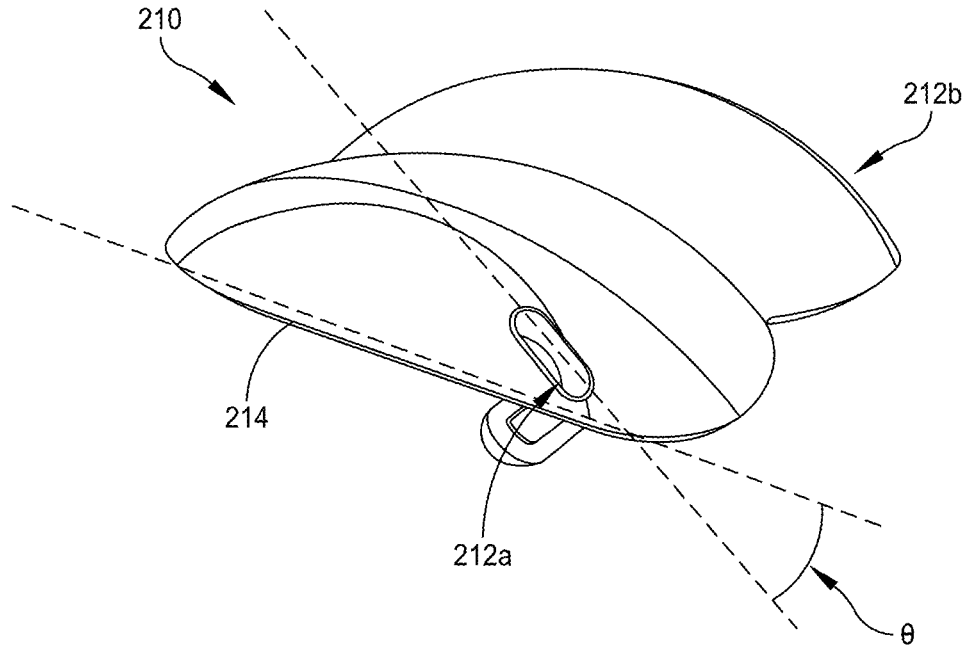
FIG. 2B shows a talar dome implant according to an embodiment of the present disclosure.

The distal end 102b of the first arm 102 comprises a first protrusion 110 configured to engage a corresponding first recess in a talar dome implant (e.g., the recess 202a in the talar dome implant 200 or the recess 212a in the talar dome implant 210, shown in FIGS. 2A and 2B, respectively). The distal end 104b of the second arm 104 comprises a second protrusion 112 configured to engage a corresponding second recess in the talar dome implant (e.g., the recess 202b in the talar dome implant 200 or the recess 212b in the talar dome implant 210, shown in FIGS. 2A and 2B, respectively). The grasping end 108 of the surgical clamp 100 securely holds the talar dome implant (e.g., the talar dome implant 200 or the talar dome implant 210, shown in FIGS. 2A and 2B) by the engagement of the first protrusion 110 and the second protrusion 112 with the respective first and second recesses 202a, 202b, 212a, 212b in the talar dome implant when the grasping end 108 is closed around the talar dome implant. In some embodiments, the first protrusion 110 and the second protrusion 112 have a hemispheric shape. The first protrusion 110 and the second protrusion 112 protrude generally towards each other.

Figure 3:
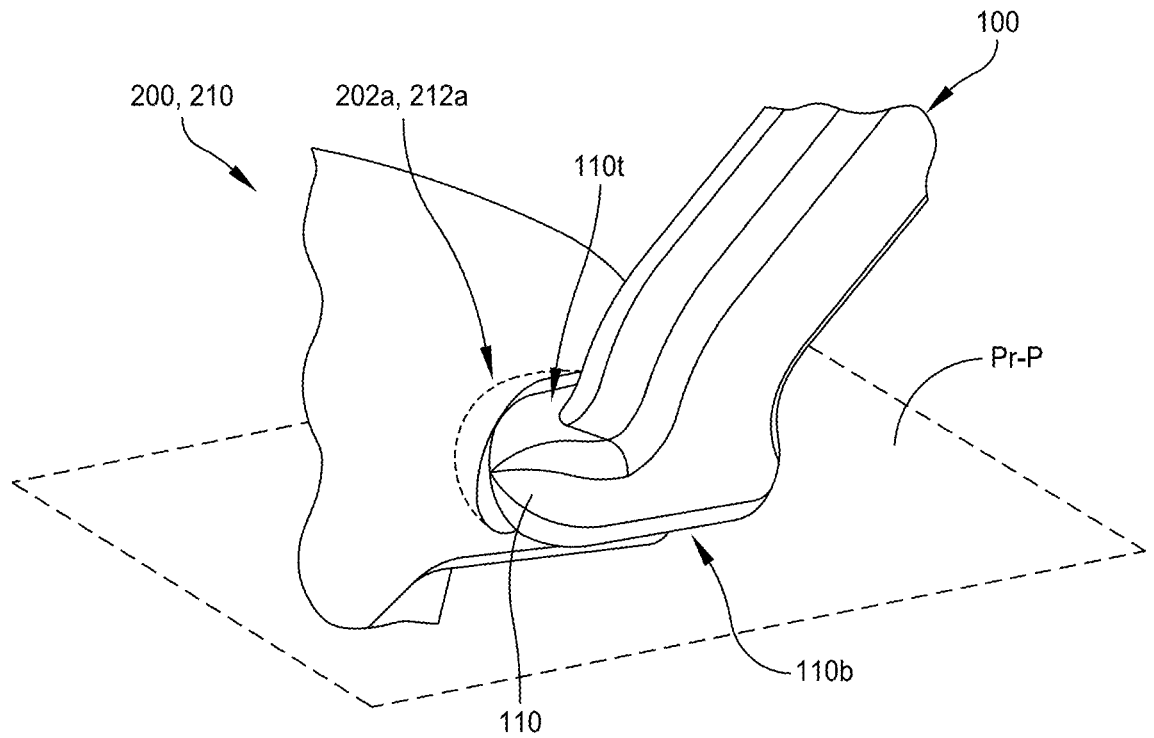
FIG. 3 shows a partial view of a surgical clamp and talar dome implant according to an embodiment of the present disclosure.
Figure 4A:
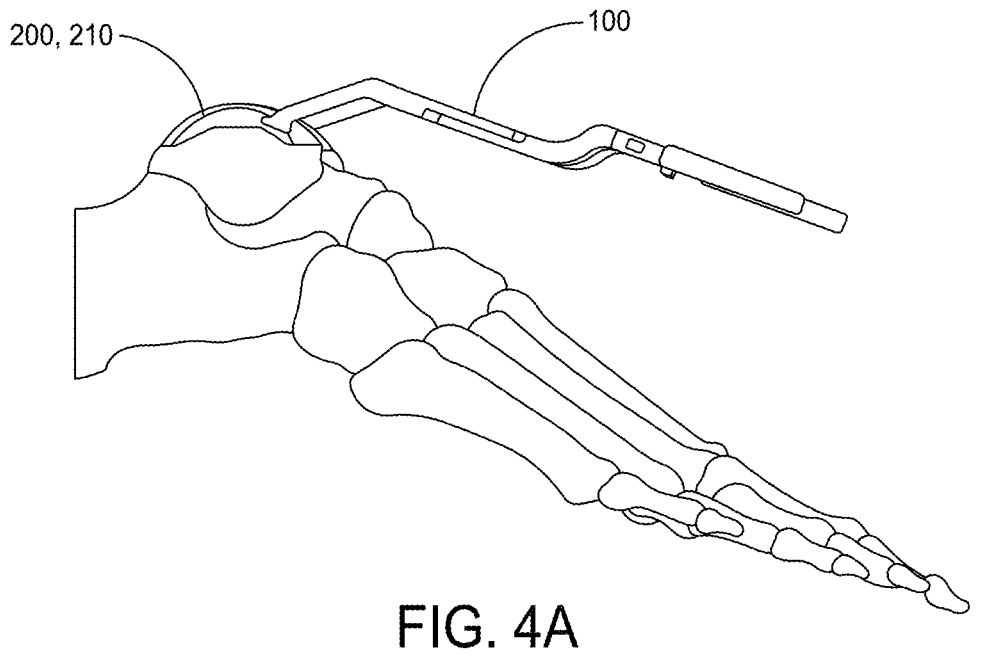
FIG. 4A shows an implant system according to an embodiment of the present disclosure.
Figure 4B:
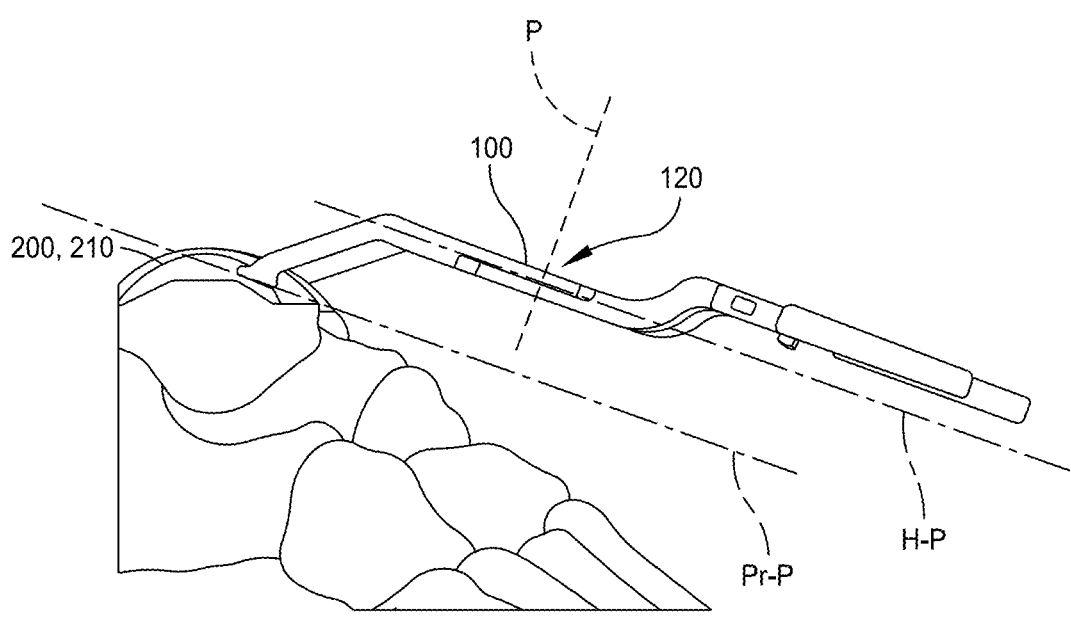
FIG. 4B shows a close-up view of FIG. 4A.

Referring to FIGS. 4A and 4B which are side views showing the surgical clamp 100 holding a talar dome implant 200 (or 210), the plane that is orthogonal to the pivotal axis (i.e. the hinge axis) P of the hinge pin 120 of the clamp 100 is identified as a Hinge-Plane H-P. It should be noted that the orientation of the protrusions 110, 112 relative to the Hinge-Plane H-P is one of the beneficial features of the surgical clamp 100. As shown in the close-up view of the protrusion 110 in FIG. 3, the protrusions 110 and 112 have generally flattened disc-like shape with substantially flat top surface 110*t* and bottom surface 110*b* that are parallel to each other, as shown in FIG. 3. A plane that is parallel to the flat top surface 110*t* and the flat bottom surface 110*b* will be referred to herein as the Protrusion-Plane labeled as Pr-P and that plane represents the orientation of the protrusions 110 and 112. Although FIG. 3 is only showing the protrusion 110 on the distal end 102*b* of the first arm 102, the protrusion 112 provided on the distal end 104*b* of the second arm 104 is configured symmetrical to the protrusion 110 and the two protrusions are oriented in the same Protrusion-Plane Pr-P. The Protrusion-Plane Pr-P is also identified in FIG. 4B.

The surgical clamp 100 is configured such that the two planes, the Protrusion-Plane Pr-P and the Hinge-Plane H-Pare parallel to each other. This ensures that as the surgical clamp 100 is opened and closed, the two protrusions 110 and 112 remain in the Pr-Plane. This allows the surgical clamp 100 to open its distal ends 102*b*, 104*b* to varying widths and still maintain the desired opposing orientation for the two protrusions 110 and 112. This allows the surgical clamp 100 to properly grip talar dome implants 200, 210 of varying sizes whose corresponding pairs of recesses 202*a*, 212*a* on a given talar dome implant are configured to be in planar alignment. If the Hinge-Plane H-P and the protrusions' Protrusion-Plane Pr-P were not in parallel configuration, the protrusions 110, 112 would arc in and out of plane relative to each other as the clamp 100 is opened and closed and could not grip different sizes of talar dome implants.

In some embodiments, the surgical clamp 100 further comprises a ratchet mechanism 114 configured to allow closing of the surgical clamp 100 while preventing opening of the surgical clamp 100 unless the ratchet mechanism 114 is temporarily unlocked. Starting from its open configuration, where the ratchet mechanism 114 allows this one-way motion by allowing the two arms 102, 104 to pivot or rotate about the pivot axis P in one direction that brings the proximal ends 102*a*, 104*a* toward each other but selectively preventing the proximal ends 102*a*, 104*a* from opening in the opposite direction.

In the illustrated example surgical clamp 100, the ratchet mechanism 114 comprises a rack 116 and a pawl 118*a*. The rack 116 is configured with a plurality of teeth 116*a* that face toward the pawl 118*a*. The pawl 118*a* is configured with one or more teeth as shown. The pawl 118*a* is pivotally attached to the first arm 102 by a pivot pin 118*b* in the configuration shown and the pawl 118*a* is urged against the teeth 116*a* of the rack 116. The urging of the pawl 118*a* against the teeth 116*a* can be accomplished by one of many known spring-like mechanisms. The result is that when the proximal ends of the first and second arms 102, 104 are being closed so that the first arm 102 is moving towards the second arm 104, the pawl 118*a* is on the trailing side of the first arm 102 and the one or more teeth on the pawl 118*a* will be ratchet over the row of the plurality of teeth 116*a*. If a surgeon tries to open the proximal ends of the first and second arms 102, 104, however, the pawl 118*a* now being on the leading side of the first arm 102 will be pushed against the row of the plurality of teeth 116*a* on the rack 116, thus, preventing the first arm 102 from moving further in that direction. Thus, when the surgical clamp 100 is clamped onto a talar dome, the surgical clamp 100 automatically locks in the closed position and prevent any unwanted accidental opening of the surgical clamp 100.

To open and unclamp the surgical clamp 100, the ratchet mechanism 114 can be unlocked by pulling the lever 118 portion of the pawl 118*a* in the direction away from the rack 116. This will disengage the one or more teeth on the pawl 118*a* from the teeth 116*a* of the rack 116 allowing the proximal ends 102*a* and 104*a* of the first and second arms 102, 104 to open.

In some embodiments, the proximal end 102*a* of the first arm 102 and the proximal end 104*a* of the second arm 104 are configured to receive a user's fingers for gripping the surgical clamp 100 and operating the surgical clamp. For example, in the illustrated example shown in FIG. 1, the proximal end 102*a* is provided with a first hole 122 and the proximal end 104*a* is provided with a second hole 124. A surgeon may insert her fingers into the two holes to grip and operate the surgical clamp 100.

FIG. 2A illustrates one example of a talar dome implant 200 according to some embodiments. The talar dome implant 200 comprises a first recess 202*a* and a second recess 202*b* (not visible) on the opposite side of the talar dome implant 200. According to some embodiments, the recesses 202*a*, 202*b* are located on the talar dome implant 200 away from the articular surface of the talar dome plant and also located on the anterior portion of the talar dome implant to avoid the surrounding soft tissue when the talar dome implant 200 is installed in a patient's ankle. Additionally, the angle $\theta$ of the recesses 202*a*, 202*b* on the talar dome implant controls the ergonomics of the clamp 100 with respect to the patient's foot. The angle $\theta$ is noted in FIGS. 2A and 2B. Thus, talar dome implants can be provided in predetermined variety of the angle of the recesses 202*a*, 202*b*. The talar dome implant 200 is an example of a chamfered version of a talar dome implant and thus further comprises a chamfered bottom surface 204.

FIG. 2B illustrates one example of a talar dome implant 210 according to some other embodiments. The talar dome implant 210 comprises a first recess 212*a* and a second recess 212*b* (not visible) on the opposite side of the talar dome implant 210. The talar dome implant 210 is an example of a flat cut version of a talar dome implant and thus further comprises a flat cut bottom surface 214.

In some prior art implant systems, chamfered talar dome implants were inserted into the joint space by hand and flat cut talar dome implants were inserted into the joint space using a threaded rod. However, as illustrated in FIGS. 4A, 4B, with the present implant system, a surgeon can use the surgical clamp 100 to insert any one of a chamfered, flat cut, or stemmed talar dome implant (e.g., 200, 210) into the joint space.

The hemispheric shape of the protrusions 110 and 112 allows the surgical clamp 100 to be used for multiple sizes of talar dome implants as well, adding to its versatility. This design configuration utilizing the hemispherical shape for the protrusions 110 and 112 allows very robust means of gripping the talar dome implants of varying sizes because the curvature of the hemispherical shape of the protrusions 110, 112 and the corresponding recesses on the talar dome implants allow the protrusions and the recesses to maintain intimately contacting engagement at varying angles as the clamp 100 is opened and closed to varying degrees where the angle of the distal ends of the clamp's first and second arms change. The surgical clamp 100 also provides much more stability and maneuverability than a surgeon would have when performing the insertion by hand or using a threaded rod. FIG. 3 illustrates a close-up view of the protrusion 110 of the surgical clamp 100 engaging a recess 202a, 212a of the talar dome implants 200, 212.

Figure 4C:
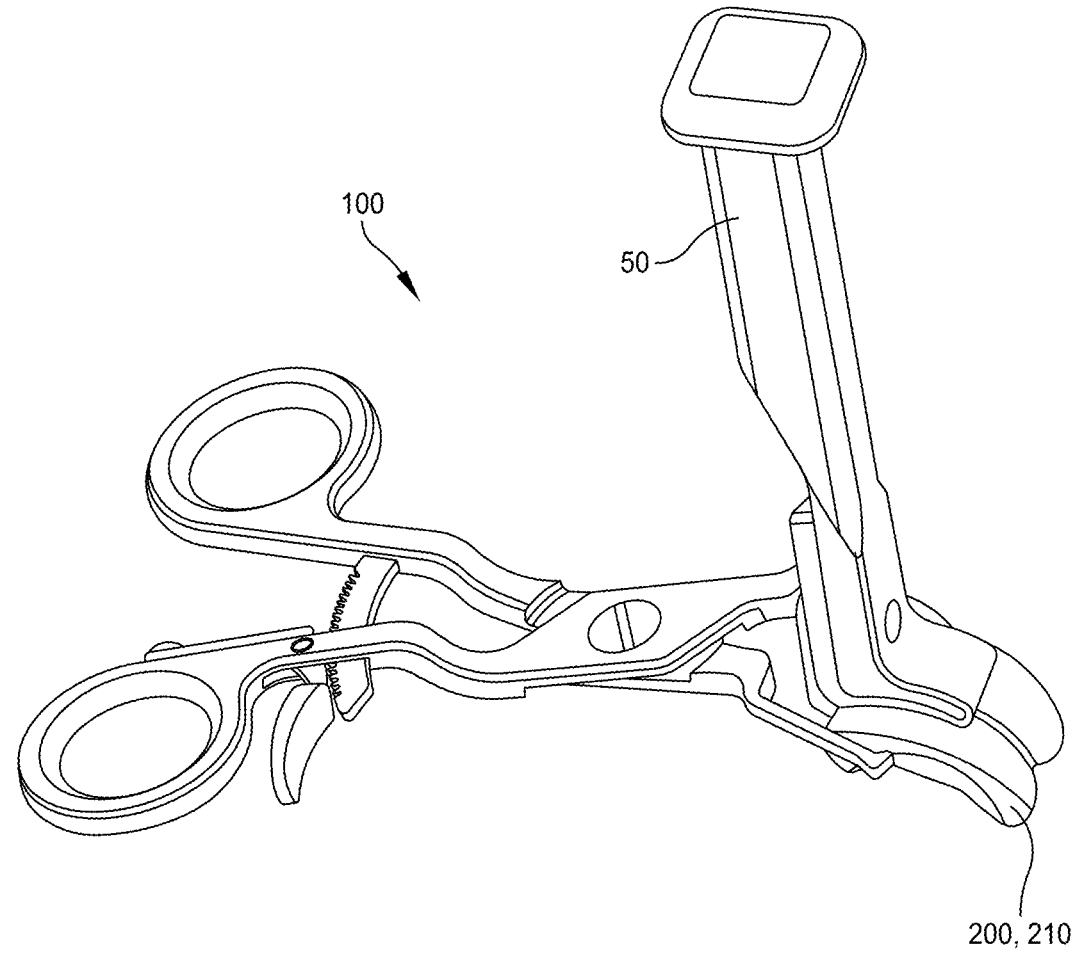
FIG. 4C is an illustration of the surgical clamp of FIG. 1 being used to hold a talar dome implant in place while an impactor is used to secure the talar dome implant to a talus.

FIG. 4 illustrates one example of an implant system 400 according to some embodiments. The implant system 400 comprises the surgical clamp 100 and at least one of the talar dome implants 200, 210. The surgical clamp 100 is described in detail above with reference to FIG. 1. The talar dome implants 200, 210 are described in detail above with reference to FIGS. 2A, 2B. The surgical clamp 100 will allow the surgeon to securely hold the talar dome implant 200, 210 as the surgeon inserts it into the joint space, as illustrated in FIGS. 4A, 4B. The surgeon can hold the talar dome implant using the surgical clamp 100 as shown during impaction also. Once the talar dome implant 200, 210 is in the joint space, the surgeon may release the talar dome implant 200, 210 by depressing the lever 118, unlocking the ratchet mechanism 114, which will allow the proximal ends 102a, 104a of the first arm 102 and the second arm 104, respectively, to open and, in turn, open the grasping end 108 release the grip on the talar dome implant 200, 210. FIG. 4C is an illustration of the surgical clamp 100 being used to hold a talar dome implant 200, 210 in place while an impactor 50 is used to secure the talar dome implant to a talus.

[Concept 2]

Figure 5A:
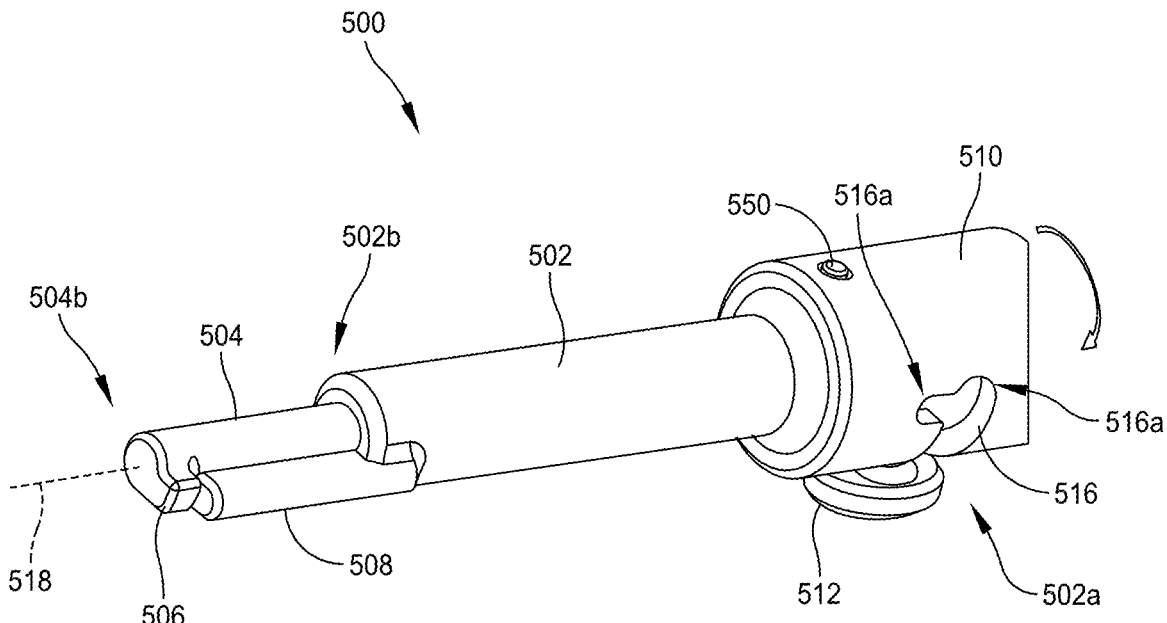
FIG. 5A shows a partial view of a holder apparatus according to an embodiment of the present disclosure.

FIGS. 5A-7C are illustrations of a holder apparatus 500 according to the present disclosure. FIG. 5A illustrates a partial view of one example of the holder apparatus 500 according to some embodiments. The holder apparatus 500 may be used by a surgeon to engage and hold an implant component or a trial component that are configured with appropriate structures to receive the engaging end of the holder apparatus 500 and form a removable connection. Such implant component and trial component can include, but not limited to, such components are talar dome trials, poly bearing insert trials of ankle joint prostheses, spacer guides, and new inserts for chamfer preparation instruments. In the case of ankle joint arthroplasty, the surgeon may use a talar dome trial to determine the correct size talar dome implant to use in the procedure. The holder apparatus 500 of the present disclosure can be used to securely hold and manipulate each talar dome trial as the surgeon may try talar dome trials of a variety of sizes.

In some embodiments, the holder apparatus 500 further comprises a handle portion 510, a tubular sleeve housing 502, and a stem 504. A longitudinal axis 518 can be defined through the length of the holder apparatus 500. The tubular sleeve housing 502 has a proximal end 502a, a distal end 502b, and an internal bore 502c extending longitudinally through the length of the tubular sleeve housing 502.

The handle portion 510 comprises a proximal end 510a, a distal end 510b (labeled in FIG. 6), and a cylindrical recess (or cavity) 510c provided at the distal end 510b that is configured to receive the proximal end 502a of the tubular sleeve housing 502. The tubular sleeve housing 502 can be rotated about the longitudinal axis 518 within the cylindrical recess 510c. As shown in FIG. 5A, the stem 504 is positioned within the tubular sleeve housing 502 and extends distally out of the distal end 502b of the tubular sleeve housing 502. The longitudinal axis 518 of the holder apparatus 500 defines the longitudinal axis of the handle portion 510 and the longitudinal axis of the cylindrical recess 510c.

Figure 5B:
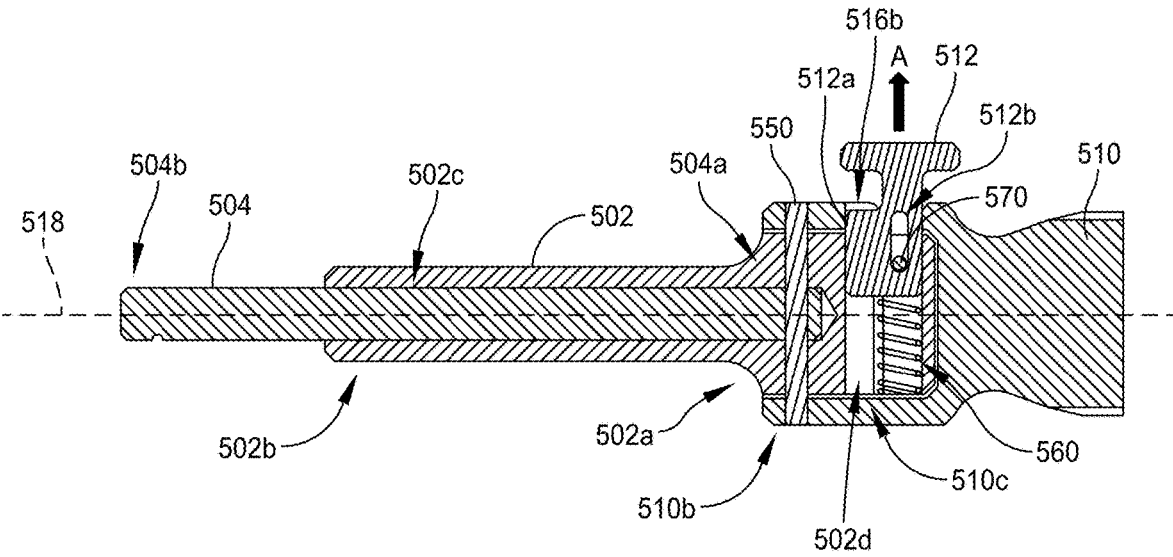
FIG. 5B shows a longitudinal cross-sectional view of the working portion of the holder apparatus of FIG. 5A.

Referring to the longitudinal cross-section view of the holder apparatus 500 shown in FIG. 5B, the stem 504 is received in the internal bore 502c of the tubular sleeve housing 502 and the stem 504 can be rotated about the longitudinal axis 518 within the internal bore 502c. The stem 504 is connected to the handle portion 510 so that the stem 504 can be rotated about the longitudinal axis 518 by turning the handle portion 510 about the longitudinal axis 518. The longitudinal axis 518 is the common longitudinal axis for the stem 504, the tubular sleeve housing 502, as well as the holder apparatus 500 itself.

Referring to the cross-sectional view shown in FIG. 5B, the stem 504 and the handle portion 510 are connected by a pin 550. The pin 550 extends from one side of the distal end 510b of the handle portion 510, through the proximal end 502a of the tubular sleeve housing 502 and the proximal end 504a of the stem 504, and to the opposite side of the distal end of the handle portion 510 as shown. The pin 550 is affixed to the distal end of the handle portion 510 and the proximal end 504a of the stem 504, and the proximal end 502a of the tubular sleeve housing 502 is configured with two opposing slots (not shown) that are circumferentially oriented through which the pin 550 extends. The circumferentially oriented slots allow the pin 550 to sweep through the circumferentially oriented slots when the handle 510 is rotated about the longitudinal axis 518 relative to the tubular sleeve housing 502. Because the stem 504 is affixed to the pin 550, when the handle portion 510 is rotated about the longitudinal axis 518, the stem 504 rotates in unison relative to the tubular sleeve housing 502. Thus, the rotational and longitudinal motions of the tubular sleeve housing 502 with respect to the stem 504 are all motions with respect to the handle portion 510 also. In other words the handle portion 510 and the stem 504 are connected to each other and rotate as one unit with respect to the other unit which is the combination of the tubular sleeve housing 502 and the knob 512 which are also connected to each other.

As described below in connection with FIGS. 5C and 5D, the first and second configurations of the holder apparatus involves the stem 504 and the tubular sleeve housing 502 being rotated about 90 degrees (i.e. ¼ turn) with relative to each other, the circumferentially oriented opposing slots on the tubular sleeve housing 502 have appropriate length to allow for the 90 degree rotation.

The internal bore 502c of the tubular sleeve housing 502 extends from the proximal end 502a to the distal end 502b of the tubular sleeve housing 502. In the illustrative example shown in FIG. 5B, the internal bore 502c is closed at the proximal end 502a of the tubular sleeve housing 502 and does not extend completely through. However, the internal bore 502c can be open at least to the cavity 502d provided at the proximal end 502a of the tubular sleeve housing 502. Because the stem 504 is held in place by the pin 550 preventing any longitudinal translation of the stem 504, having the internal bore 502c open to the cavity 502d would not pose any interference with the mechanism residing within the cavity 502d.

As can be seen in FIG. 5A, the stem 504 extends a distance distally out of the tubular sleeve housing 502. The stem 504 comprises a first arm 506 provided at the distal end 504b of the stem 504 and protrudes orthogonal to the longitudinal axis 518. The first arm 506 is spaced apart from the distal end 502b of the tubular sleeve housing 502.

The tubular sleeve housing 502 comprises a second arm 508 provided at the distal end 502b of the tubular sleeve housing 502. The second arm 508 extends distally from the distal end 502b of the tubular sleeve housing 502 adjacent to the stem 504 and protrudes orthogonal to the longitudinal axis 518.

The tubular sleeve housing 502 and the stem 504 are configured to rotate about the longitudinal axis 518 with respect to each other so that the first arm 506 and the second arm 508 can be rotated with respect to one another between a first configuration and a second configuration.

Figure 5C:
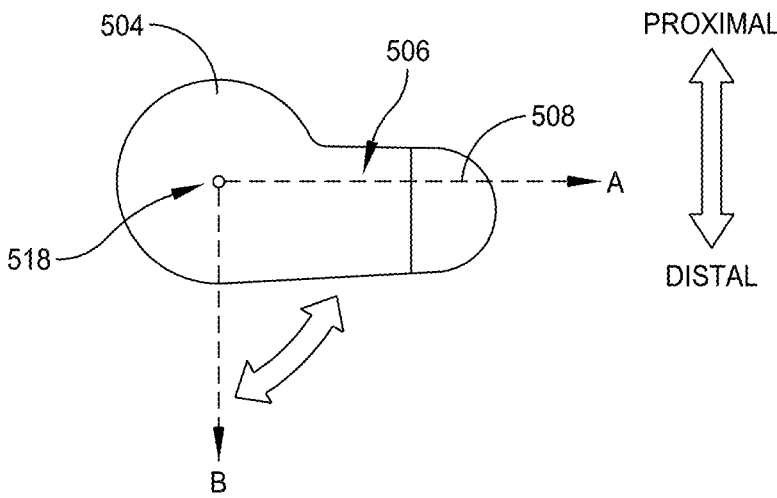
FIG. 5C is a schematic illustration of the holder apparatus viewed from the distal end showing the radially aligned first configuration of the first arm of the stem and the second arm of the tubular sleeve housing.

In the first configuration, the first arm 506 and the second arm 508 are radially aligned as shown in FIGS. 5A and 5C. Radially aligned configuration refers to the protruding directions (orthogonal to the longitudinal axis 518) of the first arm 506 and the second arm 508 being in the same radial direction when viewed from the distal end of the holder apparatus 500. FIG. 5C is a schematic illustration of the holder apparatus 500 viewed from the distal end showing the radially aligned configuration. The first arm 506 of the stem 504 and the second arm 508 of the tubular sleeve housing 502 are both protruding in the same radial direction A.

Figure 5D:
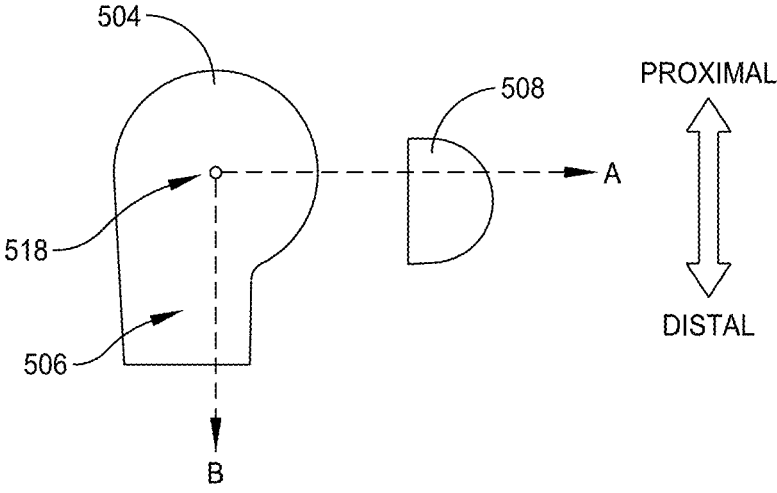
FIG. 5D is a schematic illustration of the holder apparatus viewed from the distal end showing the radially offset second configuration of the first arm of the stem and the second arm of the tubular sleeve housing.

Referring to FIG. 5D, in the second configuration, the stem 504 has been rotated 90 degrees in clock-wise direction with respect to the tubular sleeve housing 502 so that the first arm 506 has been rotated and now protrudes in the radial direction B. The first arm 506 is no longer in radial alignment with the second arm 508. In the second configuration, the first arm 506 and the second arm 508 can be referred to as being radially offset.

The proximal end 502a of the tubular sleeve housing 502 and the distal end 510b of the handle portion 510 are configured to cooperate in a way that can lock the two parts (one part being the tubular sleeve housing 502, and the other part being the connected combination of the stem 504+the handle portion 510) in two rotational positions that correspond to the first configuration and the second configuration of the first arm 506 and the second arm 508 described above.

In some embodiments, this locking configuration can be achieved by the following structures. As shown in FIG. 5A, the handle portion 510 can comprise a slot 516 that opens into the cavity 510c. The slot 516 comprise a main slot portion 516a that extends circumferentially and a distally extending portion 516b at each of the two ends of the main slot portion 516a. The main slot portion 516a extends circumferentially and orthogonal to the longitudinal axis 518 and guides the movement of the knob 512 within the slot 516. The distally extending portion 516b extends parallel to the longitudinal axis 518 and enables the locking function that locks the holder apparatus 500 in the first configuration and the second configuration.

Figure 6:
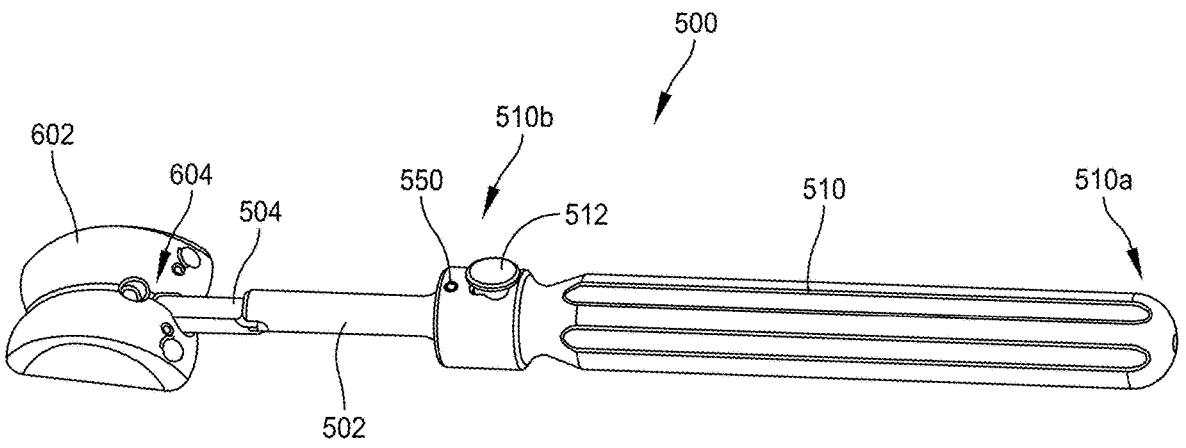
FIG. 6 shows the holder apparatus of FIG. 5A engaging a talar dome trial according to an embodiment of the present disclosure.

As can be seen in FIGS. 5A and 6, a knob 512 that is connected to the proximal end 502a of the sleeve housing 502 extends through the slot 516. Because the knob 512 is connected to the sleeve housing 502, when the sleeve housing 502 rotates about the longitudinal axis 518 with respect to the handle portion 510 and the stem 504, the knob 512 translates within the slot 516. FIG. 5A shows one of the two distally extending portion 516b at one end of the main slot portion 516a. The second of the two distally extending portion 516b is not visible in the view shown in FIG. 5A because of the angle of the view. The knob 512 can be seen as being in position at the end of the main slot portion 516a that is opposite from the end that is visible in FIG. 5A.

Because the knob 512 is connected to the tubular sleeve housing 502, when the handle portion 510 is turned with respect to the tubular sleeve housing 502, the knob 512 will correspondingly be moved within the slot 516. Thus, the limits on the amount of relative rotational movement between the tubular sleeve housing 502 and the handle portion 510 (and in turn the stem 504 since the stem and the handle portion are connected) can be defined by the length of the main slot portion 516a.

Accordingly, in some embodiments, the length of the main slot portion 516a is configured so that when the knob 512 is in position at one end of the main slot portion 516a, the first arm 506 and the second arm 508 are in their first configuration, and when the knob 512 is in position at the other end of the main slot portion 516a, the first arm 506 and the second arm 508 are in their second configuration. In some embodiments, the length of the main slot portion 516a is configured to rotate the tubular sleeve housing 502 90° about the longitudinal axis 518 with respect to the stem 504.

As shown in FIG. 5A, in the first configuration, the stem 504 extends further distally than the second arm 508 of the tubular sleeve housing 502 so that the first arm 506 extends out radially over the distal tip of the second arm 508. This prevents the tubular sleeve housing 502 from being moved distally.

In the second configuration, because the first arm 506 and the second arm 508 are radially offset as shown in FIG. 5D, the first arm 506 does not interfere with the second arm 508 being extended further distally. Thus, the tubular sleeve housing 502 can be configured to slide longitudinally further, i.e., extended, in distal direction with respect to the stem 504 so that the distal portion of the second arm 508 is adjacent to the first arm 506 of the stem 504. This will be referred to as the third configuration. In this third configuration, the stem 504 and the tubular sleeve housing's 502 ability to rotate about one another is limited because the first arm 506 and the second arm 508 will interfere with each other. Thus, the tubular sleeve housing 502 is prevented from rotating back to the first configuration.

In I some embodiments, the knob 512 is configured to cooperate with the distally extending portions 516b at the two ends of the slot 516 to lock the holder apparatus 500 in the first configuration and the second configuration. Referring to FIG. 5B, the knob 512 is positioned within a cavity 502d provided at the proximal end 502a of the tubular sleeve housing 502. The knob 512 is urged radially outward, in the direction shown by the arrow A, by an expanding member, such as a coil spring 560.

As shown in FIG. 5B, the knob 512 further comprises a slot 512b provided in a neck portion of the knob that remains within the cavity 502d of the tubular sleeve housing 502. A detent pin 570 that is affixed to the tubular sleeve housing 502 extends through the slot 512b. The detent pin 570 functions to retain the knob 512 within the cavity 502d and also limits how far the knob 512 can be urged outward in the direction A and retains the knob 512 within the proximal end of the tubular sleeve housing 502.

The knob 512 can further comprise a detent 512a that protrudes out on one side of the knob 512. When the knob 512 is within the main slot portion 516a, because the detent 512a portion of the knob 512 is wider than the width of the main slot portion 516a, the detent 512a portion remains on the interior of the cavity 510c of the handle portion 510 and the handle 510 and the knob 512 can be rotated relative to each other.

The distally extending portions 516b are wider than the main slot portion 516a and are sufficiently wide to allow at least a portion of the detent 512a to enter the distally extending portion 516b. Thus, when the knob 512 and the handle 510 are turned to a point where the knob 512 is in alignment with one of the distally extending portions 516b of the slot 516, the detent portion 512a is in alignment with the distally extending portion 516b. The urging force of the spring 560 pushes the knob 512 outward in the direction A and the detent portion 512a slides into the distally extending portion 516b of the slot 516. At this point, the detent pin 570 keeps the knob 512 from being ejected completely out of the cavity 502d and the handle portion 510. This is the configuration shown in FIG. 5B.

This configuration of the holder apparatus 500 will be referred to as the locked configuration because the detent portion 512a of the knob 512 is positioned within the distally extending portion 516b of the slot 516 and prevents the two parts of the holder apparatus 500 from being rotated relative to each other, the two parts being: (1) the stem 504/handle 510 assembly; and (2) the tubular sleeve housing 502/knob 512 assembly. Each of the two ends of the main slot portion 516a is provided with a distally extending portion 516b to lock the holder apparatus 500 in the first configuration and the second configuration of the first arm 506 and the second arm 508 discussed above.

The locked second configuration corresponds to the locking arrangement achieved between the holder apparatus 500 and a mating component, such as the talar dome trial 602, shown in FIG. 7C which is discussed in detail below.

Figure 6A:
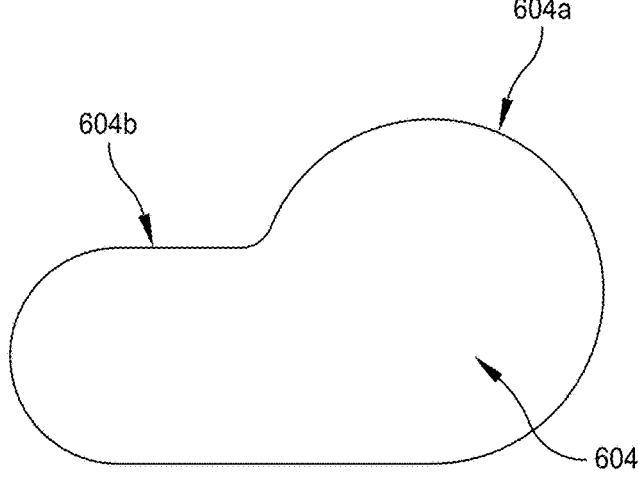
FIG. 6A shows an outline of the shape of the opening of the recess 604 in the talar dome trial that is shaped to receive the distal end of the holder apparatus 500.

FIG. 6 illustrates one example of the holder apparatus 500 engaging and holding a talar dome trial 602. The talar dome trial 602 comprises a recess 604 that receives the distal end of the holder apparatus 500. FIG. 6A shows an outline of the shape of the opening of the recess 604 that is shaped to receive the distal working end of the holder apparatus 500. In some embodiments, the recess 604 in the talar dome trial 602 comprises a keyhole design. The keyhole shape of the recess 604 comprises a main lobe 604a and a side lobe 604b. The two lobes generally extend orthogonal to each other so that the keyhole recess 604 has an asymmetric opening.

Figure 7B:
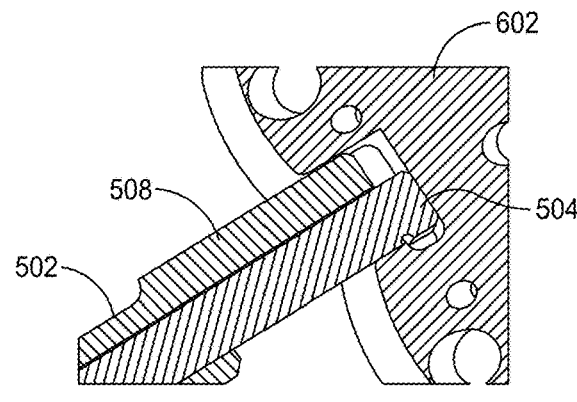
FIG. 7B shows a partial top view of the holder apparatus of FIG. 5 engaging a talar dome trial according to an embodiment of the present disclosure.
Figure 7A:
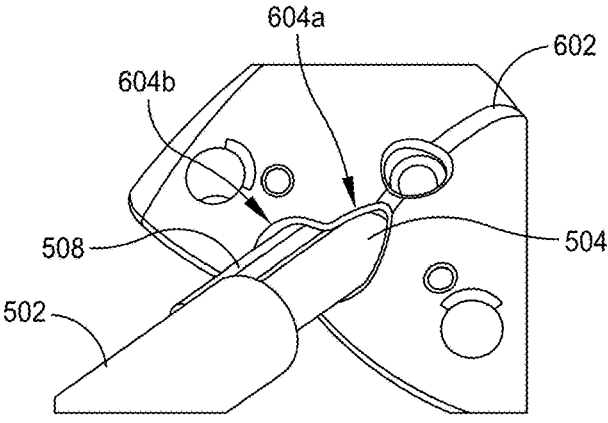
FIG. 7A shows a partial bottom view of the holder apparatus of FIG. 5 engaging a talar dome trial according to an embodiment of the present disclosure.
Figure 7C:
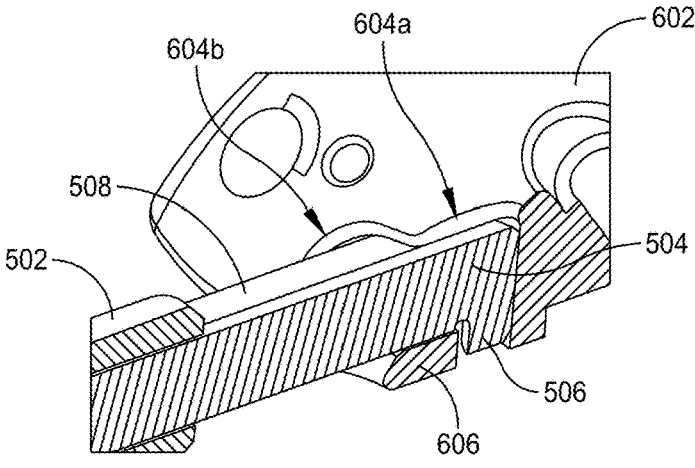
FIG. 7C shows a partial cross-sectional view of the holder apparatus of FIG. 5 engaging a talar dome trial according to an embodiment of the present disclosure.

FIGS. 7A-7C show detailed views of the locking engagement between the holder apparatus 500 and the talar dome trial 602 via cooperation of the working distal end of the holder apparatus 500 and the keyhole recess 604 of the talar dome trial 602.

The holder apparatus 500 is configured so that the distal end of the holder apparatus 500 is first inserted into the keyhole recess 604 with the first arm 506 and the second arm 508 of the holder apparatus 500 in their first configuration (sec FIG. 5C). The result is shown in FIG. 7A.

As shown, the stem 504 of the holder apparatus 500 mates into the main lobe 604a and the second arm 508 of the tubular sleeve housing 502 mates into the side lobe 604b of the keyhole recess 604. In this initial insertion step, because the first arm 506 and the second arm 508 are in their first configuration, the first arm 506 of the stem 504 would be radially aligned and oriented in the same direction as the second arm 508 and the first arm 506 enters the side lobe 604b of the keyhole recess 604 while the stem 504 itself enters the main lobe 604a.

Then, to lock the holder apparatus 500 to the talar dome trial 602, the first arm 506 and the second arm 508 are placed into their second configuration (see FIG. 5D) by turning the handle portion 510 with respect to the tubular sleeve housing 502. This step may require first unlocking the holder apparatus 500 from its first configuration by pressing on the knob 512 toward the longitudinal axis 518 of the apparatus 500 (i.e., the direction opposite of the arrow A shown in FIG. 5B) to release the detent 512a from the distally extending portion 516b of the slot 516. This allows the stem 504 to be rotated about the longitudinal axis 518 within the main lobe 604a with respect to the second arm 508 of the tubular sleeve housing 502 which allows the first arm 506 to rotate downward with respect to the talar dome trial 602 so that the first arm 506 is positioned behind a bottom ledge 606 of the keyhole recess 604. The bottom ledge 606 can be better seen in the sectional view of the talar dome trial/holder apparatus assembly in FIG. 7C, in which the section is taken longitudinally through the holder apparatus 500. This sectioned view in FIG. 7C shows the first arm 506 that has been rotated 90° downward with respect to the tubular sleeve housing 502 and the talar dome trial 602 and is now positioned behind the bottom ledge 606 of the keyhole recess 604 in the talar dome trial 602. At this point, the holder apparatus 500 will automatically lock itself in this second configuration by the operation of the locking feature of the knob 512 and its detent 512a described above. This second configuration locks the talar dome trial 602 and the holder apparatus 500 together because the interference between the first arm 506 and the bottom ledge 606 prevents the holder apparatus 500 from being pulled out of the keyhole recess 604. This enables a surgeon to securely hold the talar dome trial 602 and insert the talar dome trial 602 into the joint space during an ankle joint prosthetic procedure.

After the use of the talar dome trial 602 is completed, the holder apparatus 500 can be separated from the talar dome trial 602 by unlocking the holder apparatus 500, rotating the handle portion 510 with respect to the tubular sleeve housing 502 and placing the holder apparatus 500 to its first configuration, then pulling the holder apparatus 500 out of the keyhole recess 604. As described above, unlocking of the holder apparatus 500 would involve pressing on the knob 512 toward the longitudinal axis 518 of the apparatus 500 (i.e., the direction opposite of the arrow A shown in FIG. 5B) to release the detent 512a from the distally extending portion 516b of the slot 516.

In some embodiments, the securement between the holder apparatus 500 and the talar dome trial 602 can be further enhanced by placing first and second arms 506, 508 of the holder apparatus 500 into their third configuration described above. As discussed, in their third configuration, because the tubular housing 502 is prevented from rotating back to the first configuration, any accidental rotation of the tubular housing 502 is prevented and minimizes chances of accidental disengagement of the holder apparatus 500 from the talar dome trial 602.

Figure 8:
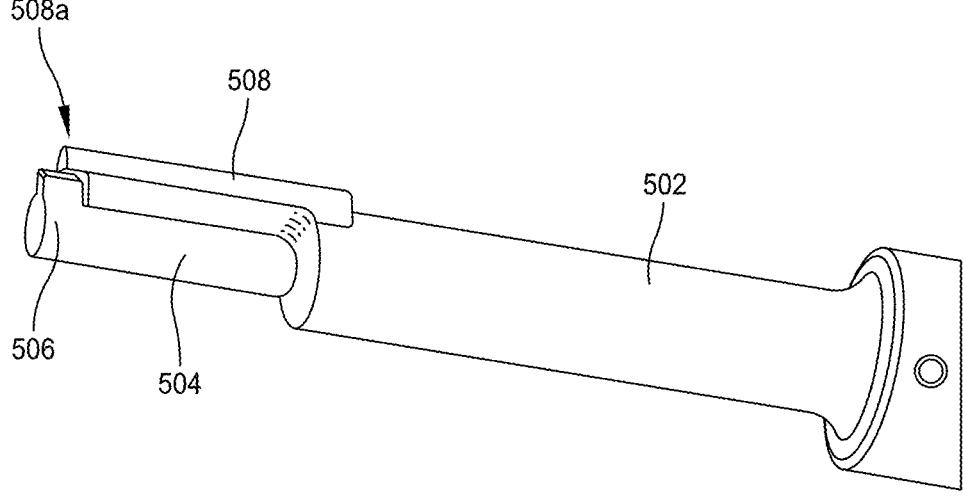
FIG. 8 shows a detailed view of the distal end of the holder apparatus of FIG. 5.
Figure 9A:
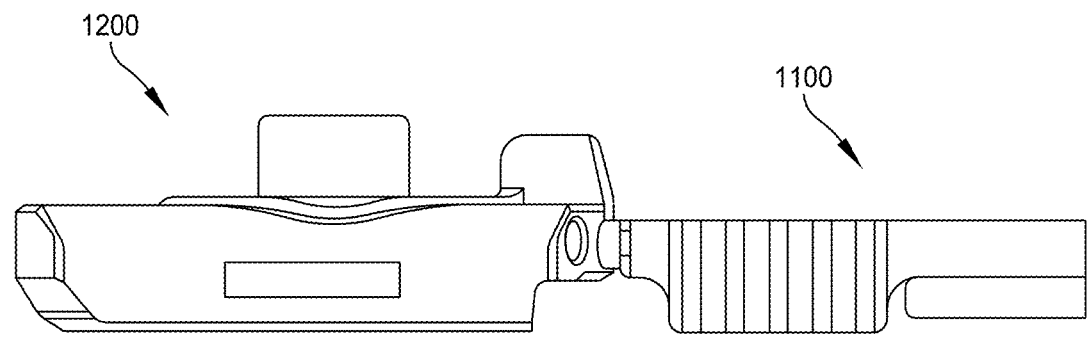
FIG. 9A shows an ankle joint replacement system according to an embodiment of the present disclosure.
Figure 9B:
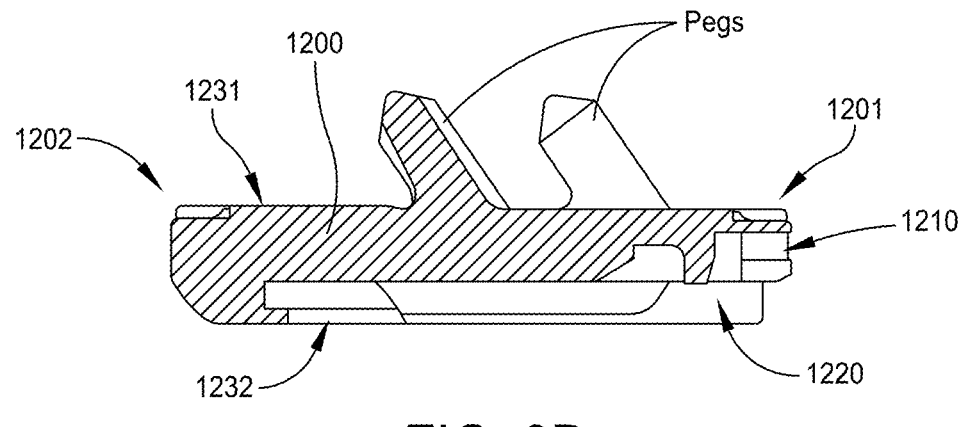
FIG. 9B shows a longitudinal cross-section of a tibia tray according to an embodiment of the present disclosure.
Figure 9C:
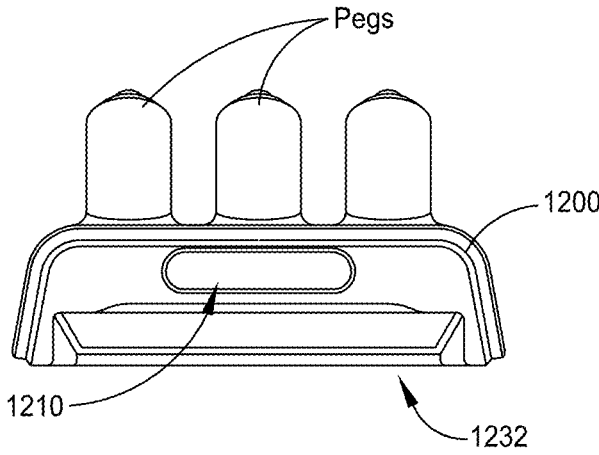
FIG. 9C shows a view from the front end portion of the tibia tray of FIG. 9B.
Figure 9D:
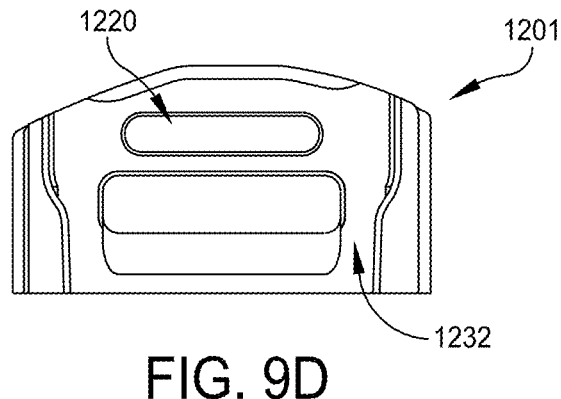
FIG. 9D shows a view from the bottom surface of the front end portion of the tibia tray of FIG. 9B.
Figure 10:
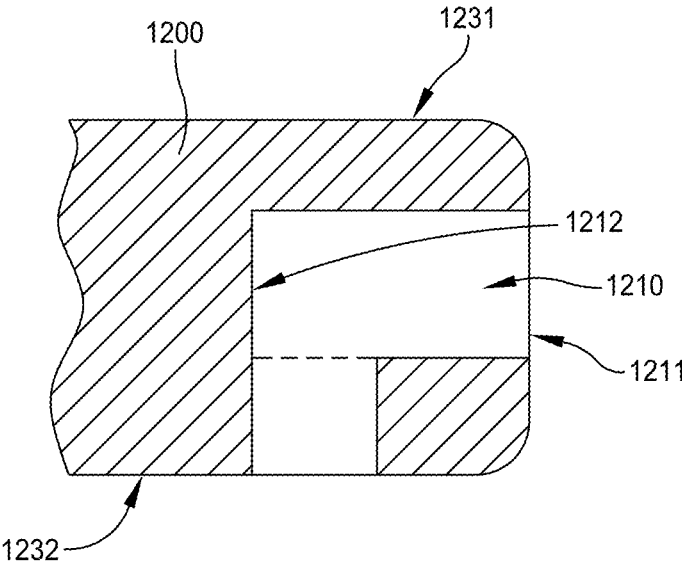
FIGS. 10-11 show close up views of a partial cross-section of the front end portion of the tibia tray showing the two orthogonally oriented blind slots that cooperate to provide improved attachment of the tibia tray to various surgical instruments.
Figure 11:
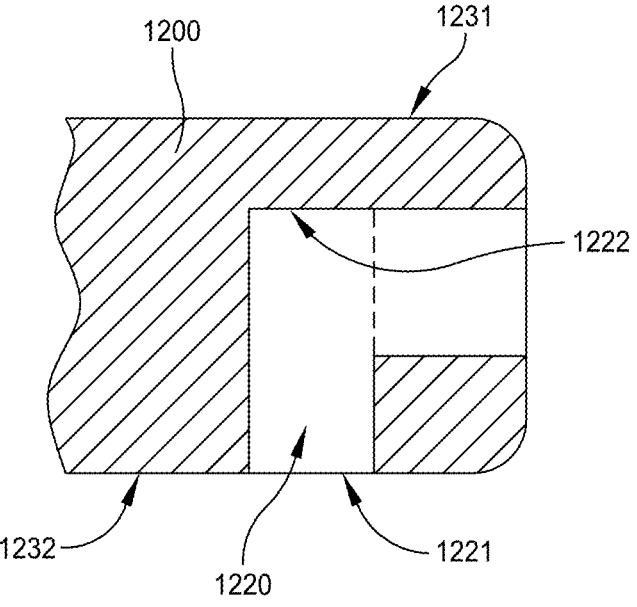

FIG. 8 illustrates a variation of the holder apparatus 500 according to some embodiments. In this embodiment, the second arm 508 has an extended tip 508a that extends the length of the second arm over the first arm 506. The extended tip 508a provides the distal end of the holder apparatus 500 with a smoother contour that facilitates initial insertion of the holder apparatus 500 into the keyhole recess 604 of the talar dome trial 602.

[Concepts 3 & 4]

Referring to FIGS. 9A-15, according to some embodiments, provided is an ankle joint replacement system 1000 comprising a tibia tray 3200, and an instrument 1100 for holding the tibia tray. The tibia tray 3200 comprises a first end 1201 configured to receive the instrument 1100 for holding the tibia tray 3200, a second end 1202, a top surface 1231 configured for engaging a distal end of a tibia bone, and a bottom surface 1232 configured for engaging a bearing component (not shown) of the ankle joint replacement system. The bearing component is generally made of a polymer material and engages the articulating surface of a talar dome implant.

The tibia tray 3200 comprises two orthogonally oriented blind slots 1210, 1220 that intersect each other. Each of the blind slots 1210, 1220 has a width and comprises an opening at one end and a blind end at a second end. For example, in the illustrated example of the tibia tray 3200 shown in FIGS. 9A-11, the first end 1201 is provided with a first blind slot 1210 that has an opening 1211 that opens to the first end 1201 and a blind end 1212 at the opposite end of the blind slot 1210. The first end 1201 is also provided with a second blind slot 1220 that is orthogonally oriented from the first blind slot 1210. The second blind slot 1220 has an opening 1221 that opens to the bottom surface 1232 of the tibia tray and a blind end 1222 at the opposite end of the blind slot 1220.

Figure 12:
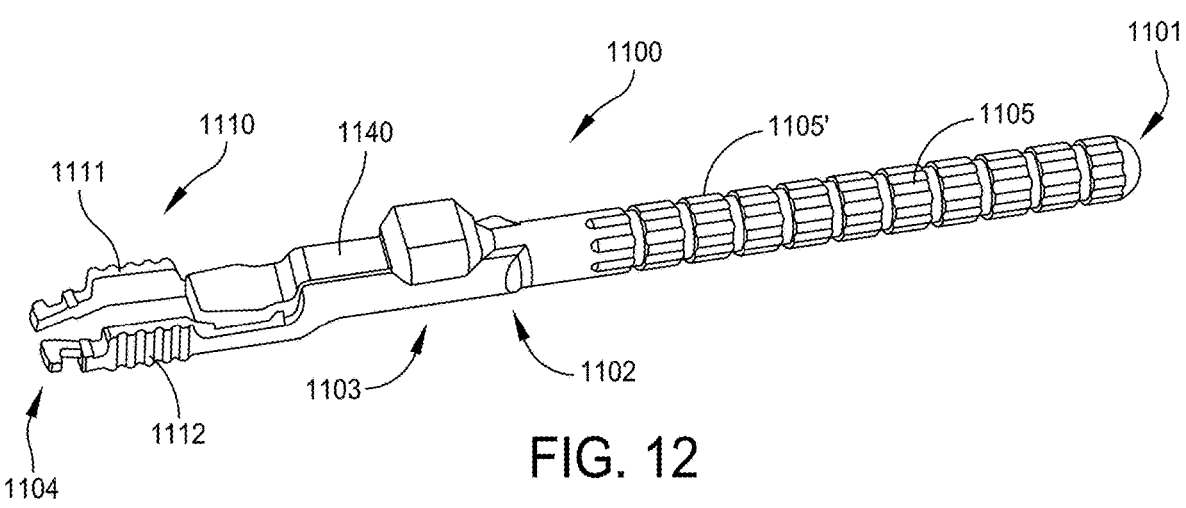
FIGS. 12-13B are isometric views of a tibia tray holding instrument according to an embodiment of the present disclosure.

Referring to FIG. 12, the instrument 1100 comprises an elongated handle 1105, and a forked clip portion 1110. The elongated handle comprises a proximal end 1101 and a distal end 1102 and the forked clip portion 1110 is provided at the distal end 1102, where the forked clip portion 1110 comprises two opposing arms 1111 and 1112. The forked clip portion 1110 has a distal end 1104 and a proximal end 1103 that is joined to the distal end 1102 of the elongated handle 1105.

Figure 13A:
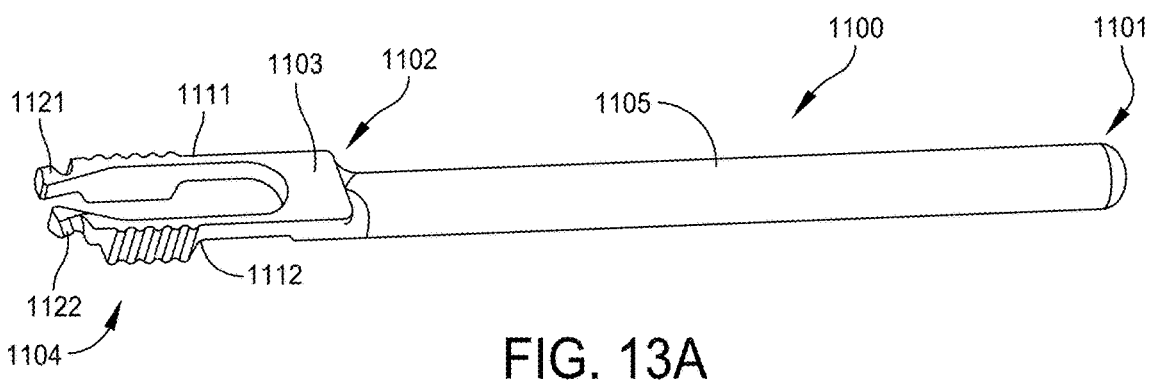
Figure 13B:
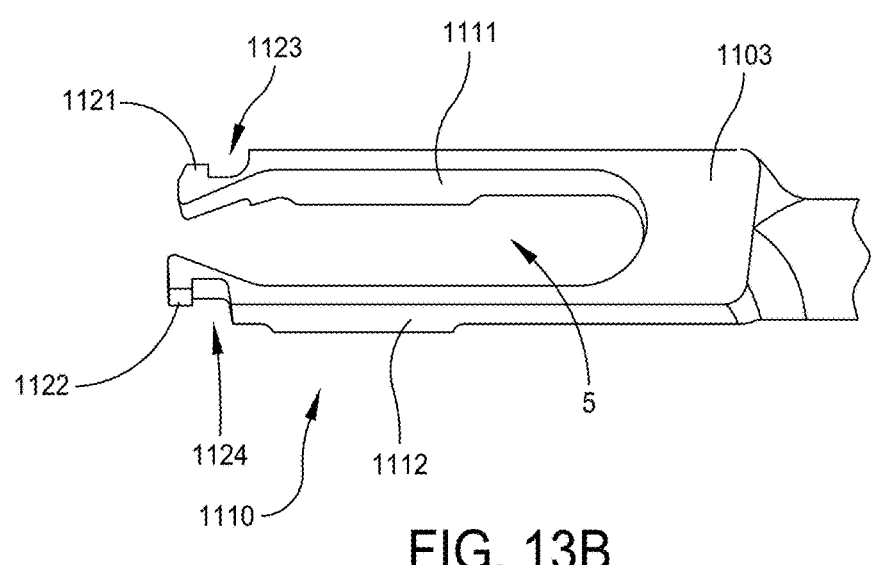

Referring to FIG. 13B, each of the two opposing arms 1111 and 1112 are joined to the proximal end 1103 of the forked clip portion 1110 and extends distally from the proximal end 1103 of the forked clip portion 1110 to its distal end. The two opposing arms 1111 and 1112 can also be thought of as extending further from the distal end 1102 of the elongated handle 1105 to their distal ends.

As shown in FIGS. 9A-11, the first blind slot 1210 of the two blind slots 1210, 1220 in the tibia tray 1200 opens to the first end 1201 of the tibia tray. The second blind slot 1220 of the two blind slots 1210, 1220 opens to the bottom surface 1232 of the tibia tray.

Figure 14A:
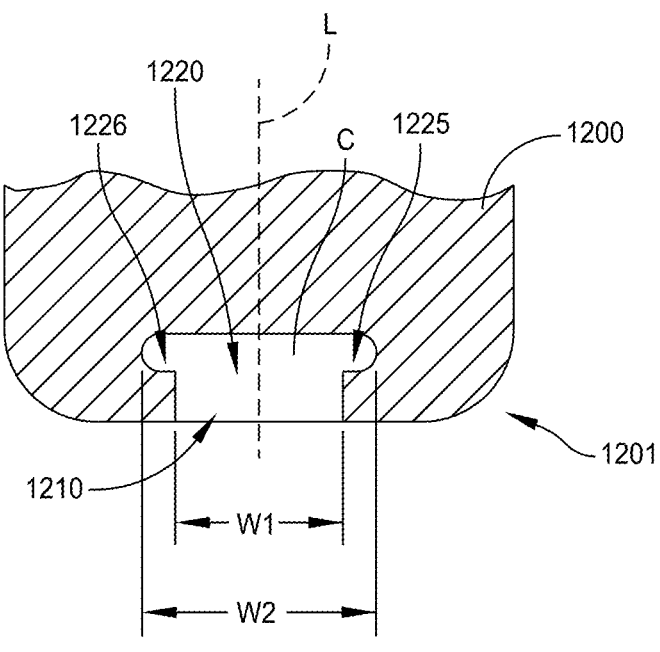
FIGS. 14A-14B are partial lateral cross-sectional views of the front end portion of the tibia tray shown in FIGS. 11-13.

Referring to FIG. 14A, the first blind slot 1210 has a width W1 and the second blind slot 1220 has a width W2. The width W2 of the second blind slot 1220 is wider than the width W1 of the first blind slot 1210. As a result of this difference in the widths and because the two orthogonally oriented blind slots intersect each other near their blind ends, the second blind slot 1220 effectively forms a cavity portion C at the blind end of the first blind slot 1210. Because the second blind slot 1220 is wider, the cavity portion C is wider than the width W1 of the first blind slot 1210 and thereby forms two side pockets 1225 and 1226 located at each side of the blind end of the first blind slot 1210. The two side pockets 1225, 1226 are separated by a distance that is equal to the width W1 of the first blind slot 1210.

The distal ends of the two opposing arms 1111 and 1112 of the forked clip portion 1110 are configured to engage the two pockets 1225 and 1226 at the blind end 1212 of the first blind slot 1210 and hold the tibia tray 1200 when the forked clip portion 1110 is fully inserted into the first blind slot 1210.

The term "blind slot" is used herein to describe a groove, a slit, a slot, or an elongated hole that does not extend completely through but only partially through a body of structure.

Figure 14B:
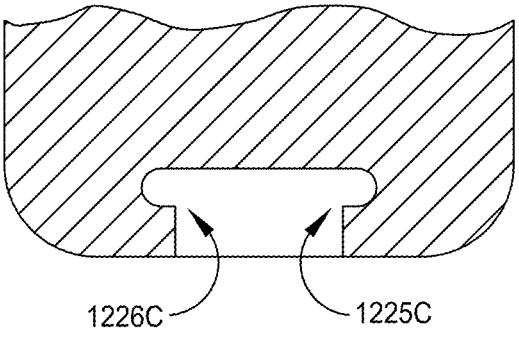

As shown in FIG. 14B, the tibia tray 1200 has a longitudinal axis L defined through its midline extending from the first end 1201 to the second end 1202.

Each of the two side pockets 1225, 1226 at the blind end 1212 of the first blind slot 1210 extends laterally outward with respect to the longitudinal axis L of the tibia tray 1200 and form a respective convex corner 1225C and 1226C at the transition point between the first blind slot 1210 and the pocket 1225, 1226.

With the provision of the side pockets 1225, 1226, the distal end of each of the two opposing arms 1111, 1112 of the forked clip portion 1110 are configured to catch or engage by interference, the respective convex corners 1225C, 1226C, when the forked clip portion is fully inserted into the first blind slot 1210 and the two opposing arms 1111, 1112 are urged outward.

Figure 15:
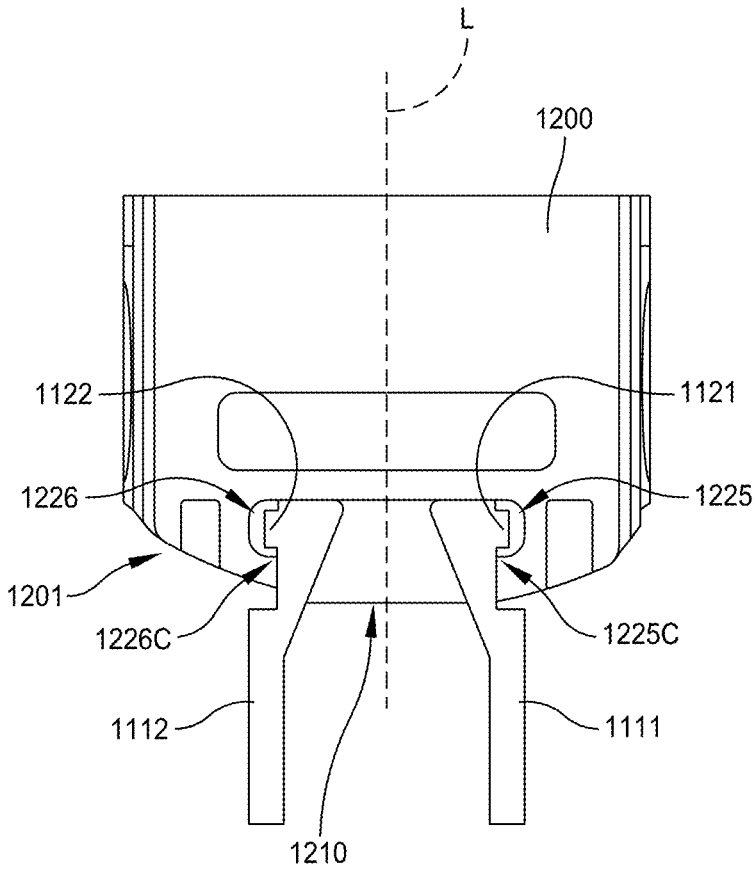
FIG. 15 is a partial lateral cross-sectional view of the front end portion of the tibia tray shown in FIGS. 9-11, and 14A-14B, shown in engagement with the forked clip portion of the tibia tray holding instrument of FIG. 12 that has been fully inserted into the first blind slot with the two opposing arms being urged outward so that the distal tips of the two opposing arms are engaged with the side pockets at the blind end of the first blind slot.
Figure 16A:
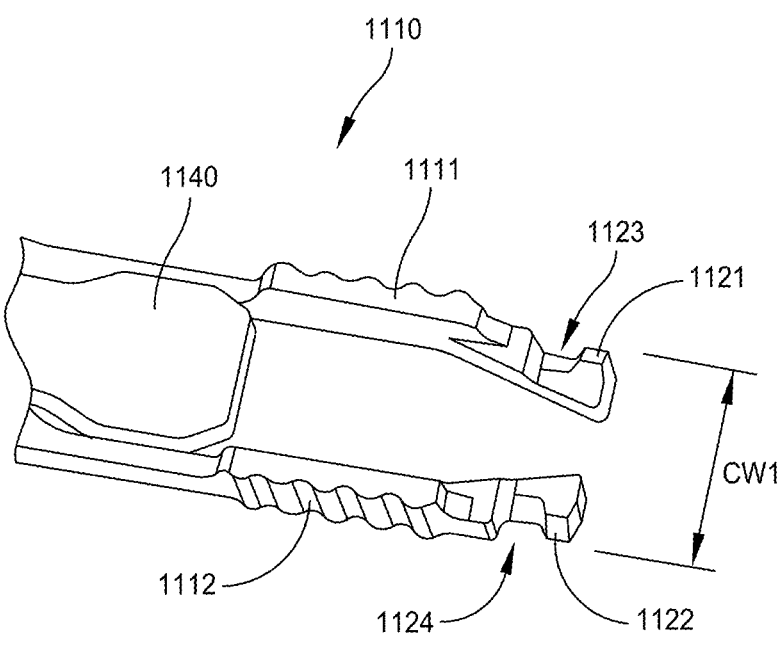
FIG. 16A shows the forked clip portion in normally open configuration.

Referring to FIG. 16A, in some embodiments of the ankle joint replacement system 3000, the two opposing arms 1111,

1112 of the forked clip portion are configured to be in normally open configuration in which the distal ends of the two opposing arms have a width CW1 that is incrementally larger than the distance between the two pockets (which is effectively the width W1 of the first blind slot 1210). Because the width CW1 is slightly larger than the width W1, the distal ends of the two opposing arms 1111, 1112 need to be squeezed together to be inserted into the first blind slot 1210 and the two opposing arms will try to spring back to their original open configuration and be urged laterally outward (i.e. away from the longitudinal axis L of the tibia tray) against the sides of the first blind slot 1210. Then, when the forked clip portion 1110 is fully inserted into the first blind slot 1210 as shown in FIG. 15, as the distal ends of the two opposing arms clear the convex corners 1225C, 1226C, the distal ends are urged outward and catch or engage by interference, the convex corners. The two opposing arms 1111, 1112 remain in this normally urged outward state when the forked clip portion is fully inserted into the first blind slot.

The instrument 1105 can further comprise a sliding cam 1140 located between the two opposing arms that is configured to be slidable distally in the direction shown by the arrow A toward the distal ends of the two opposing arms. In this embodiment, where the two opposing arms 1111, 1112 are in normally open configuration, the sliding cam 1140 can be used to lock the arms in the engaged position after the arms are fully inserted into the first blind slot 1210 as shown in FIG. 15. By sliding the cam 1140 up against the distal ends of the two opposing arms, the cam 1140 will prevent the two arms from being closed and thus lock the instrument 1150 and the tibia tray 1200 locked together and prevent the tibia tray 1200 from being dislodged when being handled.

Figure 16B:
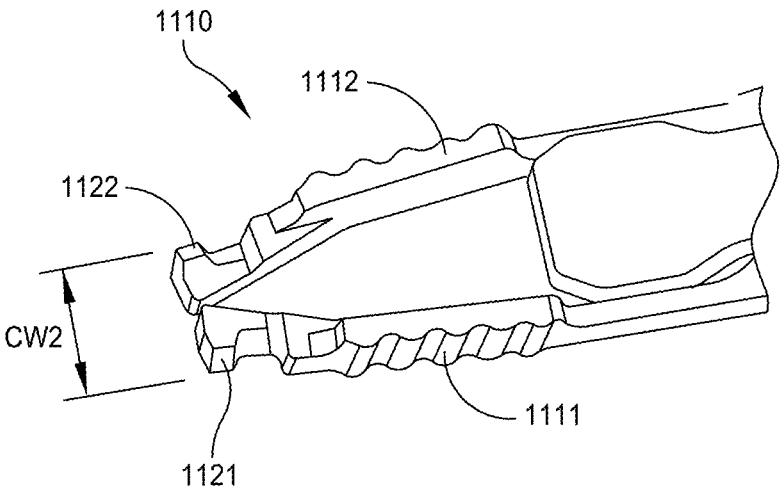
FIG. 16B shows the forked clip portion in normally closed configuration.

Referring to FIG. 16B, in some embodiments of the ankle joint replacement system 1000, the two opposing arms 1111, 1112 of the forked clip portion are configured to be in normally closed configuration in which the distal ends of the arms are close together at rest as shown. The distal ends of the two opposing arms have a width CW1. The width CW1 is narrower than the width W1 of the first blind slot 1210 so the forked clip portion 1110 can be easily inserted into the first blind slot 1210 for engaging the tibia tray 1200.

In these embodiments, the instrument 1105 can further comprise a sliding cam 1140 located between the two opposing arms that is configured to be slidable distally in the direction shown by the arrow A toward the distal ends of the two opposing arms. After the two opposing arms are fully inserted into the first blind slot 1210, the two opposing arms are urged outward by sliding the cam 1140 so that the distal ends of the two opposing arms engage the side pockets 1225, 1226, and the convex corners 1225C, 1226C and securely attach the tibia tray 1200 to the instrument 1105.

Referring to FIGS. 16A and 16B, in the embodiments discussed above, the distal end of each of the two opposing arms 1111, 1112 comprises an outwardly extending detent 1121, 1122, respectively. The detents 1121, 1122 interfere with the convex corners 1225C, 1226C when the forked clip portion 1110 is fully inserted into the first blind slot 1210 and the two opposing arms are urged outward. This engagement prevents the instrument 1105 from disengaging the tibia tray 1200 by preventing the forked clip portion 1110 from being pulled out of the first blind slot 1210.

Because the detents 1121 and 1122 protrude outward at the distal ends of the two opposing arms 1111 and 1112, respectively, a recessed neck portion 1123 and 1124, respectively, are formed behind each of the detents 1121 and 1122, respectively. As can be seen in FIG. 15, the recessed neck portions 1123, 1124 provides a clearance space for the convex corners 1225C, 1226C as the detents 1121, 1122 engage the side pockets 1225, 1226 and the convex corners 1225C, 1226C.

[Concept 5]

Figure 17:
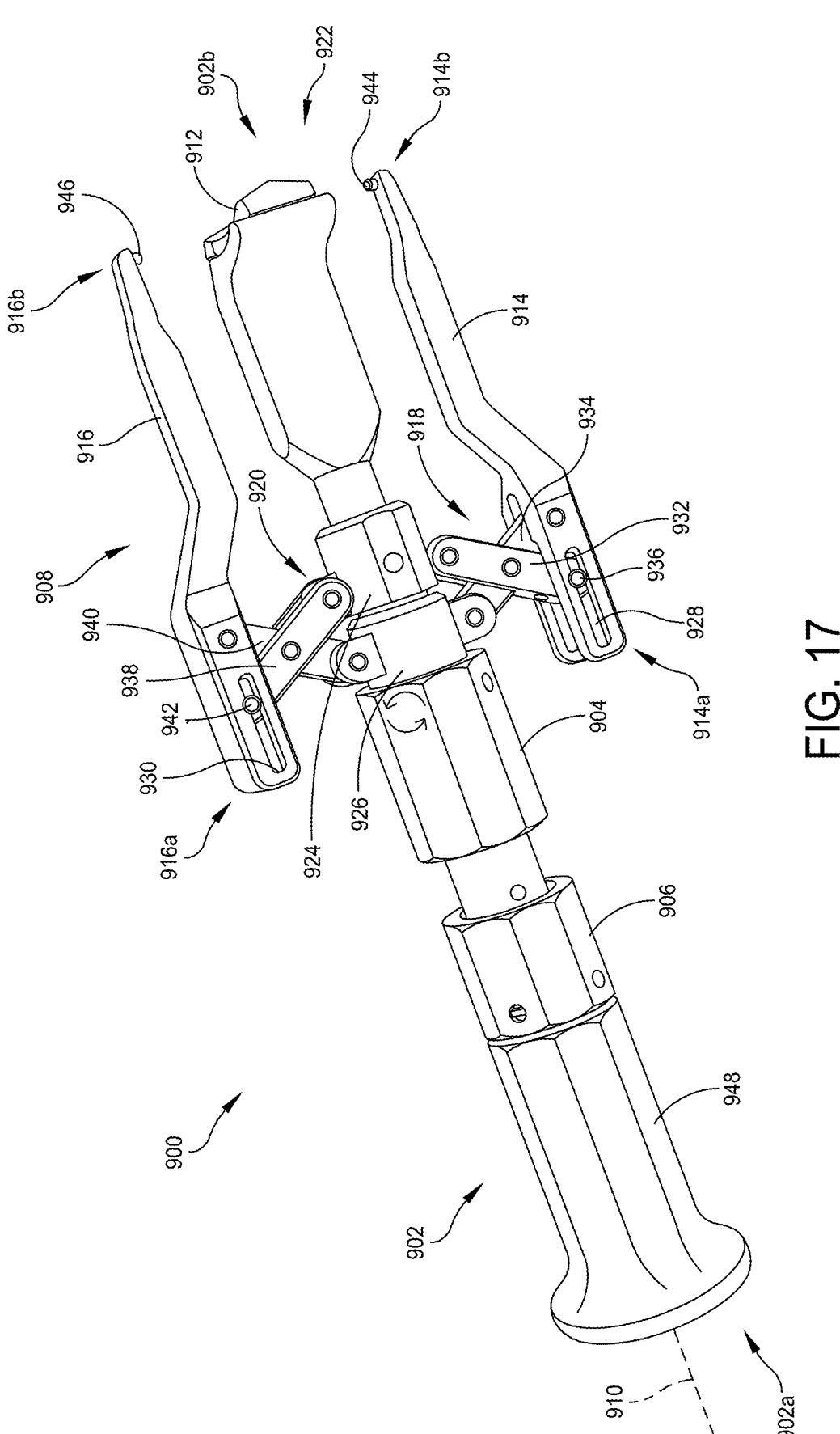
FIG. 17 illustrates one example of a holder apparatus 900 according to some embodiments.

FIG. 17 illustrates one example of a holder apparatus 900 according to some embodiments. The holder apparatus 900 may be used by a surgeon to hold a talar dome implant component of an ankle joint replacement system and insert it into a joint space during an ankle joint arthroplasty procedure. The holder apparatus 900 enables a surgeon to securely hold a talar dome implant. Once the talar dome implant is in position in the joint space, with the holder apparatus 900 still holding the talar dome implant, the holder apparatus 900 can be used as an impactor to impact the talar dome implant into the prepared talus. This eliminates the need for two separate instruments (e.g., a talar dome holder apparatus and a separate impactor) to secure the talar dome implant in the joint space.

The holder apparatus 900 comprises an impactor 902, a first knob 904, a second knob 906, and a grasping assembly 908. The impactor 902 has a proximal end 902*a* and a distal end 902*b*. The impactor's longitudinal axis 910 defines longitudinal axis of the holder apparatus 900. The impactor 902 comprises an impactor tip 912 at the distal end 902*b*.

The first knob 904 is configured to rotate about the longitudinal axis 910, and the second knob 906 is configured to rotate about the longitudinal axis 910.

Figure 18A:
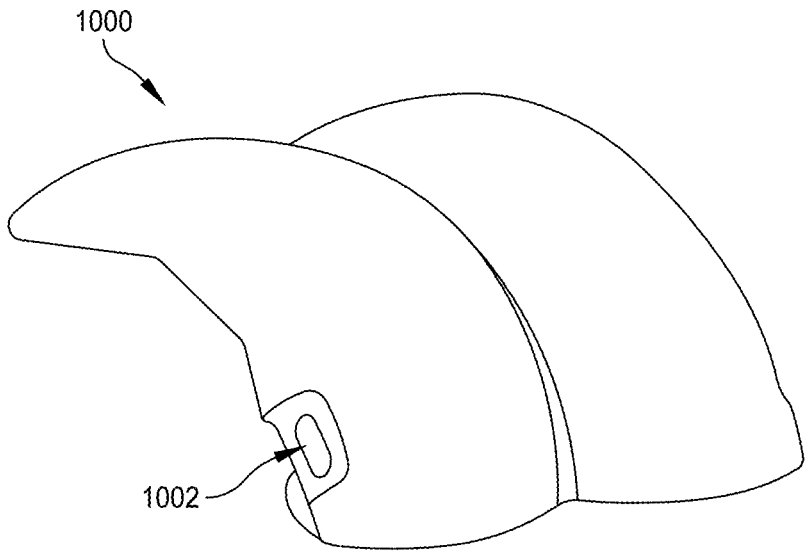
FIGS. 18A and 18B illustrate one example of a talar dome implant, that is configured to be engaged by the holder apparatus shown in FIG. 17.
Figure 18B:
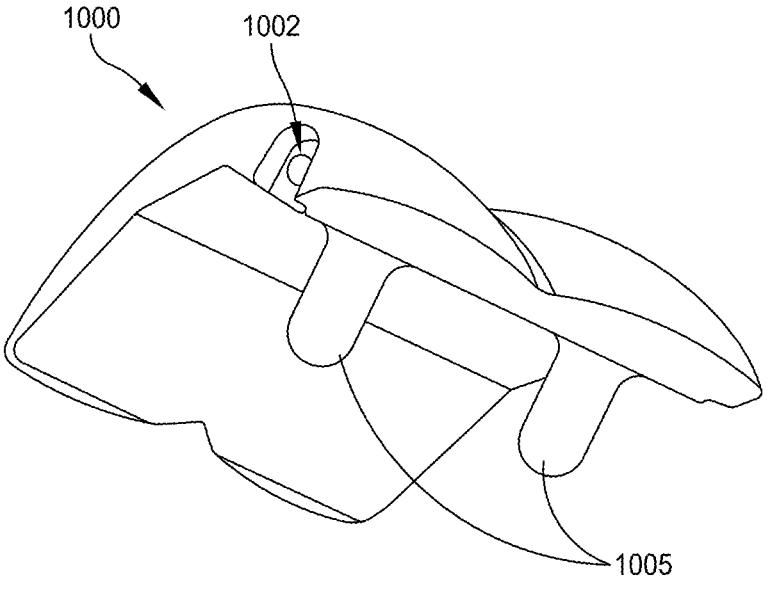

The grasping assembly 908 is slidingly coupled to the impactor 902 and configured to securely grasp a talar dome implant (e.g., talar dome implant 1000, shown in FIGS. 18A and 18B). The grasping assembly 908 is capable of pulling the talar dome implant (e.g., talar dome implant 1000) up against the impactor tip 912. The grasping assembly 908 comprises a first arm 914, a second arm 916, a first scissor joint arrangement 918, and a second scissor joint arrangement 920. The first arm 914 has a proximal end 914*a* and a distal end 914*b*, and the second arm 916 has a proximal end 916*a* and a distal end 916*b*. The distal end of the first arm 914*b* and the distal end of the second arm 916*b* form a grasping end 922 of the grasping assembly 908. A surgeon may use the grasping end 922 to securely grasp a talar dome implant (e.g., talar dome implant 1000). The first arm 914 and the second arm 916 are arranged in opposing positions about the longitudinal axis 910. The first scissor joint arrangement 918 connects the first arm 914 to a first collar 924 and a second collar 926, and the second scissor joint arrangement 920 connects the second arm 916 to the first collar 924 and the second collar 926.

The first knob 904 is coupled to the first collar 924 and configured to draw the first arm 914 and the second arm 916 toward each other by rotating the first knob in a first direction which, in turn, collapses the two scissor joint arrangements 918, 920 by sliding the first collar 924 distally along the longitudinal axis 910. The first knob 904 is configured to draw the first arm 914 and the second arm 916 away from each other by rotating the first knob 904 in an opposite direction from the first direction which, in turn, expands the two scissor joint arrangements 918, 920 by sliding the first collar 924 proximally along the longitudinal axis 910. Rotating the first knob 904 adjusts the width of the grasping end 922, which allows the holder apparatus 900 to clamp onto talar dome implant of varying sizes, making it a versatile instrument. The second knob 906 is coupled to the second collar 926 and configured to slide the second collar 926 proximally which, in turn, slides the grasping assembly 908 proximally along the longitudinal axis 910. Once the grasping end 922 is clamped around a talar dome implant (e.g., talar dome implant 1000), a surgeon may rotate the second knob 906 in order to pull the talar dome implant proximally until it contacts the impactor tip 912.

In some embodiments, the impactor 902 comprises a handle 948 at the proximal end 902*a*. The handle 948 may comprise grooves or ridges on its surface that enable a surgeon to more easily grip the handle 948. In some embodiments, the impactor 902 is configured to receive an impact force at the proximal end of the impactor 902*a* and configured to transmit the impact force to the talar dome implant (e.g., talar dome implant 1000) through the impactor tip 912. For example, when securing a talar dome implant to pre-drilled holes in a talus, a surgeon may strike the proximal end of the impactor 902*a* with a hammer (or other suitable instrument) and the impactor 902 would transmit the impact force to the talar dome implant via the impactor tip 912 to drive the pegs 1005 on the bottom surface of the talar dome implant into the pre-drilled holes in the talus. The pre-drilled holes have slightly smaller diameter than the pegs 1005 so that an interference fit is achieved between the pegs 1005 and the pre-drilled holes.

In some embodiments, the first arm 914 comprises a slot 928 at the proximal end of the first arm 914*a*, and the second arm 916 comprises a slot 930 at the proximal end of the second arm 916*a*. In some embodiments, the first scissor joint arrangement 918 comprises a first support 932 configured to attach the first arm 914 to the first collar 924 and a second support 934 configured to attach the first arm 914 to the second collar 926. The first support 932 comprises a pin 936 configured to slide within the slot 928 of the first arm 914, which assists with changing the width of the grasping assembly 908. In some embodiments, the first support 932 is pivotally coupled to the second support 934.

In some embodiments, the second scissor joint arrangement 920 comprises a third support 938 configured to attach the second arm 916 to the first collar 924 and a fourth support 940 configured to attach the second arm 916 to the second collar 926. The third support 938 comprises a pin 942 configured to slide within the slot 930 of the second arm 916, which assists with changing the width of the grasping assembly 908. In some embodiments, the first scissor joint arrangement 918 and the second scissor joint arrangement 920 are positioned 180 degrees apart about longitudinal axis 910. In some embodiments, the third support 938 is pivotally coupled to the fourth support 940.

FIGS. 18A and 18B illustrate one example of a talar dome implant 1000 according to some embodiments. FIG. 18A is a perspective view showing the proximal articulating surface of the talar dome implant and FIG. 18B is a perspective view showing the opposite, the distal surface of the implant.

In some embodiments, the distal end of the first arm 914*b* comprises a first protrusion 944 configured to engage a corresponding first recess 1002 in the talar dome implant 1000, and the distal end of the second arm 916*b* comprises a second protrusion 946 configured to engage a corresponding second recess (not shown) in the talar dome implant 1000. In some embodiments, the first protrusion 944 and the second protrusion 946 each comprise sides that are straight and orthogonal to the longitudinal axis 910. In some embodiments, the first protrusion 944 and the second protrusion 946 protrude towards each other. The first protrusion 944 and second protrusion 946 at the grasping end 922 enable a surgeon to securely grasp a talar dome implant (e.g., talar dome implant 1000) using holder apparatus 900 when preparing to insert the talar dome implant into the joint space. Once the surgeon has grasped the talar dome implant using the grasping end 922, the surgeon can pull the talar dome implant proximally towards the impactor tip 912 by twisting the second knob 906, even further securing the talar dome implant to the holder apparatus 900. The surgeon can then easily and securely insert the talar dome implant into the joint space and subsequently impact the talar dome implant into the prepared talus by applying an impact force to the proximal end of the impactor 902a.

[Concept 6]

FIGS. 19-27B illustrate one example of a system for preparing an intramedullary path in the tibia from the distal end for receiving a tibia component of an ankle prosthesis. In some embodiments, the system comprises a clip 2100, a cartridge 2200, a reamer tip 2300, a reamer shaft 2400, and a C-bracket 2600. The cartridge 2200 may be positioned in a resected ankle joint space formed by resected tibia in the ankle and is designed to aid the surgeon in aligning and assembling a surgical tool 2500 within the resected joint space. In the illustrated example, the surgical tool 2500 is a reaming tool for reaming the intramedullary path in the tibia from the distal end.

The surgical tool 2500 comprises a reamer shaft 2400 and the reamer tip 2300, assembled along a central axis of the tool. The cartridge 2200 and the clip 2100 are configured to cooperate for aligning the reamer shaft 2400 and the reamer tip 2300 and assembling them within the resected joint space into the surgical tool 2500.

Figure 21A:
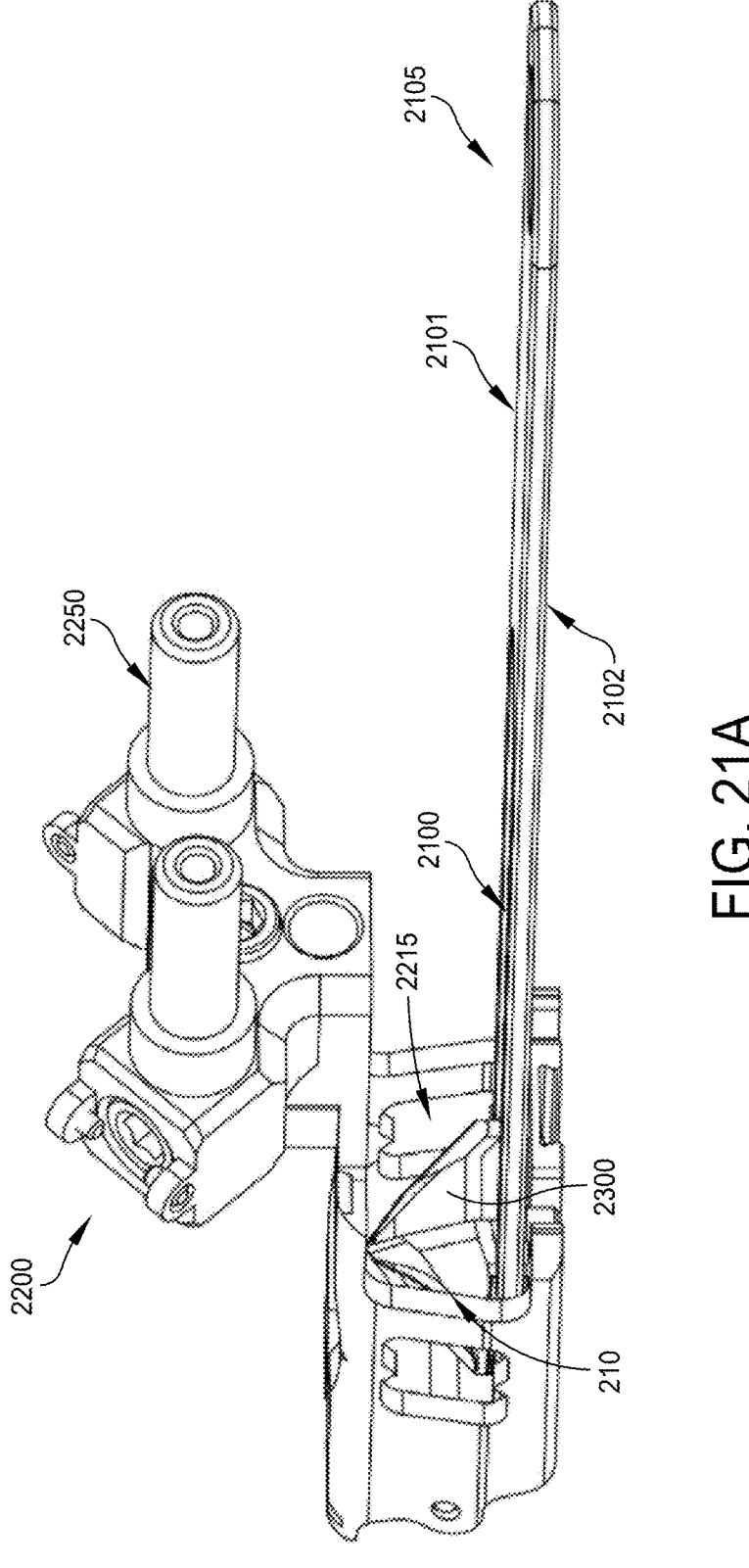
FIGS. 21A-21C are illustrations showing the clip of FIG. 19 and the hollow body cartridge of FIGS. 20A-20C in cooperating engagement.

With the cartridge 2200 positioned in the resected joint space, the reamer tip 2300 is provisionally retained by the clip 2100 and positioned within the cartridge 2200 to a predetermined position. The clip 2100 is configured and arranged to hold and align the reamer tip 2300 in the predetermined position within the cartridge 2200. A reamer shaft 2400 is then introduced into the cartridge 2200 to engage and couple with the reamer tip 2300 to complete the assembly of the surgical tool 2500. The positioning of the reamer tip 2300 within the cartridge 2200 using the clip 2100 is shown in FIG. 21A.

The C-bracket 2600 is an alignment jig that can be attached to the cartridge 2200 and assist with guiding the reamer shaft 2400 along an axis that is in a desired alignment with the reamer tip 2200 when the reamer shaft 2400 is being introduced into the cartridge 2200. Thus, the C-bracket 2600 facilitates alignment of the reamer shaft 2400 with the reamer tip 2300 within the cartridge.

The combination of these elements enables in-situ assembly of a surgical tool 2500 within the resected bone space, which may otherwise be too invasive to insert pre-assembled. The size and arrangement of the abutting surfaces within the system enables locating components at a predetermined position to facilitate in-situ assembly of the surgical tool 2500.

Figure 19:
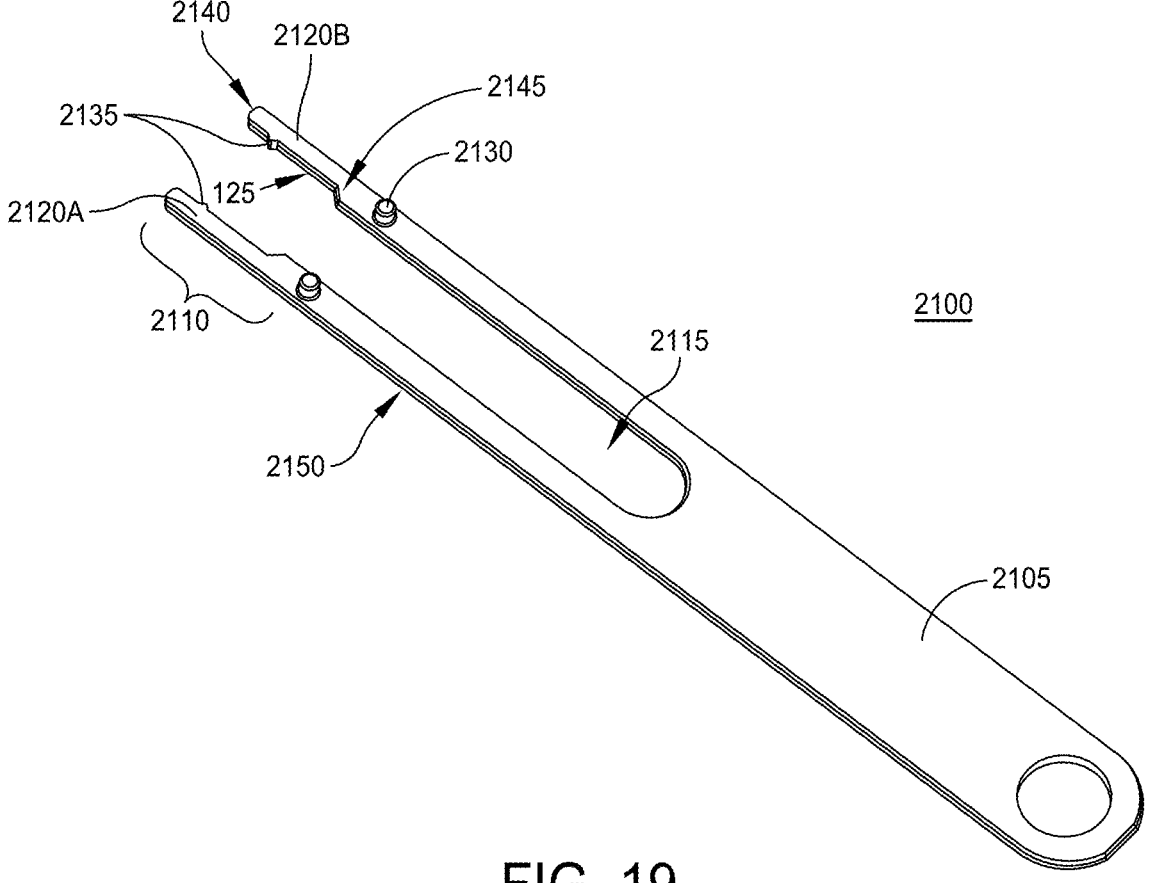
FIG. 19 illustrates one example of a clip that is part of a system for preparing an intramedullary path in the tibia according to the present disclosure.

FIG. 19 illustrates one example of the clip 2100 according to some embodiments. The clip 2100 comprises a body with a handle end 2105 opposite a tool engaging end 2110. A slot 2115 is defined within the body. The slot 2115 is open at the tool engaging end 2110 and extends partly toward the handle end 2105. The open end of the slot 2115 thus splits the tool engaging end 2110 into two arms 2120A, 2120B. The slot 2115 is sized and arranged to allow the tool engaging end 2110 to flex and splay open for loading and unloading of the reamer tip 2300. The two arms 2120A, 2120B of the tool engaging end 2110 are arranged for engaging the reamer tip 2300 and hold the reamer tip. The two arms 2120A, 2120B are configured and arranged to seat within the cartridge 2200 at a specific spaced apart relationship. The tool engaging 2110 end further defines a distal end 2140 at each of the two arms 2120A, 2120B.

In some embodiments, the two arms 2120A, 2120B are configured and arranged to serve as a depth stop when inserting the reamer tip 2300 into the cartridge 2200 using the clip 2100, whereby the reamer tip 2300 is located within the cartridge 2200 at a predefined position.

The two arms 2120A, 2120B of the tool engaging end 2110 includes inner surfaces 2125 sized and arranged to abut and grip the reamer tip 2300 from two opposing sides. The inner surface 2125 on each of the two arms includes a bump or a tab 2135 and a ledge 2145. The tab 2135 is sized and arranged to allow provisionally holding the reamer tip 2300 in a predetermined position within the clip 2100.

Figure 21B:
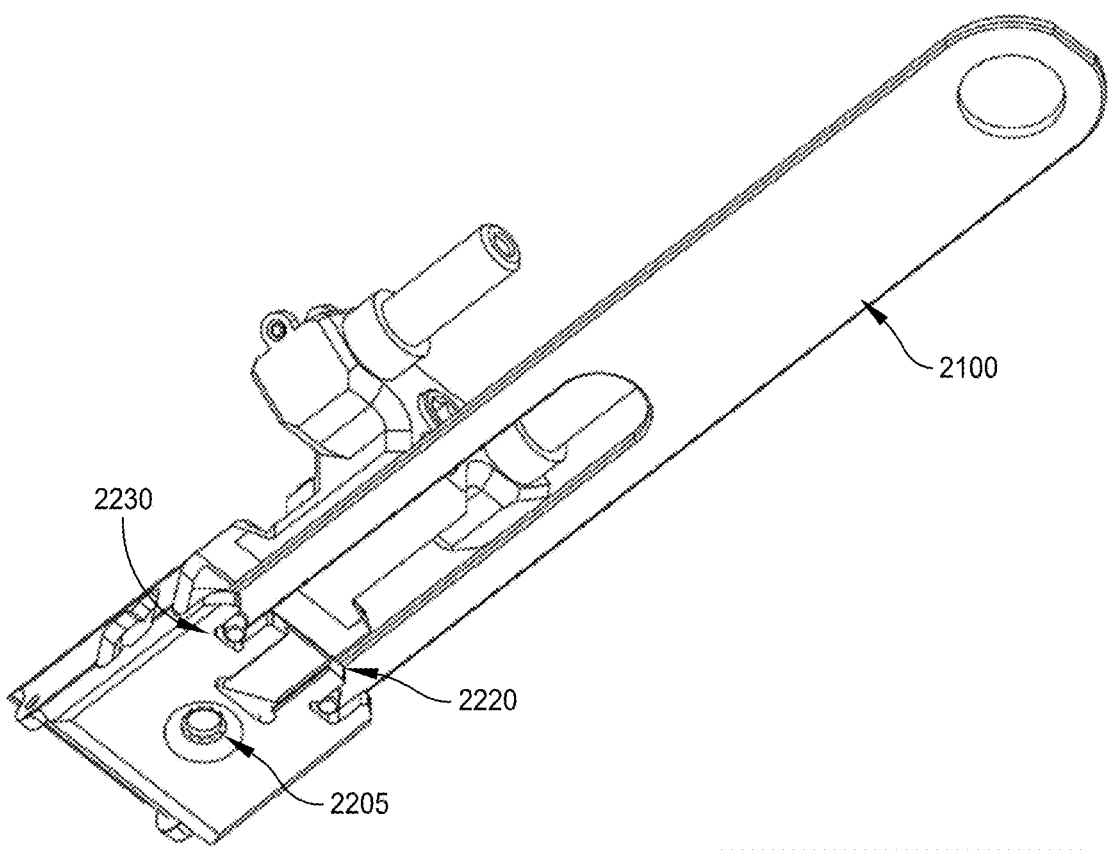
Figure 21C:
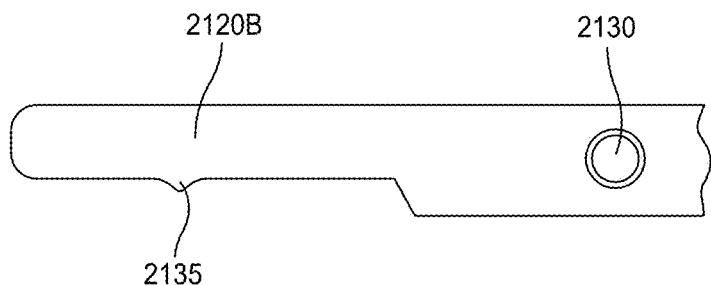

A close-up of the tab 2135 on the arm 2120B is shown in FIG. 21C. The reamer tip 2300 is configured with corresponding recesses that receive the tabs 2135 when the two arms 2120A, 2120B of the clip are clipped onto the reamer tip 2300. The tabs 2135 are sized to allow insertion and retention of the reamer tip 2300 between the two arms 2120A, 2120B, but also small enough that the tabs 2135 do not project inward (i.e., toward the longitudinal center of the clip 2100) too far so that they do not prevent the reamer tip 2300 from being unloaded/released from the clip 2100 without having to open the two arms 2120A, 2120B too much because the space within the cartridge 2200 can be limited.

The ledges 2145 are also sized and arranged to provisionally retain the reamer tip 2300 in a predetermined position within the clip 2100. In one embodiment, the ledges 2145 are larger than the tabs 2135 and provides a more secure engagement of the reamer tip 2300 by the two arms 2120A, 2120B.

The clip 2100 can include at least one protrusion or peg 2130 on the bottom surface of each of the arms 2120A, 2120B as shown in the embodiment of FIG. 19. The protrusions 2130 are configured to function as a depth stop when the clip 2100, while holding the reamer tip 2300 at its tool engaging end 2110, is used to insert the reamer tip 2300 into the cartridge 2200. After the tool engaging end 2110 is inserted into the cartridge 2200 a predetermined amount, the protrusions 2130 will come into contact with predetermined portions of the cartridge 2200 that are configured to abut against and cooperate with the protrusions 2130 and prevent the tool engaging end 2110 of the clip 2100 from advancing further into the cartridge 2200. The details of these cooperating structures will be described further below.

For example, the protrusion 2130 is sized and arranged to abut either the cartridge's front surface 2220 or recesses 2230 provided on the front surface 2220. This allows the clip 2100 to be seated within the cartridge 2200 at a predetermined position. The engagement between the protrusions 2130 and the recesses 2230 are shown in FIG. 21B.

It can be appreciated by one skilled in the art that any combination of abutting surfaces may enable a constraint in various degrees of freedom, whereby alignment at a predetermined position may be achieved.

In some embodiments, the cartridge 2200 can include a feature, such as a protrusion or a surface, that functions as a depth stopping surface when abutting the clip 2100.

Figure 20A:
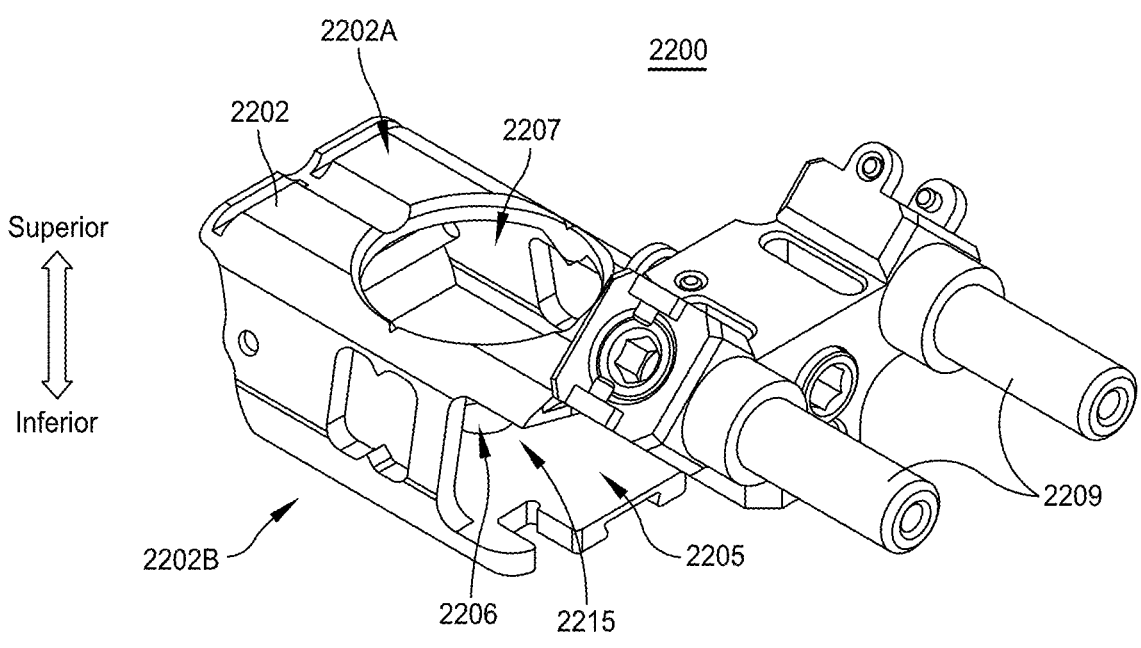
FIGS. 20A-20C are illustrations showing an example of a hollow body cartridge that cooperate with the clip of FIG. 19 for aligning a reamer tip with a reamer shaft within the joint space formed at the end of a resected tibia.
Figure 20B:
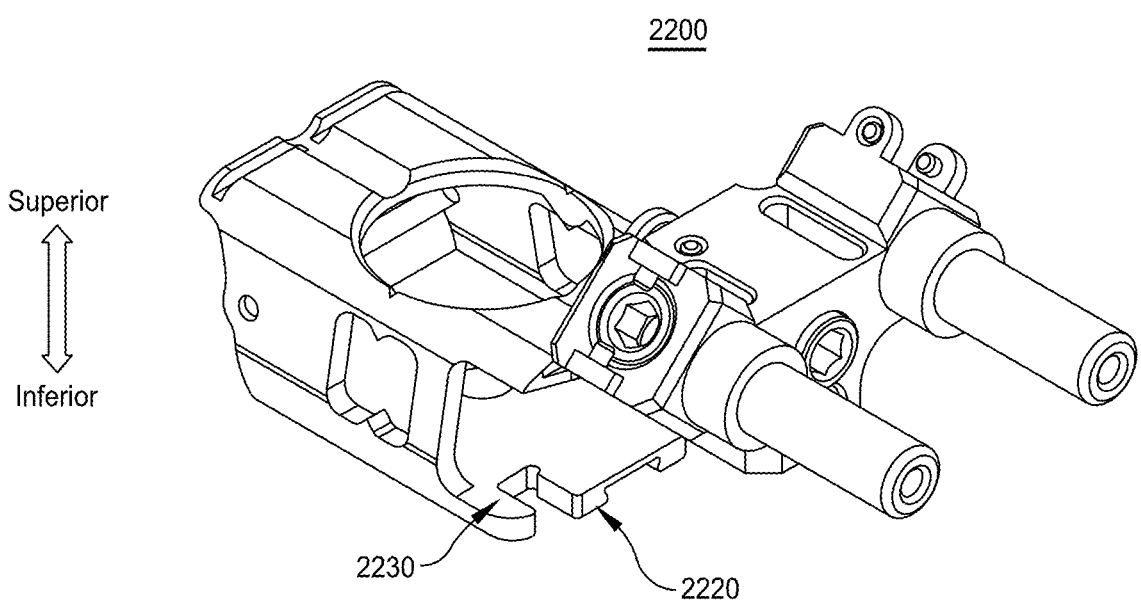
Figure 20C:
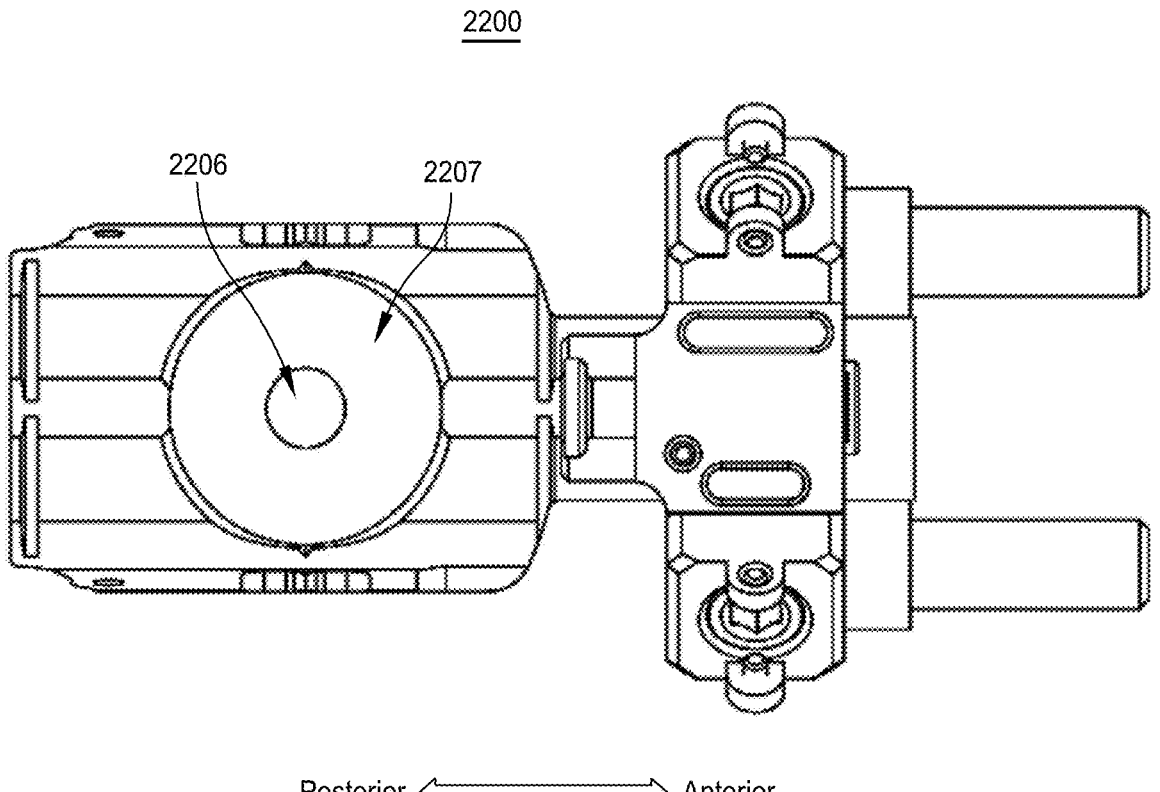
Figure 24:
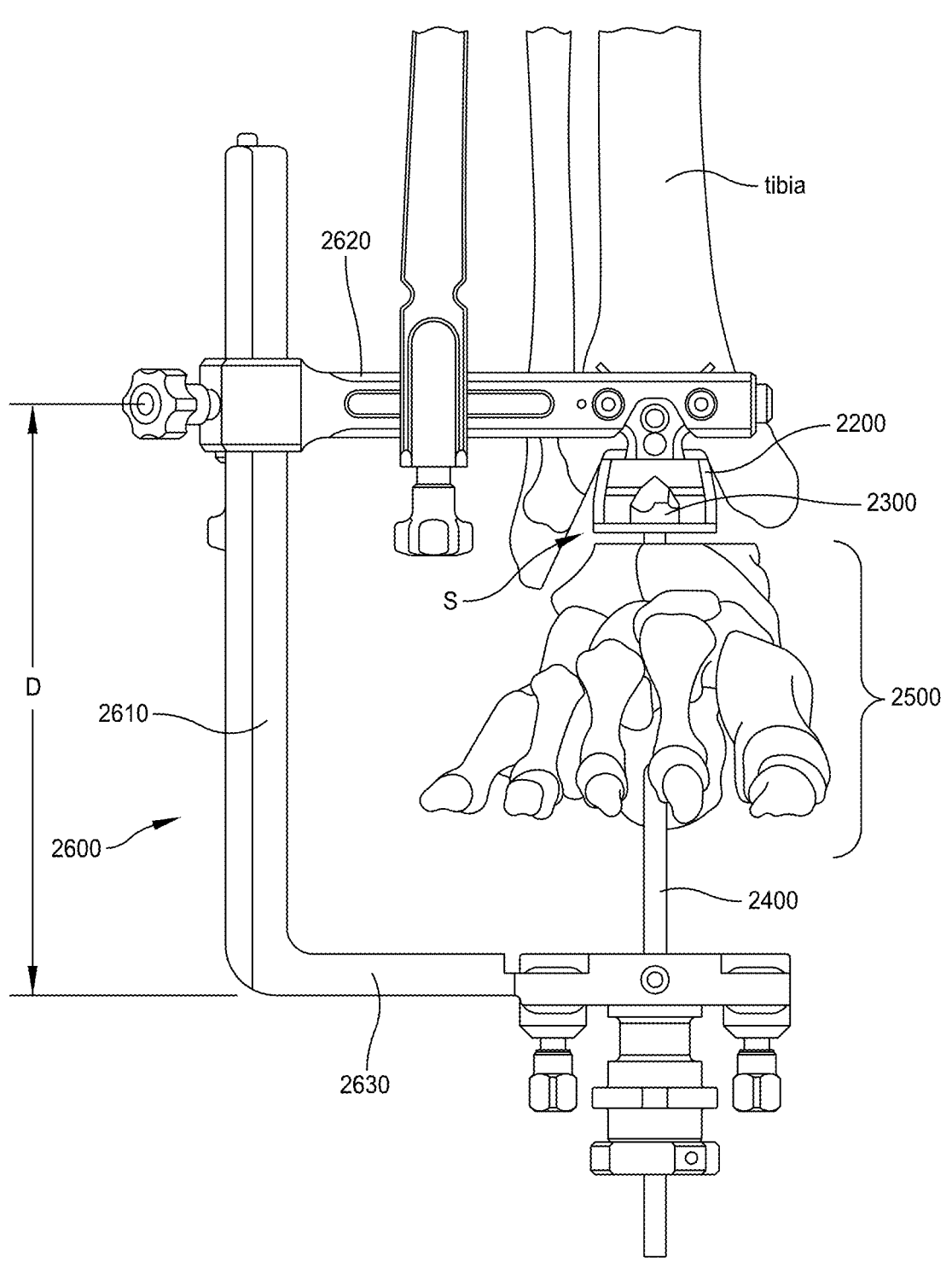
FIG. 24 shows the assembly of the system for preparing an intramedullary path in the tibia along with an illustration of a patient's bones forming an ankle joint.

FIGS. 20A-20C illustrate one example of the cartridge 2200. FIGS. 20A and 20B are the same isometric views of the cartridge 2200. FIG. 20C is a top-down view of the cartridge. The cartridge 2200 comprises a hollow body 2202 that includes a top portion (superior side) 2202A, a bottom portion (inferior side) 2202B, and two side portions 2202C that define a cartridge cavity 2215 therein. The cartridge 2200 is intended to be positioned within the resected joint space S prepared at the distal end of a tibia as shown in FIG. 24. Thus, the anatomical directions, superior, inferior, anterior, and posterior indicated in FIGS. 20B and 20C show the orientation of the cartridge 2200 with respect to the patient.

Referring to FIG. 20A, the hollow body 2202 of the cartridge 2200 comprises an aperture or is open at least at its anterior side so that the cartridge cavity 2215 is accessible from the anterior side. The cartridge 2200 also includes an aperture 2207 at its superior side 2202A and another aperture 2206 at its inferior side 2202B. Thus, these two apertures also provide access to the cartridge cavity 2215. The superior side aperture 2207 and the inferior side aperture 2206 are axially aligned. This alignment can be seen in the top-down view in FIG. 20C.

The superior side aperture 2207 is sized large enough to allow the reamer tip 2300 to fit through without interference. The inferior side aperture 2206 is sized large enough to allow the reamer shaft 2400 to fit through without interference.

In some embodiments, the inferior side aperture 2206 has a smaller diameter than the superior side aperture 2207, as can be seen in FIG. 20C. The diameter of the inferior side aperture 2206 is also smaller than the diameter of the reamer tip 2300 so that the reamer tip 2300 cannot pass through the inferior side aperture 2206.

In use, the cartridge 2200 is attached to a C-bracket 2600 and positioned in the resected joint space S as shown in FIG. 24. The combination of the C-bracket 2600 and the cartridge 2200 functions as an alignment guide that aligns the reamer shaft 2400 with the reamer tip 2300 that is positioned within the cartridge cavity 2215 of the cartridge 2200.

As shown in FIG. 24, the C-bracket 2600 comprises main stem 2610, a first arm 2620 at one end thereof to which the cartridge 2200 is attached, and the other end of the C-bracket 2600 is provided with a second arm 2630 that is configured with a hole for guiding the reamer shaft 2400 toward the predetermined location within the cartridge cavity 2215.

With the cartridge 2200 attached to the first arm 2620, when the cartridge 2200 is positioned within the resected joint space S and the main stem 2610 is aligned with the patient's tibia, the second arm 2630 is configured to guide the reamer shaft 2400 in the direction of the predetermined location within the cartridge cavity 2215. This alignment will direct and guide the reamer shaft 2400 through the patient's calcaneus bone into the resected joint space S, then through the inferior end aperture 2206 of the cartridge 2200 and into the cartridge cavity 2215. Using the clip 2100, the reamer tip 2300 can be positioned within the cartridge cavity 2215 before the reamer shaft 2400, after the reamer shaft 2400, or simultaneously with the reamer shaft 2400.

Once both the reamer shaft 2400 and the reamer tip 2300 are within the cartridge cavity 2215 and aligned, the reamer tip can be attached to the reamer shaft, thus forming/assembling a reaming tool 2500. The reaming procedure can then be carried out. The attachment between the reamer tip 2300 and the reamer shaft 2400 can be enabled by any one of the known mechanical connection structures. An example is by screw threads.

The reaming procedure involves, pushing the reamer tool 2500 superiorly so that the reamer tip 2300 passes through the superior end aperture 2207 of the cartridge 2200 and engage the distal end of the tuba for reaming. The reaming forms a hole/recess into the distal end of the tibia for receiving a tibia component of an ankle prosthesis system.

Figure 22A:
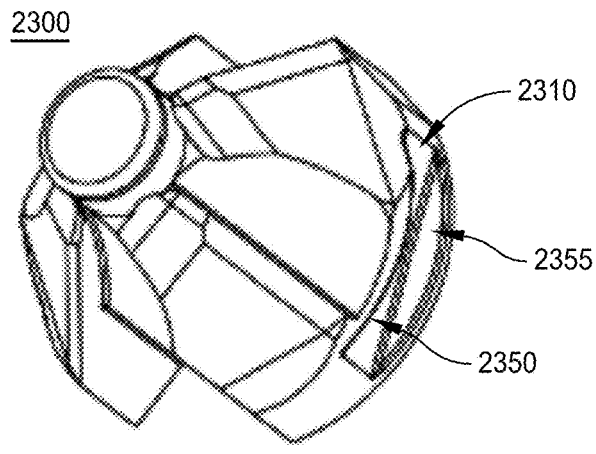
FIGS. 22A-22B are illustrations showing an isometric view and a side view of a reamer tip, respectively.
Figure 22B:
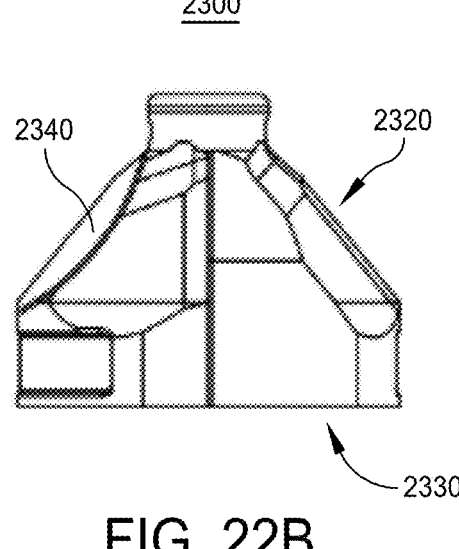

FIGS. 22A-22B illustrate one example of the reamer tip 2300. The reamer tip 2300 may be blunt or include sharp cutting flutes 2340 on the cutting surface 2320. Opposite the cutting surface 2320 is a reamer bottom 2330. The reamer bottom 2330 defines a recess for engagement to the reamer shaft 2400. In one embodiment, the reamer tip 2300 attaches to the reamer shaft 2400 with a threaded arrangement. In another embodiment, the engagement may be a tongue and groove, O-ring, or another quick connect drive feature. The reamer tip includes at least one groove 2310, configured and arranged to receive the arm 2120 of the clip 2100. The groove 2310 is sized and arranged to fit within the tool engaging end 2110 of the clip, abutting the inner surface 2125 within the notch 2135 and the ledge 2145. The groove is defined by a top shelf 2350 and a bottom shelf 2355, accommodating for the thickness of the clip 2100.

Figure 23A:
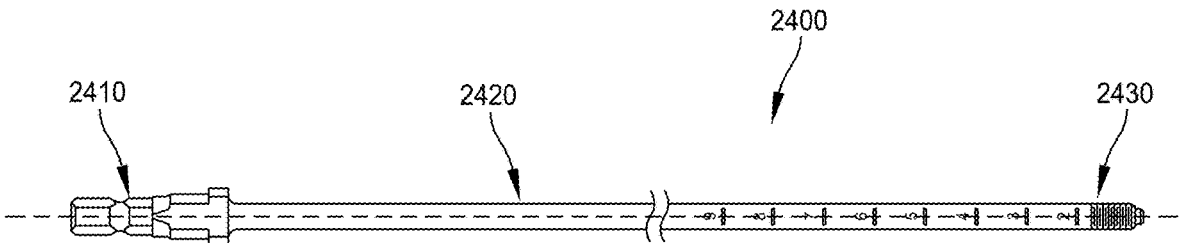
FIG. 23A shows a reamer shaft.
Figure 23B:
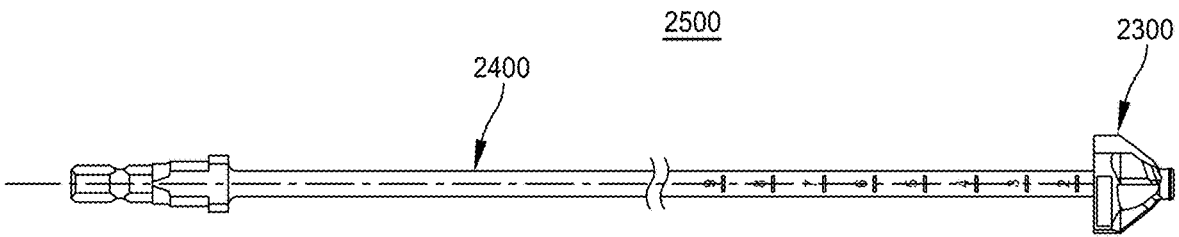
FIG. 23B shows a reamer tool that is formed by assembling the reamer shaft of FIG. 23A with the reamer tip of FIG. 22A.

FIGS. 23A-23B illustrates one example of the reamer tool 2500. FIG. 23A shows a reamer shaft 2400. FIG. 23B shows a reamer tool 2500 that is formed by assembling the reamer shaft 2400 of FIG. 23A with the reamer tip 2300 of FIG. 22A. The reamer shaft 2400 includes a quick connect end 2410, a driveshaft 2420, and tool end 2430. The quick connect end 2410 is configured to attach to a handle or power tool. The drive shaft 2420 is sized and arranged to pass through patient anatomy and transmit adequate torque. The tool end 2430 is sized and arranged to attach to the reamer tip 2300 within the cartridge cavity 2215. In the current embodiment, the tool end 2430 includes external threads. In the illustrated example, the tool end 2430 is configured with male type screw thread to engage the reamer tip 2300 by threading. As described above, the surgical tool 2500 is reversibly assembled within the cartridge cavity 2215. In the current embodiment, the surgical tool is used to ream the patient's tibia shaft proximal of the cartridge 2200 and ankle joint, wherein the reamer shaft 2400 extends out the plantar side of the foot and through the C-bracket 2600.

Thus, the present disclosure provides a system for establishing an intramedullary path in a bone, for example, at the distal end of a tibia in an ankle joint. Such system can comprise a cartridge 2200 and a clip 2100. The cartridge 2200 is sized and configured to be positioned in a resected ankle joint space S of a patient. The cartridge 2200 comprises an anterior side, a posterior side, a medial side, a lateral side, a superior side, and an inferior side corresponding to the anatomical directions when positioned in the resected joint space S. The cartridge 2200 comprises: a body 2202 that defines a cartridge cavity 2215 and includes: a first aperture 2205 that extends into the cartridge cavity 2215 from the anterior side in the anterior-posterior direction and defining an anterior opening for receiving a reamer tip 2300 and the clip 2100; a second aperture 2206 provided on the inferior side providing access to the cartridge cavity 2215 and sized and configured to pass a reamer shaft 2400 therethrough; and a third aperture 2207 provided on the superior side providing access to the cartridge cavity 2215 and sized and configured to pass a reamer tip 2300 therethrough. The clip 2100 comprises a top surface 2101, a bottom surface 2102, handle end 2105, and a tool engaging end 2110 that comprises a space, defined by a slot 2115, to receive and hold the reamer tip 2300. The clip 2100 and the cartridge 2200 are configured to co-operate with each other to position the clip in a predefined relationship with respect to the cartridge as the clip is advanced into the cartridge cavity through the first aperture while the clip is holding the reamer tip. The reamer tip is thereby positioned at a predetermined location within the cartridge cavity 2215 that allows the reamer tip 2300 to be aligned for receiving the reamer shaft 2400 that is passed through the second aperture. [Concept 6A]

Figure 25A:
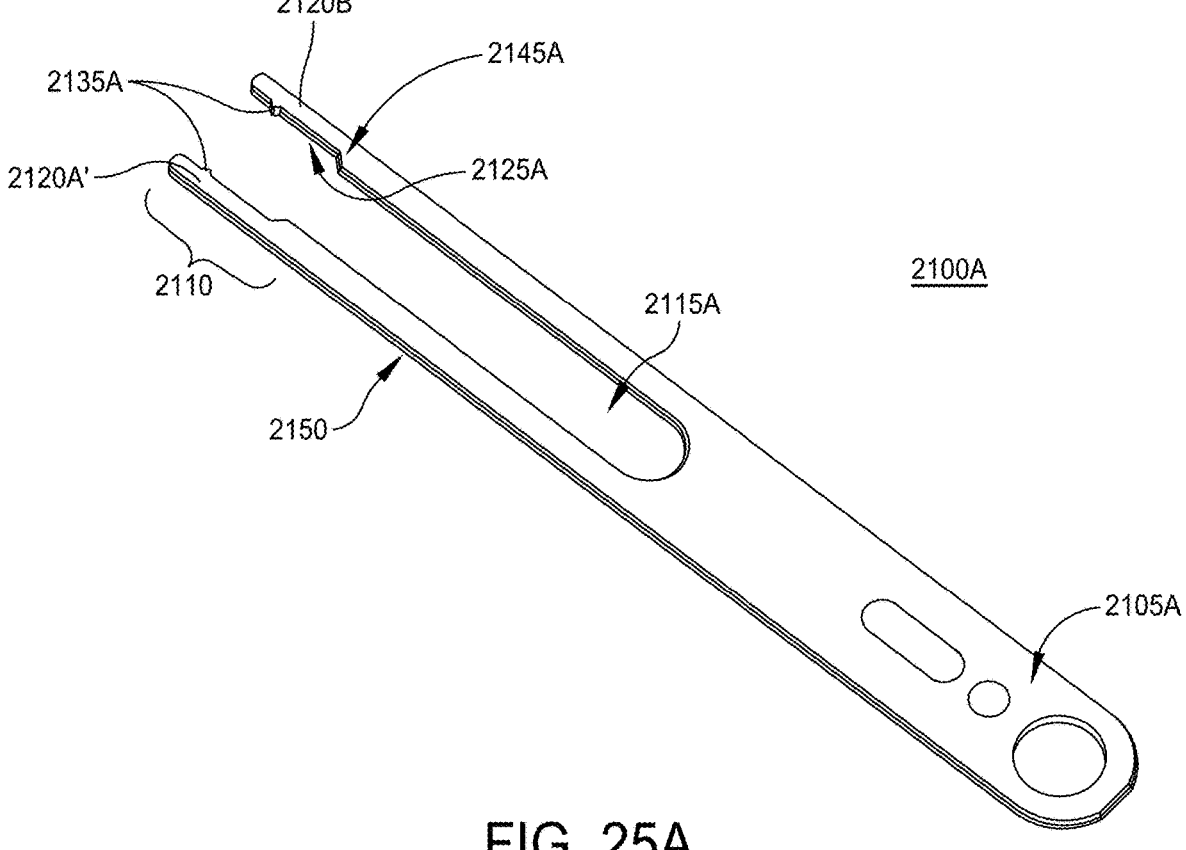
FIGS. 25A-25B are illustrations showing another embodiment of the clip of FIG. 19.
Figure 25B:
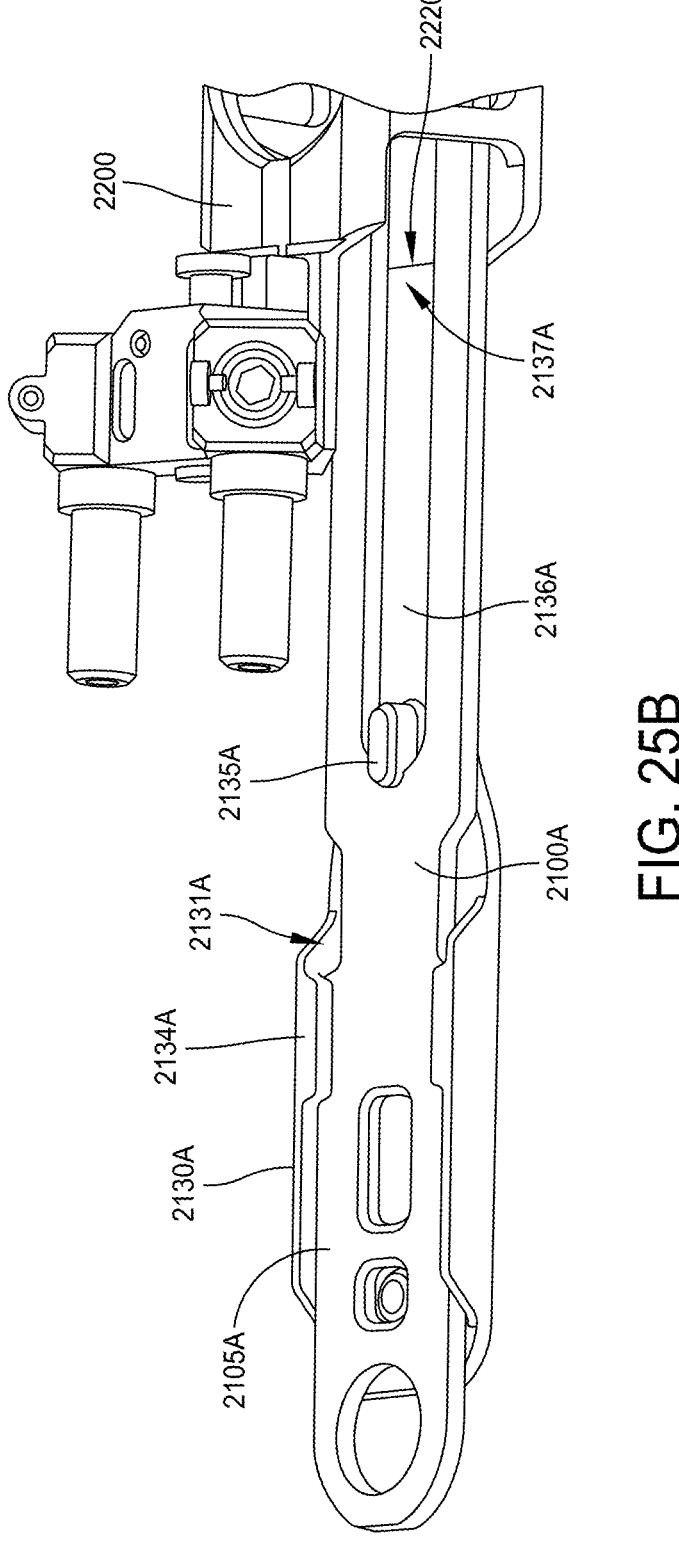

FIGS. 25A-25B illustrate an example of a second embodiment clip 2100A that is an alternate embodiment of the clip 2100. The second embodiment clip 2100A comprises a body with a handle end 2105A opposite a tool engaging end 2110A. A slot 2115A is defined within the body. The slot 2115A is open at the tool engaging end 2110A and extends partly toward the handle end 2105A. The tool engaging end 2110A is configured to grasp and hold a reamer tip 3100. Thus, the tool engaging end 2110A is configured with the same structures as the tool engaging end 2110 of the clip 2100 except for the omission of the protrusions 2130. The open end of the slot 2115A thus splits the tool engaging end 2110A into two arms 2120A', 2120B'. The slot 2115A is sized and arranged to allow the tool engaging end 2110A to flex and splay open for loading and unloading of the reamer tip 2300. The two arms 2120A', 2120B' of the tool engaging end 2110A are arranged for engaging the reamer tip 2300 and hold the reamer tip. The two arms 2120A', 2120B' are configured and arranged to seat within the cartridge 2200 at a specific spaced apart relationship. The tool engaging 2110A end further defines a distal end 2140A at each of the two arms 2120A', 2120B'.

The two arms 2120A', 2120B' of the tool engaging end 2110A includes inner surfaces 2125A sized and arranged to abut and grip the reamer tip 2300 from two opposing sides. The inner surface 2125A on each of the two arms includes a bump or a tab 2135A and a ledge 2145A. The tab 2135A is sized and arranged to allow provisionally holding the reamer tip 2300 in a predetermined position within the clip 2100A. The tabs 2135A are sized to allow insertion and retention of the reamer tip 2300 between the two arms 2120A', 2120B', but also small enough that the tabs 2135A do not project inward (i.e., toward the longitudinal center of the clip 2100A) too far so that the reamer tip 2300 can be unloaded, or released, without having to open the two arms 2120A', 2120B' too much because the space within the cartridge 2200 can be limited.

The ledges 2145A are also sized and arranged to provisionally retain the reamer tip 2300 in a predetermined position within the clip 2100A. In one embodiment, the ledges 2145A are larger than the tabs 2135A and provides a more secure engagement of the reamer tip 2300 by the two arms 2120A', 2120B'.

Rather than the one or more protrusions 2130 provided in the clip 2100, the second embodiment clip 2100A is accompanied by a clip-on depth stop piece 2130A that serves as a depth stop when inserting the reamer tip 2300 into the cartridge 2200 using the second embodiment clip 2100A. Like the first embodiment clip 2100, the second embodiment clip 2100A enables the reamer tip 2300 to be located within the cartridge 2200 at a predefined position.

As shown in FIG. 25B, the clip-on depth stop piece 2130A is a separate piece that is configured to be clipped on to the second embodiment clip 2100A. The clip-on depth stop piece 2130A comprises a channel 2131A that receives the handle end 2105A of the clip 2100A. The channel 2131A is flanked by at least two opposing tabs 2134A that allows the clip-on depth stop piece 2130A to be clipped on to the handle end 2105A. The clip-on depth stop piece 2130A has a an elongated body with two ends. The at least two opposing tabs 2134A are near one of the two ends and a depth stop surface 2137A is at the other of the two ends of the clip-on depth stop piece 2130A. When clipped onto the clip 2100A, the elongated body is aligned with the clip

2100A so that the tabs 2134A are closer to the handle end 2105 and the depth stop surface 2137A is closer to the tool engaging end 2110A of the clip 2100A. The at least two opposing tabs 2134A comprise portions that extend toward each other so that the two tabs 2134A overhanging the second embodiment clip 2100A. The clip-on depth stop piece 2130A can be made of a material that is flexible enough to allow the tabs 2134A, for example, to flex when the clip-on depth stop piece 2130A is being clipped onto the second embodiment clip 2100A.

With the clip-on depth stop piece 2130A clipped onto the clip 2100A, when the tool engaging end 2110A of the clip 2100A is advanced into the cartridge cavity 2215 through the anterior opening of the cartridge 2200, by bringing the depth stop surface 2137A of the clip-on depth stop piece 2130A to come in contact with and abut against the front surface 2220 of the cartridge 2200, the depth to which the tool engaging end 2110A of the clip 2100A is advanced into the cartridge cavity 2215 can be limited to a predetermined amount. Thus, the depth stop surface 2137A contacting the front surface 2220 registers the Anterior-Posterior position of the reamer to the reamer shaft 2400.

In some embodiments, the clip-on depth stop piece 2130A is also configured with a third tab 2135A that engages the slot 2115A of the clip 2100A at the closed end of the slot 2115A (i.e. the end closer to the handle end 2105A). The third tab 2135A prevents the clip 2100A from sliding with respect to the clip-on depth stop piece 2130A in the direction toward the depth stop surface 2137A. Thus the third tab 2135A ensures that the position of the clip 2100A is maintained at a fixed position with respect to the depth stop surface 2137A so that the depth stop function of the assembly works properly.

Thus, as with the first embodiment clip 2100, after the cartridge 2200 is positioned within the resected joint space S in the patient's ankle joint with the help of the C-bracket 2600, the second embodiment clip 2100A can be used to locate the reamer tip 2300 at a desired location within the cartridge cavity 2215 to be assembled in situ with a reamer shaft 2400 that is advanced through the calcaneus and talus of the patient into the resected joint space S to form a reamer tool 2500. [Concept 6B]

Figure 26:
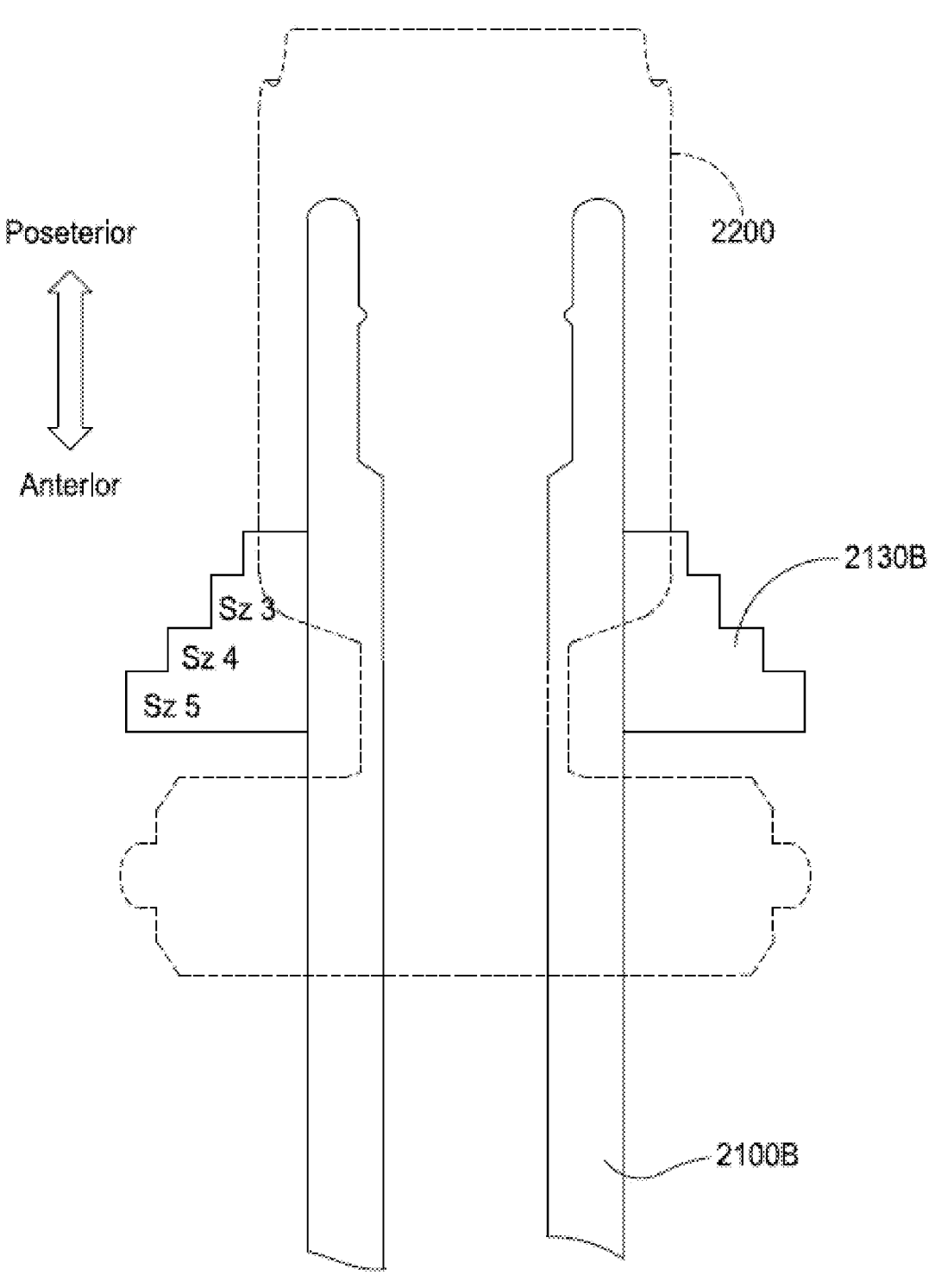
FIG. 26 is an illustration showing another embodiment of the clip of FIG. 19.

FIG. 26 illustrates an example of a third embodiment clip 2100B that is an alternate embodiment of the clip 2100. Rather than the protrusions 2130, the third embodiment clip 2100B comprises a stepped registration guide structure 2130B, that references the sidewalls of the cartridge 2200 as the clip 2100B is advanced into the cartridge cavity 2215 from the anterior side.

The stepped registration guide structure 2130B comprises a pair of appendages attached to or extending from each of the arms 2120A, 2120B. Because the cartridge 2200 also functions as a trial for tibia tray implant components, the cartridge 2200 are provided in multiple sizes to account for different size tibia tray implants. Thus, the distance that the clip 2100B needs to be advanced into the cartridge cavity 2215 is different for different size cartridge. For example, for larger cartridges, the clip 2100B needs to advance further into the cartridge cavity 2215 for the reamer tip 2300 to reach the desired location. This different registration required for different size cartridge is accomplished by the stepped registration guide structure 2130B. Each appendage of the stepped registration guide structure 2130B can be configured with multiple steps, each step making the clip wider toward the anterior direction. Each step is keyed for a particular size of the cartridge. For example, in the example shown in FIG. 26, the step labeled as "Sz 5" is the widest step and the step labeled as "Sz 4" is one step narrower and is keyed to register with a cartridge that is one size smaller than the cartridge that corresponds to the step "Sz 5." The step "Sz 5" is positioned further in the anterior direction than the smaller step "Sz 4" so the step "Sz 5" allows the clip 2100B to be advanced further into the cartridge 2200. As the clip 2110B, while holding the reamer tip 2300, is advanced into the cartridge cavity 2215 through the anterior opening of the cartridge 2200, the step that corresponds to the particular size of the cartridge will come into contact with the sidewalls of the cartridge and stop the clip from advancing further into the cartridge cavity 2215.

[Concept 7]

Figure 27A:
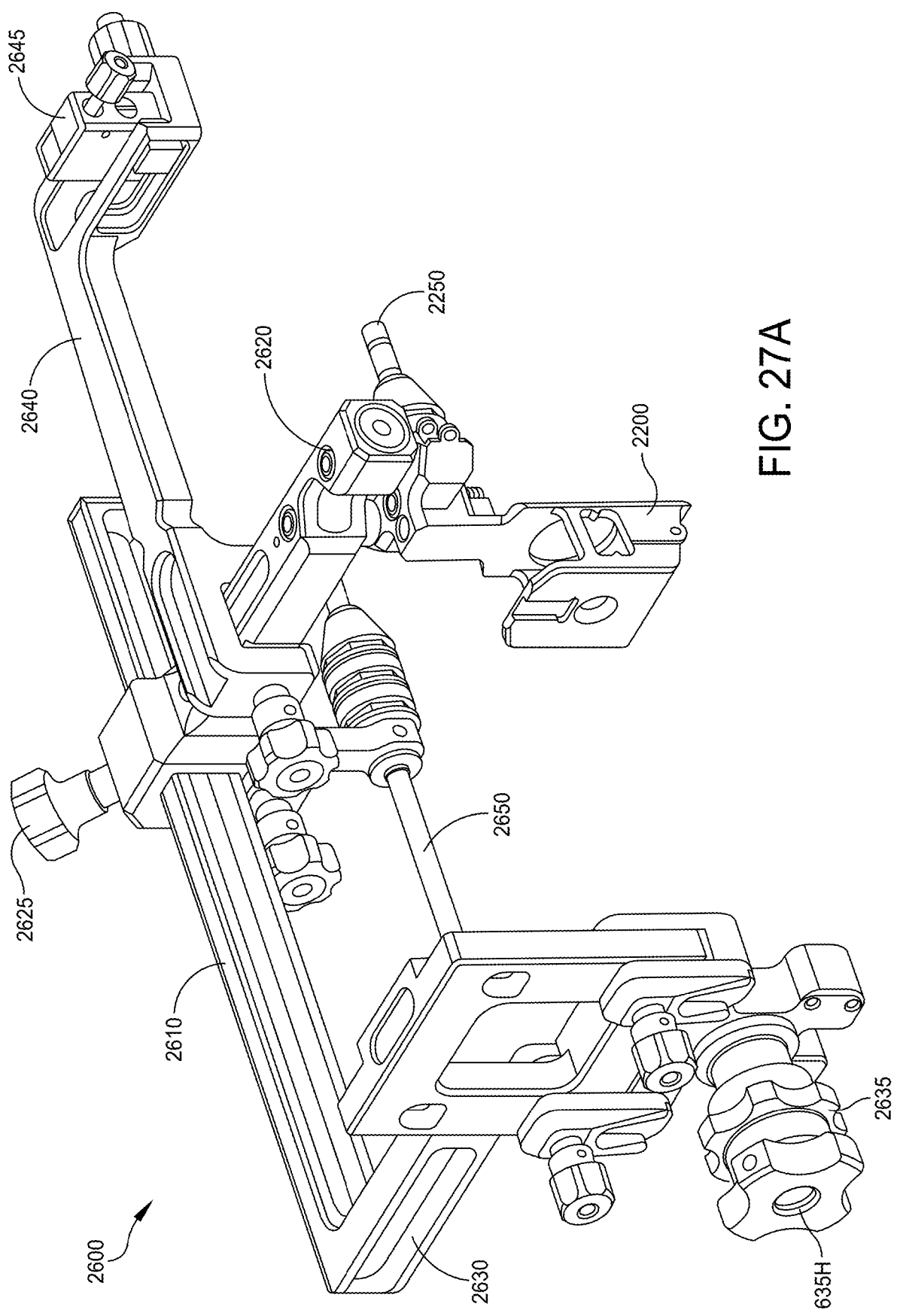
FIGS. 27A-27B are illustrations showing a C-bracket.
Figure 27B:
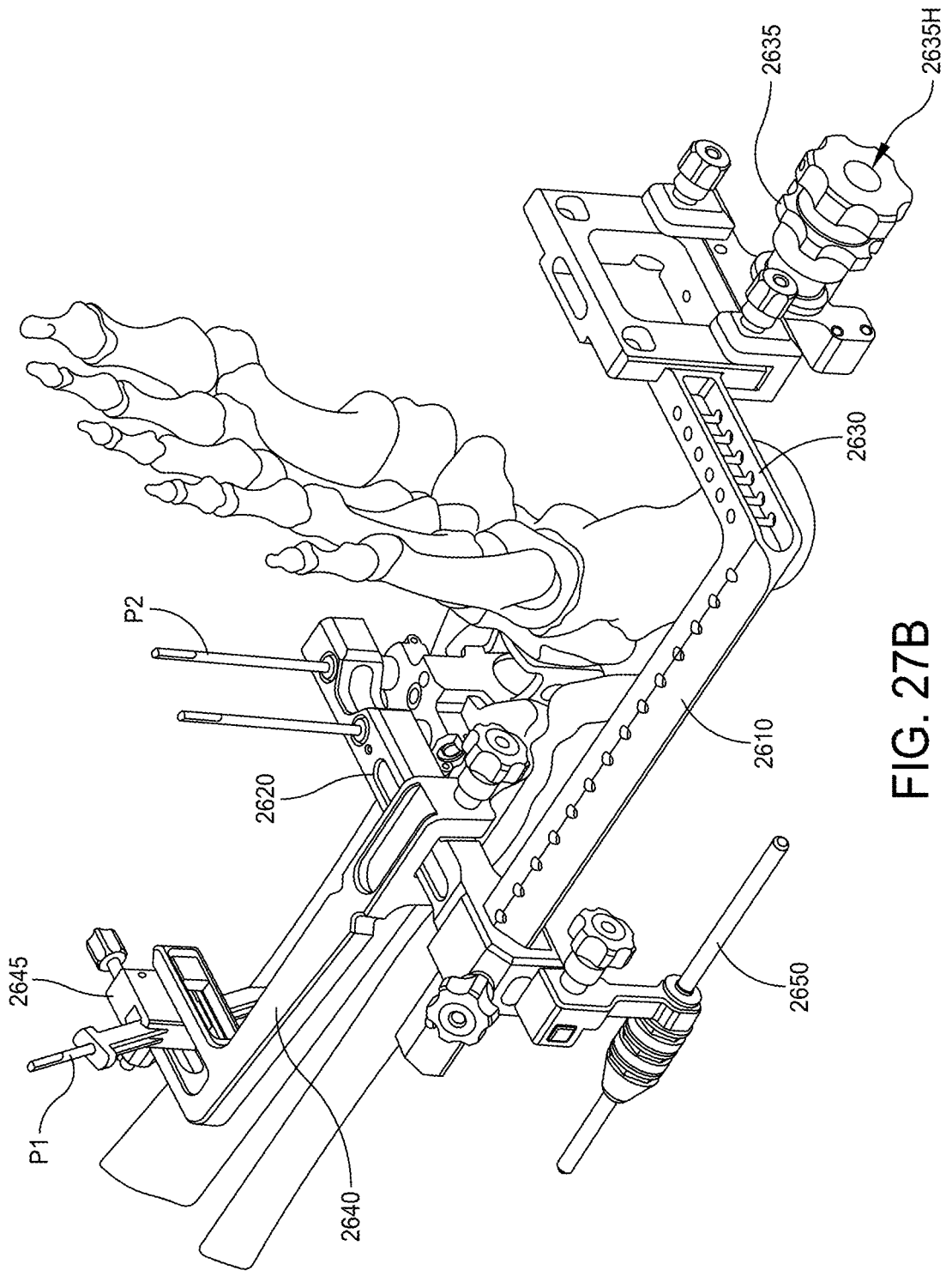
Figure 28:
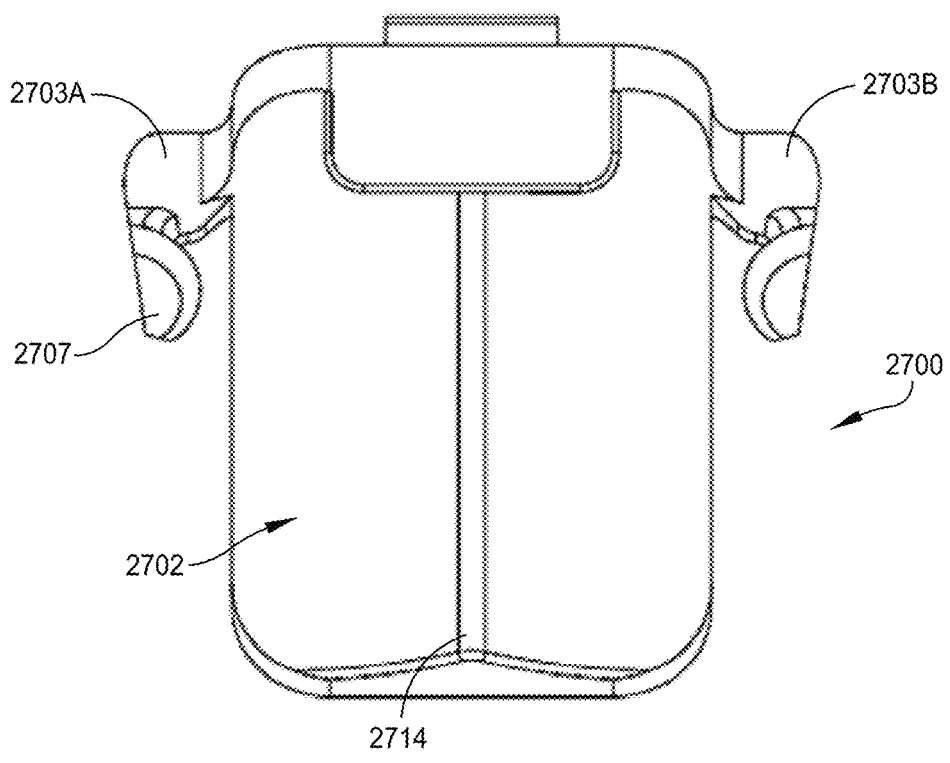
FIG. 28 shows a clip-on talar dome protector according to an embodiment of the present disclosure.
Figure 29:
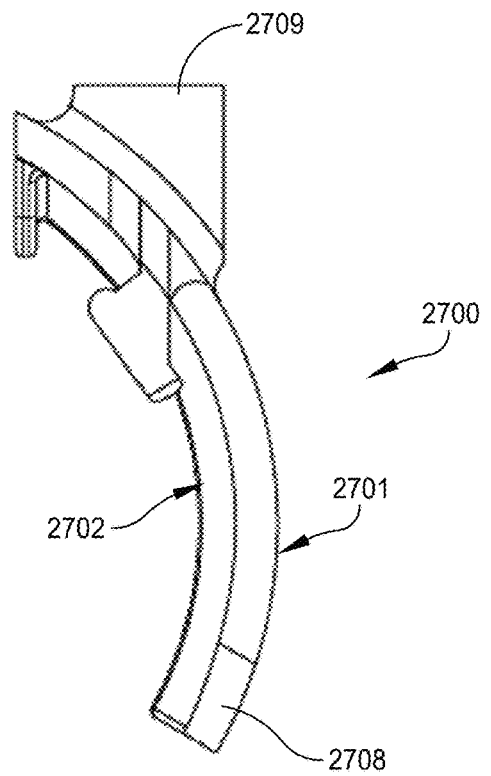
FIG. 29 shows a clip-on talar dome protector according to an embodiment of the present disclosure.
Figure 30:
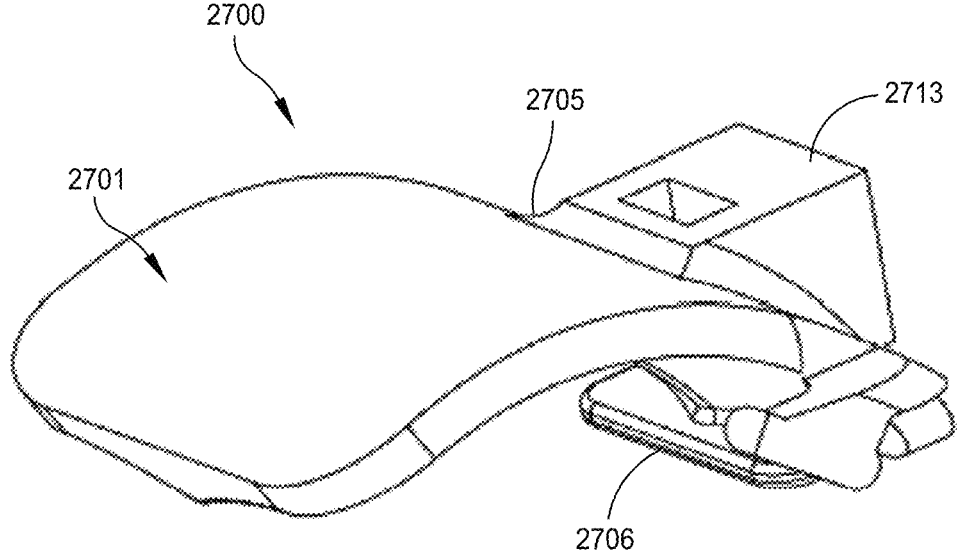
FIG. 30 shows a clip-on talar dome protector according to an embodiment of the present disclosure.
Figure 31:
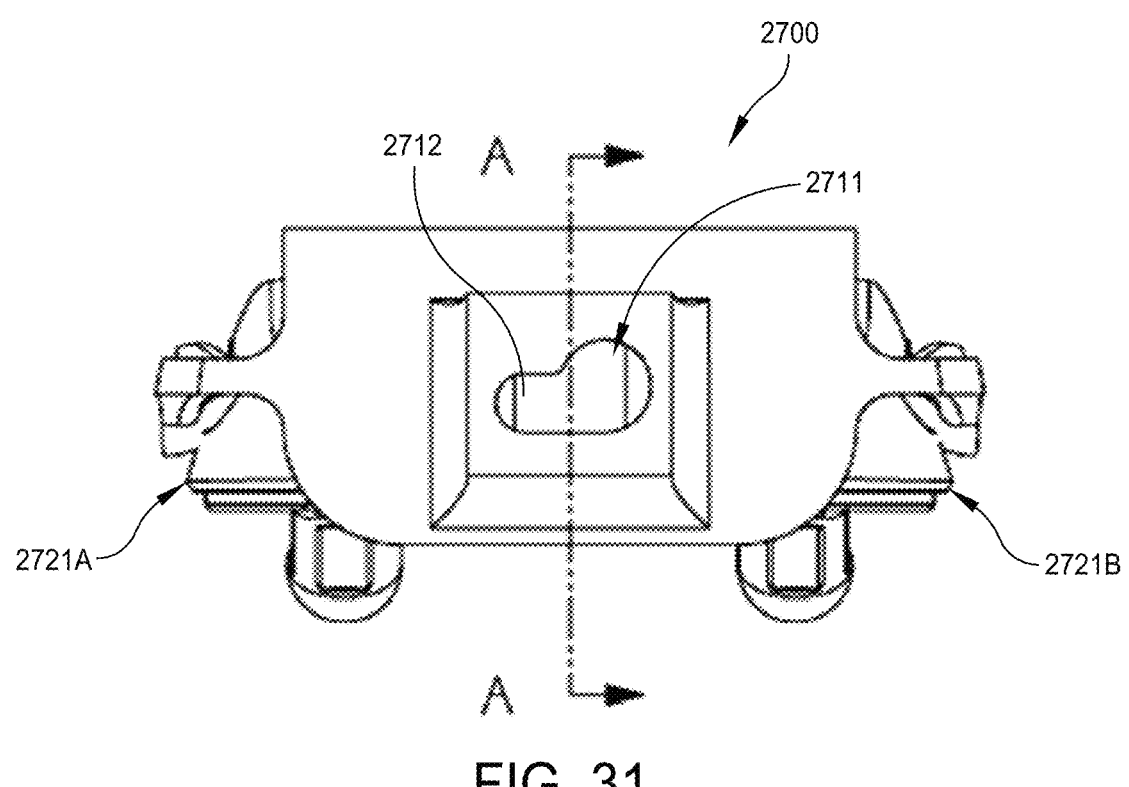
FIG. 31 shows a clip-on talar dome protector and a talar dome implant according to an embodiment of the present disclosure.
Figure 32:
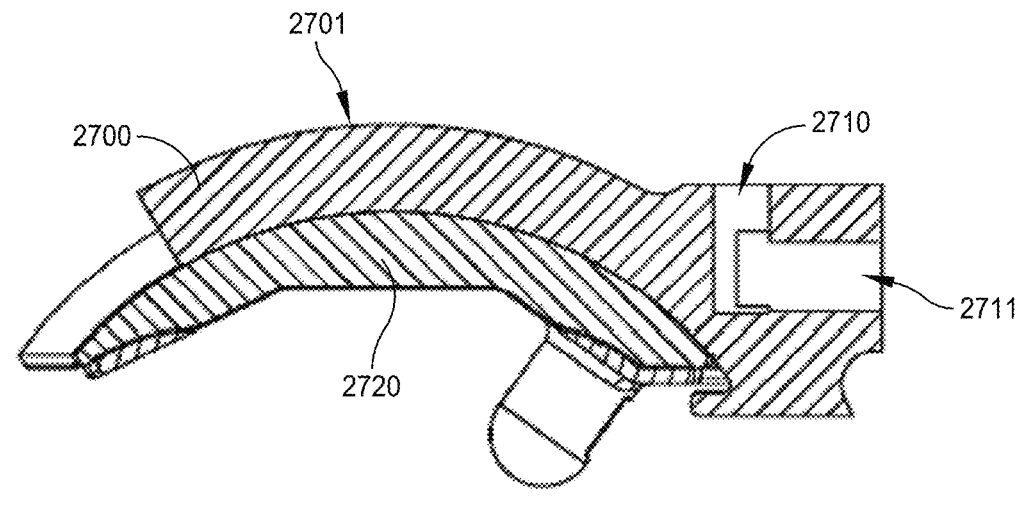
FIG. 32 shows a clip-on talar dome protector and a talar dome implant according to an embodiment of the present disclosure.
Figure 33:
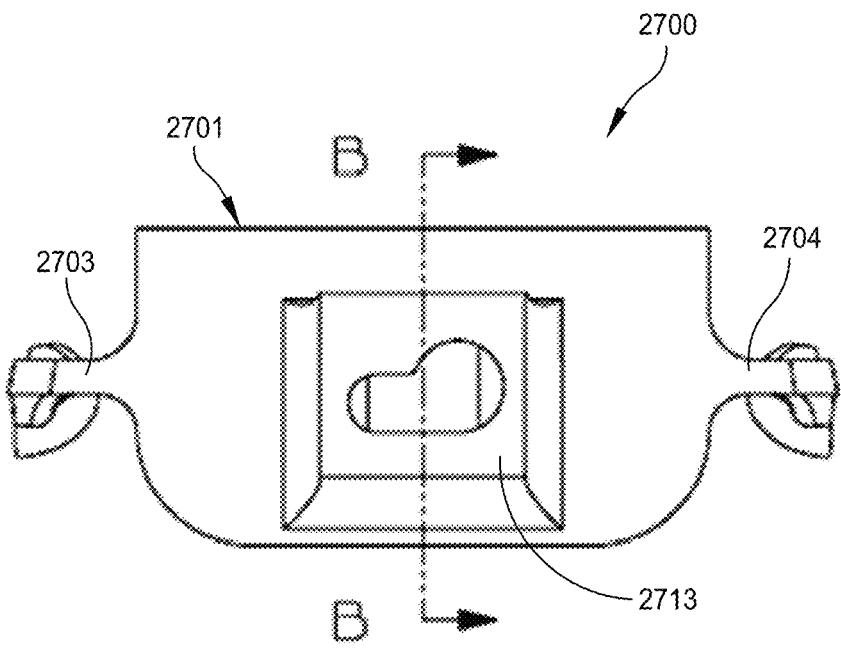
FIG. 33 shows a clip-on talar dome protector according to an embodiment of the present disclosure.
Figure 34:
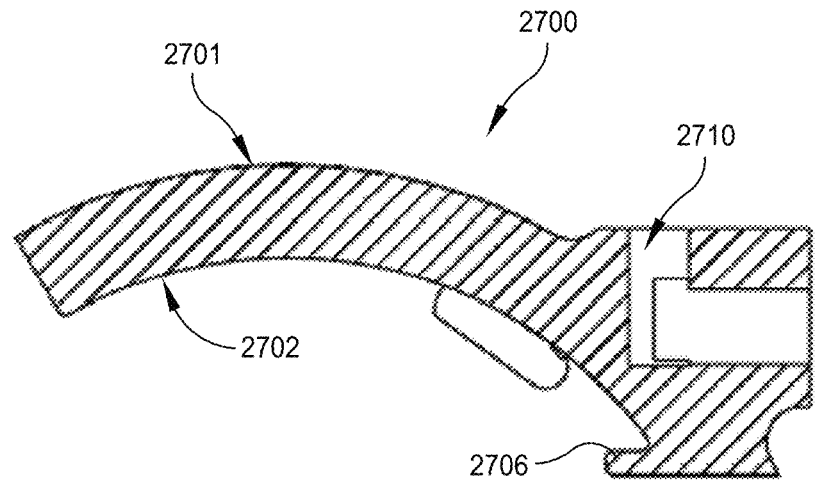
FIG. 34 shows a clip-on talar dome protector according to an embodiment of the present disclosure.

FIGS. 27A-27B illustrate one example of the C-bracket 2600 in more detail. The C-bracket 2600 is an instrument for aligning ankle joint implant trials and implants. The C-bracket 2600 also guides the reaming tool 2500 for establishing an intramedullary path, for example, at the distal end of a tibia in an ankle joint so that the tibia can receive the tibia tray component of an ankle prosthesis.

As described above in connection with FIG. 24, the C-bracket 2600 can be used to position and hold the cartridge 2200 in the resected joint space S in alignment with the reamer shaft 2400 that is guided into the resected joint space S, and thus into the cartridge cavity 2215.

Additionally, the C-bracket 2600 can be used to position and hold other versions of tibia tray trials in the resected joint space S preparing the tibia for receiving one of a variety of tibia tray implants.

As mentioned above, the C-bracket 2600 comprises the main stem 2610, the first arm 2620, and the second arm 2630. The first and second arms 2620, 2630 both extend in the same direction from the main stem 2610. In this embodiment, the second arm 2630 is at a stationary or a fixed location at one end of the main stem 2610. In some embodiments, the second arm 2630 and the main stem 2610 are two portions of a monolithic structure. The first arm 2620, however, can be adjustably connected to the main stem 2610 at a distance D away from the second arm 2630. The adjustable connection between the main stem 2610 and the first arm 2620 allows the distance D to be adjusted for the particular patient's physical dimensions.

One end of the first arm 2620, referred to hereinafter as the proximal end, is configured to be adjustably attached to the main stem 2610. The opposite end of the first arm 2620, referred to hereinafter as the distal end, is configured to be attached to the cartridge 2200 or other tibia tray trials.

The attachment between the proximal end of the first arm 2620 and the main stem 2610 can be achieved by the use of a locking screw 2625 that locks the first arm 2620 to the main stem 2610. The attachment between the distal end of the first arm and the cartridge 2200 (or other tibia tray trials) can be removable. The end of the second arm 2630 that is not attached to the main stem 2610, referred to herein as the distal end, is configured with an alignment hole 2635H that allows the reaming shaft 2400 to extend through the second arm 2630 toward the cartridge 2200 that is attached to the first arm 2620. The distal end of the second arm 2630 can be configured with a bushing 2635 which provides the alignment hole 2635H.

The C-bracket 2600 can further comprise a stabilizing arm 2640 that can be removably attached to the first arm 2620 as shown in FIGS. 27A and 27B. When the C-bracket 2600 is positioned about a patient's ankle joint, the stabilizing arm 2640 extends proximally from the ankle along the anterior side of the patient's tibia to engage the tibia to assist in holding the C-bracket 2600 assembly in the desired registration with the patient's tibia. For example, the distal end (i.e., the end away from the first arm 2620) of the stabilizing arm 2640 can be configured with a sleeve 2645 through which a fixation pin P1 can be inserted and into the tibia. The sleeve 2645 can be configured to lock the fixation pin P1 in place after the fixation pin is placed in the tibia.

As shown in FIG. 27B, the first arm 2620 can be configured to accommodate one or more fixation pins P2 for securing the cartridge 2200 to the first arm 2620 and affix the whole assembly to the distal end of the tibia near the resected joint space S.

In some embodiments, the C-bracket 2600 also comprises a sagittal alignment rod 2650 for checking and verifying the alignment of the reamer shaft 2400 being inserted through the alignment hole 2635H in the patient's sagittal plane because the alignment of the reamer shaft 2400 determines the orientation and direction of the intramedullary path to be reamed into the tibia which will then receive the stem of the tibia tray implant. In the illustrated example, the sagittal alignment rod 2650 is attached to the first arm 2620 but the alignment rod 2650 may be attached to the C-bracket 2600 at a different location.

Referring to FIG. 27A, in some embodiments the C-bracket 2600 can comprise a coronal alignment rod 2250 for checking and verifying the alignment of the reamer shaft 2400 being inserted through the alignment hole 2635H in the patient's coronal plane. In the illustrated example, the coronal alignment rod 2250 is attached to the first arm 2620 at the end where the tibia cartridge 2200 attaches to the first arm.

The disclosed devices and systems may be used in a wide variety of surgical methods and procedures. The disclosed devices and systems advantageously enable orthopedic surgical procedures (e.g., ankle joint prosthetic procedures). For example, the disclosed devices and systems enable talar dome trial insertion and removal in order to prepare for a talar dome implant insertion procedure. Further, the disclosed devices and systems enable talar dome implant insertion and removal.

[Concept 8]

FIGS. 28-34 are illustrations of one example of an implant protector 2700 for a talar dome implant 2720. The implant protector 2700 may be used by a surgeon to insert a talar dome implant 2720 or remove a talar dome implant 2720 from a joint space during an ankle joint prosthetic procedure. The implant protector 2700 is utilized to provisionally grasp the implant during implantation while also protecting the smooth articular surface 2725 of the implant prior to completion of the surgical procedure. The talar dome implant 2720 may be a component of an ankle joint prosthesis, designed to engage with a tibia tray implant 2725 and a polymer articulating implant component (not shown). The implant protector 2700 comprises a body with an insertion end 2708, opposite a handle end 2709. The body is sized and configured to couple to a talar dome implant 2720 to protect the talar dome implant's articular surface, where the body comprises a concave surface 2702 and a convex surface 2701 opposite from the concave surface. The concave surface 2702 is contoured to substantially conform to the articular surface of the talar dome implant.

The body can include the insertion end 2708 and a handle end 2709. The handle end 2709 can be configured and arranged to receive a handle 2730.

The implant protector 2700 also comprises a first arm 2703A extending medially from the body, and configured to partially wrap around a first edge of the talar dome implant, and a second arm 2703B extending laterally from the body, opposite the first arm, and configured to partially wrap around a second edge of the talar dome implant.

The implant protector 2700 forming a convex surface 2701 opposite a concave surface 2702. The handle end 2709 includes a housing 2713, and is configured to form a recess 2711 to receive a handle 2730. The recess 2711 comprises a keyed slot portion 2712 and a handle tip recess 710 to receive and engage with the handle 2730. The keyed slot portion 2712 provides axial control of rotation for positioning the talar dome implant 2720 with an attached handle 2730. The convex surface 2701 includes an impaction surface 2705. The impaction surface 2705 is configured and arranged to be struck with an impaction tool, mallet, or other surgical instrument. The impaction surface 2705 may comprise a textured surface to enhance stability during impact. The thickness between the concave surface 2703 and the convex surface 2701 is adequate to not break during use. It is understood that a variety of materials may be used.

In the current embodiment, the talar dome implant 2700 is a polymer and may range in size with a thickness between 0.5 mm and 10 mm. The concave surface 2702 includes a ridge 2714 configured and arranged to engage with the implant sulcus 2723 or trough. The concave surface 2702 is non-abrasive and configured to protect the smooth articular surface 2725 of the talar dome implant 2720. Extending from the body of the implant protector 2700 is the first arm 2703A, the second arm 2703B, a lip 2706, and at least one protrusion 2707 extending from the first arm 2703A or second arm 2703B. The protrusion 2707 is configured to securely grasp the talar dome implant 2700 throughout impaction into patient anatomy. The protrusion 2707 may correspondingly engage a recess 2724 in a talar dome implant 2700. The lip 2706 is oriented obliquely from the body of the implant protector 2700 at the handle end 2709. The lip 2706 is configured and arranged to reversibly clip the implant protector 2700 to the talar dome implant 2720 to securely engage during impaction strikes for surgical implantation. The lip 2706 and arms 2703A-2703B are arranged to strongly resist disengagement between the implant protector 2700 and the talar dome implant 2720 in some directions, while loosely engaged in other directions. In this embodiment, the configuration stays securely attached while being impacted toward the patient and easily will release when being pulled away from the patient. In this embodiment, the first arm 2703A extends from the implant protector 2700 opposite the second arm 2703B. In some embodiments, not shown, the relative orientation and position of the arms may be offset in a spaced apart relation on any side of the implant protector 2700.

The body has a thickness between the concave surface 2702 and the convex surface 2701 that is sufficient for the body to receive strikes from an impaction instrument.

Figure 35:
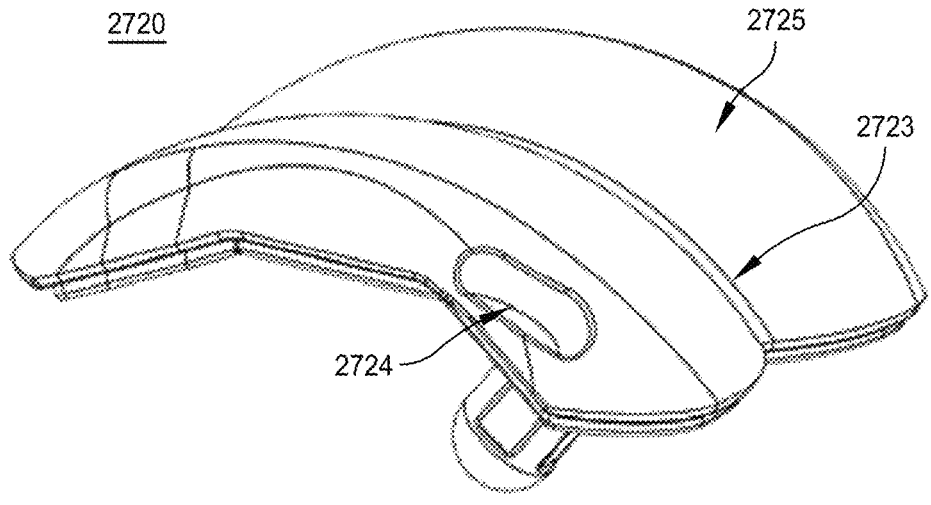
FIG. 35 shows a talar dome implant.
Figure 36:
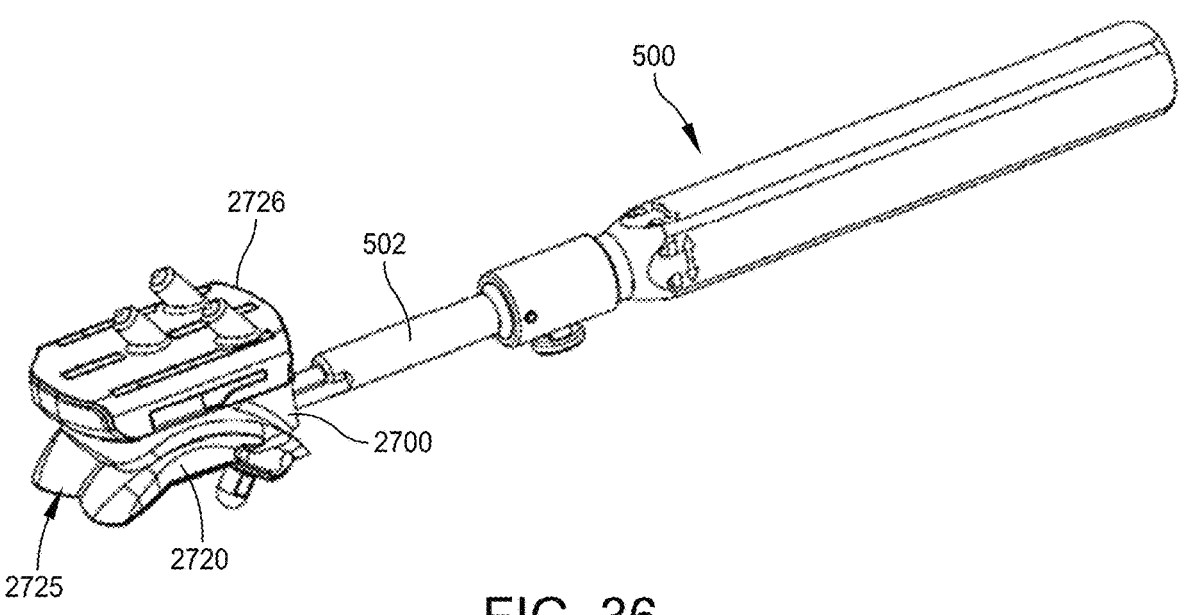
FIG. 36 shows a tibia tray implant, clip-on talar dome protector, a talar dome implant, and a handle according to an embodiment of the present disclosure.

FIGS. 35-36 are illustrations of the implant protector 2700 connected with a handle 2730 and positioned between a talar dome implant 2720 and a tibia tray implant 2726. The implant protector 2700 is protecting the articular surface 2725 from the sharp edges of the tibia tray component 2726 prior to placement of a polymer articulating implant component (not shown). The arms 2703A-2703B are reversibly snapped into the relief slot 2734. The ridge 2714 is aligned and nested within the implant sulcus 2723. The handle 2730 may include threads, locks, pins, or other features for engaging the handle end 2709 with the implant protector 2700.

Figure 37:
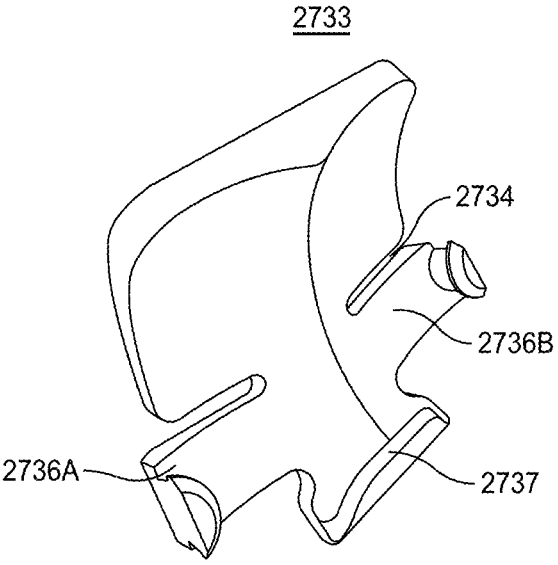
FIG. 37 shows a slotted clip-on talar dome protector according to an embodiment of the present disclosure.
Figure 38:
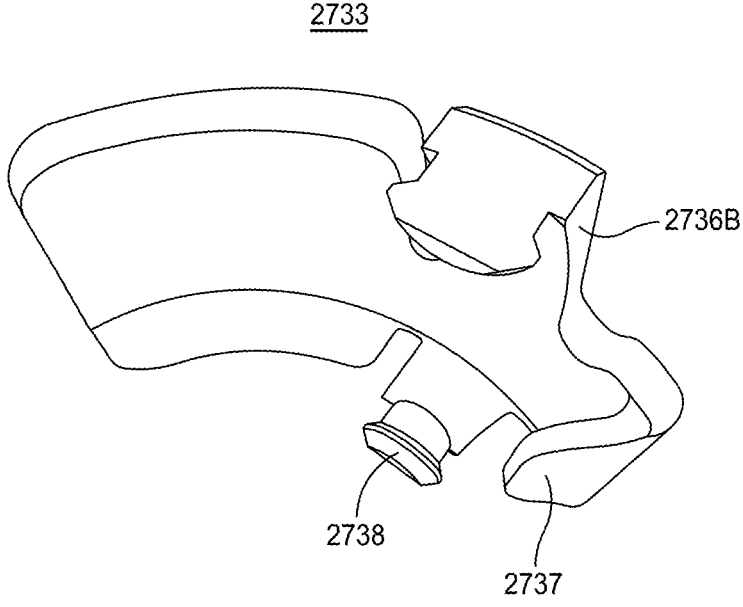
FIG. 38 shows a slotted clip-on talar dome protector according to an embodiment of the present disclosure.

FIGS. 37-38 are illustrations of one example of a slotted talar dome protector 2733, comprising a body which defines a slot 2734 to enable flexibility and a snap-fit relation with the talar dome implant 2720. The slot 2734 is configured and arranged to match the contours of the mating talar dome implant 2720, while ensuring secure attachment during impaction with a flexible release when the slotted talar dome protector is withdrawn. The slotted talar dome protector includes a first arm 2736A, a second arm 2736B, a proximal lip 2737, and a rounded protrusion 2738.

Figure 39:
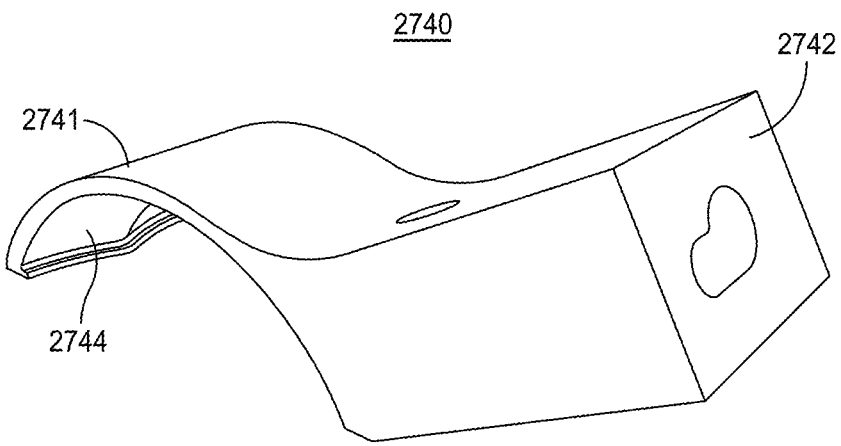
FIG. 39 shows a narrow clip-on talar dome protector according to an embodiment of the present disclosure.
Figure 40:
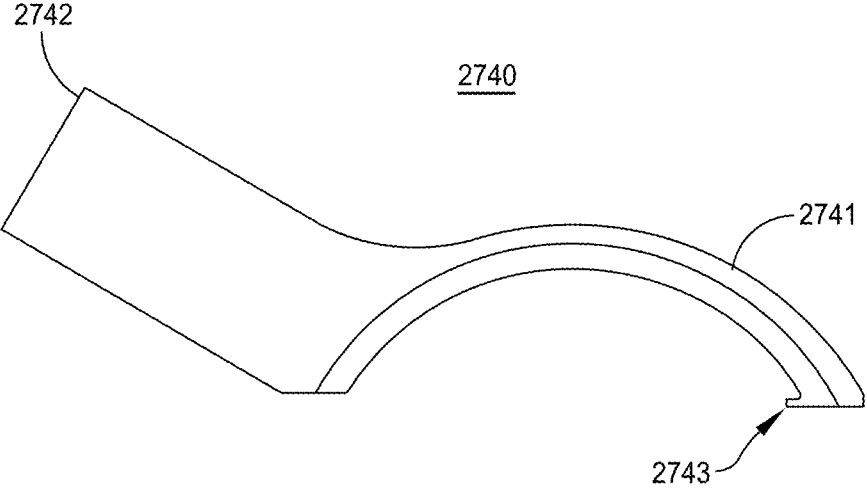
FIG. 40 shows a narrow clip-on talar dome protector according to an embodiment of the present disclosure.

FIGS. 39-40 are illustrations of one example of a narrow talar dome protector 2740, comprising a body defined by an insert end 2741 and a handle end 2742. The insert end includes a proximal lip 2743 and a ridge 2744, which are configured to releasably attach to a talar dome implant 2720. The narrow talar dome protector 2740 does not require arms and is sized and arranged to capture various sizes of implant widths. Using the talar dome protector 2740 can eliminate the need for a tibia tray protector or impactor spacer/bumper when a talar dome implant is being installed onto a talar bone using the impactor as the impactor can be hammered onto the snap-on talar dome protector directly.

[Concept 9]

Figure 41A:
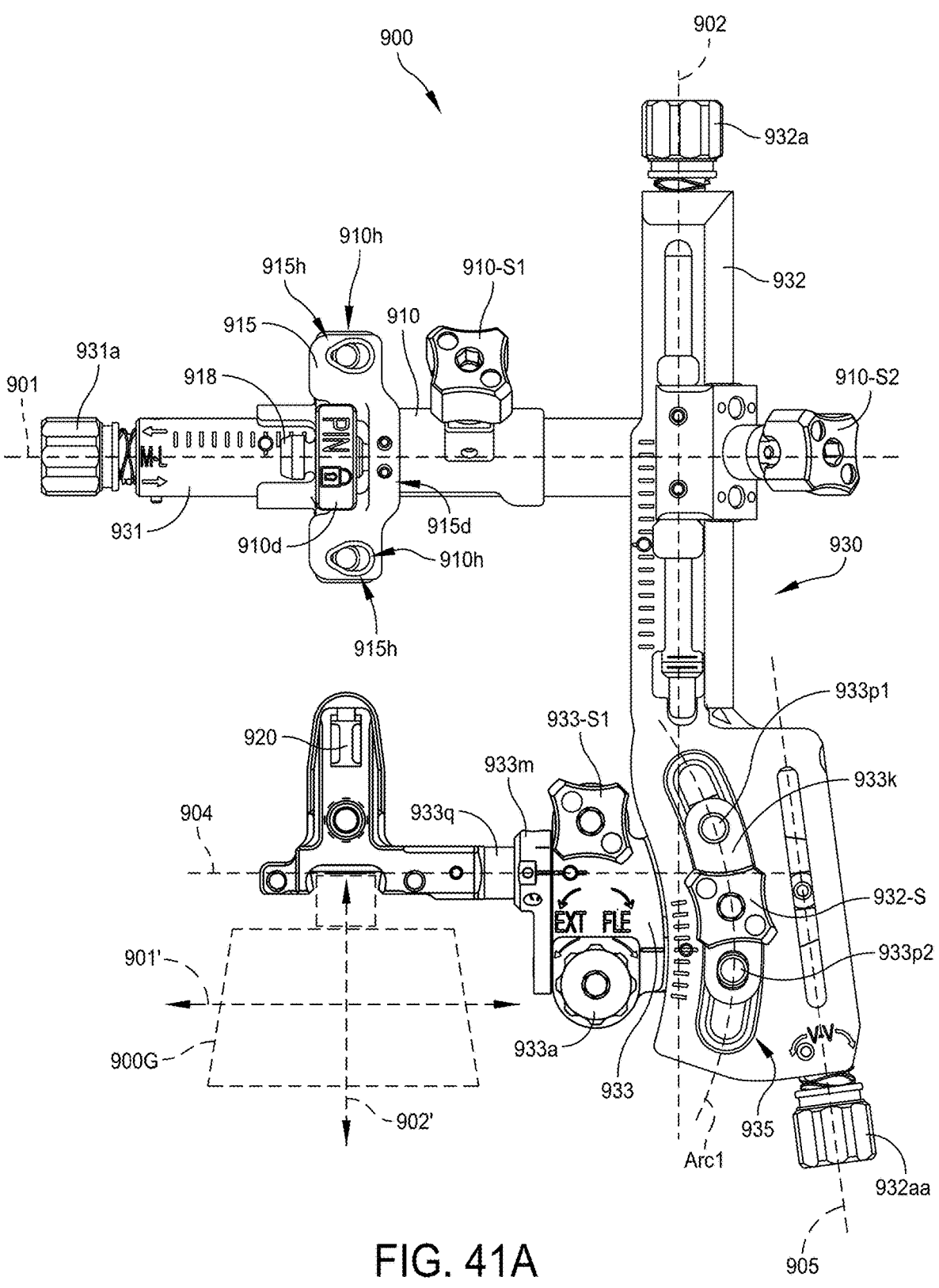
FIGS. 41A-41B are illustrations of one example of a guiding instrument according to the present disclosure.

Referring to FIG. 41A is a guiding instrument 900 for adjusting the position and attitude of a bone-cutting guide 900G. The attitude of the bone-cutting guide 900G refers to the bone-cutting guide's position and/or angular orientation with respect to a bone.

The guiding instrument 900 is useful and helpful in preparing an ankle joint space at the distal end of the patient's tibia as part of the total ankle arthroplasty procedure. The guiding instrument 900 is useful in aligning the bone-cutting guide 900G accurately with the tibia so that properly located cuts of proper dimensions can be made to the tibia to form the required ankle joint space. The guiding instrument 900 disclosed herein is particularly useful because the instrument combines the ability to adjust the attitude of the bone-cutting guide 900G in multiple directions, namely, the position of the bone-cutting guide 900G in two linear axes and angular orientation of the bone-cutting guide 900G in two different planes can be adjusted. The two linear axes can correspond to the superior/inferior position adjustment and medial/lateral position adjustment. The angular orientation in two different planes can correspond to the varus/valgus angle adjustment and flexion/extension angle adjustment for the ankle joint space.

In use, the user (e.g., a surgeon) affixes two fixation pins to the distal tibia and then attaches the guiding instrument 900 to the pins.

Another beneficial feature of the guiding instrument 900 is that the main mechanisms are offset from (i.e., away from) the tibia to allow good fluoroscopic visibility of the tibia. This is particularly beneficial for planning/positioning when using stemmed tibia implants.

Figure 41B:
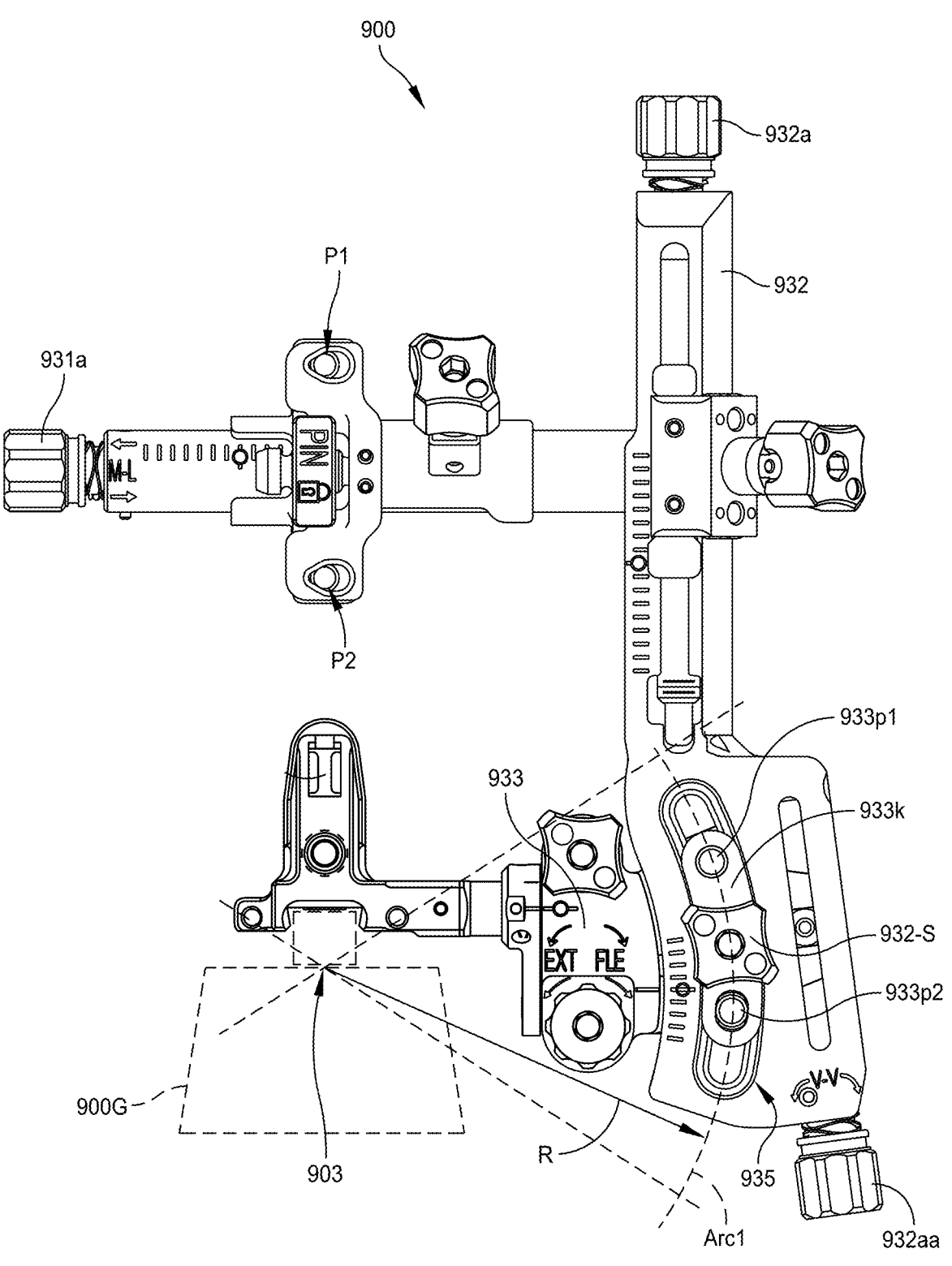
Figure 41C:
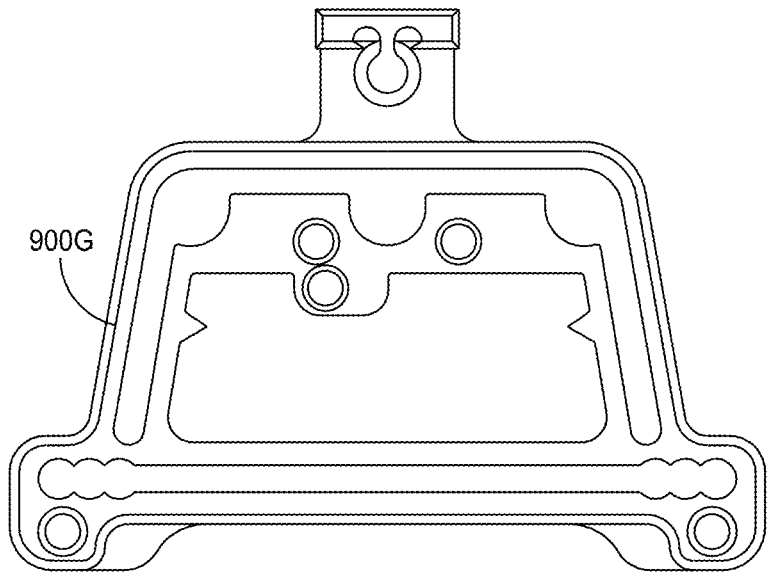
FIG. 41C is an illustration of an example of a bone-cutting guide.
Figure 42:
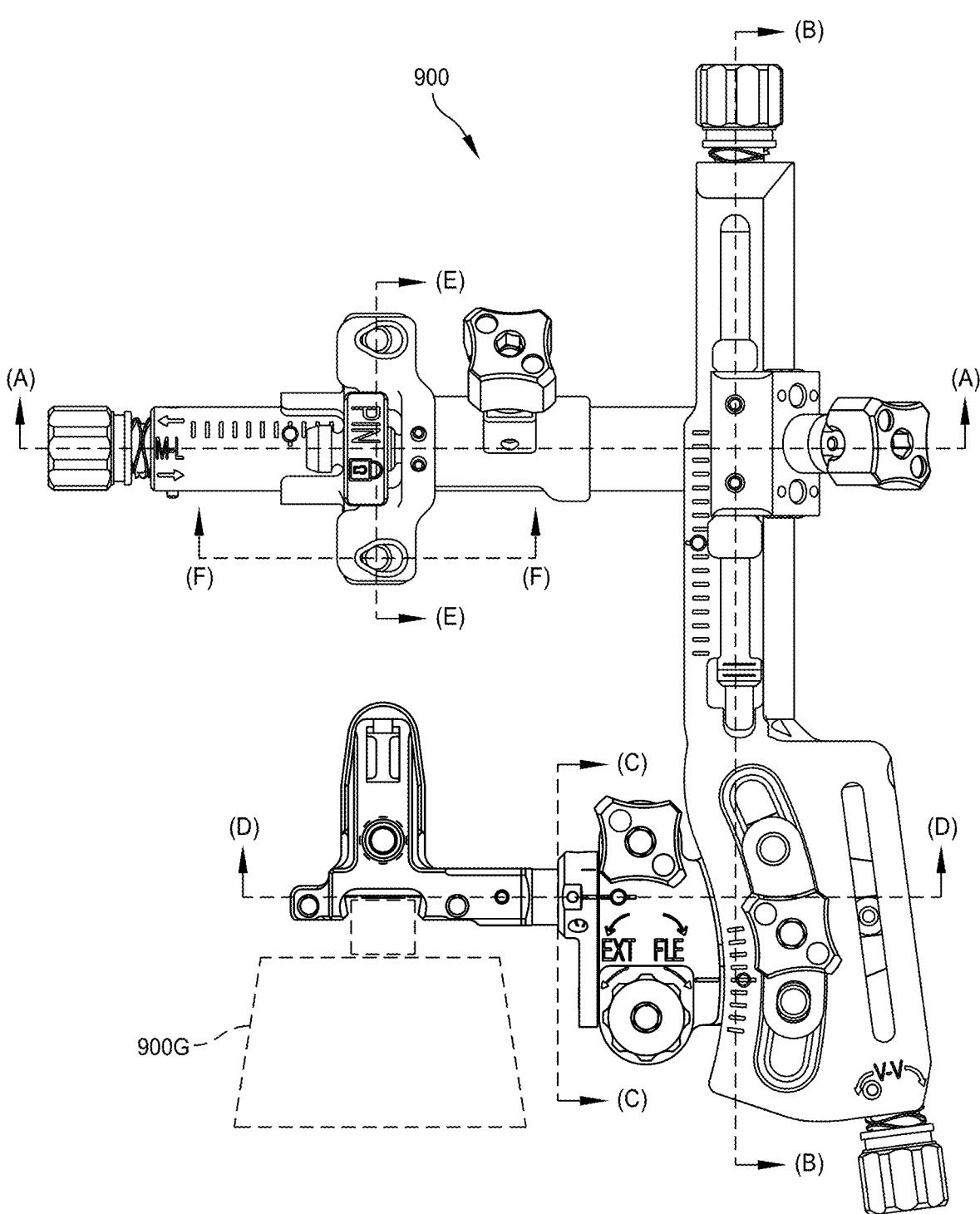
FIG. 42 is an illustration of the guiding instrument of FIG. 41A marked up to identify the various sectional views shown in FIGS. 42A-42F.

In the illustrated example, the guiding instrument 900 comprises a primary element 910, a secondary element 920, and an intermediary assembly 930 that connects the primary element 910 and the secondary element 920. In FIGS. 41A, 41B, and 42, the bone-cutting guide 900G is shown with just an outline in dashed lines to illustrate where the bone-cutting guide 900G would be attached to the guiding instrument 900. FIG. 41C is an illustration of an example of a bone-cutting guide 900G with its associated guiding slots and guiding holes.

The primary element 910 is configured to be affixed to the bone and establish a reference point on the bone. The secondary element 920 is configured to hold the bone-cutting guide 900G. The intermediary assembly 930 comprises a first part 931, a second part 932; and a third part 933.

The first part 931 of the intermediary assembly 930 is configured for adjusting the position of the bone-cutting guide 900G linearly along a direction that is parallel to the first axis 901 with respect to the primary element 910. This is achieved by a configuration that enables the first part 931 to be controllably moved linearly along the first axis 901 until a desired position is reached then lock that position. An example of such configuration will be described with reference to FIGS. 41A, 42, and 42A.

FIG. 42 shows the instrument 900 marked up with notations identifying the various cross-sectional views (A) through (F) that are illustrated in FIGS. 42A-42F to illustrate examples of the detailed structures that enable the novel functions of the instrument 900.

Figure 42A:
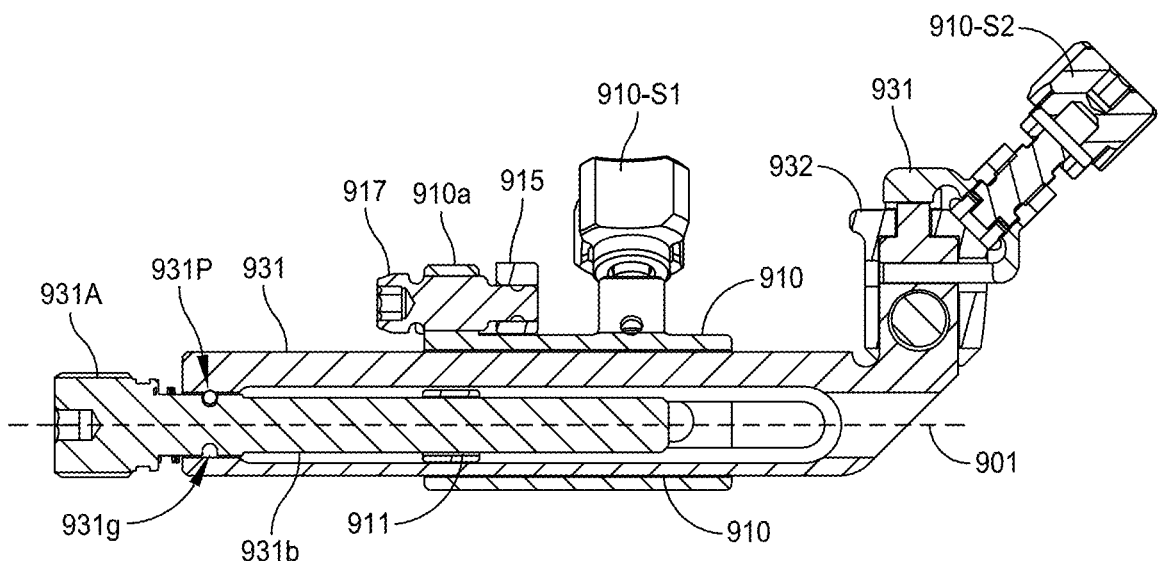
FIG. 42A is a cross-section view of the guide instrument of FIG. 41A taken through the section line (A)-(A) shown in FIG. 42.

FIG. 42A shows a cross-sectional view (A) of the assembly of the primary element 910 and the first part 931. The first part 931 forms a linear actuation mechanism in combination with the primary element 910. The first part 931 comprises a leadscrew 931a and the primary element 910 comprises a threaded nut 911. The leadscrew 931a has a threaded shaft portion 931b that threadedly engages the nut 911. The nut 911 is appropriately configured with a female type thread to establish a threaded engagement with the threaded shaft portion 931b. By turning the leadscrew 931a, the leadscrew 931a can be moved linearly back and forth along the first axis 901.

The leadscrew 931a can be rotated about the first axis 901 within the first part 931 but the leadscrew 931a is held in place by a locking pin 931p that is placed through the first part 931 and positioned so that the pin 931p goes through one side of an annular groove 931g that is provided around the neck portion of the leadscrew 931a. The cooperation between the locking pin 931c and the annular groove 931g allows the leadscrew 931a to be turned about the first axis 901 but prevents the leadscrew 931a from linearly translating with respect to the first part 931. Therefore, when the leadscrew 931a is rotated so that the leadscrew 931a translates linearly through the nut 911 along the first axis 901, the first part 931 moves with the leadscrew 931a and also translates linearly along the first axis 901. This linear motion, in turn, moves the bone-cutting guide 900G linearly along a M-L axis 901' that is parallel to the first axis 901 because the bone-cutting guide 900G is connected to the first part 931. This allows the position of the bone-cutting guide 900G to be adjusted in medial-lateral directions with respect to the patient's ankle. The spatial relationship between the first axis 901 and the M-L axis 901' can be better seen in FIG. 41A.

In some embodiments, the primary element 910 further comprises a set screw 910-S1 for locking the first part 931 with respect to the primary element 910 so that the position of the first part 931 along the first axis 901 can be locked. This, in turn, locks the position of the bone-cutting guide 900G along the M-L axis 901' that is parallel to the first axis 901. The set screw 910-S1 is threaded through the primary element 910 and contacts the first part 931. As shown, the set screw 910-S1 comprises a knob that can be used to turn the set screw.

The second part 932 of the intermediary assembly 930 can be configured for adjusting the position of the bone-cutting guide 900G linearly along a direction that is parallel to a second axis 902 with respect to the first part 931, where the second axis 902 is orthogonal to the first axis 901. This is achieved by a configuration that enables the second part 932 to be controllably moved linearly along the second axis 902 until a desired position is reached then lock that position. An example of such configuration will be described with reference to FIGS. 41A, 42, and 42B.

Figure 42B:
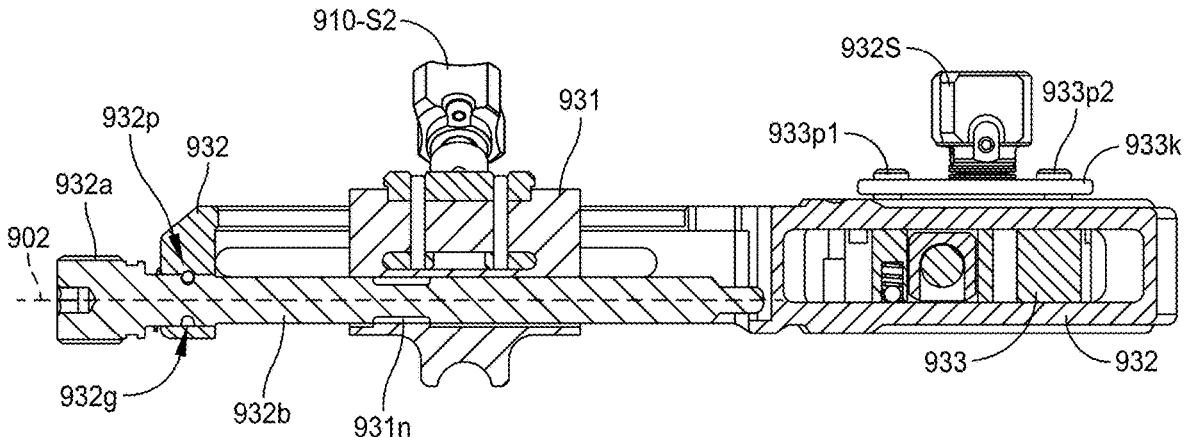
FIG. 42B is a cross-section view of the guide instrument of FIG. 41A taken through the section line (B)-(B) shown in FIG. 42.

FIG. 42B shows a cross-sectional view (B) of the assembly of components of the second part 932 and the first part 931. The second part 932 forms a linear actuation mechanism in combination with the first part 931. The second part 932 comprises a leadscrew 932a and the first part 931 comprises a nut 931n. The leadscrew 932a has a threaded shaft portion 932b that threadedly engages the nut 931n. The nut 931n is appropriately configured with a female type thread to establish a threaded engagement with the threaded shaft portion 932b. By turning the leadscrew 932a, the leadscrew 932a can be moved linearly back and forth along the second axis 902.

The leadscrew 932a can be rotated about the second axis 902 within the second part 932 but the leadscrew 932a is held in place by a locking pin 932p that is placed through the second part 932 and positioned so that the pin 932p goes through one side of an annular groove 932g that is provided around the neck portion of the leadscrew 932a. The cooperation between the locking pin 932p and the annular groove 932g allows the leadscrew 932a to be turned about the second axis 902 but prevents the leadscrew 932a from linearly translating with respect to the second part 932. Therefore, when the leadscrew 932a is rotated, the second part 932 translates linearly along the second axis 902 along with the leadscrew 932a. This motion, in turn, moves the bone-cutting guide 900G linearly along a direction parallel to the second axis 902 because the bone-cutting guide 900G is connected to the second part 932. This allows the position of the bone-cutting guide 900G to be adjusted in the superior-inferior directions along a S-I axis 902' with respect to the patient's ankle. The spatial relationship between the second axis 902 and the S-I axis 902' can be better seen in FIG. 41A.

In some embodiments, the first part 931 further comprises a set screw 910-S2 for locking the second part 932 with respect to the first part 931 so that the position of the second part 932 along the second axis 902 can be locked. This, in turn, locks the position of the bone-cutting guide 900G along the S-I axis 902' that is parallel to the second axis 902. The set screw 910-S2 is threaded through the first part 931 and contacts the second part 932. As shown, the set screw 910-S2 comprises a knob that can be used to turn the set screw.

Referring to FIGS. 41A, 41B, 43A, and 43B, the third part 933 of the intermediary assembly 930 is configured to cooperate with the second part 932 for adjusting the angular orientation of the third part 933, and in turn the angular orientation of the bone-cutting guide 900G, about a third axis 903. The third axis 903 is orthogonal to both the first axis 901 and the second axis 902. The third axis 903 is defined to be located at the point labeled as 903 in FIG. 41B. Accordingly, because the third axis 903 is orthogonal to both the first axis 901 and the second axis 902, the third axis 903 extends orthogonally through the image plane of FIG. 41B. The angular orientation of the bone-cutting guide 900C about the third axis 903 represents the varus/valgus angle in the frame of reference of the patient's ankle when the instrument 900 is affixed to the tibia during an ankle arthroplasty.

Figure 43A:
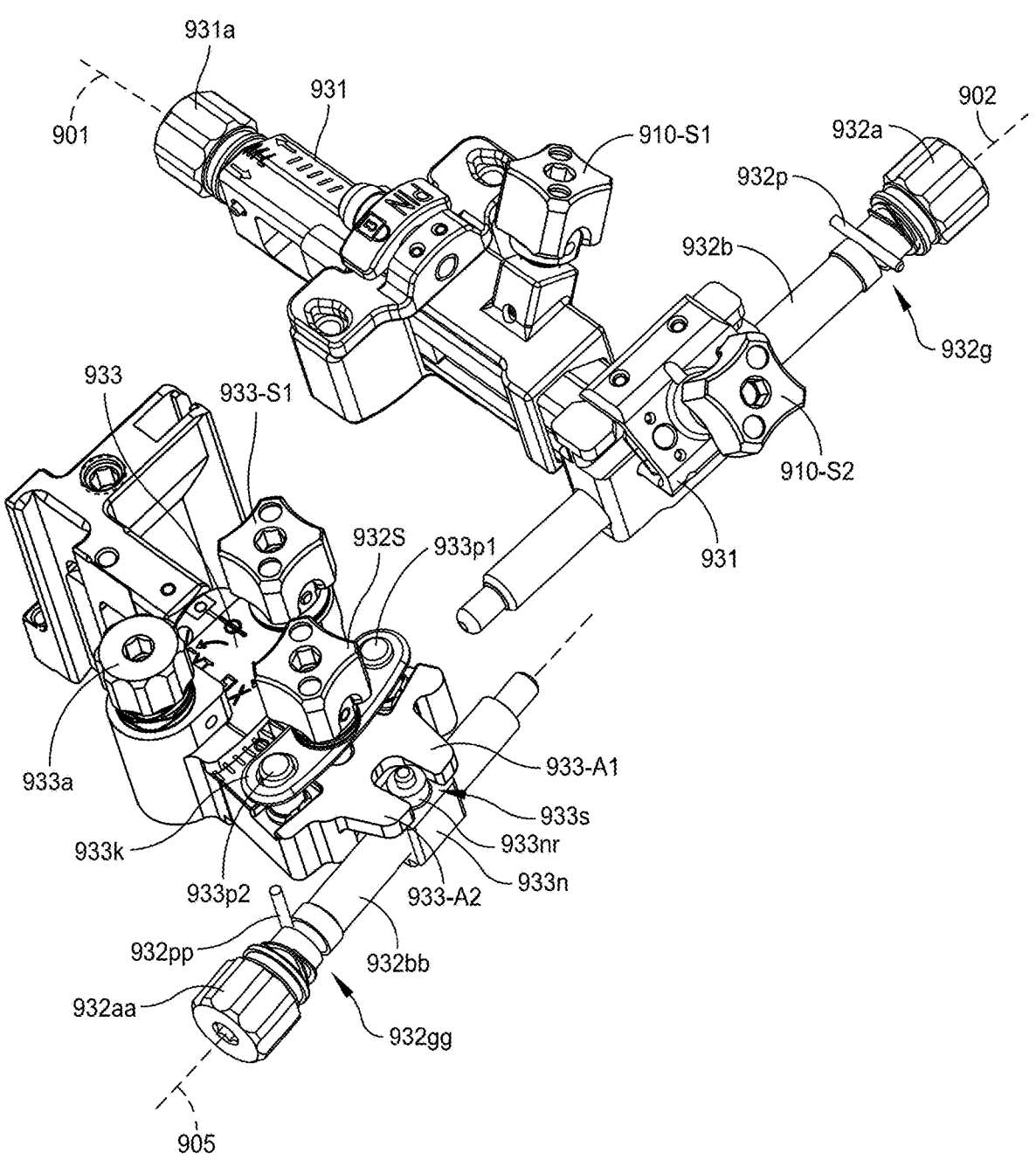
FIGS. 43A-43B are detailed views of the components of the guiding instrument of FIG. 41A without the outer portion of the second part.
Figure 43B:
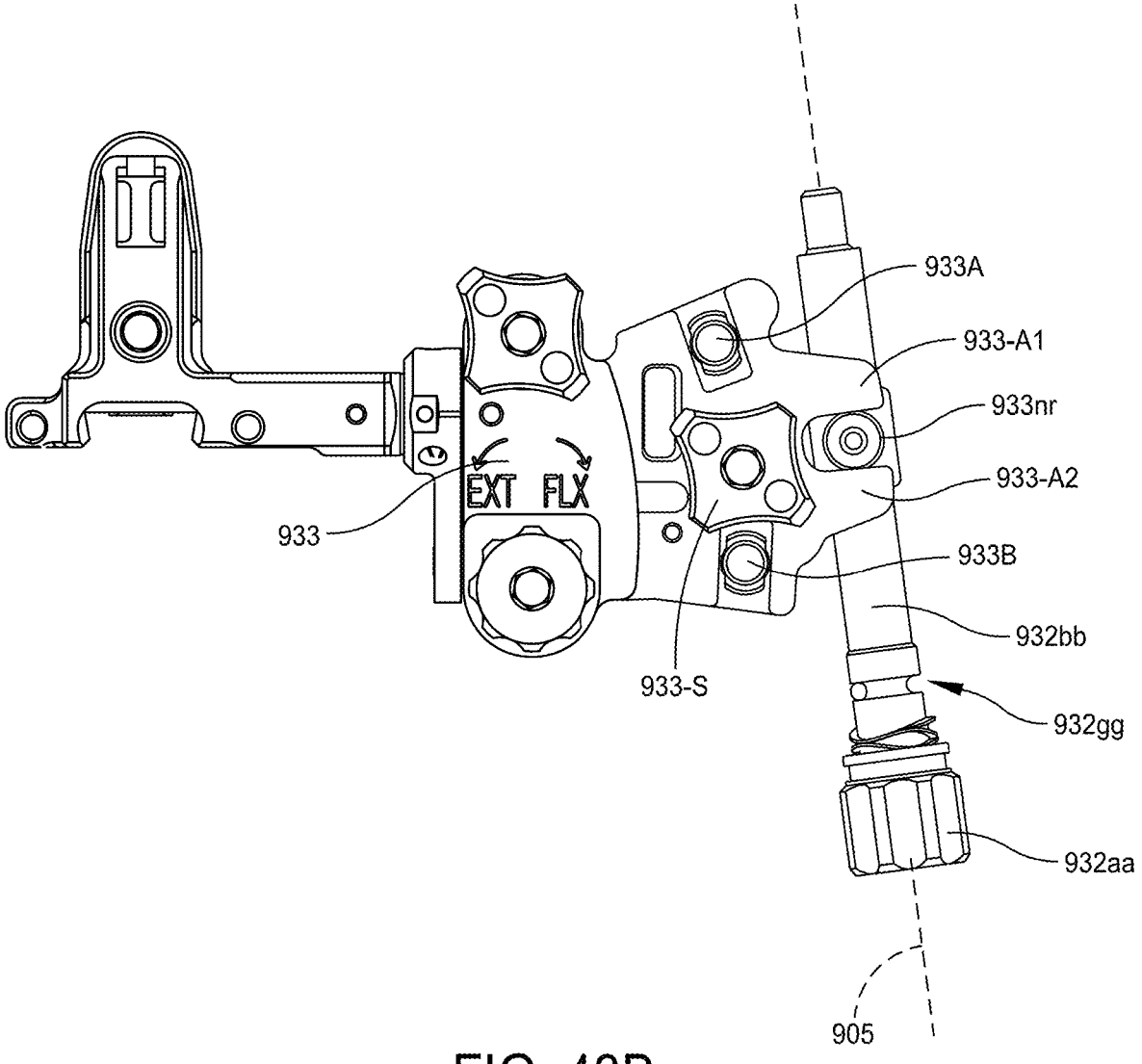

FIGS. 43A and 43B referenced in the following description show the structures of the guiding instrument 900 without the outer shell portion of the second part 932 so that the structures of the third part 933 are more visible.

Referring to FIG. 41B, to accomplish the capability to adjust the angular orientation of the third part 933 about the third axis 903, the second part 932 comprises a second leadscrew 932*aa* that cooperates with the third part 933 to move the third part 933 along a first arc Arc1. The curvature of the first arc Arc1 is a circular arc that has a radius of curvature R such that the center of the radius R that defines the first arc Arc1 is on the third axis 903. Thus, moving the third part 933 along the first arc Arc1 means pivoting the third part 933 about the third axis 903.

When the guiding instrument 900 is in use, the bone-cutting guide 900G is attached to the third part 933. Thus, the result of the configuration of the second part 932 and the third part 933 involving the third axis 903 and the first arc Arc1 is that adjusting the angular orientation of the third part 933 along the first arc Arc1 also adjusts the angular orientation of the bone-cutting guide 900G along the first arc Arc1 about the third axis 903. In other words, adjusting the angular orientation of the third part 933 along the first arc Arc1 results in rotating (i.e., pivoting) the bone-cutting guide 900G about the third axis 903.

FIGS. 43A-43B are detailed views of the components of the guiding instrument 900 shown without the outer portion of the second part 932. Referring to FIGS. 43A-43B, the third part 933 comprises a bifurcated end that engages with the second part 932. The bifurcated end has two arms 933-A1 and 933-A2 with a slot 933*s* defined between the two arms 933-A1 and 933-A2. The third part 933 also comprises a threaded nut 933*n* that has a roller guide pin 933*nr* that establishes the engagement between the bifurcated ends of the third part 933 and the second part 932. That engagement is a non-rigid engagement as the roller guide pin 933*nr* can slide within the slot 933*s* toward and away from the center of the curvature of the first arc Arc1 which is the third axis 903. The roller guide pin 933*nr* is situated within the slot 933*s* between the two arms 933-A1 and 933-A2.

The second part 932 comprises a second leadscrew 932*aa* having a threaded shaft portion 932*bb* that threadedly engages the threaded nut 933*n*. The nut 933*n* is appropriately configured with a female type thread to establish a threaded engagement with the threaded shaft portion 932*bb*. By turning the second leadscrew 932*aa*, the threaded nut 933*n* and the leadscrew 932*aa* can be moved relative to each other back and forth along a fifth axis 905.

The second leadscrew 932*aa* is affixed to the second part 932 by a locking pin 932*pp* that is placed through the second part 932 and positioned so that the pin 932*pp* goes through one side of an annular groove 932*gg* that is provided around the neck portion of the second leadscrew 932*aa*. The cooperation between the locking pin 932*pp* and the annular groove 932*gg* allows the second leadscrew 932*aa* to be turned about the fifth axis 905 but prevents the second leadscrew 932*aa* from linearly translating with respect to the second part 932.

Therefore, when the second leadscrew 932*aa* is rotated, the threaded nut 933*n* translates linearly along the fifth axis 905 with respect to the second leadscrew 932*aa*.

The second part 932 further comprises a curved slot 935 on each face. In FIGS. 41A, 41B, and 42, the front face (i.e., anterior face) of the guide instrument 900 is visible and the curved slot 935 on the front face is visible. The rear face of the guide instrument 900 is provided with a matching curved slot 935. Because the guide instrument 900 is intended to be used on a patient's ankle joint by being affixed to the anterior side of the patient's tibia, the front face of the guide instrument 900 visible in FIGS. 41A, 41B, and 42 will be referred to as the anterior side to be consistent with the patient's anatomical directions.

The curvature of each of the curved slots 935 matches the curvature of the first arc Arc1 and each slot 935 extends along the first arc Arc1 for a predetermined length as shown in FIGS. 41A and 41B.

As can be seen in FIGS. 41A, 41B, and the sectional view (B) in FIG. 42B, the third part 933 extends into a portion of the second part 932 and the anterior face and the posterior face of the second part 932 sandwich the third part 933. The third part 933 comprises two guide pins 933*p*1 and 933*p*2 that extend through each of the curved slots 935 on the anterior face and the posterior face of the second part 932. The engagement of the two guide pins 933*p*1 and 933*p*2 with the curved slots 935 converts the linear translation between the second leadscrew 932*aa* and the threaded nut 933*n* into a rotational motion (or pivoting motion) of the third part 933 about the third axis 903. This motion, in turn, pivots the bone-cutting guide 900G about the third axis 903 because the bone-cutting guide 900G is connected to the third part 933. This allows the ability to adjust the angular orientation of the bone-cutting guide 900G about the third axis 903.

In the disclosed embodiments, where the bone-cutting guide 900G is a guide for cutting the distal end of a tibia to prepare a joint space for total ankle arthroplasty, the angular orientation of the bone-cutting guide 900G about the third axis 903 represents the varus/valgus angular orientation of the ankle joint space to be cut. Thus, adjusting the angular orientation of the bone-cutting guide 900-G about the third axis 903 adjusts the varus/valgus angle of the ankle joint space to be prepared using the bone-cutting guide 900G.

As the threaded nut 933*n* of the third part 933 linearly translates with respect to the second leadscrew 932*aa*, the non-rigid engagement between the roller guide pin 933*nr* of the threaded nut 933*n* and the bifurcated end of the third part 933 allows the non-linear motion of the third part 933 that is guided and determined by the path of the two guide pins 933*p*1 and 933*p*2 within the curved slots 935. Thus, the movement of the third part 933 driven by turning of the second leadscrew 932*aa* will follow the curvature of the curved slots 935 which is the first arc Arc1 denoted in FIG. 41B. Because the curvature of the first arc Arc1 is a circular curve with a center located at the third axis 903, the pivoting motion of the third part 933 translates into a pivoting motion of the bone-cutting guide 900G about the third axis 903 which is the varus/valgus angular adjustment.

In some embodiments, the engagement between the second leadscrew 932*aa* and the third part 933 can be achieved by a worm gear drive mechanism for adjusting the angular orientation of the bone-cutting guide about the third axis 903.

In some embodiments, the third part 933 also comprises a plate 933*k* that is connected to the two guide pins 933*p*1 and 933*p*2 and extends between the two guide pins 933*p*1 and 932*p*2. As shown in FIGS. 41A, 41B, and the cross-section view (D) shown in FIG. 42D, the plate 933*k* is wider than the width of the curved slot 935 and is positioned in front of the front face of the second part 932. This can be better seen in the cross-section view (D) in FIG. 42D. A set screw 932S is provided for locking the position of the third part 933 along the first arc Arc1 within the range of positions allowed by the curved slot 935 with respect to the second part 932. The set screw 932S extends through the plate 933*k* and is threaded into the third part 933 at a location between the two guide pins 933*p*1 and 933*p*2. Thus, the plate 933*k* is captured between the neck portion of the set screw 932S and the curved slot 935. Threading the set screw 932S into the third part 933 presses the plate 933*k* against the shoulders of the curved slot 935 and lock the position of the plate 933*k*, and thus the third part 933, with respect to the second part 932. The positioning of the plate 933*k* over the curved slot 935 is better seen in the cross-section view (D) in FIG. 42D.

In the disclosed embodiments, the third part 933 is also configured to cooperate with the secondary element 920 for adjusting the angular orientation of the bone-cutting guide 900G about a fourth axis 904, where the fourth axis 904 is parallel with the first axis 901 and orthogonal with the second axis 902.

Figure 42C:
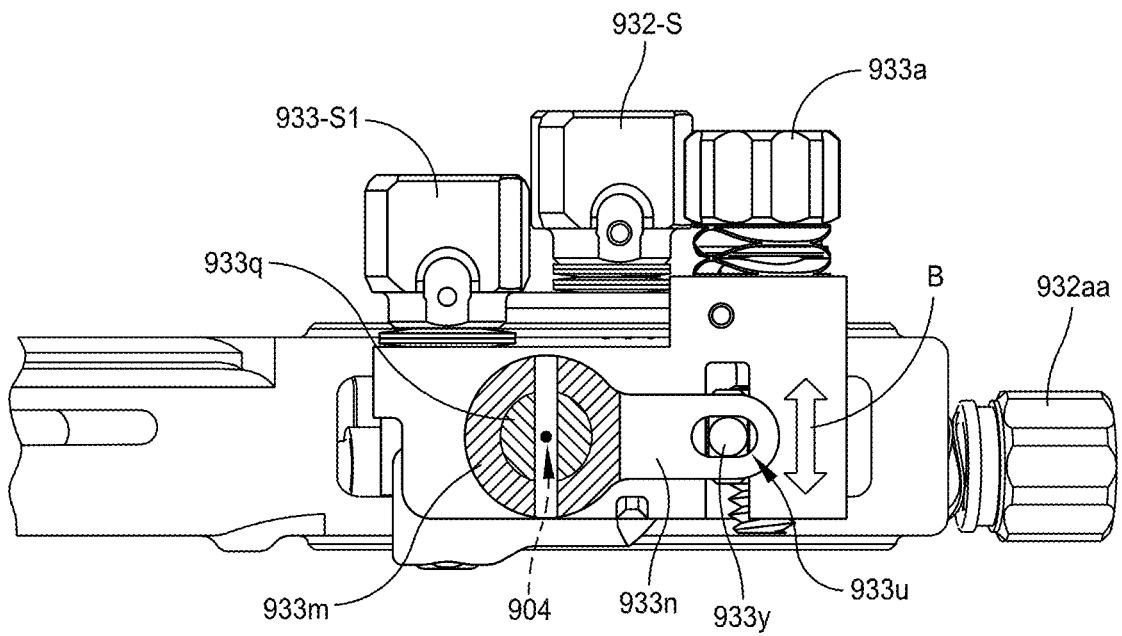
FIG. 42C is a cross-section view of the guide instrument of FIG. 41A taken through the section line (C)-(C) shown in FIG. 42.
Figure 42D:
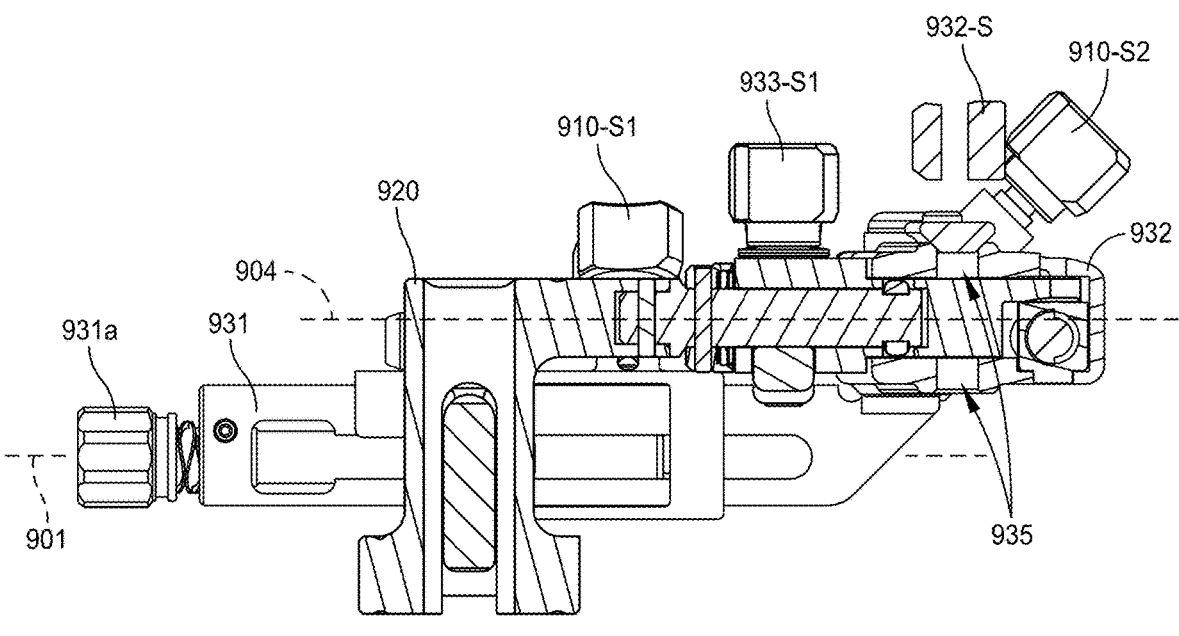
FIG. 42D is a cross-section view of the guide instrument of FIG. 41A taken through the section line (D)-(D) shown in FIG. 42.

FIG. 42C shows a cross-sectional view (C) of the assembly of components of the third part 933 that enables the third part 933 to adjust the angular orientation of the bone-cutting guide 900G about the fourth axis 904. The third part 933 comprises a leadscrew 933*a* that is oriented orthogonal to the fourth axis 904. The leadscrew 933*a* is configured to linearly translate a guide pin 933*y* back and forth in directions denote by the two-headed arrow B by turning the leadscrew 933*a*. This can be achieved by a leadscrew/threaded nut configuration similar to the leadscrew 931*a* and threaded nut 911 configuration discussed above. The third part 933 further comprises a connecting arm 933*n* that forms a connection between the guide pin 933*y* and an arm 933*q* that connects the secondary element 920 to the third part 933. The arm 933*q* extends along the fourth axis 904. The connecting arm 933*n* has a base portion 933*m* at one end that connects the connecting arm 933*n* to the arm 933*q*. The connecting arm 933*n* has an elongated opening 933*u* at the opposite end that connects to the guide pin 933*y*. When the guide pin 933*y* is linearly translated, within the elongated opening 933*u*, along the directions denoted by the arrow B in FIG. 42C, by the leadscrew 933*a*, the connecting arm 933*n* converts that linear motion into a rotational motion by pivoting about the fourth axis 904. The fourth axis 904 would be extending through the arm 933*q* along the longitudinal axis of the arm 933*q*. Thus, in the view shown in FIG. 42C, the fourth axis 904 would be extending orthogonally out of the viewing plane at the center of the connecting arm 933*n*.

In the disclosed embodiments, where the bone-cutting guide 900-G is a guide for cutting the distal end of a tibia to prepare a joint space for total ankle arthroplasty, the angular orientation of the bone-cutting guide 900G about the fourth axis 904 represents the flexion/extension angular orientation of the ankle joint space to be cut. Thus, adjusting the angular orientation of the bone-cutting guide 900G about the fourth axis 904 adjusts the flexion/extension angle of the ankle joint space to be prepared using the bone-cutting guide 900G.

(Affixing the Primary Element to the Bone)

In some embodiments of the disclosed guiding instrument 900, the primary element 910 is configured with one or more holes 910*h* for receiving one or more fixation pins for affixing the primary element 910 to a bone such as the patient's tibia. In FIG. 41B, exemplary fixation pins P1 and P2 are shown extending through the holes 910*h* in the primary element 910.

Figure 42E:
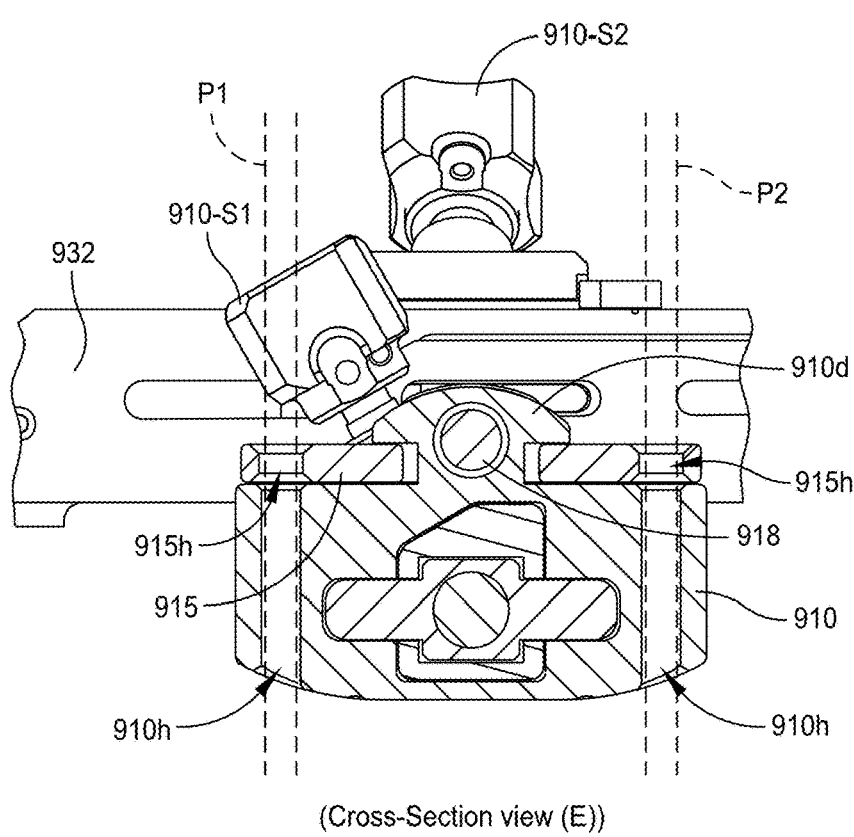
FIG. 42E is a cross-section view of the guide instrument of FIG. 41A taken through the section line (E)-(E) shown in FIG. 42.
Figure 42F:
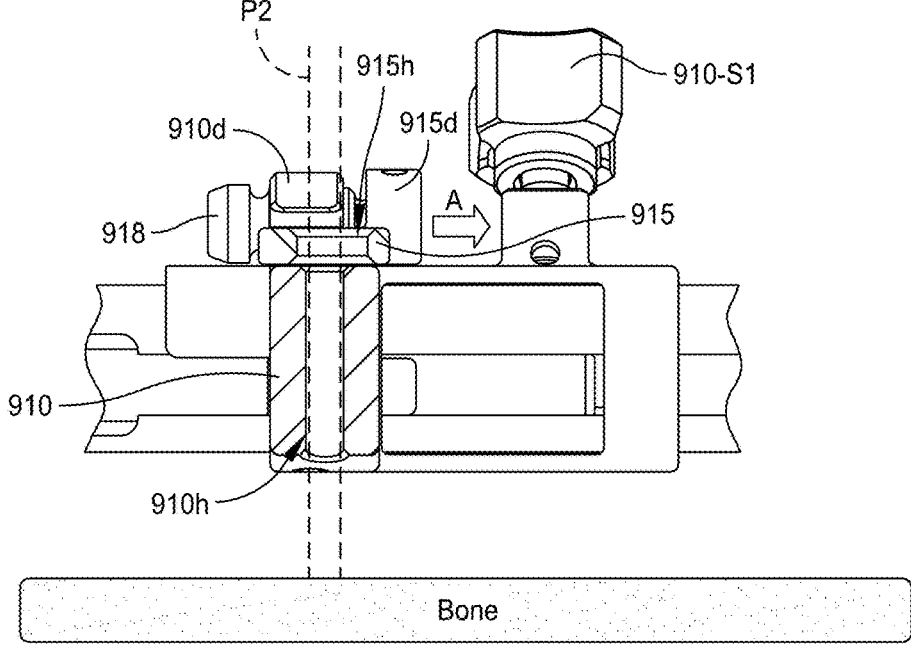
FIG. 42F is a cross-section view of the guide instrument of FIG. 41A taken through the section line (F)-(F) shown in FIG. 42.

In some embodiments, the primary element 910 can be configured with a locking mechanism for locking the primary element to the fixation pins. The locking mechanism will be described with reference to FIGS. 42E and 42F. FIG. 42E shows the cross-section view (E) taken through the section line (E)-(E) identified in FIG. 42. FIG. 42F shows the cross-section view (F) taken through the section line (F)-(F) identified in FIG. 42.

The fixation pins P1 and P2 extending through the holes 910*h* in the primary element 910 and into a bone are illustrated with dashed lines. The primary element 910 comprises a sliding plate 915 that cooperates with the primary element 910 for locking the fixation pins is provided on the anterior side of the guiding instrument 900. Thus, the sliding plate 915 is provided on the side opposite from the bone as illustrated in FIG. 42F. The sliding plate 915 is provided with one or more holes 915*h* that are aligned with the one or more holes 910*h* provided in the primary element 910 so that the fixation pins P1, P2 can extend through the holes 915*h* and the holes 910*h* and into the bone as illustrated in FIG. 42F. With the fixation pins in this position, sliding the sliding plate 915 laterally with respect to the primary element 910 until the sidewalls of the holes 915*h* in the sliding plate contacts the fixation pins P1, P2 and urging the sliding plate 915 against the fixation pins with some force can lock the guiding instrument 900 to the fixation pins by mechanical interference.

Figure 42G:
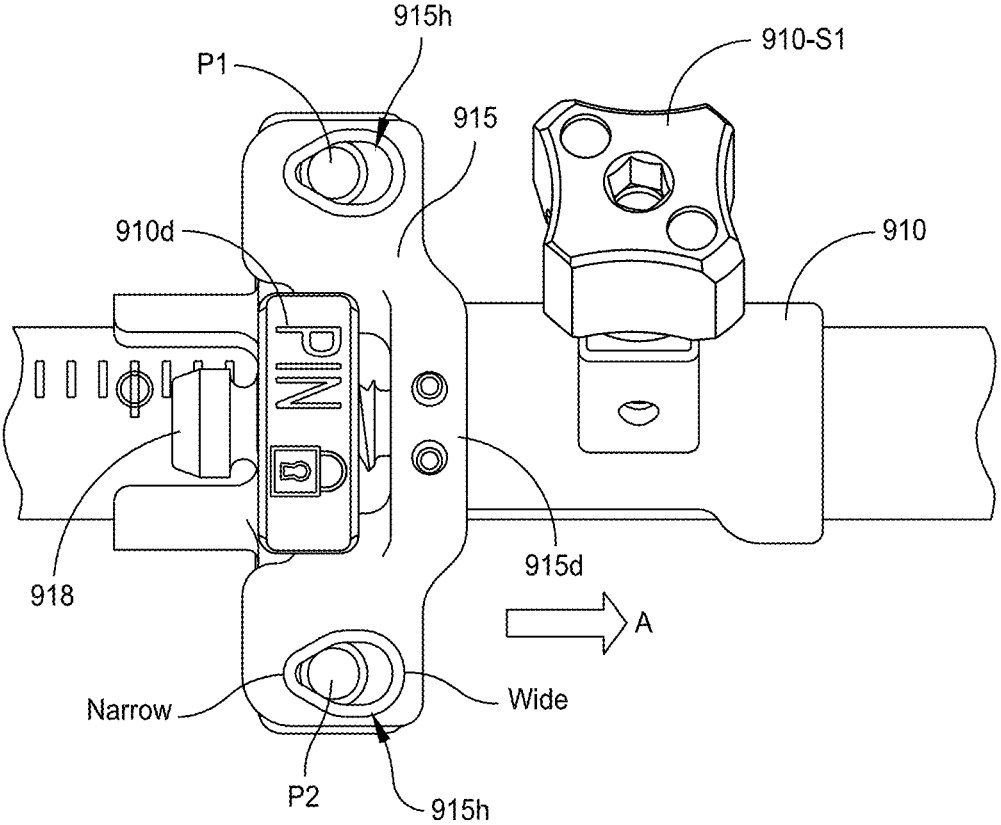
FIG. 42G is a detailed view of the primary element 910 of the guiding instrument of FIG. 41A.

To facilitate this locking motion, the sliding plate 915 comprises a protruding portion 915*d* and the primary element 910 has a corresponding protruding portion 910*d*. The protruding portion 910*d* is configured with a locking screw 918 that is threaded through the protruding portion 910*d* and butts up against the protruding portion 915*d* of the sliding plate 915. This configuration can be better seen in FIGS. 42F and 42G. Threading the locking screw 918 into the protruding portion 910*d* and pushing the protruding portion 915*d* and, thus, the sliding plate 915 in the direction of the arrow A shown in FIGS. 42F and 42G, until the sidewalls of the holes 915*h* of the sliding plate 915 urges against the fixation pins P1, P2 with some force accomplishes the locking.

To enhance the locking function of the sliding plate 915, the holes 915*h* provided in the sliding plate 915 have a non-symmetric elongated or a teardrop shape. This can be seen in FIG. 41A and the cross-section views in FIGS. 42E, 42F, and the detailed view in FIG. 42G. The width of the holes 915*h* along the direction of the section line (E)-(E) is substantially the same as the diameter of the holes 910*h*. However, the width of the holes 915*h* along the direction of the section line (F)-(F) is wider than the diameter of the holes 910*h*. Thus, by sliding the sliding plate 915 in the direction of the arrow A will force the fixation pins P1, P2 into the narrower end of the holes 915*h*. This configuration can enhance the locking function by minimizing any side movement of the fixation pins P1, P2 and make the mechanical interference locking of the pins more rigid.

Figure 44A:
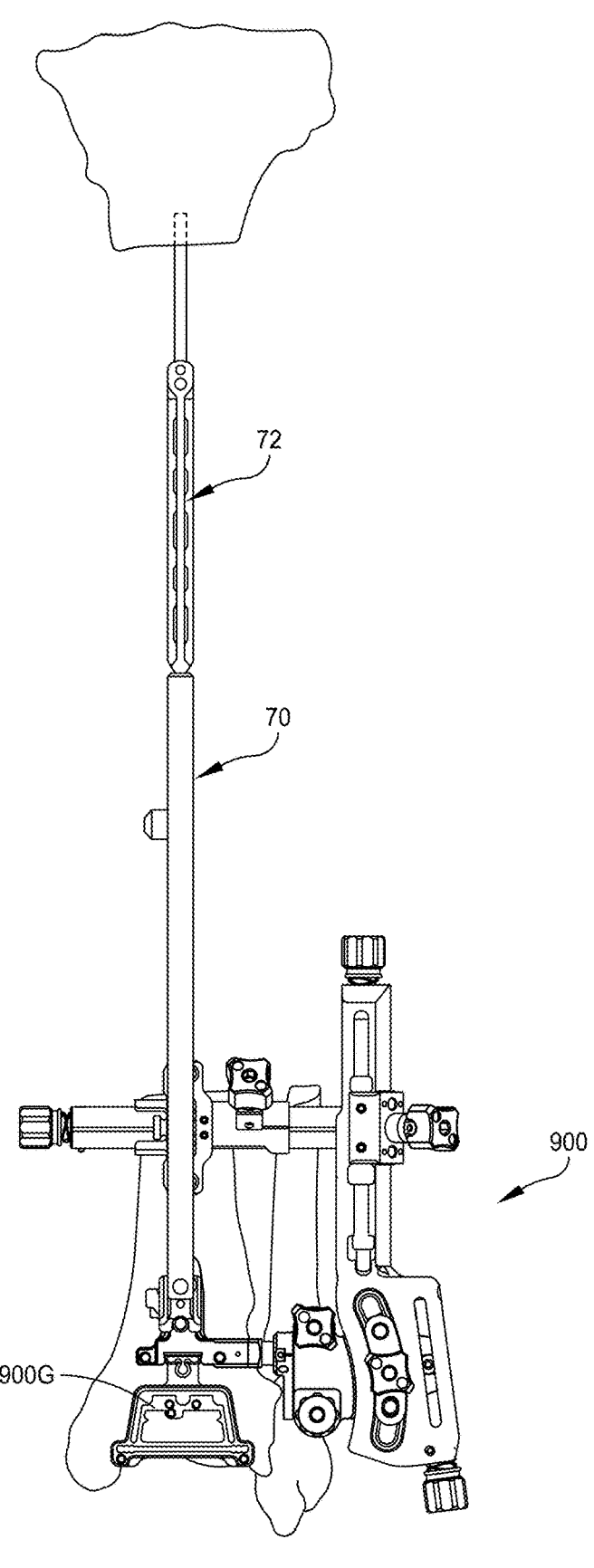
FIGS. 44A-44B are illustrations showing the guiding instrument of FIG. 41A in in-use position with respect to a patient's tibia.
Figure 44B:
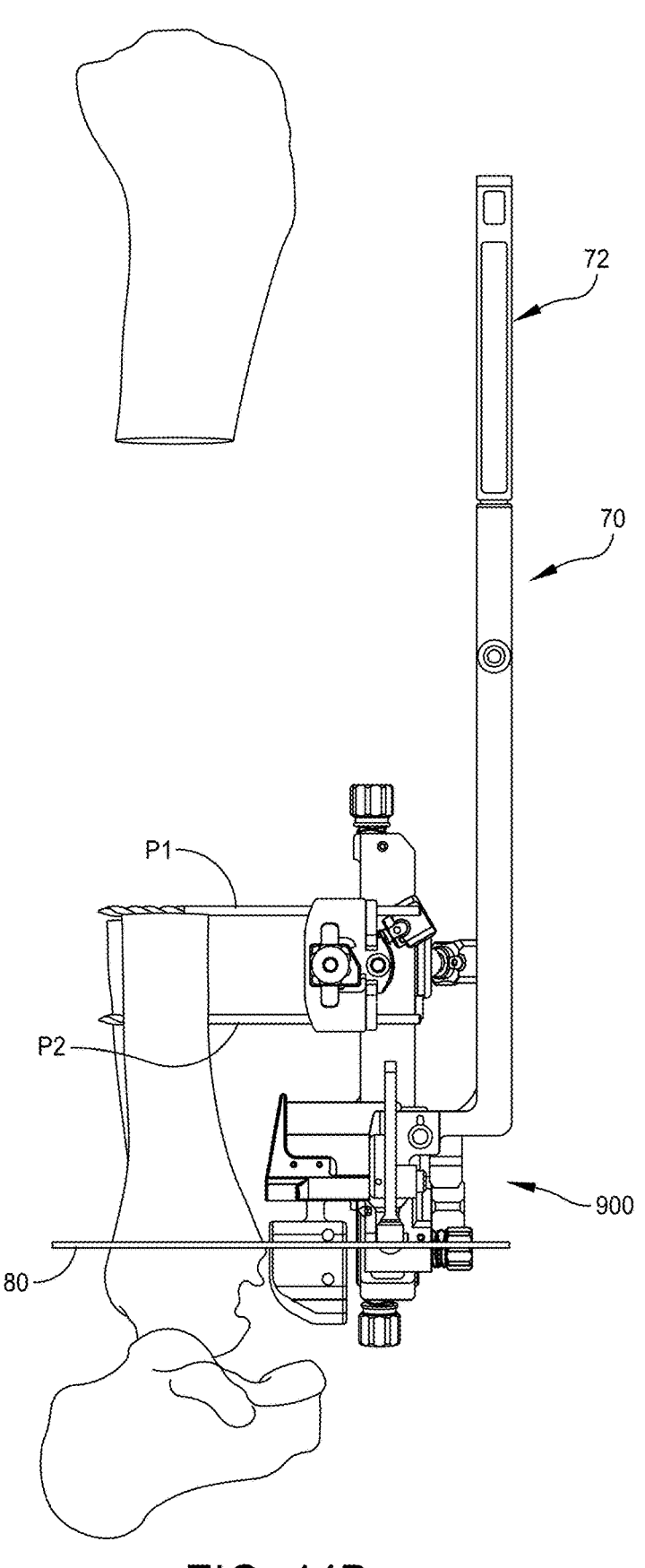

FIG. 44A-44B are illustrations showing the guiding instrument of FIG. 41A in in-use position with respect to a patient's tibia.

[Concept 10]

Figure 45:
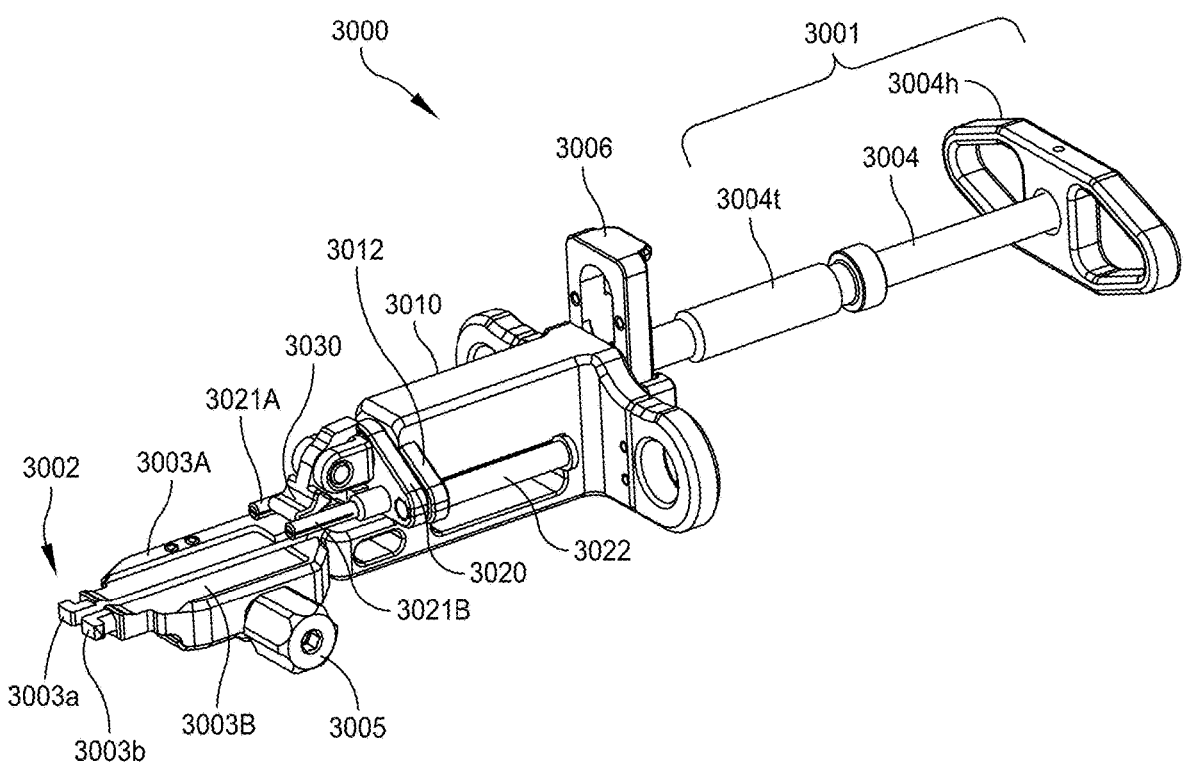
FIG. 45 is an isometric view of an example of a polymer insert implant inserter according to the present disclosure.
Figure 45A:
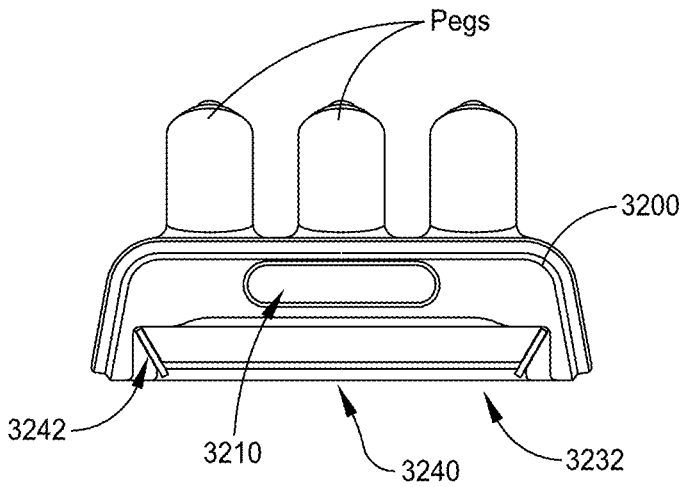
FIG. 45A is an anterior side view of a tibia tray.
Figure 45B:
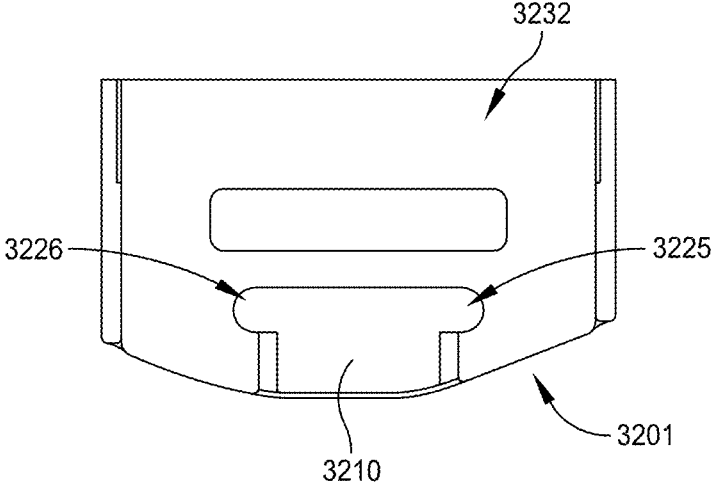
FIG. 45B is an inferior side view of the tibia tray shown in FIG. 45A.
Figure 45C:
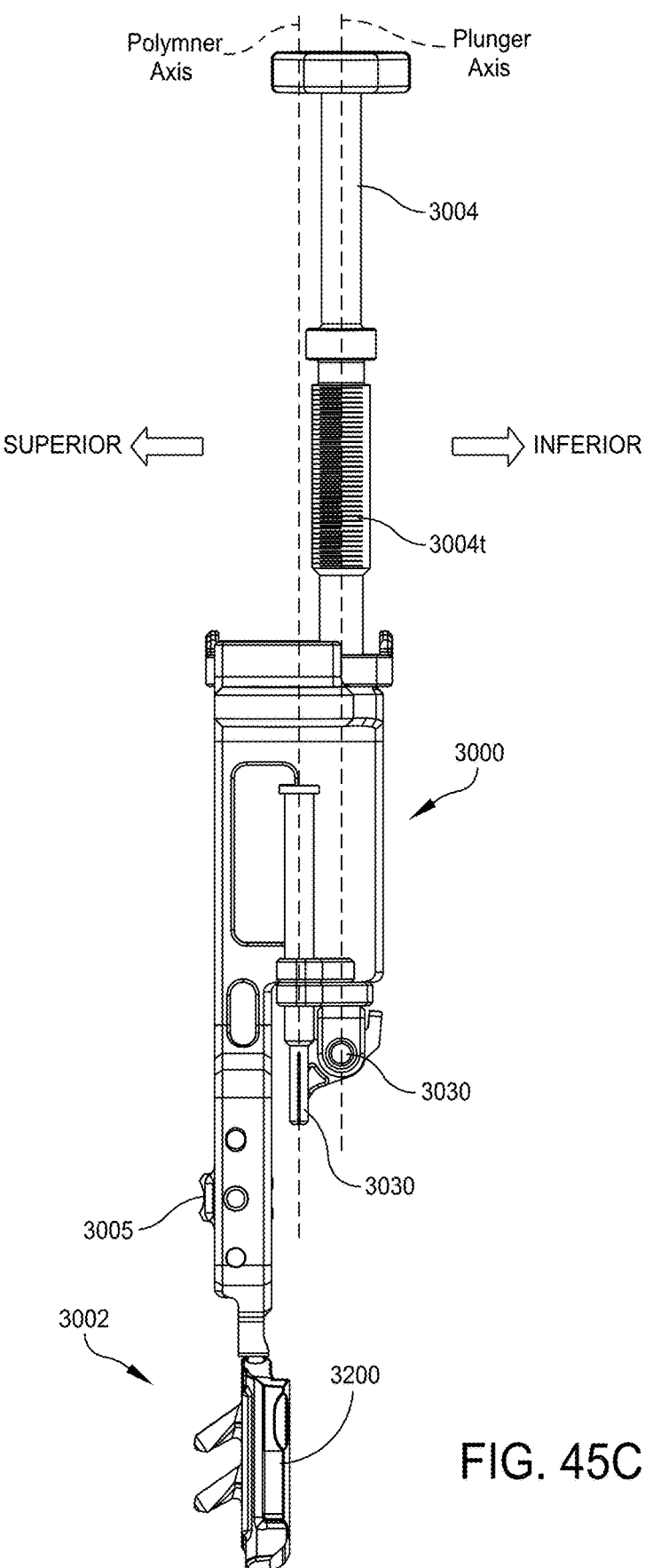
FIG. 45C is a sideview of the polymer insert implant inserter denoting the offset between the longitudinal axis of the pusher and the longitudinal axis of the polymer insert implant.
Figure 45D:
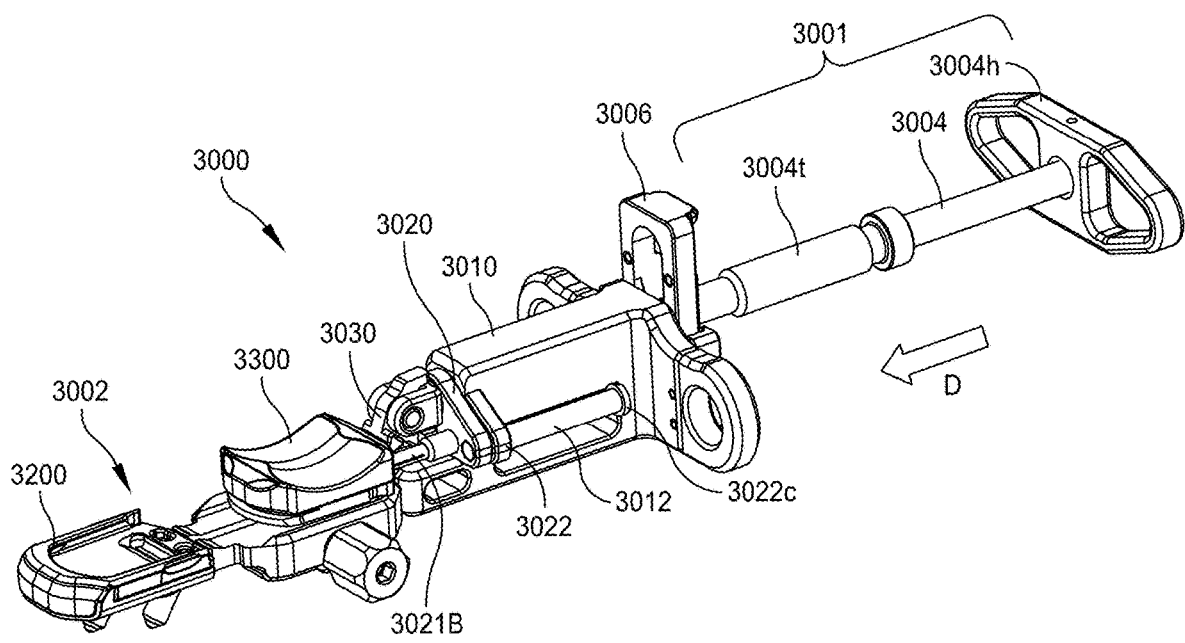
FIGS. 45D-45G are isometric views of the polymer insert implant inserter of FIG. 45 in sequence showing the plunging action of the instrument through the process of inserting a polymer insert implant into a tibia tray.
Figure 45E:
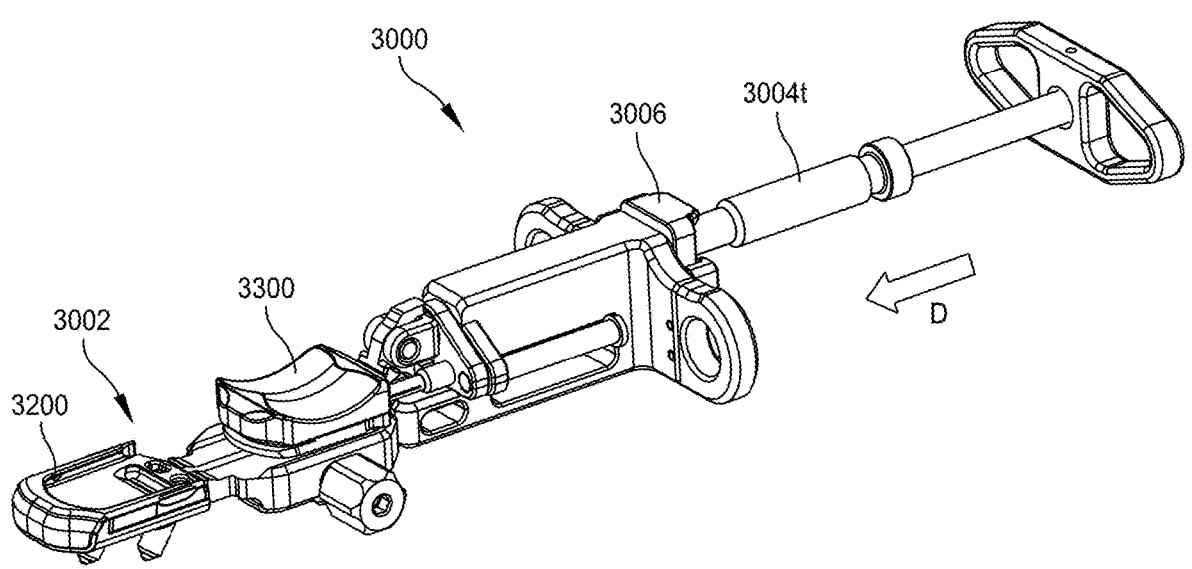
Figure 45F:
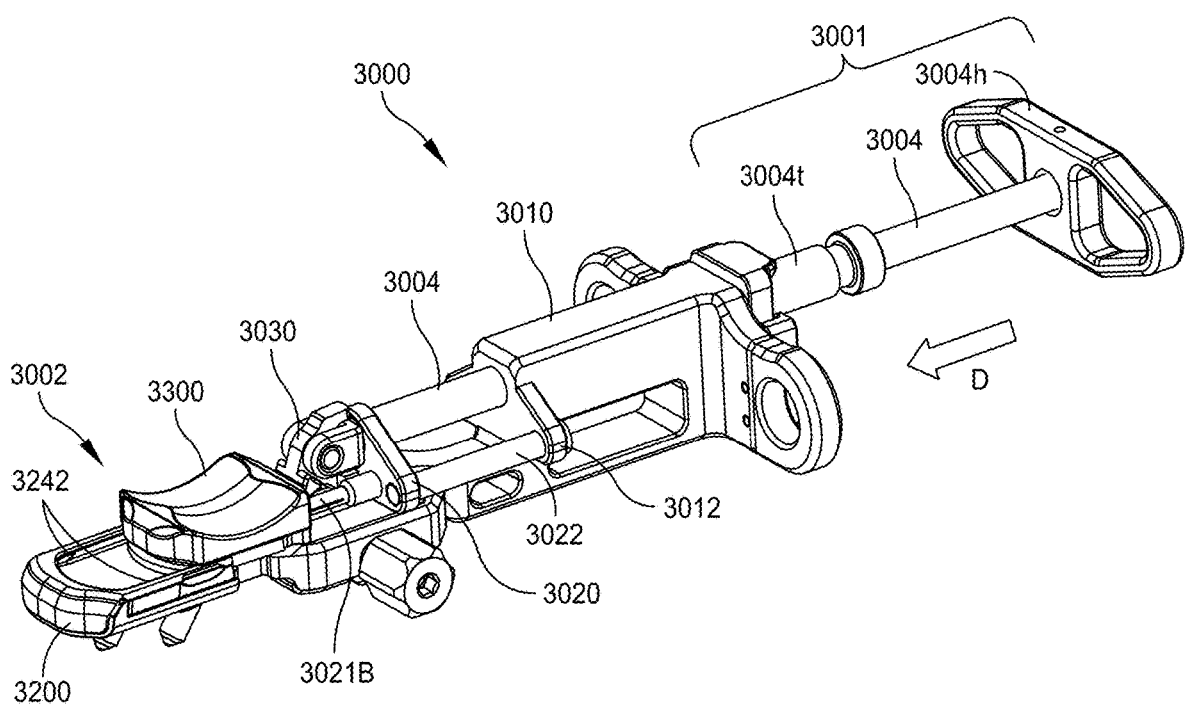
Figure 45G:
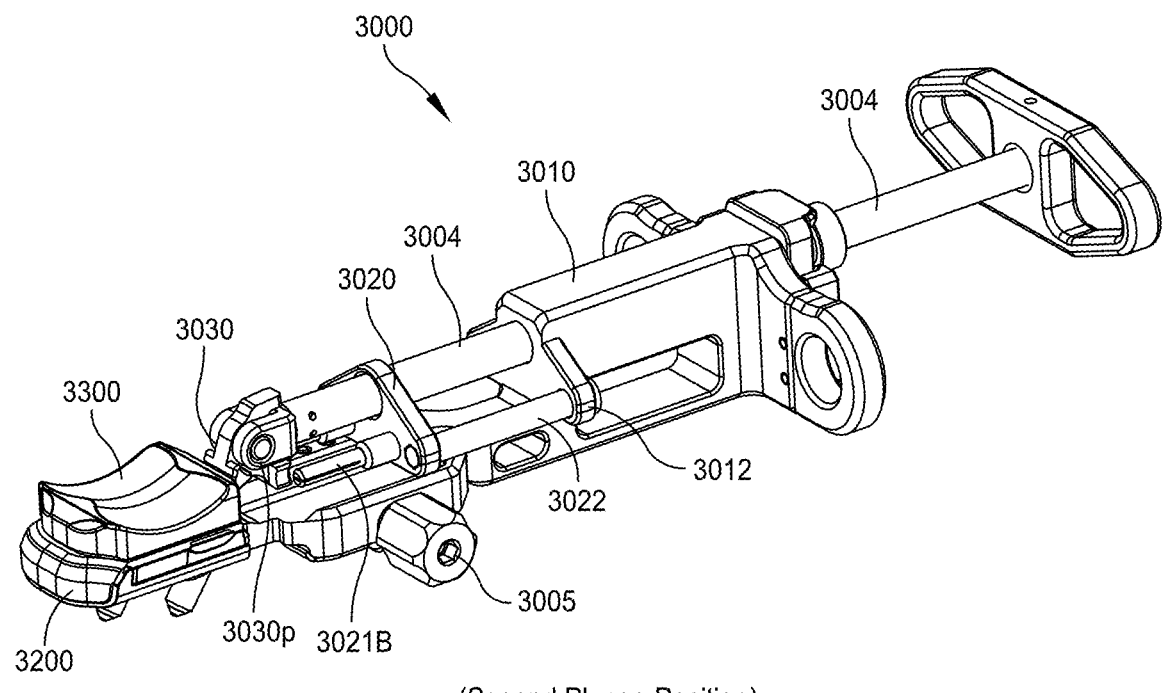
Figure 45H:
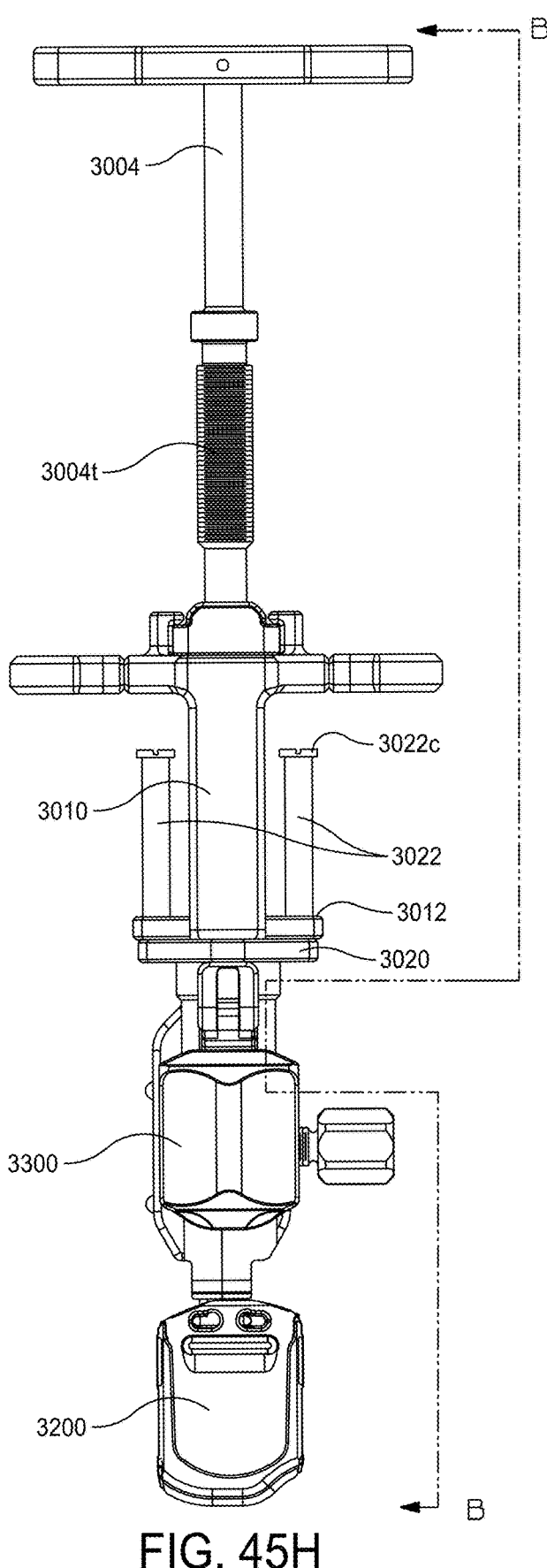
Figure 45I:
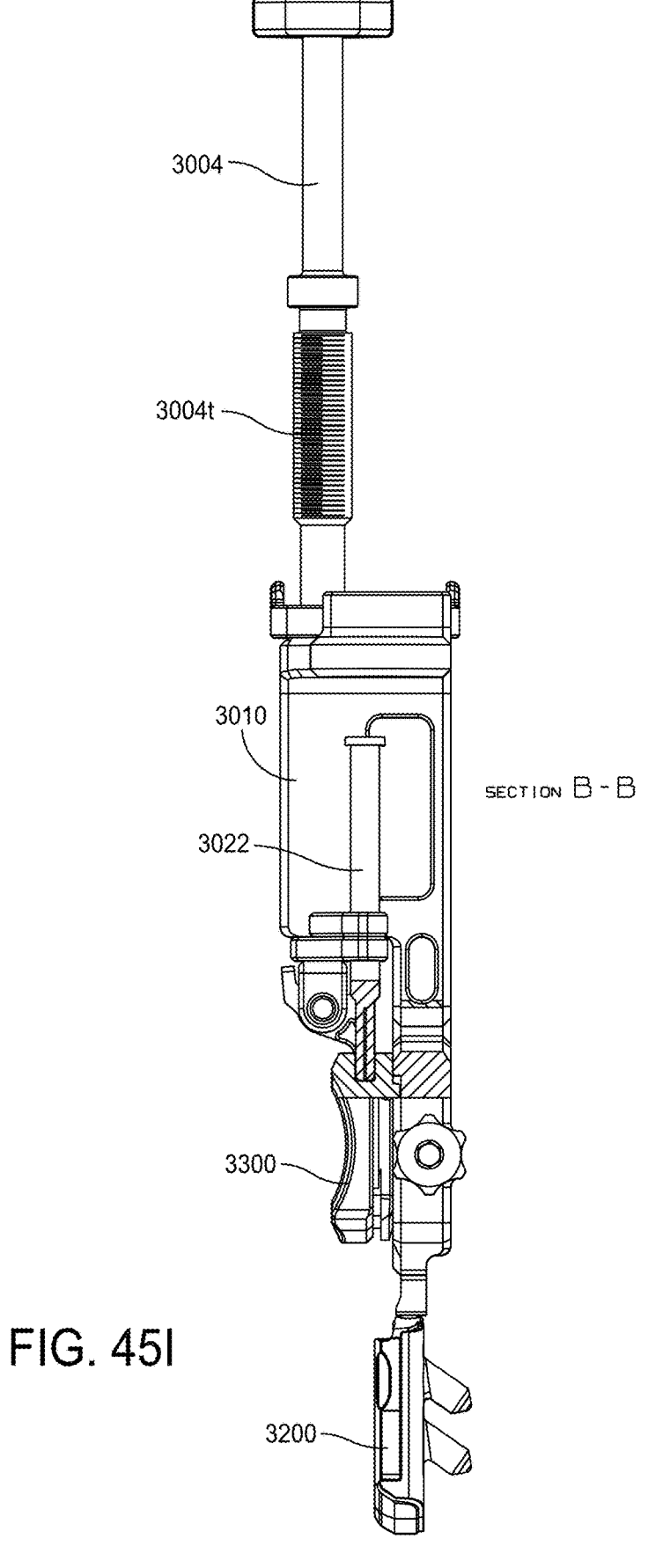
Figures 45K, 45L, 45M, 45N:
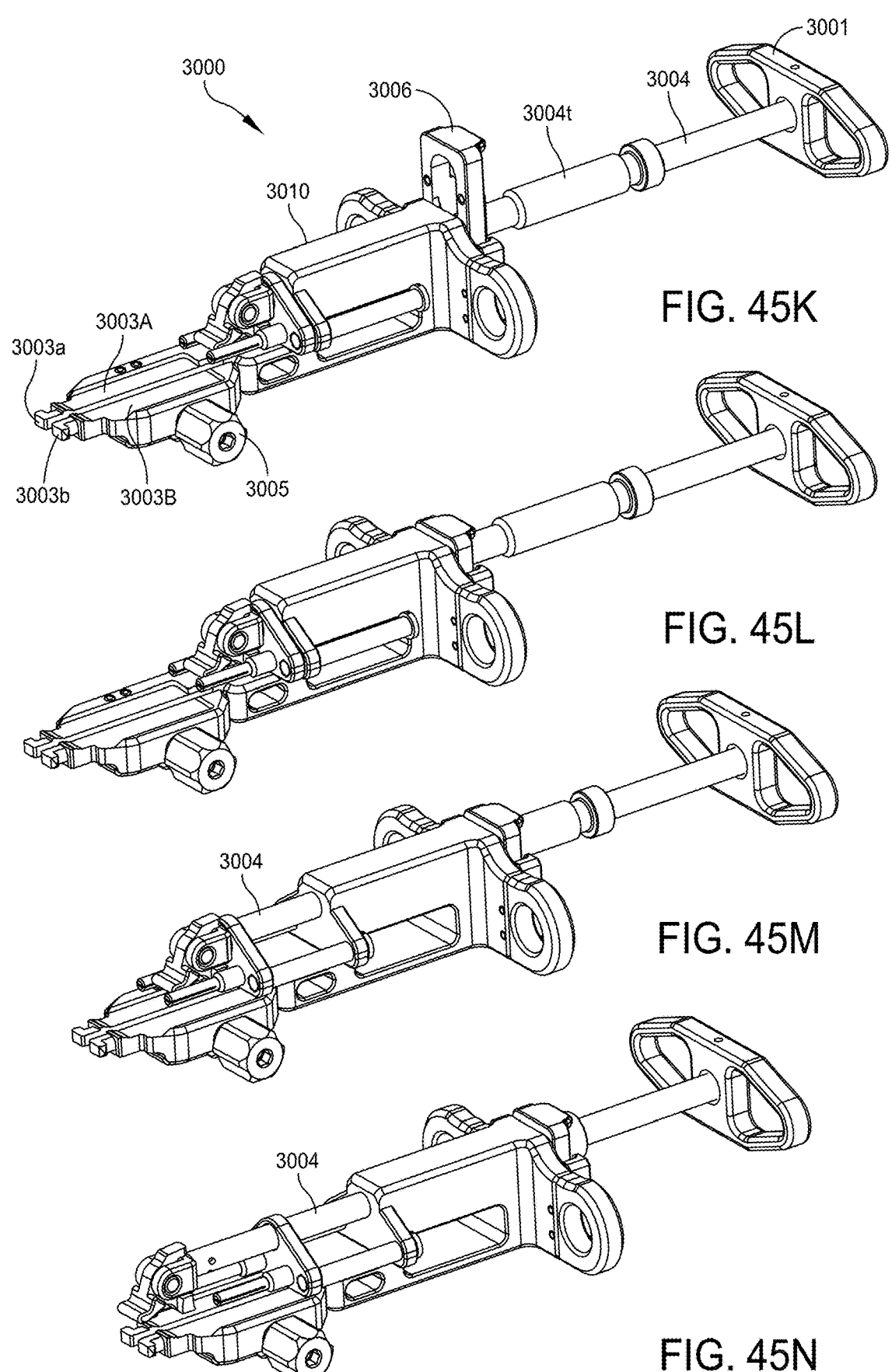
FIGS. 45K-45N are isometric views of the polymer insert implant inserter of FIG. 45 in the same sequence of the plunging action shown in FIGS. 45D-45G but without the polymer insert implant or the tibia tray.
Figure 45O:
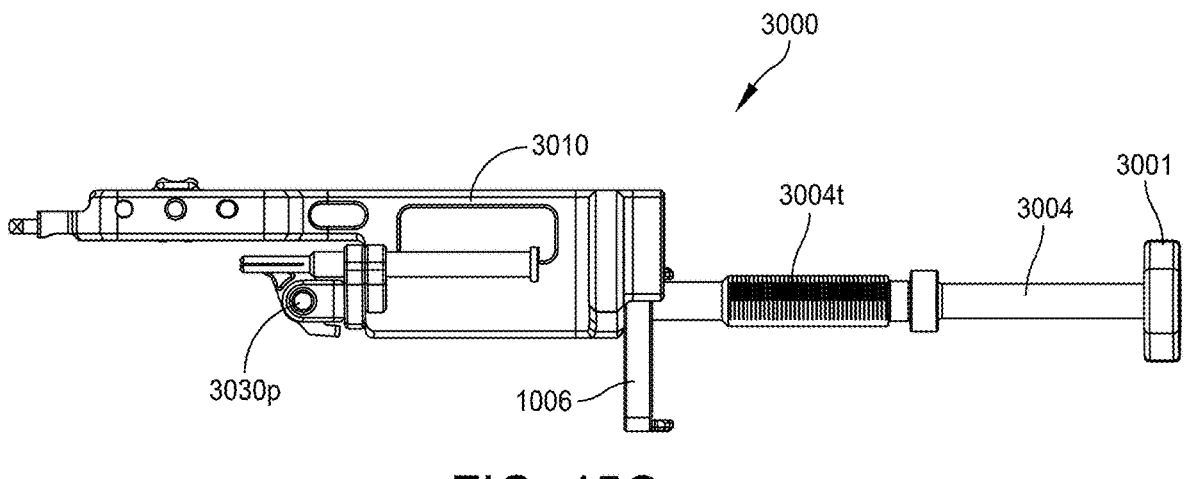
FIGS. 45O-45R are side views of the same sequence shown in FIGS. 45K-45N.
Figure 45P:
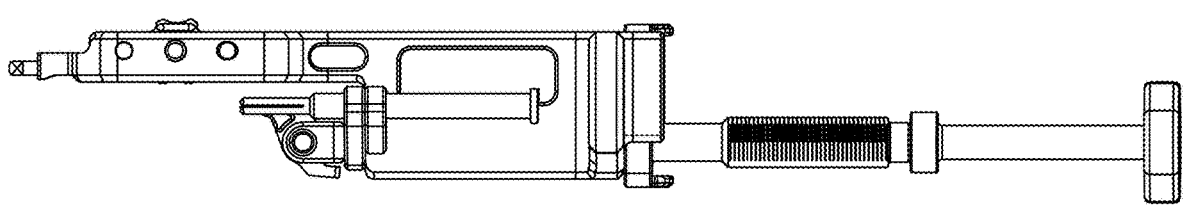
Figure 45Q:
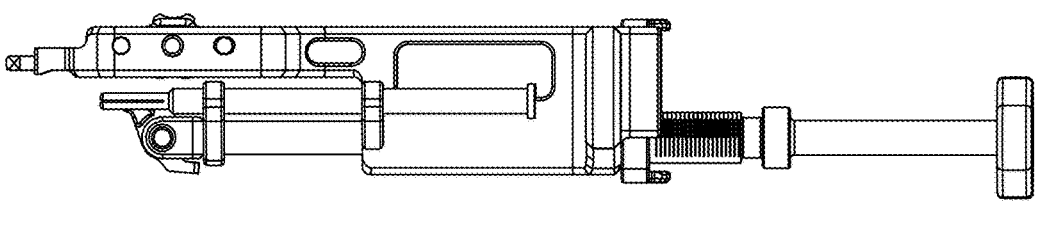
Figure 45R:
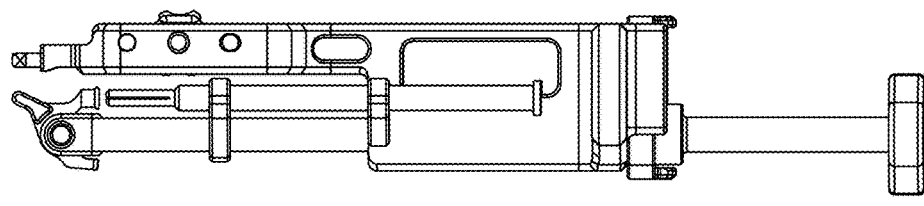

Referring to FIGS. 45-45R, an improved insertion tool 3000 for inserting a polymer insert implant into a tibia tray for an ankle joint prosthesis is disclosed. The insertion tool 3000 is designed to be used in an ankle joint arthroplasty after a tibia tray has been placed in position at the distal end of a prepared tibia to attach a polymer insert implant to the tibia tray.

The insertion tool 3000 comprises a main body 3010, a plunger assembly 3001 at one end and a bifurcated working end 3002 at the opposite end. The bifurcated working end 3002 comprises two jaws 3003A and 3003B that are configured for securely engaging a tibia tray implant. The tips of each of the two jaws 3003A and 3003B are configured with outwardly facing hooks 3003*a*, and 3003*b*, respectively. The two jaws 3003A and 3003B are configured to cooperate with a threaded screw 3005 for opening and closing the two jaws 3003A and 3003B.

The plunger assembly 3001 comprises a plunger shaft 3004, a threaded portion 3004*t* of the plunger shaft 3004, and a plunger handle 3004*h*. The insertion tool 3000 also comprises a polymer insert holder 3020 and a pusher tip 3030.

FIG. 45A shows an anterior end view of a tibia tray 3200 that is part of a surgical kit intended to be used with the insertion tool 3000. FIG. 45B shows an inferior surface 3232 view of the tibia tray 3200 near its anterior end. The tibia tray 3200 is configured with a slot 3210 that opens to the anterior end 3201 of the tibia tray 3200 for receiving the hooks 3003*a* and 3003*b* to form a secure engagement. The slot 3210 is T shaped and has side pockets 3225 and 3226 on the medial and lateral sides of the slot 3210. The side pockets 3225, 3226 receive and engage the hooks 3003*a* and 3003*b* so that when the two jaws 3003A and 3003B are expanded in Medial/Lateral direction the hooks 3003*a* and 3003*b* catch the side pockets 3225, 3226 and prevent the jaws 3003A, 3003B from being pulled out of the slot 3210.

To engage and lock onto the tibia tray 3200, the two jaws 3003A and 3003B are first closed by turning the screw 3005 in one direction. Then, the hooks 3003*a* and 3003*b* are inserted into the slot 3210 in the tibia tray 3200. Next, the screw 3005 is turned in opposite direction to open and expand the jaws 3003A and 3003B, whereby the outwardly facing hooks 3003*a*, 3003*b* expand and engage two side pockets 3225, 3226 of the slot 3210 so that the hooks hold the tibia tray 3200. FIG. 45C shows a side view of the insertion tool 3000 that has engaged the tibia tray 3200.

Figure 46:
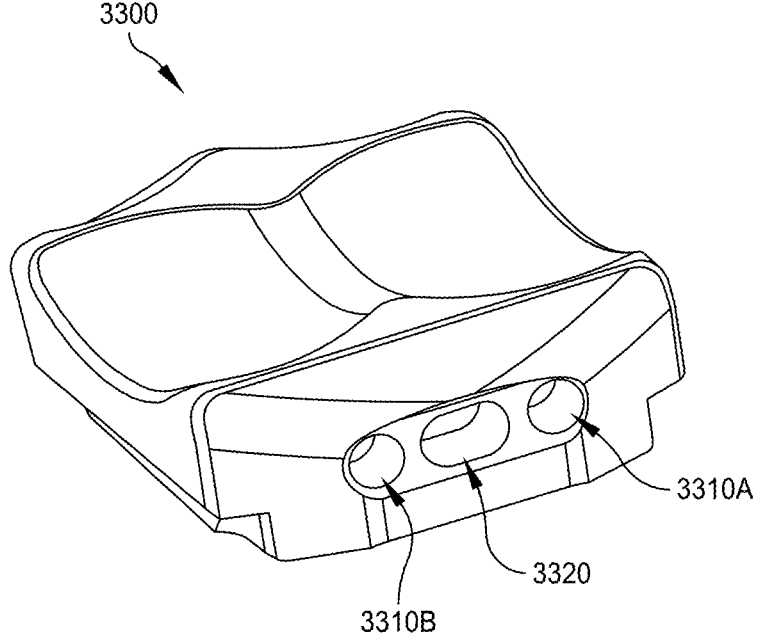
FIG. 46 is an illustration showing an example of a polymer insert implant that can be used with the polymer insertion tool of FIG. 45.

Once the tibia tray 3200 is attached to the end of the polymer insert insertion tool 3000 a polymer insert implant 3300 is positioned in place to be inserted into the tibia tray 3200 as shown in FIG. 45D. To hold the polymer insert implant 3300 for the insertion procedure, the polymer insert insertion tool 3000 comprises two interference connection pins 3021A, 3021B and the polymer insert implant 3300 has corresponding two blind holes 3310A, 3310B that receives the connection pins 3021A, 3021B to establish interference-fit engagement. An example of the polymer insert implant 3300 is shown in FIG. 46. The connection pins 3021A, 3021B are part of the polymer insert holder 3020 and extend out from the base 3020*b* of the polymer insert holder 3020 in the posterior direction parallel to the longitudinal axis Plunger Axis of the plunger assembly 3001 (See FIG. 45C). The connection pins 3021A, 3021B are designed to be compressible and the corresponding holes are sized such that the connection pins fit tightly. When the polymer insert implant 3300 is pushed onto the connection pins 3021A, 3021B by aligning the two blind holes in the polymer insert implant 3300 to the connection pins 3021A, 3021B get compressed inside the connection pins and they form a snug fit connection but not a permanent connection. Thus, after the polymer insert implant 3300 is fully inserted into the tibia tray 3200, the connection pins 3021A, 3021B can be disengaged from the polymer insert implant 3300 by pulling them out.

FIGS. 45J-A to 45J-C show the structure of the polymer insert holder 3020 connection pins 3021A, 3021B. FIG. 45J-A is a view of the polymer insert holder 3020 looking straight at the base 3020*b* of the polymer insert holder 3020 from the ends of the connection pins 3021A, 3021B. FIG. 45J-B is a cross-section view of the polymer insert holder 3020 taken through the section line A-A shown in FIG. 45J-A. FIG. 45J-C is a cross-section view of the polymer insert holder 3020 taken through the section line B-B shown in FIG. 45J-A. The connection pins 3021A, 3021B each has a slot 3021*s* cut longitudinally into the pins so that the slots

3021*s* are open at the ends of the connection pins 3021A, 3021B. The slots 3021*s* make the connection pins compressible for forming the interference-fit engagement with the polymer insert implant 3300.

The insertion tool 3000 is configured to be able to lock the plunger assembly 3001 in the initial configuration shown in FIG. 45. In the initial configuration, the plunger assembly 3001 is fully retracted and ready to accept the tibia tray 3200 and the polymer insert implant 3300. The locking function can be achieved by a locking slider 3006. In FIG. 45D, the locking slider 3006 is shown in locked configuration, in which the locking slider 3006 is pulled up. When in the locked configuration, the plunger assembly 3001 cannot be pushed in the direction of the arrow D shown in FIG. 45D. Once the polymer insert implant 3300 is attached to the polymer insert holder 3020 as shown in FIG. 45D, the plunger assembly 3001 is unlocked by pushing the locking slider 3006 down. This unlocked configuration is shown in FIG. 45E. Now, the plunger assembly 3001 can be plunged in the direction of the arrow D.

Next, the plunger assembly 3001 is plunged into its first plunge position, which is shown in FIG. 45F. The plunger shaft 3004 extends through the main body 3010 and is connected to the polymer insert holder 3020. The main body 3010 is provided with a through hole sufficiently sized to allow the shaft 3004 to slide in and out of the main body 3010 along the longitudinal axis Plunger Axis of the plunger shaft 3004.

As the plunger assembly 3001 is plunged in the direction of the arrow D, the polymer insert holder 3020 is pushed out in the direction of the arrow D by the plunger shaft 3004 which, in turn, pushes the polymer insert implant 3300 in the direction of the arrow D toward the tibia tray 3200 so that the polymer insert implant 3300 engages the tibia tray 3200.

As shown in FIG. 45A, the tibia tray 3200 comprises a recess 3240 on the inferior side for receiving and engaging the polymer insert implant 3300. The recess 3240 is configured with side rail structures 3242 that enables the tibia tray and the polymer insert implant to slide into the recess 3240 and allow the two components to engage and hold together.

In the first plunge position, just the leading end of the polymer insert implant 3300 has started to engage the side rail structures 3242 of the tibia tray 3200 and the polymer insert implant 3300 is not yet fully inserted and seated in the tibia tray 3200.

The first plunge position is also the furthest point the polymer insert holder 3020 can extend toward the working end 3002 of the insertion tool 3000. This limit on the extent of the first plunge action is accomplished by two motion limiting pins 3022. The motion limiting pins 3022 are connected to the polymer insert holder 3020 and extend backwards toward the plunger handle 3004*h*. The main body 3010 of the insertion tool 3000 comprises two flanges 3012 that extend out laterally from the main body 3010. The flanges 3012 are provided with holes that allow the motion limiting pins 3022 to extend through the flanges 3012. The ends of the motion limiting pins 3022 have capped portions 3022*c* that have larger diameter than the motion limiting pins themselves. The capped portions 3022*c* are too large to fit through the holes in the flanges 3012. Thus, as the plunger shaft 3004 is plunged in the direction of the arrow D, pushing the polymer insert holder 3020 and, in turn, the motion limiting pins 3022 in the direction of the arrow D, this motion will be stopped when the capped portions 3022*c* of the motion limiting pins 3022 reaches the flanges 3012.

Thus the length of the motion limiting pins 3022 determines the maximum length of the travel involved to reach the first plunge position.

At this point, it should be mentioned that the size of the polymer insert implant 3300 will determine how far the plunger shaft 3004 should travel to reach the first plunge position where the polymer insert implant 3300 makes the initial engagement with the tibia tray 3200. The insertion tool 3000 can easily accommodate this by adjusting the length of the motion limiting pins 3022. Alternatively, this adjustment can also be achieved by using different length caps that form the capped portion 3022c of the motion limiting pins 3022.

Next, to fully insert the polymer insert implant 3300 into the tibia tray 3200 and engage the tibia tray 3200, the polymer insert implant 3300 needs to be advanced further into the tibia tray 3200 from the position in the first plunge position. This will be referred to as the second plunge of the insertion tool 3000. At this point, the threaded portion 3004t of the plunger shaft 3004 has reached the main body 3010. The hole in the main body 3010 through which the plunger shaft 3004 extends is configured with appropriate threads to engage the threads on the threaded portion 3004t. Because of this threaded arrangement, by turning the plunger shaft 3004 the threaded portion 3004t will engage the threads in the main body 3010 and the plunger shaft 3004 will advance further in the direction of the arrow D. The plunger shaft 3004 is connected to a plunger handle 3004h which is configured to facilitate turning of the plunger shaft 3004.

Referring to FIGS. 45J-A and 45J-C, the polymer insert holder 3020 is provided with a hole 3020h through which the plunger shaft 3004 extends and is connected to the pusher tip 3030. As the plunger shaft 3004 is advanced further from the first plunge position, the plunger shaft 3004 pushes the pusher tip 3030 in the direction of the arrow D and, in turn, pushes the polymer insert implant 3300 in the same direction. This motion will push the polymer insert implant 3300 away from the polymer insert holder 3020 and disengage from the connection pins 3021A, 3021B. The user continues to turn the plunger shaft 3004 until the polymer insert implant 3300 has fully advanced into and fully seated in the tibia tray 3200. This is the second plunge position illustrated in FIG. 45G. As shown, the polymer insert implant 3300 has now been fully disengaged from the connection pins 3021A, 3021B. The insertion tool 3000 can now be disengaged from the tibia tray 3200 by loosening the two jaws 3003A and 3003B turning the threaded screw 3005 and pull away from the ankle joint space.

FIG. 46 shows an illustration of the polymer insert implant 3300 that shows a recess 1320 that is configured to receive and engage the pusher tip 3030.

FIGS. 45K-45N are isometric view illustrations of the insertion tool 3000 shown in sequence through the plunging actions described above but without the tibia tray 3200 and the polymer insert implant 3300. The sequence illustrated in FIGS. 45K-45N corresponds to the sequence illustrated in FIGS. 45D-45G. FIGS. 45O-45R are side view illustrations of the polymer insert tool 3000 shown in the same sequence as in FIGS. 45K-45N.

One of the beneficial features of the insertion tool 3000 is that the Plunger Axis of the plunger assembly and the longitudinal axis Polymer Axis of the polymer insert implant 3300 are offset. This offset is noted in the side view of the polymer insert implant inserter shown in FIG. 45C. The longitudinal axis Plunger Axis of the plunger is offset from the longitudinal axis Polymer Axis of the polymer insert implant in the inferior direction, in other words, the Plunger Axis is further away from the tibia tray 3200 than the Polymer Axis. This offset makes the pusher tip 3030 to tilt or rotate in the superior direction and push the polymer insert implant 3300 toward the tibia tray 3200 as the polymer insert implant 3300 is pushed into the tibia tray during the second plunger action. This helps form more intimate assembly between the tibia tray 3200 and the polymer insert implant 3300. This rotation or tilting of the pusher tip 3030 is illustrated in FIG. 45R. The pusher tip 3030 pivots about the connection point 3030p where the pusher tip 3030 is connected to the pusher shaft 3004. The pusher tip 3030 is also configured to rotate about the longitudinal axis Plunger Axis of the plunger shaft 3004.

[Concept 11]

Figure 47:
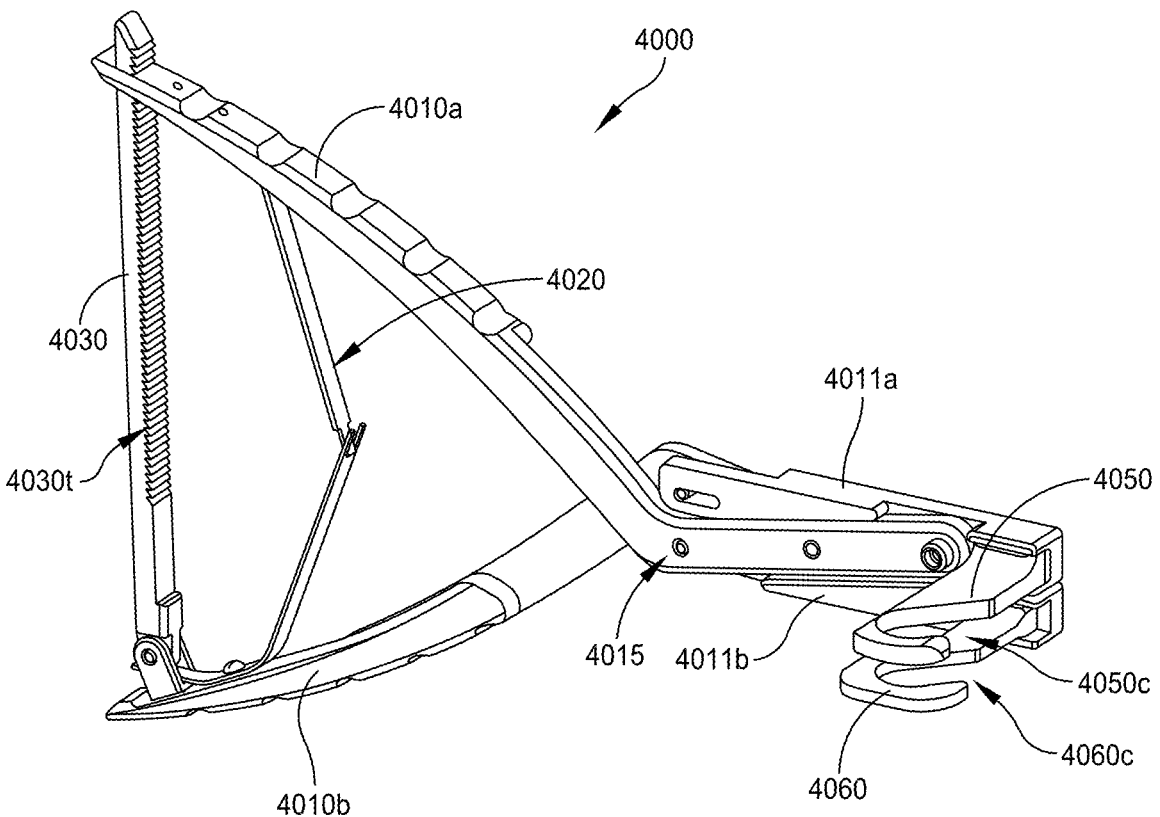
FIG. 47 is an illustration of a new distractor tool.

FIG. 47 shows an example of a new distractor 4000. The distractor 4000 is designed to distract the angle joint and keep the foot in neutral position to aid implantation of a stem construct version of tibia tray. The distractor 4000 comprises two handle pieces 4010a, 4010b that are pivotally joined at a pivot point 4015. Each of the two handle pieces 4010a, 4010b comprises a hand grip end and a working end and the pivot point 4015 joins the two handle pieces 4010a, 4010b between the hand grip end and the working end.

The pivoting joint formed at the pivot point 4015 provides a scissor-like action of the distractor 4000. Each of the working ends of the two handle pieces 4010a, 4010b is provided with a paddle 4050 and 4060, respectively. By operation of the scissor-like action, opening and closing of the hand grip ends of the two handle pieces 4010a, 4010b closes and opens the working ends.

In some embodiments, each of the working ends of the two handle pieces 4010a, 4010b may be provided with working pieces 4011a, 4011b and the paddles 4050 and 4060 attached to the working pieces 4011a, 4011, respectively, the distractor that is on the opposite side of the pivot point 4015.

In use, the distractor can be inserted into the ankle joint space so that one paddle 4050 contacts the tibia and the other paddle 4060 contacts the talus. The tibial paddle 4050 can be provided in multiple sizes and match the size of the tibial resection. The tibial paddle 4050 can also match the shape of the tibial resection. The talar paddle 4060 can also be provided in multiple sizes. Both paddles can be constructed as modular units or they can be permanently attached to the working pieces 4011a, 4011b. Each of the paddles 4050 and 4060 can comprise a cut out 4050c and 4060c, respectively, that provides a clearance space that can accommodate a tibial stem implant that is in the patient's ankle joint space.

In some embodiments, the distractor 4000 can comprise a leaf spring arrangement 4020 that connects the two hand grip ends and keeps the two hand grip ends apart as a resting configuration.

In some embodiments, a releasable ratchet mechanism 4030 can be provided that extends between the two hand grip ends of the two handle pieces 4010a and 4010b. The ratchet mechanism 4030 can hold a desired degree of distraction at the working end of the distractor. The working end of the distractor is the end where the two paddles 4050, 4060 are provided. One end of the ratchet mechanism 4030 can be attached to the hand grip end of one of the two handle pieces (in the illustrated example, the handle piece 4010b), and a second end of the ratchet mechanism 4030 can be provided with a series of ratchet teeth 4030t that cooperate with the hand grip end of the other of the two handle pieces (in the illustrated example, the handle piece 4010a) to hold a desired degree of distraction at the working end of the distractor.

[Concept 12]

Figure 48:
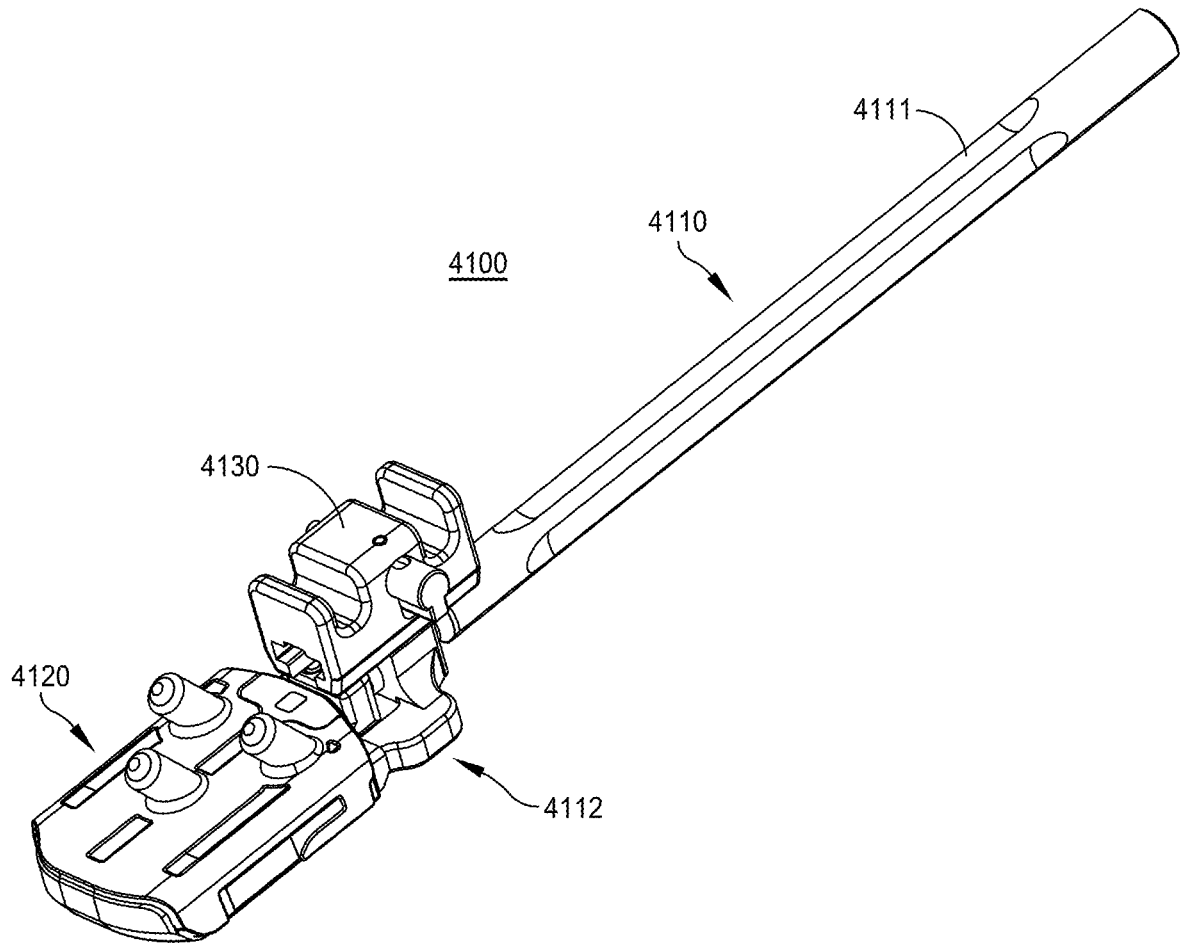
FIG. 48 shows an ankle joint replacement system according to an embodiment of the present disclosure.

Shown in FIG. 48 is an ankle joint implant system 4100 comprising a tibia tray 4120, and an instrument 4110 configured to hold the tibia tray 4120. The instrument 4110 can be useful in an ankle joint arthroplasty procedure for inserting the tibia tray 4120 into a prepared ankle joint space and enabling impacting the tibia tray to the distal end of the patient's tibia. The instrument 4110 is configured to engage the tibia tray 4120 on the bottom surface of the tibia tray 4120 and pinch-hold the tibia tray.

Referring to FIGS. 49A-49E, the tibia tray 4120 comprises a first end 4121 configured to receive the instrument 4110 for holding the tibia tray 4120, a second end 4122, a top surface 4123 configured for engaging a distal end of a tibia bone, and a bottom surface 4124 configured for engaging a bearing component (not shown) of the ankle joint replacement system. The bearing component is generally made of a polymer material and comprises an articulating surface that engages the articulating surface of a talar dome or a talar dome implant when the tibia tray and the bearing component are implanted in a patient.

The bottom surface 4124 of the tibia tray 4120 comprises a distal cavity 4124a that engages the bearing component of the ankle joint replacement system. Referring to the longitudinal cross-section view of the tibia tray 120 in FIG. 49A, the first end 4121 of the tibia tray comprises two orthogonally oriented blind slots 4125A and 4125B that intersect each other. Each of the blind slots 4125A, 4125B has a width and comprises an opening at one end and a blind end at a second end. For example, in the illustrated example of the tibia tray 4120 shown in FIGS. 49A-49E, the first end 4121 is provided with a first blind slot 4125A that has an opening 4125AO that opens to the first end 4121 and a blind end 4125AB at the opposite end of the blind slot 4125A. The first end 4121 is also provided with a second blind slot 4125B that is orthogonally oriented from the first blind slot 4125A. The second blind slot 4125B has an opening 4125BO that opens to the bottom surface 4124 of the tibia tray and a blind end 4125BB at the opposite end of the second blind slot 4125B. This arrangement can be better viewed in the detailed sectional views of the first end 4121 in FIGS. 49D and 49E. As described in more detail below, the second blind slot 4125B enables the locking engagement with the instrument 4110.

The part of the distal cavity 4124a at the first end 4121 of the tibia tray is open. This open end of the distal cavity 4124a functions to slidingly receive the bearing component of the ankle joint when the ankle joint implant is being assembled. This open end of the distal cavity 4124a is utilized for engaging the tibia tray holding instrument 4110 with the tibia tray 4120.

Figure 49A:
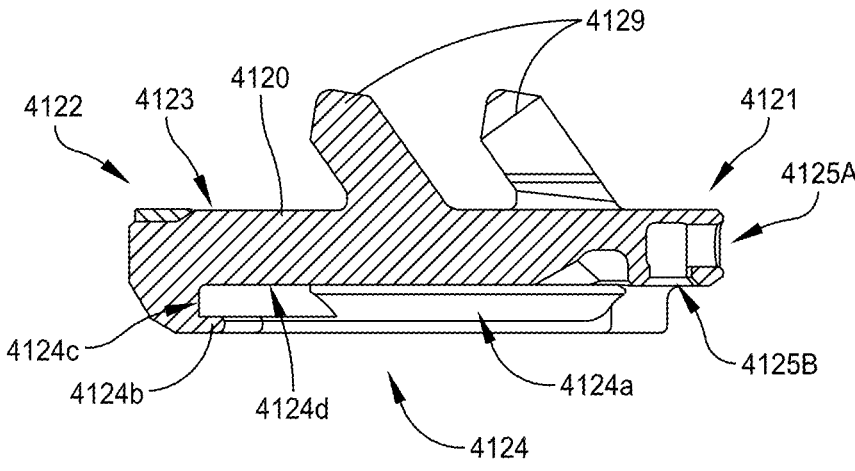
FIG. 49A shows a longitudinal cross-section of a tibia tray according to an embodiment of the present disclosure.
Figure 49B:
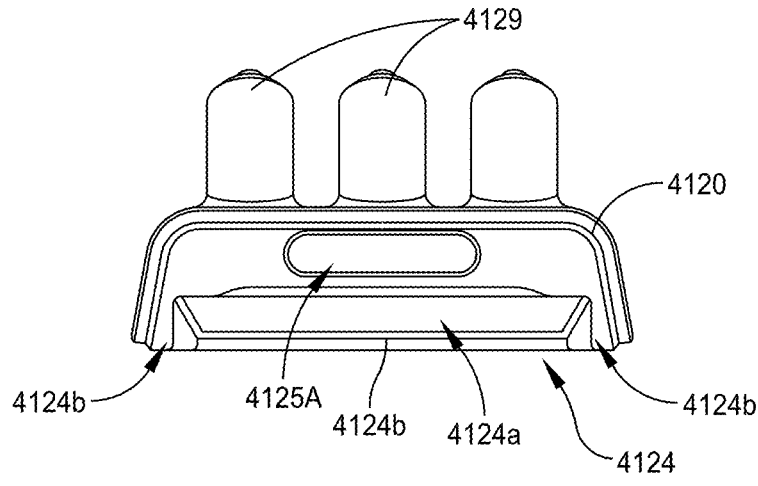
FIG. 49B shows a view from the front end portion of the tibia tray of FIG. 49A.
Figure 49C:
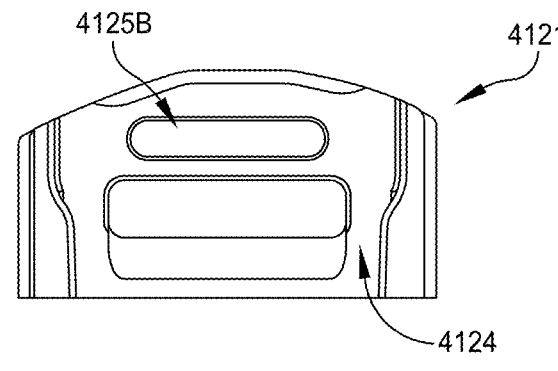
FIG. 49C shows a view from the bottom surface of the front end portion of the tibia tray of FIG. 49A.
Figure 49D:
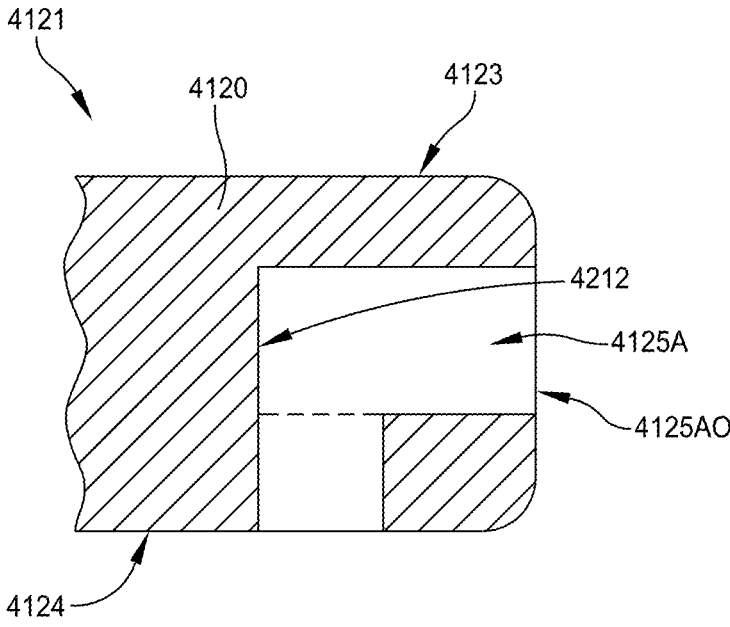
FIGS. 49D-49E show close up views of a partial cross-section of the front end portion of the tibia tray showing the two orthogonally oriented blind slots that cooperate to provide improved attachment of the tibia tray to various surgical instruments.
Figure 49E:
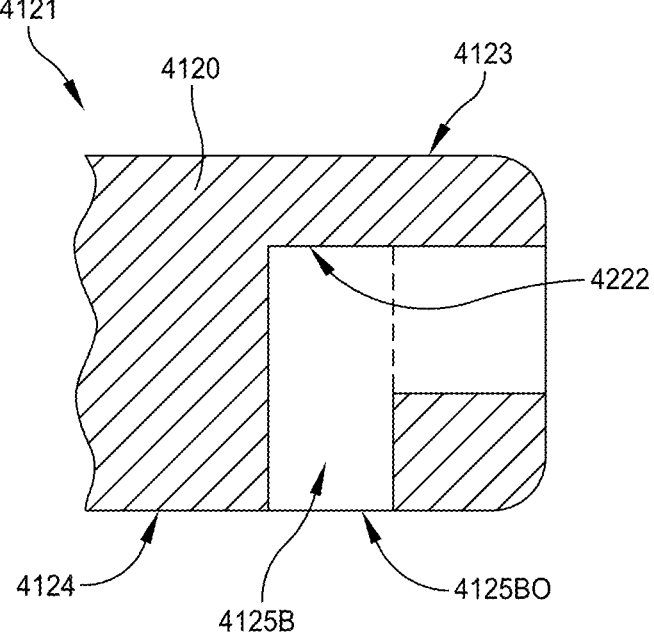

As shown in FIGS. 49A and 49B, the part of the distal cavity 4124a at the second end 4122 of the tibia tray is closed. The closed end of the distal cavity 4124a comprises a second end wall portion 4124c and a ledge 4124b. FIG. 49B is a view of the tibia tray 4120 from the first end 4121 looking into the distal cavity 4124a. The second end wall portion 4124c and the ledge 4124b can be seen at the far end of the distal cavity 4124a. The distal cavity 4124a includes a proximal (or top) surface 4124d that extends from the first end 4121 to the second end wall portion 4124c.

Figures 50A, 50B:
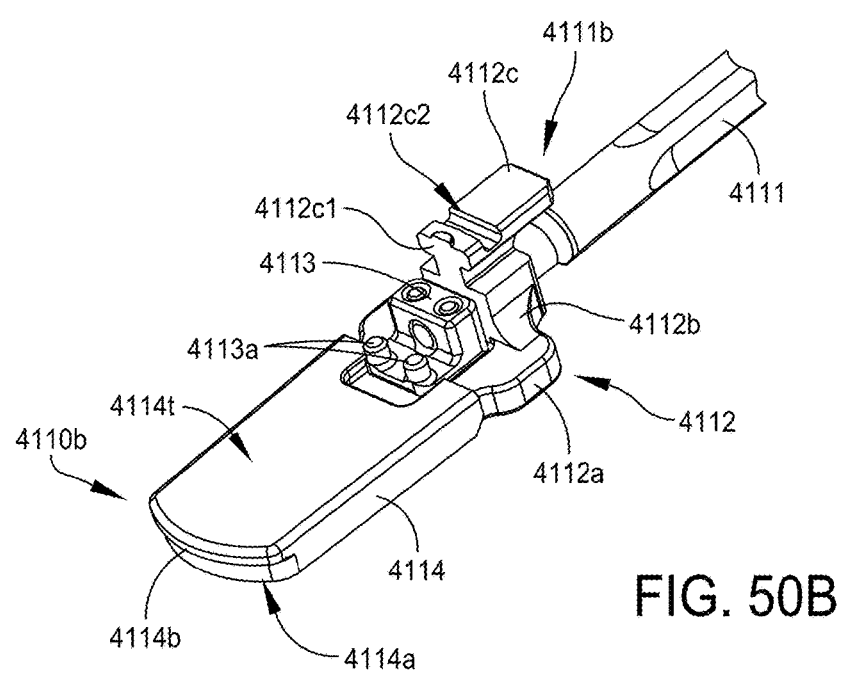
FIG. 50A shows an isometric view of the instrument for holding a tibia tray according to an embodiment of the present disclosure that is in an unlocked configuration.
FIG. 50B shows a detailed view of the working end of the instrument of FIG. 50A in a locked configuration.

Referring to FIGS. 50A-50B, the instrument 4110 has a first end 4110a and a second end 4110b. The instrument 4110 comprises a main body 4112, an elongated handle 4111 that is operatively connected to the main body 4112 and extends toward the first end 4110a, a support plate 4114 for the tibia tray that extends from the main body 4112 toward the second end 4110b, and a tibia tray grabber 4113 that is connected to the elongated handle 4111.

Figure 51A:
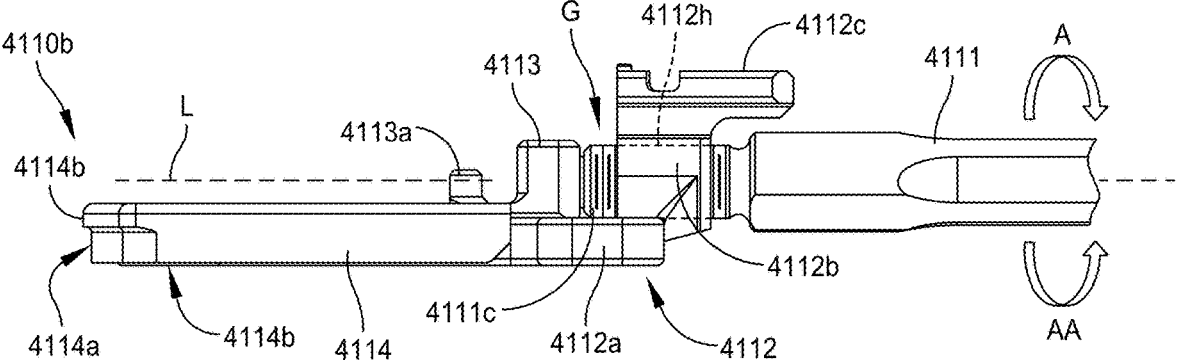
FIG. 51A shows a first configuration of the instrument of FIG. 50A in which the assembly of the handle and the tibia tray grabber is in a first position, which is the unlocked configuration.

The main body 4112 comprises a first portion 4112a that is substantially flat and extends parallel to the longitudinal axis L of the handle 4111. The main body 4112 further comprises a second portion 4112b that extends transverse to the first portion 4112a, which is also transverse to the longitudinal axis L. When viewed from side as shown in FIG. 51A, for example, the first and second portions 4112a, 4112b form a generally L shaped configuration.

Figure 51B:
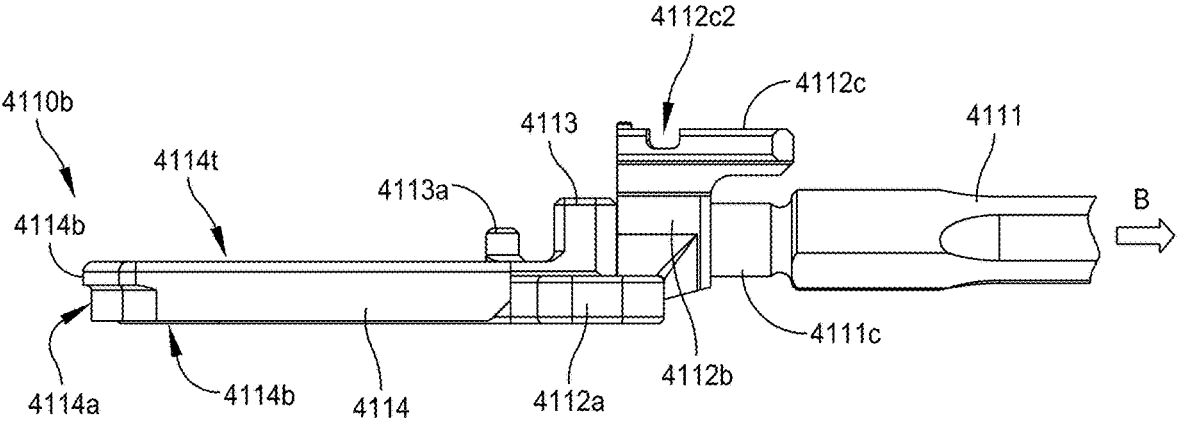
FIG. 51B shows a second configuration of the instrument of FIG. 51A in which the assembly of the handle and the tibia tray grabber is in a second position, which is the locked configuration.

The handle 4111 has a first end 4111a and a second end 4111b, whose direction coincides with the first end 4110a and the second end 4110b of the instrument 4110. The second end 4111b of the handle 4111 is operatively connected to the main body 4112. Referring to FIGS. 51A-51B, in some embodiments, the operative connection is a threaded engagement between the second end 4111b of the handle 4111 and the second portion 4112b of the main body 4112. The second portion 4112b is provided with a threaded hole 4112h extending through the second portion 4112b parallel to the longitudinal axis L. The second end 4111b of the handle 4111 comprises a threaded portion 4111c that is threadedly engaged with and extends through the threaded hole 4112h of the second portion 4112b of the main body 4112. The threaded second end 4111b is configured as a male type screw threaded body that threadedly engage and extend through the threaded hole 4112h in the main body 4112.

The end of the threaded portion 4111c of the handle 4111 is operatively connected to the tibia tray grabber 4113. The connection is configured as a rotatable connection so that the handle 4111 can be turned about the longitudinal axis L with respect to the tibia tray grabber 4113 in either direction as represented by the arrows A and AA in FIG. 51A.

Enabled by the threaded engagement between the handle 4111 and the main body 4112, the handle 4111 can be made to travel linearly along the longitudinal axis L either toward the first end 4110a or the second end 4110b of the instrument 4110 by turning the handle 4111 about the longitudinal axis L. The tibia tray grabber 4113 travels along with the handle 4111 either toward the first end 4110a or the second end 4110b of the instrument 4110 because the tibia tray grabber 4113 is connected to the end of the threaded portion 4111c. As described in more detail below, this linear motion of the tibia tray grabber 4113 enables the instrument 4110 to lock and hold a tibia tray and subsequently unlock and disengage.

The tibia tray grabber 4113 comprises one or more upwardly extending pins 4113a positioned at the tibia tray grabber's 4113 leading end (the end toward the second end 4110b). The upwardly extending pins 4113a are used for engaging the tibia tray 4120 and securely holding the tibia tray.

The particular direction of the linear travel of the handle 4111 associated with the rotational directions noted by the arrow A and arrow AA depends on the handedness of the screw threads provided on the threaded portion 4111c of the handle 4111 and the main body 4112.

FIG. 51A shows a first configuration of the instrument 4110 in which the assembly of the handle 4111 and the tibia tray grabber 4113 is in a first position where the handle 4111 is at its most advanced position toward the second end 4110b of the instrument. This configuration will be referred to as the first position of the tibia tray grabber 4113. In this first position, the handle 4111 has been fully threaded into the main body 4112 and fully advanced toward the second end 4110b of the instrument 4110 so that the tibia tray grabber 4113 and thus the upwardly extending pins 4113a are in their closest position to the second end 4110b. Because the handle

4111 and the tibia tray grabber 4113 are fully advanced toward the second end 4110*b*, there is a gap G between the tibia tray grabber 4113 and the second portion 4112*b* of the main body 4112.

FIG. 51B, on the other hand, shows a second configuration of the instrument 4110 in which the assembly of the handle 4111 and the tibia tray grabber 4113 is in a second position where the handle 4111 is at its most retracted position from the second end 4110*b* of the instrument. This configuration will be referred to as the second position of the tibia tray grabber 4113. In this second position, the handle 4111 has been backed out toward the first end 4110*a* of the instrument 4110 so that the tibia tray grabber 4113 is at its furthest position from the second end 4110*b*. Because the handle 4111 and the tibia tray grabber 4113 are fully retracted toward the first end 4110*a*, the tibia tray grabber 4113 is now backed up against the second portion 4112*b* of the main body 4112 and the gap G has been closed.

As can be seen in FIGS. 51A and 51B, the leading edge 4114*a* of the support plate 4114 at the second end 4110*b* of the instrument 4110 is configured to include a protruding lip 4114*b*.

Figure 51C:
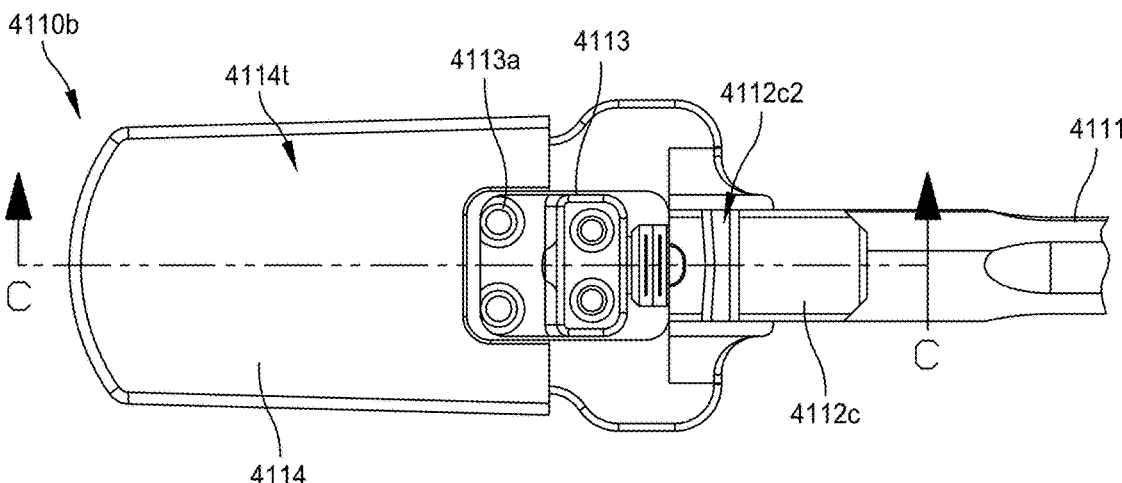
FIG. 51C is a top-down view of the instrument of FIG. 51A.
Figure 51D:
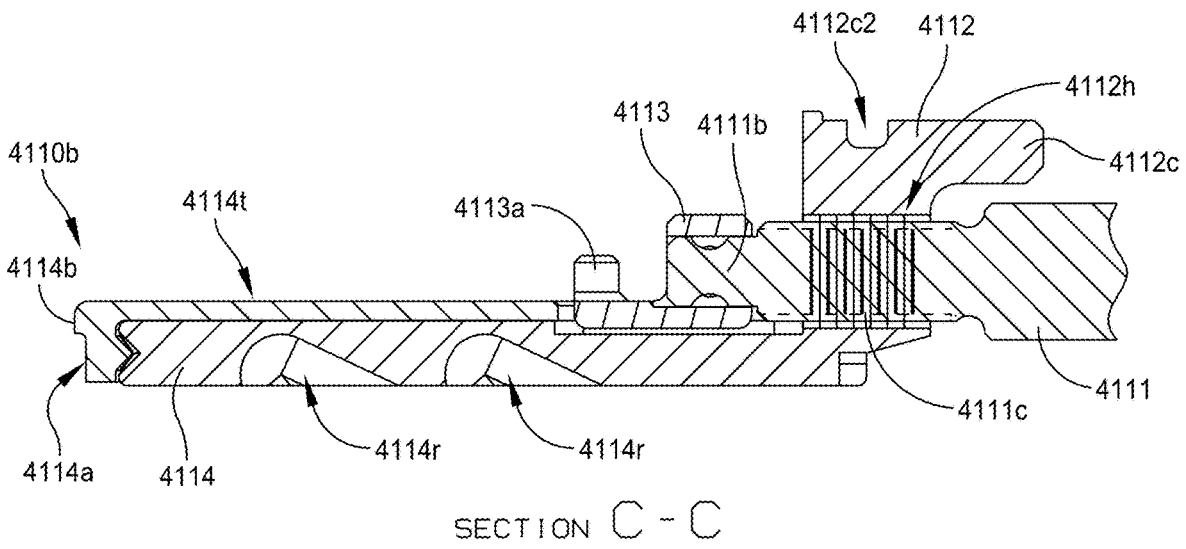
FIG. 51D is a longitudinal cross-section view of the structure shown in FIG. 51C, where the section is taken longitudinally along the section line C-C shown in FIG. 51C.

FIG. 51C is a top-down view of the instrument 4110 looking at the top surface of the support plate 4114. FIG. 51D is a longitudinal cross-section view of the structure of FIG. 51C where the section is taken longitudinally along the section line C-C shown in FIG. 51C.

FIG. 51D shows the threaded engagement between the threaded portion 4111C of the handle 4111 and the threaded hole 4112*h* of the main body 4112. FIG. 51D shows that, in some embodiments, the rotatable connection between the tibia tray grabber 4113 and the handle 4111 can be formed by the end 4111*b* of the handle configured as a spindle that is received in the tibia tray grabber 4113. This configuration allows the handle 4111 to be turned in relation to the tibia tray grabber 4113.

Figure 52A:
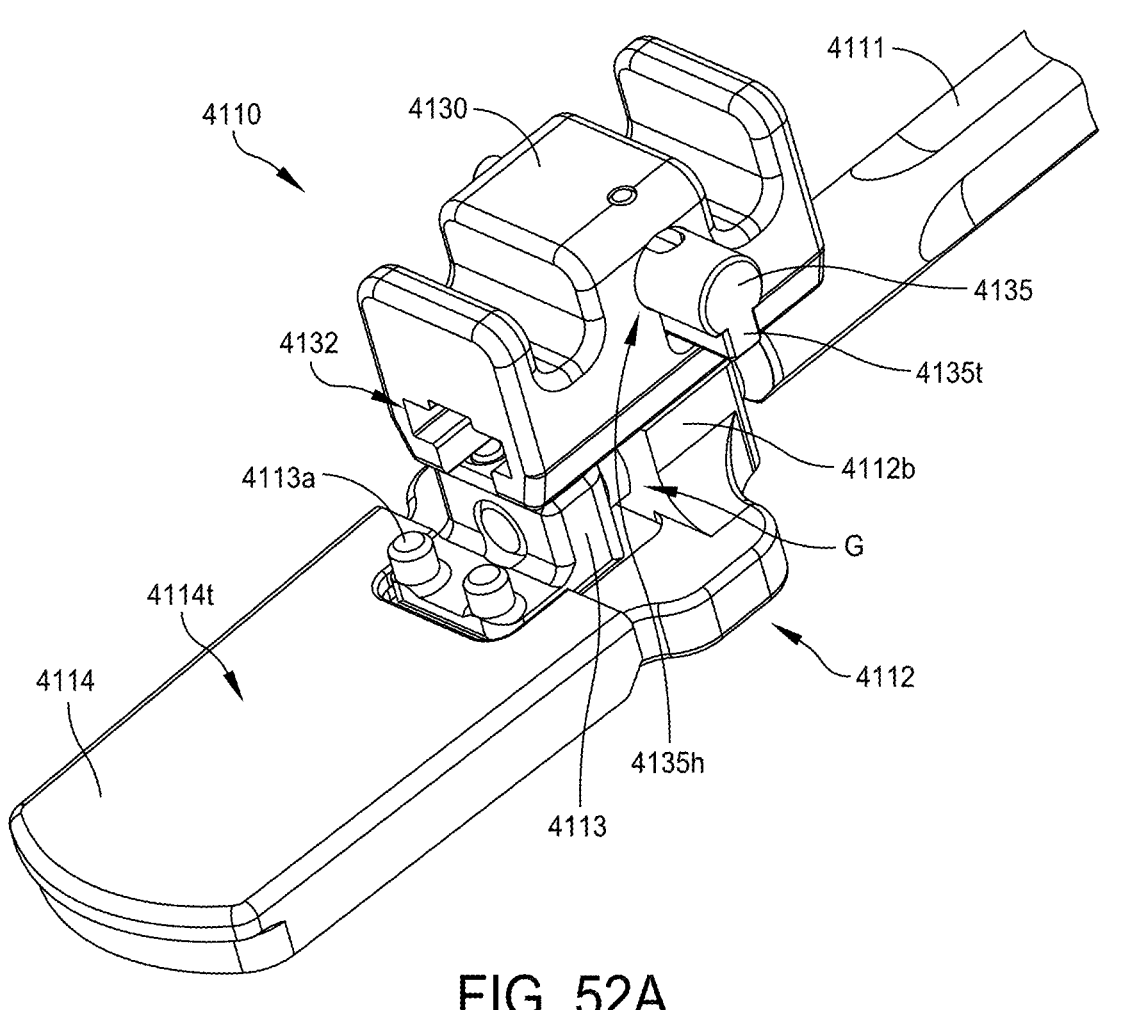
FIG. 52A shows the instrument in the first configuration as in FIG. 51A, but now with a removable depth stop mounted on the main body of the instrument.
Figure 52B:
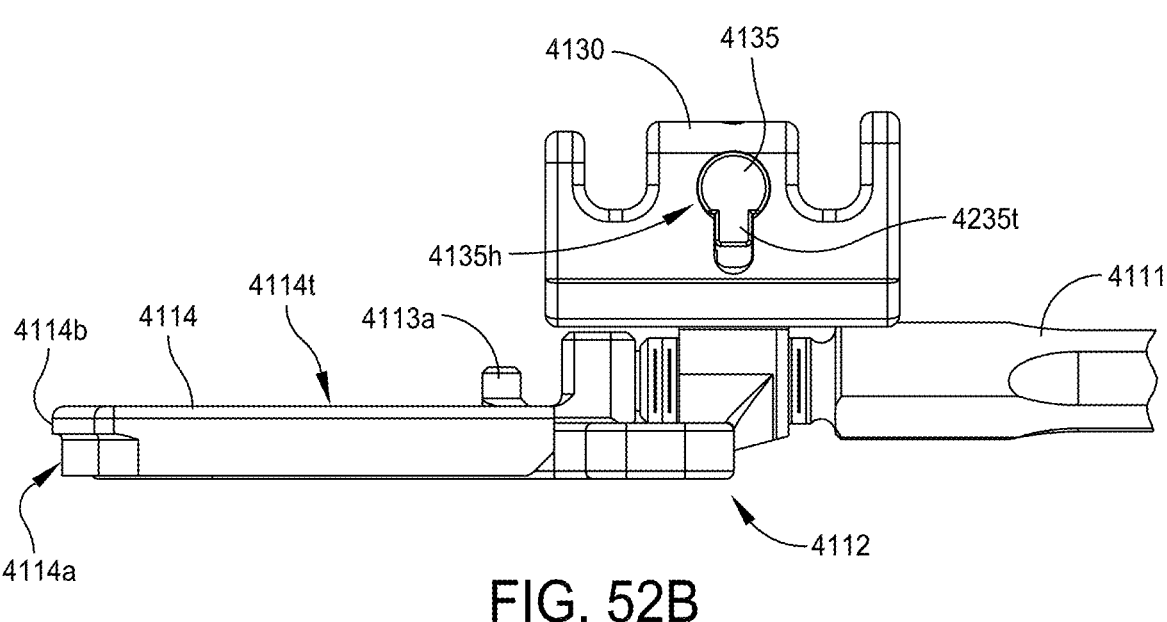
FIG. 52B shows a side view of the instrument shown in FIG. 52A.

FIG. 52A shows the instrument 4110 with a removable depth stop 4130 component mounted on the main body 4112. The top portion of the second portion 4112*b* of the main body 4112 is configured with a structure that forms a tongue and groove type connection with the depth stop 4130. In the illustrated example, the top portion of the second portion 4112*b* of the main body 4112 is configured as a tongue 4112*c* that engages a groove 4132 provided in the depth stop 130. In some embodiments, the tongue 4112*c* has a generally T-shaped cross-section as can be seen in FIGS. 50A and 50B. The groove 4132 on the depth stop 4130 is configured with a complementary shape as shown in FIG. 52A. The tongue 4112*c* extends along a direction that is parallel with the longitudinal axis L. Thus, the depth stop 4130 can be attached to the second portion 4112*b* by sliding over the T-shaped tongue 4112*c*. When necessary, the depth stop 4130 can be removed by sliding it out in reverse direction. In some embodiments, the tongue and groove structures on the depth stop and the main body 4112 can be reversed. The depth stop 4130 is an optional component of the instrument 4110 and the detailed description of its function and use is described below.

In some embodiments, the depth stop 4130 comprises a locking pin 4135, as shown in FIGS. 52A-52D, for locking the depth stop 4130 in place. The tongue 4112*c* of the main body 4112 comprises a transversely oriented slot 4112*c*2 that cooperates with the locking pin 4135 to accomplish the locking. The depth stop 4130 comprises a keyhole 4135*h* that extends transversely (in relation to the longitudinal axis L) through the width of the depth stop 4130. After the depth stop 4130 is slid into place over the tongue 4112*c* and the keyhole 4135*h* is aligned with the slot 4112*c*2, the locking pin 4135 is inserted into a keyhole 4135*h* to slide it into the slot 4112*c*2. This locks the depth stop 4130 in place and prevents the depth stop from traveling in the longitudinal direction. In some embodiments, the locking pin 4135 can be configured to have a tab portion 4135*t* that extends into the transversely oriented slot 4112*c*2 to engage with the slot 4112*c*2.

Figure 53A:
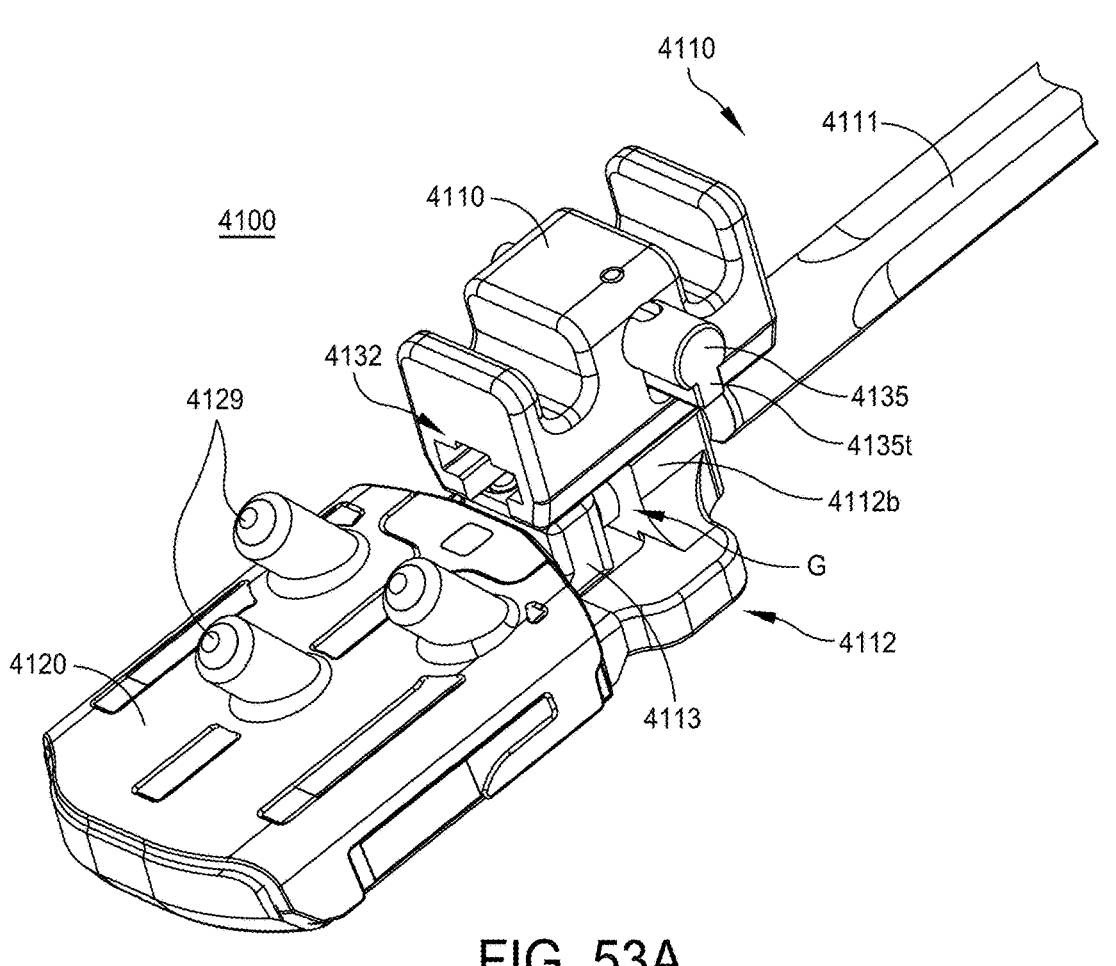
FIG. 53A shows the instrument in the first configuration as in FIG. 52A but now with a tibia tray engaged with the instrument.

As can be seen in FIGS. 52A and 53A, when the locking pin 4135 is seated in place, a portion of the locking pin 4135 can protrude from the keyhole 4135*h*. This protruding portion of the licking pin 4135 can be used as a handle to manipulate the locking pin. For example, the protruding portion can be used to pull the locking pin out when the depth stop 4130 needs to be removed.

Figure 52C:
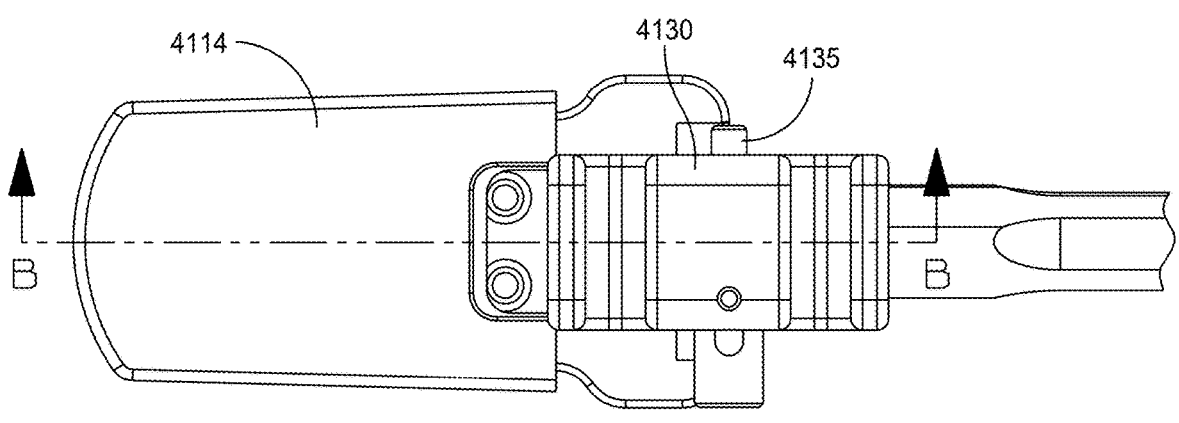
FIG. 52C is a top-down view of the instrument of FIG. 52A.
Figure 52D:
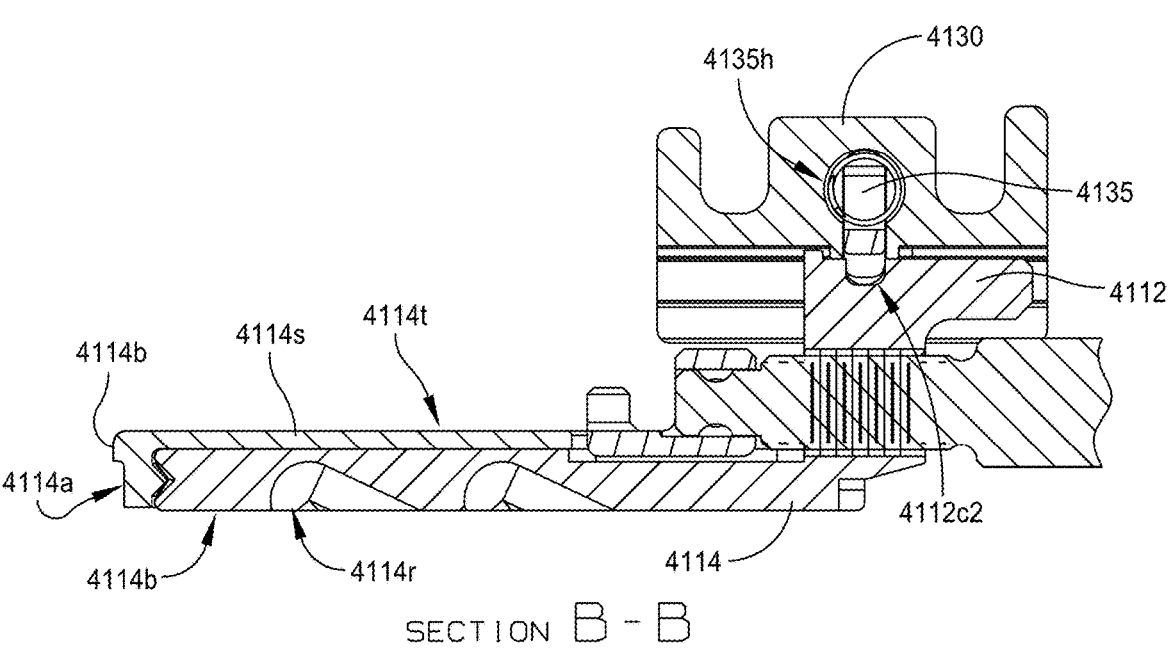
FIG. 52D is a longitudinal cross-section view of the structure shown in FIG. 52C, where the section is taken along the section line B-B shown in FIG. 52C.

FIG. 52C is a top-down view of the instrument 4110, with the depth stop 4130 attached to the main body 4112, looking at the top surface of the support plate 4114. FIG. 52D is a longitudinal cross-section view of the structure of FIG. 52C where the section is taken longitudinally along the section line B-B shown in FIG. 52C. The engagement between the locking pin 4135 and the transversely oriented slot 4112*c*2 can be seen in better detail.

To engage the tibia holding instrument 4110 with a tibia tray 4120, the leading edge 4114*a* of the support plate 4114 at the second end 4110*b* of the instrument is inserted into the distal cavity 4124*a* of the tibia tray 4120 and advanced toward the second end wall portion 4124*c* of the distal cavity 4124*a* until the protruding lip 4114*b* of the leading edge 4114*a* abuts the second end wall portion 4124*c* and be seated between the ledge 4124*b* and the proximal (or top) surface 4124*d* of the distal cavity 4124*a*.

At this point, the ledge 4124*b* holds the second end 4110*b* of the instrument 4110 in place against the tibia tray 4120 so that the instrument 4110 can pivoted about the second end 4110*b* in proximal direction so that the first end 4110*a* of the instrument can be swung proximally (upwardly) toward the first end 4121 of the tibia tray 4120 until the support plate 4114 comes in contact with the proximal surface 4124*d* of the tibia tray into the configuration shown in FIGS. 53A-53D. The support plate 4114 is configured to have a width that is narrow enough to fit within the distal cavity 4124*a*.

Figure 53B:
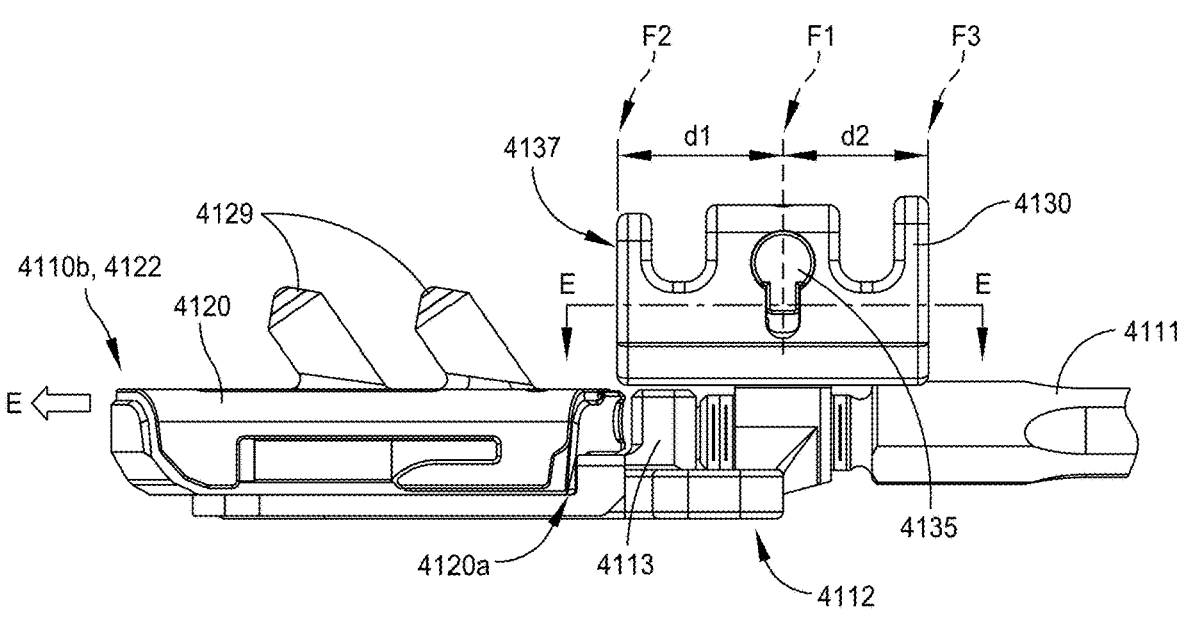
FIG. 53B shows a side view of the assembly shown in FIG. 53A.
Figure 53C:
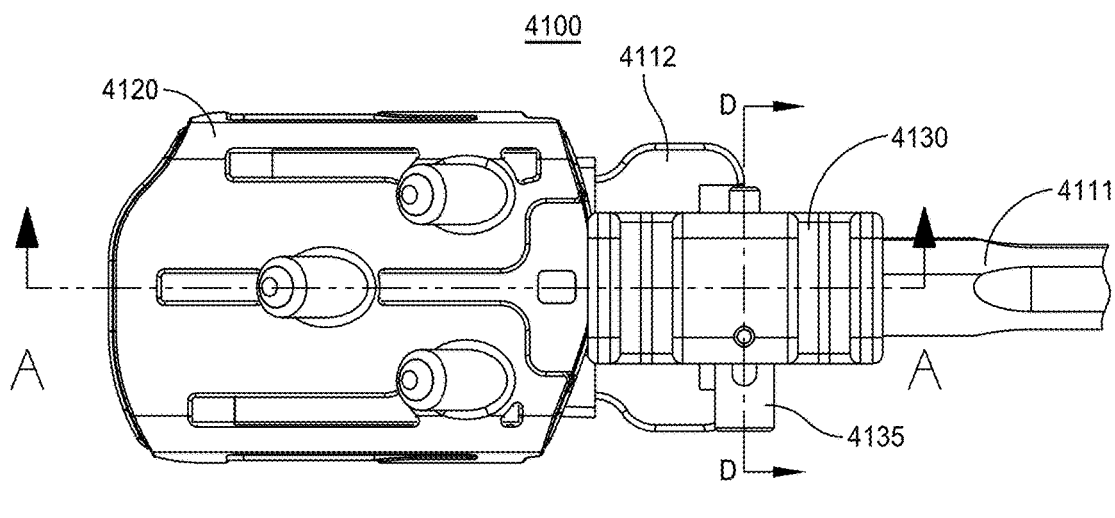
FIG. 53C is a top-down view of the assembly of FIG. 53A.
Figure 53D:
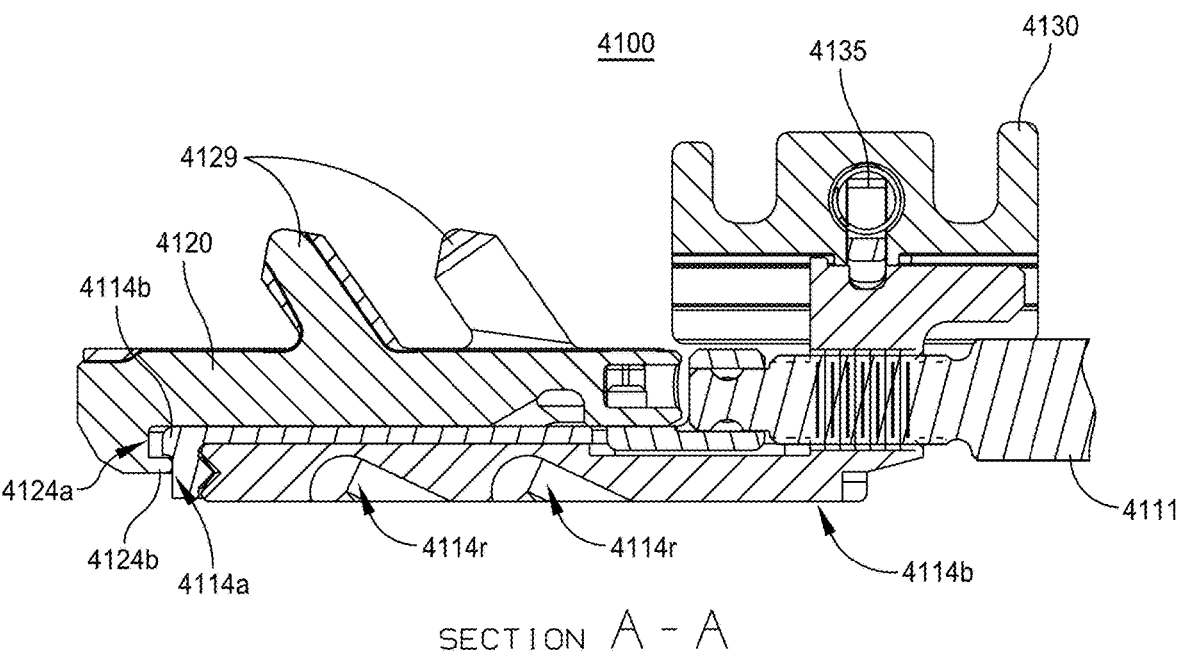
FIG. 53D is a longitudinal cross-section view of the structure shown in FIG. 53C, where the section is taken along the section line A-A shown in FIG. 53C.

As can be better seen in the longitudinal cross-sectional view of the assembly in FIG. 53D, at this point, the tibia tray grabber's 4113 upwardly extending pins 4113*a* are extending through the opening 4125BO and into the second blind slot 4125B. This engagement will be referred to herein as hooking the tibia tray grabber's 4113 upwardly extending pins 4113*a* onto the second blind slot 4125B portion of the tibia tray 4120.

The procedure of pivoting the instrument 4110 described above is conducted with the instrument 4110 in its first configuration so that the tibia tray grabber's 4113 upwardly extending pins 4113*a* align with the opening 4125BO. In the first configuration, the handle 4111 of the instrument 4110 has been advanced toward the second end 4110*b* of the instrument so that the tibia tray grabber 4113 is at its closest distance to the second end 4110*b* of the instrument.

Once the tibia tray grabber's 4113 upwardly extending pins 4113*a* are extending into the second blind slot 4125B, the instrument 4110 can be locked onto the tibia tray 4120 by putting the instrument 4110 into its second configuration. As described above, this is accomplished by turning the handle 4111 in the direction that would allow the threaded engagement between the threaded portion 4111*c* of the handle 4111 and the threaded hole 4112*h* of the main body 4112 to retract the handle 4111 and, in turn, the tibia tray grabber 4113 toward the first end 4110A of the instrument and away from the tibia tray 4120. The handle 4111 is retracted until the upwardly extending pins 4113*a* that are extending into the second blind slot 4125B pull the tibia tray 4120 toward the first end 4110A. Because the second end 4122 of the tibia tray 4120 is essentially hooked over the protruding lip 4114*b* of the leading edge 4114*a* of the support plate 4114, the pull by the tibia tray grabber 4113 places the tibia tray 4120 in tension. By turning the handle 4111 until the tibia grabber 4113 and the tibia tray 4120 are tightly in tension, the instrument 4110 securely holds the tibia tray 4120.

With the tibia tray 4120 securely being held by the instrument 4110, a surgeon can easily manipulate the tibia tray 4120 into the prepared ankle joint space of the patient and implant the tibia tray onto the distal end of the tibia. The securing may involve impacting the bone engaging features on the top surface 4123 of the tibia tray 4120 into the tibia. In the illustrated example embodiment, the tibia tray 4120 comprises one or more bone-engaging pegs 4129 that get embedded into the tibia by impaction. In some embodiments, the support plate 4114 can comprise one or more recesses 4114*r* on the bottom surface 4114*b* for accommodating and facilitating an impaction tool. The one or more recesses 4114*r* can be seen in FIGS. 51D, 52D, and 53D. Because the bone-engaging pegs 4129 are generally oriented so that the pegs lean into the direction in which the tibia tray 4120 is advanced into the ankle joint space as shown, the recesses 4114*r* can be provided to extend into the support plate 4114 at an angle that facilitate application of the impaction force in the direction that is generally similar to the leaning direction of the pegs 4129.

Figure 53E:
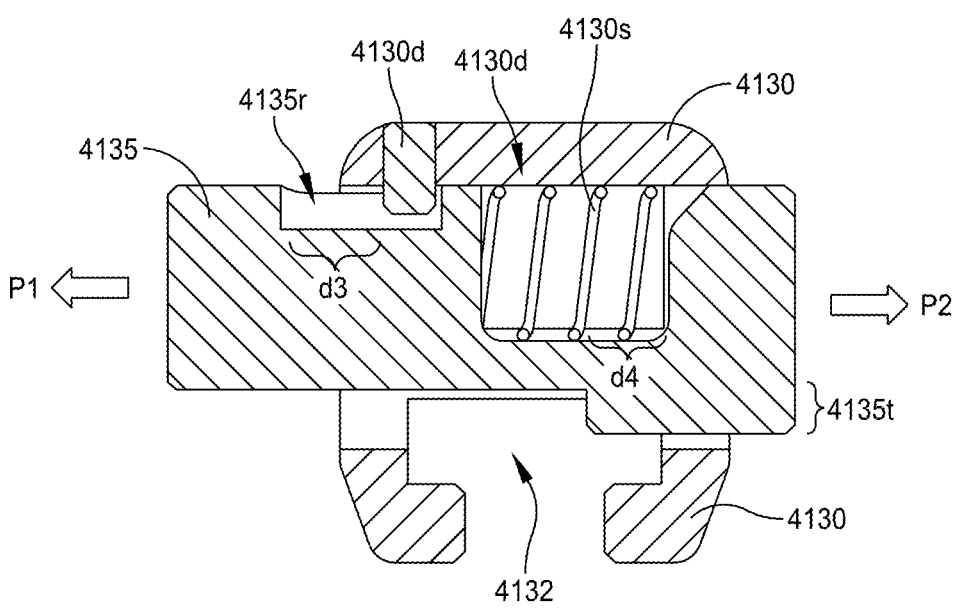
FIG. 53E is a cross-section view of the depth stop where the section is taken along the section line D-D shown in FIG. 53C.

FIG. 53A is a detailed view of the ankle joint replacement system 4100 shown in FIG. 48 where the assembly of the handle 4111 and the tibia tray grabber 4113 is in its first configuration, the unlocked configuration. In the first configuration, the tibia tray grabber 4113 has not yet been pulled back toward the first end 4110*a* of the instrument so the gap G between the tibia tray grabber 4113 and the second portion 4112*b* of the main body 4112 can be seen. FIG. 53B is a side view of the assembly shown in FIG. 53A. FIG. 53D is a top-down view of the ankle joint replacement system 4100 shown in FIG. 53A. FIG. 53E is a longitudinal section view of the ankle joint replacement system 4100 in which the section was taken through the section line A-A in FIG. 53C.

As shown in FIG. 52D, in some embodiments, the support plate 4114 can be formed as an extension of the main body 4112 so that the main body 4112 and the support plate 4114 are different portions of a monolithic structure. In some embodiments, the outer surface of the support plate portion 4114, including the top surface 4114*t* and the leading edge 4114*a* can be formed to be a layer of a material that is more compliant than the bulk portion of the support plate 4114 and the main body 4112. In such example, the bulk portion of the support plate 4114 and the main body 4112 can be made of a surgical grade metal for durability and the layer forming the top surface 4114*t* and the leading edge 4114*a* can be formed of a polymer, for example, that provides more compliant and less abrasive surface for repeatedly contacting the tibia tray which is generally formed of a surgical metal. This prevents metal-to-metal contact, which may be desired in many applications.

Referring to FIGS. 53A-53B, the depth stop 4130 is an optional component of the instrument 4110 that can be used to prevent advancing the tibia tray 4120 too far into the ankle joint space posteriorly during the impaction procedure installing the tibia tray 4120 to the distal end of the patient's tibia. Such undesirable advancement in posterior direction may happen from excessive force from impaction if the depth stop 4130 is not present. Such excessive advancement in posterior direction can result in the pegs on the tibia tray 4120 plowing through the cancellous bone on the resected distal end of the tibia. Therefore, preventing such excessive advancement of the tibia tray is desired. When the depth stop 4130 is installed on the main body 4112 of the instrument, as the tibia tray 4120, held by the instrument 4110, is advanced into the ankle joint space in the direction of the arrow E shown in FIG. 53B, and the pegs 4129 are being driven into the resected distal end of the patient's tibia, the leading surface 4137 of the depth stop 4130 will come into contact with the tibia and prevent further advancement.

In some embodiments, the depth stop 4130 is configured so that the location of the leading surface 4137 with respect to the main body 4112 and the second end 4110*b* can be changed. Because the tibia tray 4120 can be available in two different lengths, the location of the first end 4121 of the tibia tray 4120 with respect to the second portion 4112*b* of the main body 4112 will be different for the different length tibia tray. In other words, when a longer tibia tray 4120 is being used, when the instrument 4110 is engaging the tibia tray 4120, the first end 4121 of the tibia tray extends further toward the first end 4110*a* of the instrument and thus the first end 4121 is closer to the second portion 4112*b* of the main body 4112. Thus, the leading surface 4137 of the depth stop 4130 will need to be set backwards toward the first end 4110*a* of the instrument by equal distance when compared to the location of the leading surface 4137 that is required for a shorter tibia tray. This adjustment of the location of the leading surface 4137 of the depth stop 4130 is accomplished by configuring the depth stop 4130 so that the locking pin 4135 is located off-center in the longitudinal direction in the depth stop 4130.

This is illustrated in FIG. 53B. The position of the locking pin 4135 is marked by the dashed line F1. The end of the depth stop 4130 that is toward the second end 4110*b* of the instrument (also the second end 4122 of the tibia tray 4120) is marked by the line F2. The end of the depth stop 4130 that is toward the first end 4110*a* of the instrument is marked by the line F3. The distance between F1 and F2 is marked as d1. The distance between F1 and F3 is marked as d3. Because the locking pin 4135 is located off-center, d1 is greater than d2. Because of this asymmetric configuration of the depth stop, and the fact that the location of the transversely oriented slot 4112*c*2 on the top surface of the second portion 4112*b* of the main body 4112 is fixed, by removing and reattaching the depth stop 4130 reoriented 180 degrees turned, the leading surface 4137 of the depth stop 4130 can be set back away from the second end 4110*b* by the difference between d1 and d2.

Referring to FIGS. 53A-53B, a benefit of using the instrument 4110 to insert the tibia tray 4120 into the ankle joint space is that the instrument 4110 provides the surgeon a great visibility of the anterior end 4120*a* of the tibia tray 4120. As can be seen in the figures, the main body 4112 has a low profile so that a substantial portion of the anterior end 4120*a* of the tibia tray 4120 is visible from the direction of the handle 4111. This allows the surgeon to better determine whether the tibia tray 4120 is fully seated on the tibia or not when installing the tibia tray 4120 to the distal end of the patient's tibia without disengaging the instrument 4110 from the tibia tray 120.

Figure 53F:
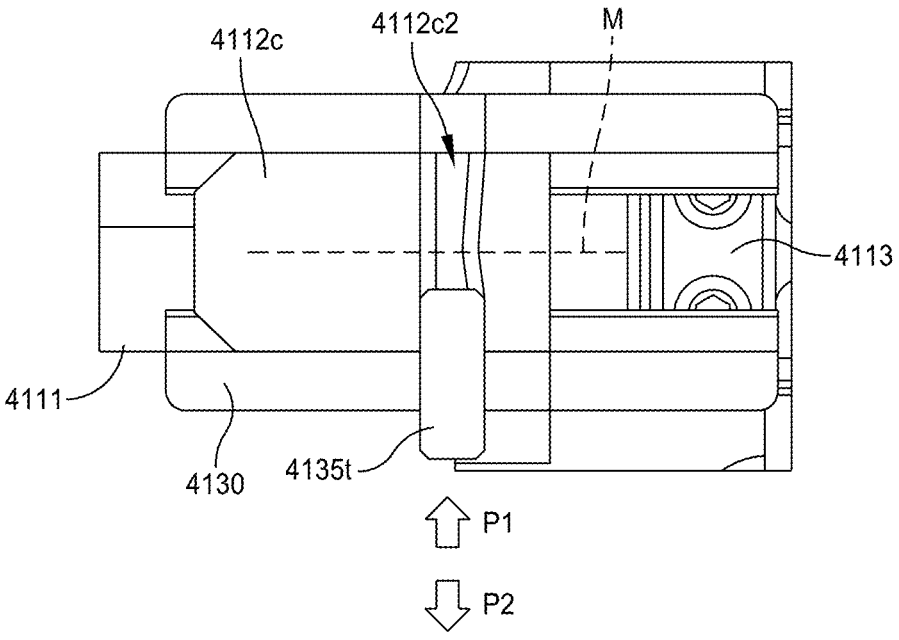
FIG. 53F is a cross-section view of the assembly of the depth stop and the main body, where the section is taken along the section line E-E shown in FIG. 53B.

Referring to FIGS. 53E-53F, in some embodiments, the assembly of the locking pin 4135 and the depth stop 4130 is configures so that the locking pin 4135 is biased to be in its locked position as the default position. FIG. 53E is a sectioned view of the depth stop 4130 taken through the section line D-D shown in FIG. 53C. The section is taken through the length of the locking pin 4135. The locking pin 4135 is spring loaded by a spring 4130s to be biased in the direction noted by the arrow P1 so that the locking pin 4135 is in the position shown in FIG. 53E as the default position. In this position, the spring 4130s has urged the locking pin 4135 in the direction P1 as far as the locking pin can go inside the keyhole 4135h. The amount of travel in the direct P1 is limited by a detent 4130d that cooperates with an elongated recess 4135r provided on the locking pin 4135. The detent 4130d extends downward from the top portion of the depth stop 4130 and extends into the elongated recess 4135r. As shown, with the spring 4130s urging the locking pin 4135 in the direction P1, the end of the recess 4135r that is toward the direction P2 comes in contact against the detent 4130d and stops the locking pin 4135. From this default position, the locking pin 4135 can be pushed in the direction P2 by a distance d3 until the end of the recess 4135r that is toward the direction P1 comes in contact against the detent 4130d.

As shown in FIG. 53E, in the default position, the tab portion 4135t of the locking pin 4135 extends into the groove 4132 of the depth stop 4130 by a distance d4. In some embodiments, the distance d3 is greater than the distance d4 so that the locking pin 4135 can be pushed in the direction P2 by a sufficient distance to completely clear the tab portion 4135t out of the groove 4132.

FIG. 53F shows a sectioned view of the assembly of the depth stop 4130 and the tongue 4112c of the main body 4112, where the section is taken through the section line E-E shown in FIG. 53B. The section plane is just above the tongue 4112c of the main body 4112 and the depth stop 4130 is mounted onto the tongue 4112c and in the locked position. Thus, the spring 4130s is urging the locking pin 4135 in the direction P1 and, thus, the tab portion 4135t of the locking pin 4135 is shown extending in the transverse slot 4112c2. The directions P1 and P2 corresponding to the directions P1 and P2 in FIG. 53E are marked in FIG. 53F also.

When the locking pin 4135 is pushed in the direction P2 sufficiently to clear the distance d4 shown in FIG. 53E, the tab portion 4135t will be disengaged from the slot 4112c2 and the depth stop 4130 can be disengaged from the tongue 4112c of the main body 4112. The depth stop 4130 can be turned 180 degrees to accommodate different length tibia tray and engage the tongue 4112c again. When the depth stop 130 is turned 180 degrees, the tab portion 135t will now engage the slot 4112c2 from the opposite end of the slot 4112c2.

In some embodiments, the transverse slot 4112c2 can be tapered as shown in FIG. 53F. The slot 4112c2 can be tapered so that the two ends of the slot 4112c2 are wider than the width of the slot at the midline M. The taper on the slot 4112c2 that narrows toward the midline M creates an interference fit as the tab portion 4135t of the locking pin 4135 is urged toward the midline by the bias of the spring 4130s. This establishes a secure engagement between the depth stop 4130 and the tongue 4112c of the main body 4112 and prevents any toggling of the assembly.

[Concept 13a]

According to another aspect of the present disclosure, FIGS. 54A-54E show a hand tool 4200 that can be used for assembling the tibia tray 4120 with an articulating insert 4170 together or disassembling the assembly of the tibia tray 4120 and the articulating insert 4170. For assembling the two components together, the hand tool 4200 can be used to compress the articulating insert 4170 together with the tibia tray 4120 to form a snap-fit engagement between the tibia tray and the articulating insert 4170. For disassembling the assembly of the two components, the hand tool 4200 can be used to perform a reverse motion of separating the articulating insert 4170 and the tibia tray 4120 apart and undo the snap-fit engagement.

The articulating insert 4170 provides the articulating surface at the distal end of the tibia. The articulating surface of the insert 4170 operates against the articulating surface of a natural talar dome or an implant talar dome.

The hand tool 4200 has a construction similar to a plier or a scissors and comprises two handle pieces 4201 and 4202 that are pivotally connected by a pivot joint 4250 in a cross-over arrangement.

The first handle piece 4201 comprises a first end 4201a and a second end 4201b. The second handle piece 4202 comprises a first end 4202a and a second end 4202b. The hand tool 4200 operates like a plier and when an operator holds the tool by the first ends 4201a, 4202a and squeeze the two first ends together, the two second ends 4201b and 4202b close toward each other.

The two second ends 4201b, 4202b form the working ends of the hand tool 4200. The second end 4201b of the first handle piece 4201 is configured to engage the anterior end of the articulating insert 4170. The second end 4201b comprises one or more projections 4201c for engaging the anterior end of the articulating insert 4170. In the illustrated example, the anterior end of the articulating insert 4170 is configured with two recesses 4170c (see FIG. 54G), and the second end 4201b of the first handle piece 4201 comprises two projections 4201c for inserting into the two recesses 4170c. The two recesses 4170c are cylindrically shaped recesses and the two projections 4201c are cylindrically shaped projections to match.

The second end 202b of the second handle piece 4202 is configured to engage the anterior end of the tibia tray 4120. The second end 4202b comprises one or more projections 4202c for engaging the anterior end of the tibia tray 4120. In the illustrated example, the anterior end of the tibia tray 4120 is configured with one elongated recess or a slot 4125A (see FIG. 54G), and the second end 4202b of the second handle piece 4202 comprises one projection 4202c for inserting into the recess 4125A. The projection 4202c has a flat tab-like shape to match the shape of the slot 4125A.

Figure 54A:
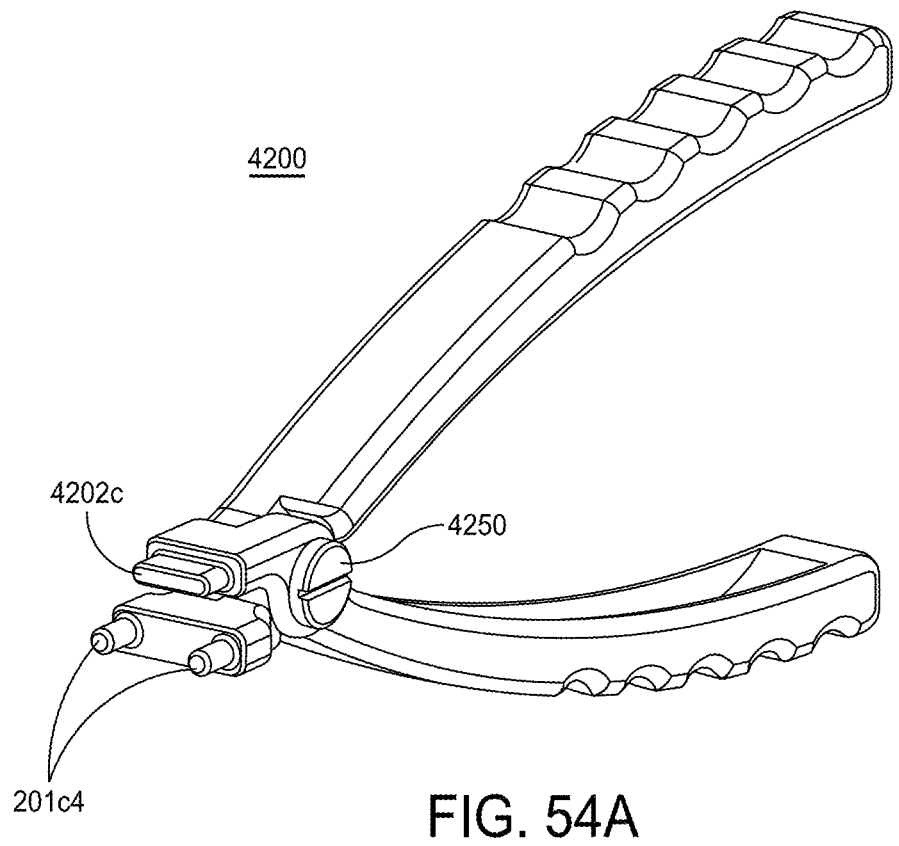
FIG. 54A is an isometric view of a clamping instrument according to the present disclosure.
Figure 54B:
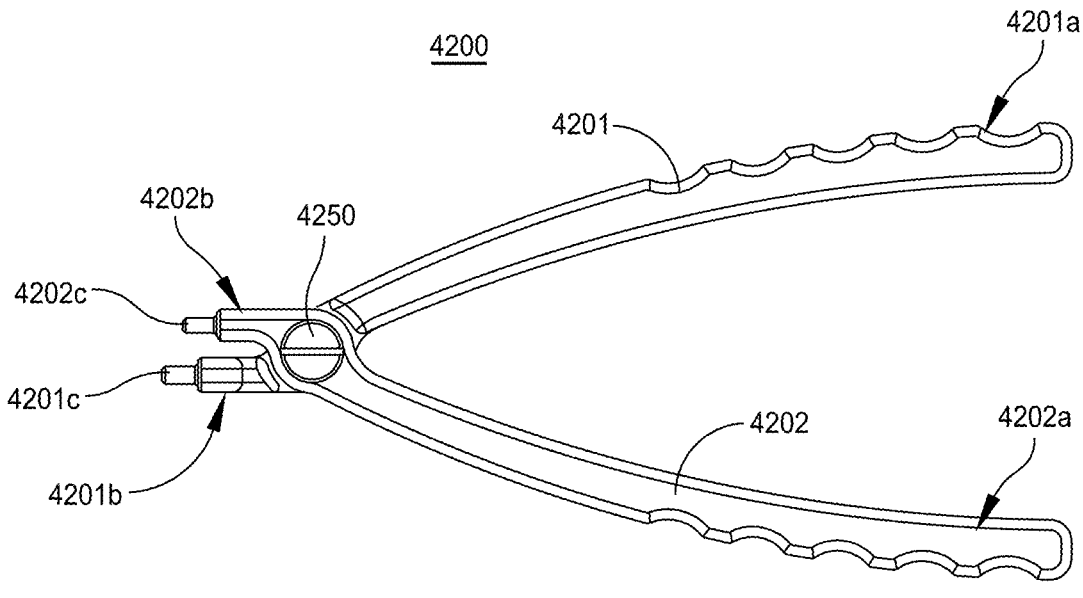
FIG. 54B is a side view of the clamping instrument shown in FIG. 54A.
Figure 54F:
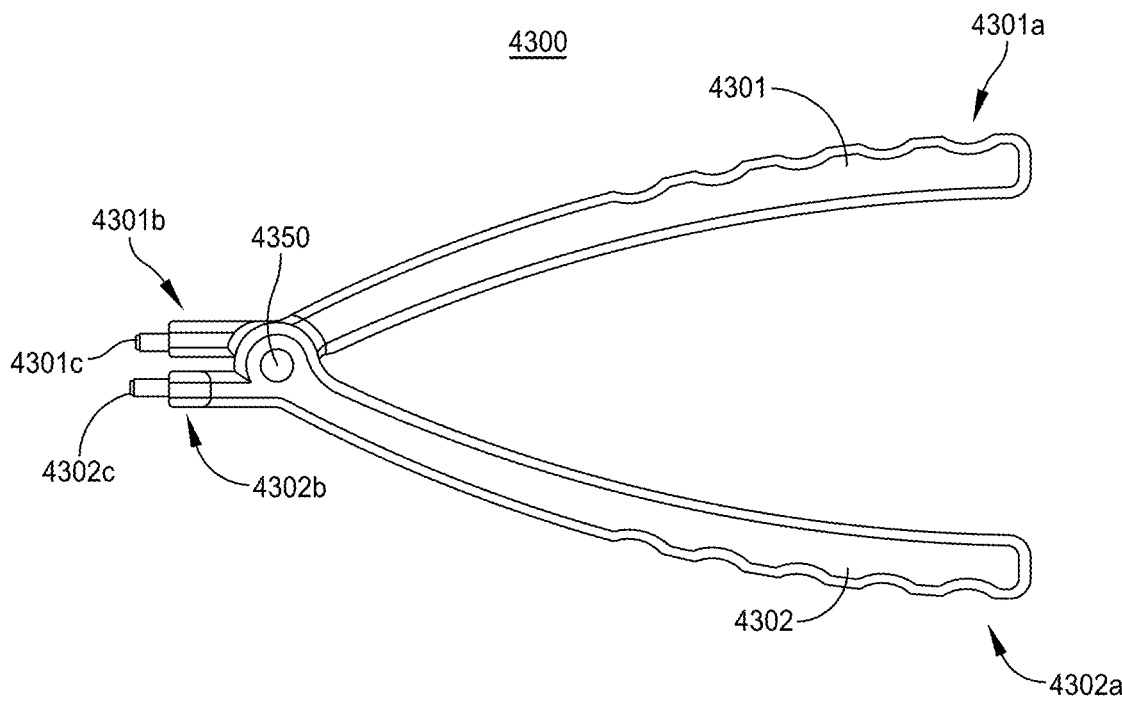
Figure 54G:
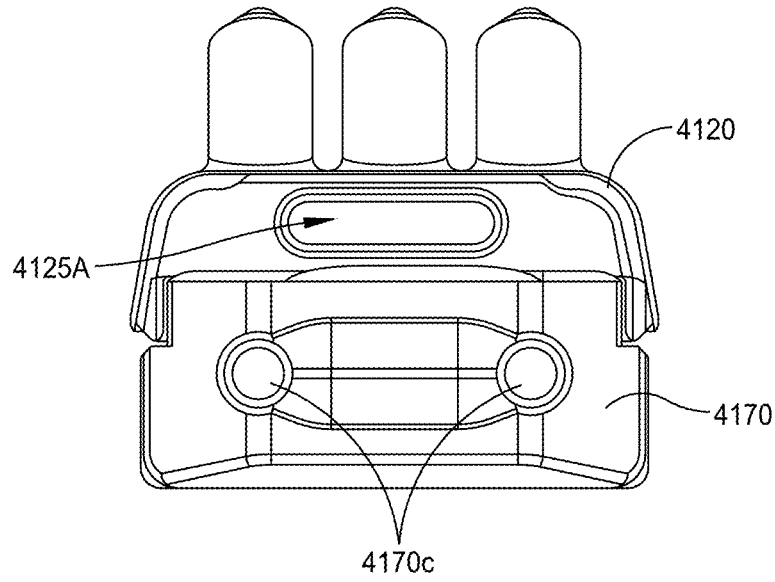
FIG. 54G is an anterior view of the assembly of a tibia tray and the corresponding articulating insert.

During the ankle arthroplasty procedure, after the tibia tray 4120 is installed on the distal end of the patient's tibia, the articulating insert 4170 is inserted into the tibia tray to form a tibia tray/articulating insert assembly as shown in FIG. 54G. At this stage, the assembly of the tibia tray and the articulating insert is not completely locked. The anterior ends of the articulating insert 170 and the tibia tray 4120 are shown in FIG. 54G.

Then, the projections 4201c and 4202c of the hand tool 4200 are aligned with the corresponding recesses 4170c and 4125A and inserted into the recesses. Next, by squeezing the handles of the hand tool 4200 together, the assembly of the tibia tray 4120 and the articulating insert 4170 is locked by clamping the tibia tray 4120 and the articulating insert 4170 together to form the tibia tray/articulating insert assembly shown in FIG. 54G. The tibia tray 4120 and the articulating insert 4170 are configured with appropriate snap-fitting structures that cooperate to lock together when clamped together.

[Concept 13b]

Referring to FIG. 54F, another hand tool 4300 is disclosed that is configured for separating the assembly of articulating insert 4170 and the tibia tray 4120 to facilitate unlocking of the tibia tray/articulating insert assembly. Similar to the hand tool 4200, the hand tool 4300 has two handle pieces 4301 and 4302 that are pivotally connected by a pivot joint 4350. The first handle piece 4301 comprises a first end 4301a and a second end 4301b. The second handle piece 4302 comprises a first end 4302a and a second end 4302b. Unlike the hand tool 4200, however, the two handle pieces 4301 and 4302 do not cross over at the pivot joint 4350. Thus, when the first ends 4301a and 4302a of the handle pieces are closed together, the respective second ends 4301b and 4302b separate from one another so that the second ends 4301b and 4302b, which are the working ends, can be used as a distractor.

The two second ends 4301b, 4302b form the working ends of the hand tool 4300. The second end 4301b of the first handle piece 4301 is configured to engage the anterior end of the tibia tray 4120.

The second end 4302b of the second handle piece 4302 is configured to engage the anterior end of the articulating insert 4170. The second end 4302b comprises one or more projections 4302c for engaging the two recesses 4170c (sec FIG. 54G) of the articulating insert 4170. The two projections 4302c are configured to match the shape of the two recesses 4170c. In the illustrated example, the two recesses 4170c are cylindrically shaped recesses and, thus, the two projections 4302c are cylindrically shaped to match.

The second end 4301b of the first handle piece 4301 is configured to engage the anterior end of the tibia tray 4120. The second end 4301b comprises one or more projections 4301c for engaging the anterior end of the tibia tray 4120. In the illustrated example, the anterior end of the tibia tray 4120 is configured with one elongated recess or a slot 4125A (see FIG. 54G), and the second end 4301b of the first handle piece 4301 comprises one projection 4301c for inserting into the recess 4125A. The projection 4301c has a flat tab-like shape to match the shape of the slot 4125A.

To dis-assemble the tibia tray/articulating insert assembly, the projections 4301c and 4302c of the hand tool 4300 are aligned with the corresponding recesses 4125A and 4170c, respectively, and inserted into the recesses. Next, by squeezing the handles of the hand tool 3300 together, the assembly of the tibia tray 4120 and the articulating insert 4170 of the tibia tray/articulating insert assembly are distracted until the snap-fitting connection is undone, thus unlocking the tibia tray/articulating insert assembly shown in FIG. 54G.

The hand tool 4300 allow the surgeons to use simple squeezing action to pry apart the tibia tray 4120 and the articulating insert 4170 that are in snap-fit engagement.

In some embodiments, the number of projections on the working ends of the hand tool 4200 and the hand tool 4300 can be varied from the illustrated example to match the number of recesses in the tibia tray and the articulating insert.

For example, in some embodiments of the hand tool 4200, the second end 4201b of the first arm 4201 has one projection 4201c configured to engage a recess in the articulating insert 4170, and the second end 4202b of the second arm 4202 has two projections 4202c. Such clamping hand tool would be used on a tibia tray/articulating insert assembly where the tibia tray has two recesses on its anterior end and the articulating insert has one recess on its anterior end.

In some embodiments of the hand tool 4200, the second end 4201b, 4202b of the first and second arms 4201, 4202, each respectively has one projection 4201c, 4202c configured to engage a recess in the articulating insert 4170 and the tibia tray 4120, respectively.

In some embodiments of the hand tool 4200, the second end 4201b, 4202b of the first and second arms 4201, 4202, each respectively has two projections 4201c, 4202c, each configured to engage a corresponding recess in the articulating insert 4170 and the tibia tray 4120, respectively, where the articulating insert 4170 and the tibia tray 4120 each have two recesses in their anterior ends.

[Concept 14a]

Figure 55A:
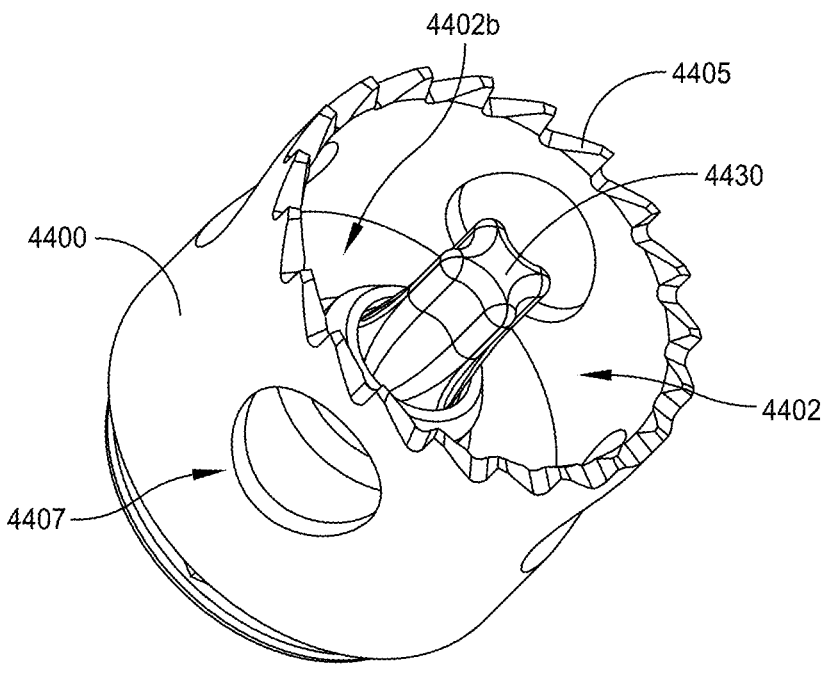
FIG. 55A is an isometric view of an embodiment of a hole cutting saw for cutting into the medullary bone of a tibia for removing a modular tibia stem component of an ankle prosthesis according to the present disclosure.
Figure 55B:
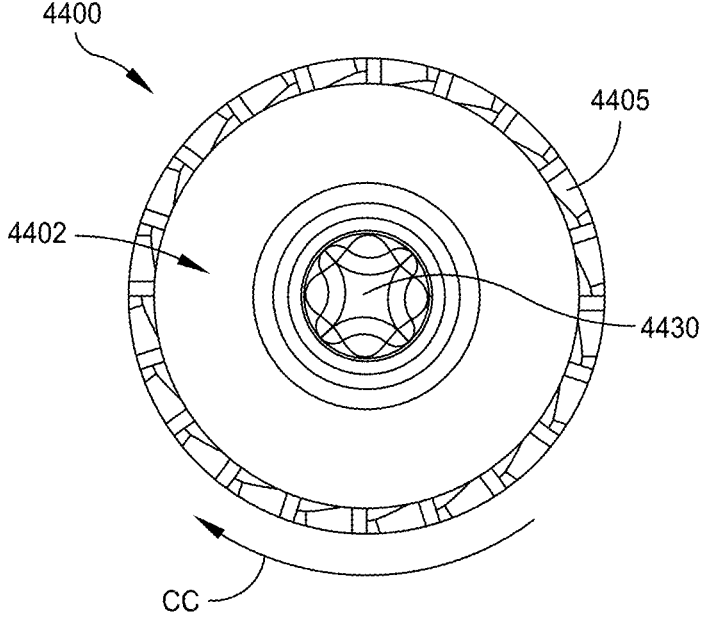
FIG. 55B is a top-down view of the hole cutting saw of FIG. 55A.
Figure 55C:
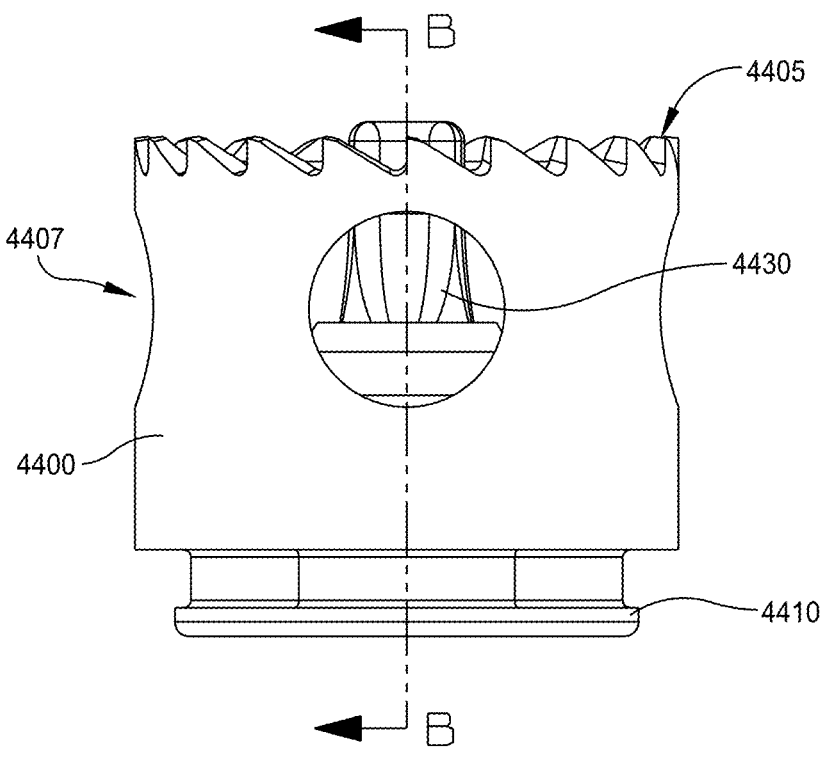
FIG. 55C is a side view of the hole cutting saw of FIGS. 55A-55B.

FIG. 55A shows an isometric view of an embodiment of a hole cutting saw 4400 for cutting into the medullary bone of a tibia for removing a modular tibia stem component of an ankle prosthesis. FIG. 55B is a top-down view and FIG. 55C is a side view of the hole cutting saw 4400. The hole cutting saw 4400 comprises a cylindrical wall body having a base portion 4410 at one end thereof and a plurality of cutting teeth 4405 at the opposite end of the cylindrical wall body.

The cylindrical wall body defines a main cavity 4402 that is open at the end with the teeth 4405 and closed at the end of the base portion 4410. The closed end of the cavity 4402 forms a cavity wall 4402b. Positioned at the geometric center of the main cavity 4402 is a drive bit 4430 extending longitudinally from the cavity wall 4402b. The drive bit 4430 is configured for engaging the bottom end of a modular tibia stem component and the bottom end of the modular tibia stem component would be configured with a complementary recess for receiving the driver bit 4430. The driver bit 4430 and the recess on the bottom end of the modular tibia stem component have complementary shape. For example, in some embodiments, the driver bit 4430 is a square shaped bit as shown in the figures because the recess on the bottom end of the modular tibia stem component has a square shaped recess. In some embodiments, the driver bit 4430 is a 6-point star shaped Torx® bit because the recess on the bottom end of the modular tibia stem component is a Torx® socket for receiving the Torx® bit.

In some embodiments, the cylindrical wall body can includes a plurality of openings 4407 between the base portion 4410 and the teeth 4405 for allowing discharge of the bone material cut by the teeth 4405 into the center cavity 4402.

Figure 55D:
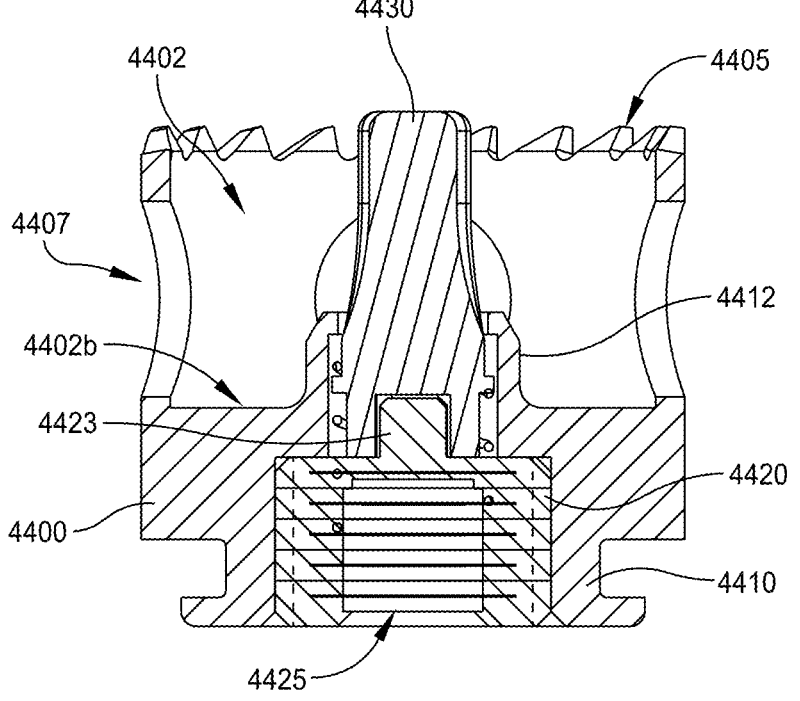
FIG. 55D is a sectional view taken through the section line B-B shown in FIG. 55C.
Figure 55E:
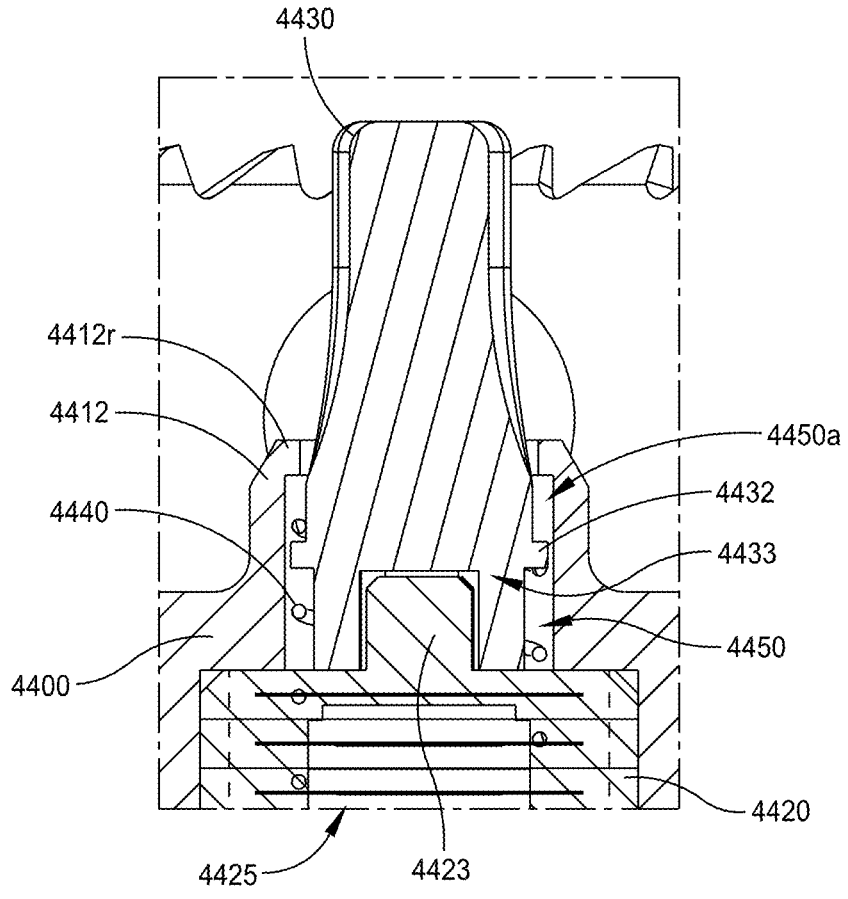
FIG. 55E is a detailed view of the portion of FIG. 55D.

FIG. 55D is a sectional view of the hole cutting saw 4400 taken through the section line B-B shown in FIG. 55C showing more details of the structure of the hole cutting saw 4400. FIG. 55E is a close up view of the driver bit 4430 arrangement in the hole cutting saw 4400. A recess 4425 is provided at the bottom end of the hole cutting saw 4400 for receiving and engaging a driving tool, usually a motorized tool.

In this embodiment, the base portion 4410 is configured as a two-piece structure with a center core 4420 extending into the base portion 4410 toward the cutting end of the hole cutting saw, the end with the teeth 4405. The cavity wall 4402b comprises an annular sleeve 4412 portion that extends upward toward the cutting end. The recess 4425 for receiving and engaging a driving tool is provided in the center core 4420.

As can be better seen in FIG. 55E, the center core 4420 and the annular sleeve 4412 define a central cavity 4450 between them. The bottom end of the driver bit 4430 sits within the central cavity 4450 and extends out of the annular sleeve 4412 toward the cutting end of the hole cutting saw 4400. The top end of the center core 4420 is provided with a boss 4423 and the bottom end of the driver bit 4430 is provided with a corresponding recess 4433 that receives the boss 4423. The boss 4423 and the recess 4433 are shaped so that torque from the driving tool is properly transferred to the driver bit 4430 so that the driver bit 4430 and the hole cutting saw 400 rotate together as one. In some embodiments, the boss 4423 has a rectangular shape often seen in powered driving tools and the corresponding recess 4433 has the corresponding rectangular shape.

The driver bit 4430 comprises a flange 4432 that circumferentially extend, at least partially, around the driver bit 4430. The flange 4432 can circumferentially extend completely around the driver bit 4430 forming a continuous structure or the flange 4432 can be broken up into multiple segments that circumferentially extend around the driver bit 4430. The flange 4432 is provided on the portion of the driver bit 4430 that sits within the central cavity 4450 and the top end of the annular sleeve 4412 is configured with an inwardly extending rim 4412*r* so that the flange 4432 interferes with the rim 4412*r* and capturing the driver bit 4430 between the rim 4412*r* and the center core 4420. The flange 4432 is positioned on the driver bit 4430 such that when the driver bit 4430 is contacting the center core 4420 so that the driver bit 4430 is at its lowest point inside the central cavity 4450, the flange 4432 is at a distance below the rim 4432*r*. This separation between the rim 4432*r* and the flange 4432 is shown in FIG. 55E by an upper portion 4450*a* of the central cavity 4450. Thus, the driver bit 4430 can be moved axially up and down inside the central cavity 4450 within the distance limited by the upper portion 4450*a*.

In this embodiment, an elastic member 4440, such as a coil spring, is provided within the central cavity 4450 in an arrangement that pushes against the flange 4432. This arrangement applies a constant force urging the driver bit 4430 upward so that the driver bit 4430 is at its maximum extension out of the central cavity 4450 toward the cutting end of the hole cutting saw 4400. However, because the driver bit 4430 is floating on the clastic member 4440, the driver bit 4430 can be pushed down into the central cavity 4450.

Figure 55F:
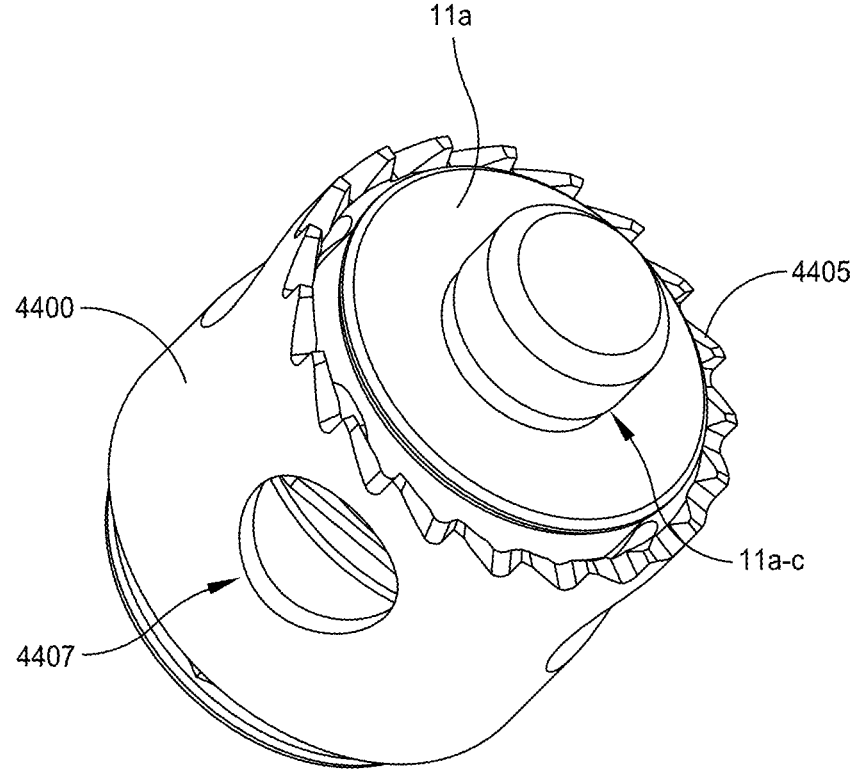
FIG. 55F shows an isometric view of the hole cutting saw of FIG. 55A engaging a modular tibia stem component after the modular tibia stem component has been removed from the patient's tibia using the hole cutting saw.

FIG. 55F shows an isometric view of the hole cutting saw 4400 engaging a modular tibia stem component 11*a* after the modular tibia stem component 11*a* has been removed from a patient's tibia using the hole cutting saw 4400. The main cavity 4402 has a diameter that is sufficiently large to receive the modular tibia stem component 11*a*.

Figure 55G:
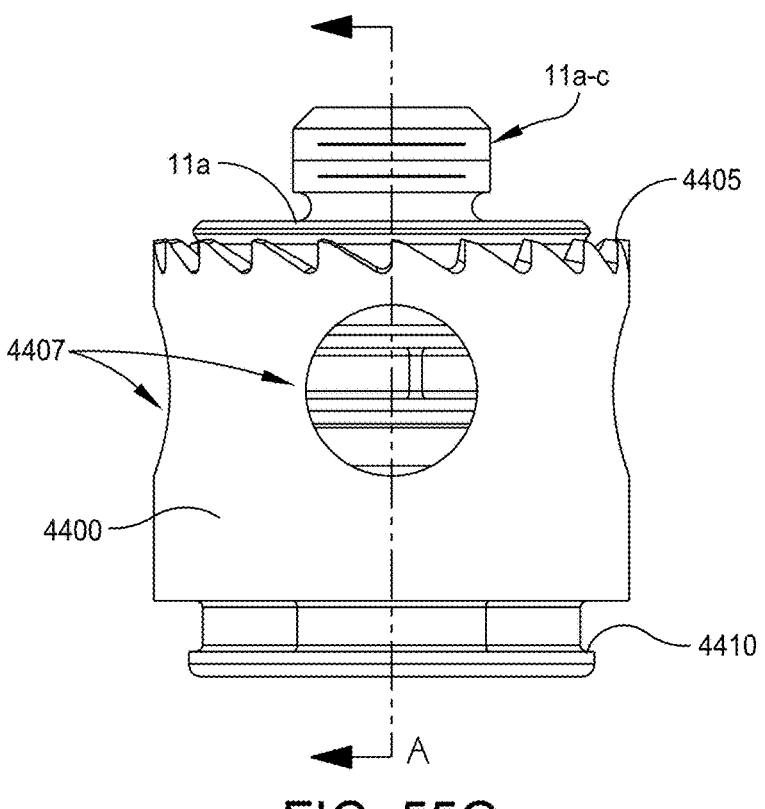
FIG. 55G is a side view of the hole cutting saw of FIG. 55A engaging a modular tibia stem.

FIG. 55G is a side view of the hole cutting saw 4400 engaging the modular tibia stem component 11*a*.

Figure 55H:
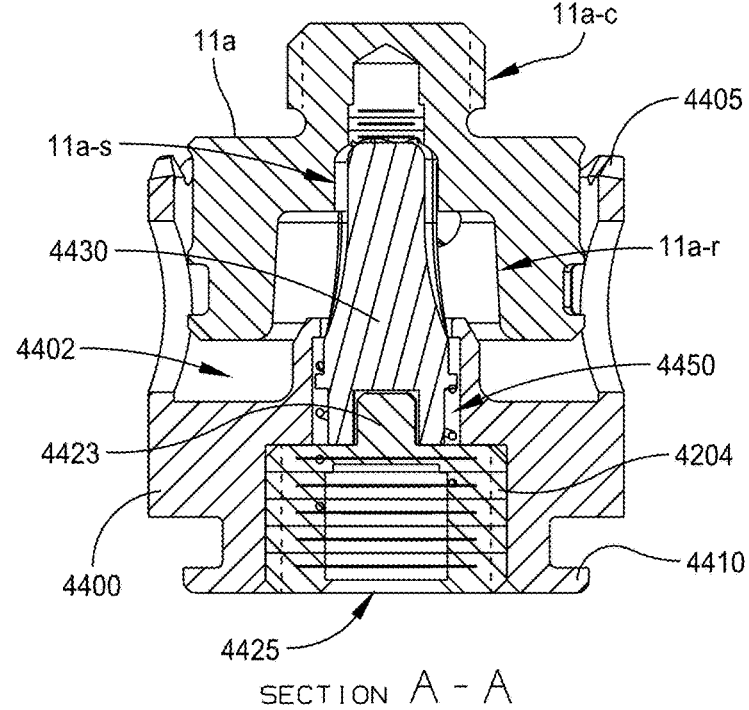
FIG. 55H is a sectional view taken through the section line A-A of the assembly shown in FIG. 55G.

FIG. 55H is a sectional view of the assembly shown in FIGS. 55F-55G taken through the section line A-A shown in FIG. 55G. As mentioned above, the bottom end of the modular tibia stem component 11*a* is configured with a recess 11*a-s* for receiving the driver bit 4430. The driver bit 4430 and the recess 11*a-s* on the bottom end of the modular tibia stem component 11*a* have complementary shape.

The assembly shown in FIGS. 55F-55H is after the modular tibia stem component 11*a* has been removed from the patient's tibia using the hole cutting saw 4400.

Figure 56:
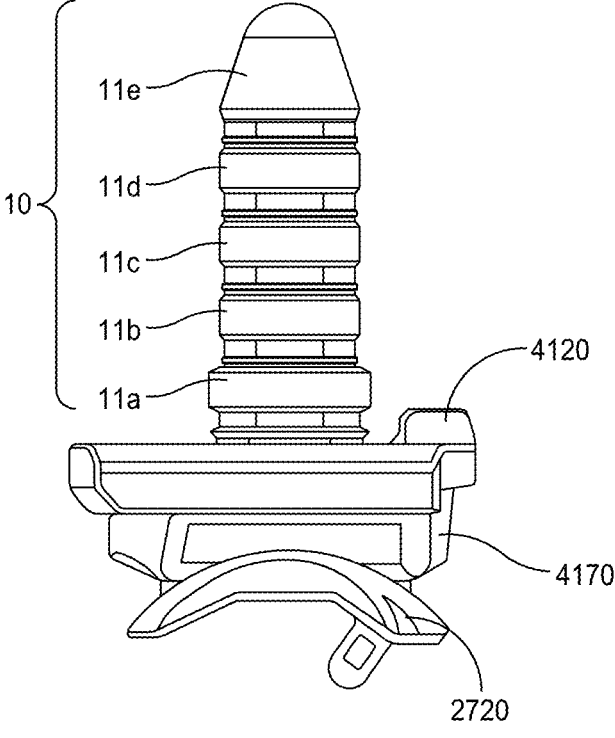
FIG. 56 is a side view of an example of a total ankle prosthesis system that includes a talar dome component, an articulating insert, and a modular tibia stem system that comprises a tibia tray and a plurality of modular tibia stem components assembled on top of the tibia tray

To provide a context for the hole cutting saw 4400, shown in FIG. 56 is an example of a total ankle prosthesis system that includes a modular tibia stem system 10. The total ankle prosthesis system includes the modular tibia stem system 10 that is mated to a tibia tray 4120, an articulating insert 4170, and a talar dome implant 4180. The modular tibia stem system 10 comprises a plurality of modular tibia stem components that are screwed into each other to form the stack shown. Each of the modular tibia stem component is configured with a threaded central stem on one end and a threaded recess on the opposite end for this purpose.

In the example shown in FIGS. 55G-55H, the first modular tibia stem component 11*a* from FIG. 56 is shown. The modular tibia stem component 11*a* has a threaded central stem 11*a-c* on top end and a threaded recess 11*a-r* on the opposite end.

The illustrated example of the modular tibia stem system 10 has five modular tibia stem components 11*a*-11*e* but can be formed with different number of modular tibia stem components depending on the needs of the patient. When implanted in a patient, the modular tibia stem system 10 is implanted in the medullary canal of the patient's tibia.

When the ankle prosthesis system is being revised, one or more of the modular tibia stem components 11*a*-11*e* may need to be removed. The disclosed hole cutting saw 4400 is useful in performing this removal procedure.

The removal procedure will now be described using the bottom-most modular tibia stem component 11*a* shown in FIG. 56 as an example. Approaching from the distal end of the patient's tibia, the hole cutting saw 4400 is aligned over the modular tibia stem component 11*a* that is embedded in the patient's tibia. While rotating the hole cutting saw 4400 at speed using an appropriate driving tool, the hole cutting saw 4400 is advanced toward the modular tibia stem component 11*a* so that the teeth 4405 cuts into the bone around a modular tibia stem component 11*a*. The bone cutting is continued until the driver bit 4430 engages the recess 11*a-s* of the modular tibia stem component 11*a*.

The rotating motion of the hole cutting saw 4400 is maintained so that the driver bit 4430 rotates the modular tibia stem component 11*a* and unscrews the modular tibia stem component 11*a* from the neighboring modular tibia stem component 11*b*. The direction of the cutting teeth 4405 is designed to match the screw thread direction of the modular tibia stem components so that the bone cutting direction for the hole cutting saw 4400 is the same direction needed for unscrewing the threaded connection between the neighboring modular tibia stem components 11*a*-11*e*. For example, the arrow CC shown in FIG. 55B represents the bone cutting direction for the hole cutting saw 4400. In this example, this direction is a counter-clockwise rotation direction when viewed from the base portion 4410 side of the hole cutting saw 4400. This counter-clockwise direction matches the unscrewing direction for the threaded connection among the modular tibia stem components 11*a*-11*e*. After the modular tibia stem component 11*a* is removed, if the next modular tibia stem component 11*b* needs to be removed, the above-described steps are repeated for the next modular tibia stem component 11*b*.

As mentioned above, the driver bit 4430 of the hole cutting saw 4400 is configured to float on the clastic member 4440. This feature can be helpful in allowing more smooth engagement between the driver bit 4430 and the recess 11*a-s* of the modular tibia stem component 11*a* during the moment of transition from pure bone cutting process to engagement between the driver bit 4430 and the recess 11*a-s*. As the rotating hole cutting saw 4400 advances into the bone around the modular tibia stem component 11*a* and the driver bit 4430 approaches the recess 11*a-s*, because the driver bit 4430 is rotating, the driver bit may chatter until its tip engages into the recess 11*a-s*. However, because the driver bit 4430 is floating on the elastic member 4440, the driver bit 4430 will be pushed incrementally backward as the edges of the driver bit 4430 chatter past the edges of the recess 11*a-s* and lessen the vibrational impact caused by the mechanical push-back during the duration of the chattering until the driver bit 4430 engages the recess 11*a-s* and stops the chattering. This results in a smooth engagement between the driver bit 430 and the recess 11*a-s*.

[Concept 14b]

Shown in FIGS. 57A-57G is a hole saw 4400' according to another embodiment. The hole saw 4400' is similar to the hole saw 4400 except that the driver bit 4430' in the hole saw 4400' is monolithically formed as part of the hole saw 4400'. Thus, the driver bit 4430' does not float on an elastic member.

Figure 57A:
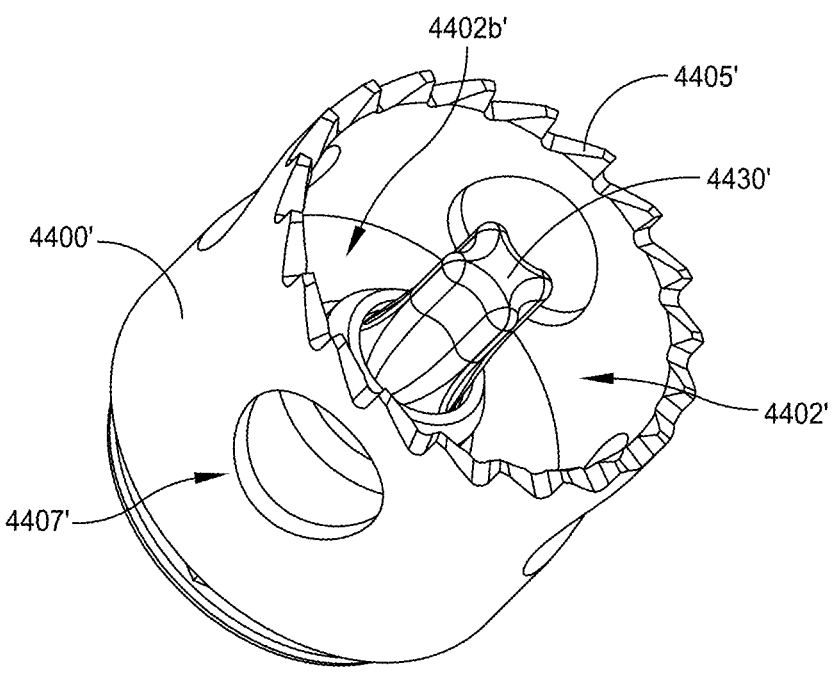
FIG. 57A is an isometric view of another embodiment of a hole cutting saw for cutting into the medullary bone of a tibia for removing a modular tibia stem component of an ankle prosthesis according to the present disclosure.
Figure 57B:
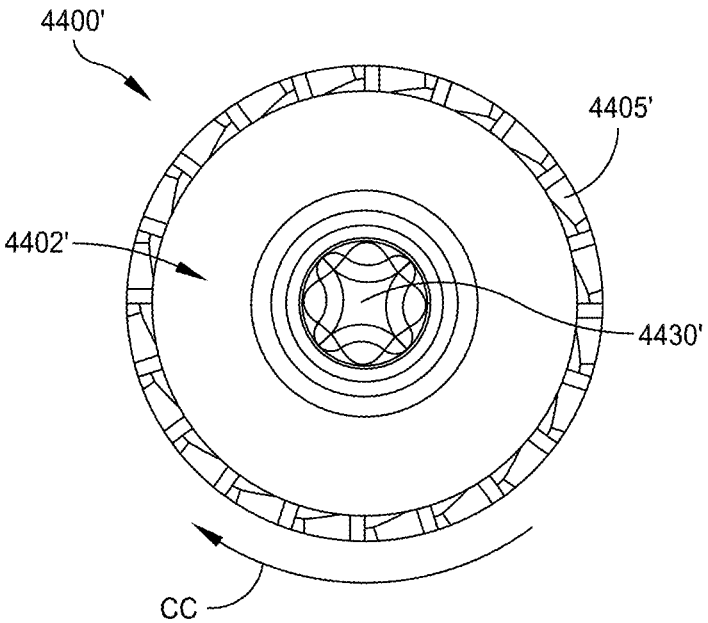
FIG. 57B is a top-down view of the hole cutting saw of FIG. 57A.
Figures 57C, 57D, 57E:
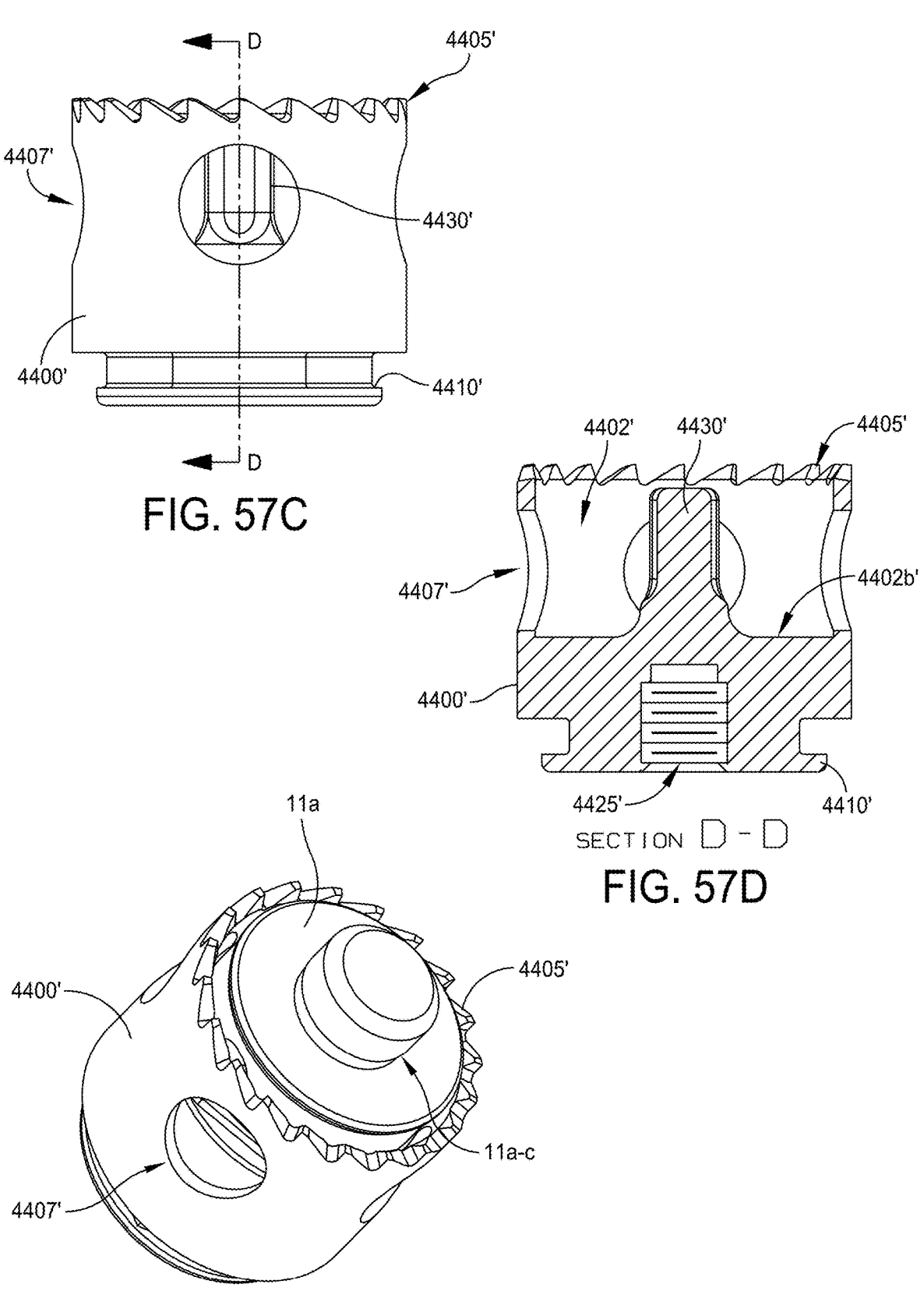
FIG. 57C is a side view of the hole cutting saw of FIGS. 57A-57B.
FIG. 57D is a sectional view taken through the section line D-D shown in FIG. 57C.
FIG. 57E shows an isometric view of the hole cutting saw of FIG. 57A engaging a modular tibia stem component after the modular tibia stem component has been removed from the patient's tibia using the hole cutting saw.

FIG. 57A shows an isometric view of an embodiment of a hole cutting saw 4400' for cutting into the medullary bone of a tibia for removing a modular tibia stem component of an ankle prosthesis. FIG. 57B is a top-down view and FIG. 57C is a side view of the hole cutting saw 4400'. The hole cutting saw 4400' comprises a cylindrical wall body having a base portion 4410' at one end thereof and a plurality of cutting teeth 4405' at the opposite end of the cylindrical wall body.

The cylindrical wall body defines a main cavity 4402' that is open at the end with the teeth 4405' and closed at the end of the base portion 4410'. The closed end of the cavity 4402' forms a cavity wall 4402b'. Positioned at the geometric center of the main cavity 4402' is a driver bit 4430' extending longitudinally from the cavity wall 4402b'. The driver bit 4430' is configured for engaging the bottom end of a modular tibia stem component and the bottom end of the modular tibia stem component would be configured with a complementary recess for receiving the driver bit 4430'. The driver bit 4430' and the recess on the bottom end of the modular tibia stem component have complementary shape. For example, in some embodiments, the driver bit 4430' is a square shaped bit as shown in the figures because the recess on the bottom end of the modular tibia stem component has a square shaped recess. In some embodiments, the driver bit 4430' is a 6-point star shaped Torx® bit because the recess on the bottom end of the modular tibia stem component is a Torx® socket for receiving the Torx® bit.

In some embodiments, the cylindrical wall body can includes a plurality of openings 407' between the base portion 4410' and the teeth 4405' for allowing discharge of the bone material cut by the teeth 4405' into the center cavity 4402'.

FIG. 57D is a sectional view of the hole cutting saw 4400' taken through the section line D-D shown in FIG. 57C showing more details of the structure of the hole cutting saw 4400'.

FIG. 57E shows an isometric view of the hole cutting saw 4400' engaging a modular tibia stem component 11a after the modular tibia stem component 11a has been removed from a patient's tibia using the hole cutting saw 4400'. The main cavity 4402' has a diameter that is sufficiently large to receive the modular tibia stem component 11a.

Figure 57F:
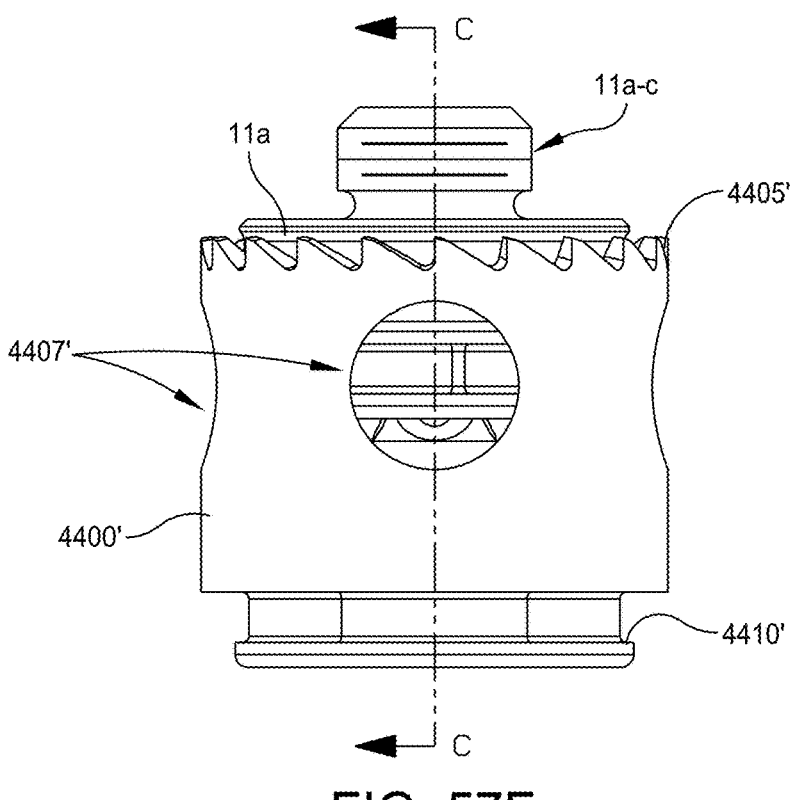
FIG. 57F is a side view of the hole cutting saw of FIG. 57A engaging a modular tibia stem.

FIG. 57F is a side view of the hole cutting saw 4400' engaging the modular tibia stem component 11a.

Figure 57G:
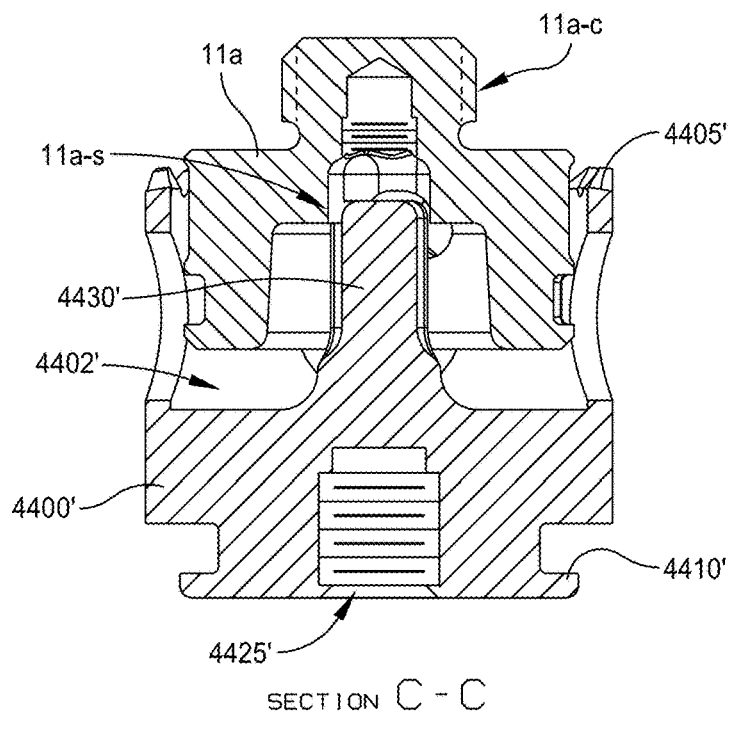
FIG. 57G is a sectional view taken through the section line C-C shown in FIG. 55F.

FIG. 57G is a sectional view of the assembly shown in FIGS. 57E-57F taken through the section line C-C shown in FIG. 57F. As mentioned above, the bottom end of the modular tibia stem component 11a is configured with a recess 11a-s for receiving the driver bit 4430'. The driver bit 4430' and the recess 11a-s on the bottom end of the modular tibia stem component 11a have complementary shape.

The assembly shown in FIGS. 57E-57G is after the modular tibia stem component 11a has been removed from the patient's tibia using the hole cutting saw 4400'.

The procedure of using the hole cutting saw 4400' for removing a modular tibia stem component such as the component 11a is similar to that described above for the hole cutting saw 4400.

Although various inventive devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A holder apparatus comprising:

a tubular sleeve housing having a proximal end and a distal end and having an internal bore extending from the proximal end to the distal end of the tubular sleeve housing; and a stem having a proximal end and a distal end, received in the bore of the tubular sleeve housing and extending a distance distally out of the tubular sleeve housing, wherein the stem's longitudinal axis defines the holder apparatus' longitudinal axis;

wherein the stem comprises a first arm provided at the distal end of the stem and protruding orthogonal to the stem's longitudinal axis, wherein the first arm is spaced apart from the distal end of the tubular sleeve housing;

wherein the tubular sleeve housing comprises a second arm provided at the distal end of the tubular sleeve housing, wherein the second arm extends distally from the distal end of the tubular sleeve housing adjacent to the stem and protruding orthogonal to the stem's longitudinal axis; and wherein the tubular sleeve housing and the stem are configured to rotate about the longitudinal axis of the stem with respect to each other so that the first and second arms can be moved between a first configuration of the holder apparatus, in which the first arm and the second arm are radially aligned, and a second configuration of the holder apparatus, in which the first arm and the second arm are radially offset.

2. The holder apparatus of claim 1, wherein when in their second configuration, the tubular sleeve housing and the stem are configured to slide longitudinally with respect to each other so that a distal portion of the second arm is adjacent to the first arm of the stem, thus limiting the stem and the tubular sleeve housing's ability to rotate about one another.

3. The holder apparatus of claim 1, further comprising:

a handle portion having a proximal end and a distal end, wherein the handle portion comprises an opening at the distal end defining a cylindrical cavity into which the proximal end of the tubular sleeve housing is received;

wherein the longitudinal axis of the stem also defines longitudinal axis of the handle portion and longitudinal axis of the cylindrical cavity;

wherein the proximal end of the stem is affixed to the proximal end of the handle portion;

whereby the handle portion and the stem can be rotated about the longitudinal axis of the stem in unison with respect to the tubular sleeve housing.

4. The holder apparatus of claim 3, wherein the cylindrical cavity at the distal end of the handle portion comprises:

a sidewall; and a slot provided in the sidewall, wherein the slot is defined by two ends and extends circumferentially and orthogonal to the longitudinal axis of the stem along the sidewall; and the holder apparatus further comprises a knob including a portion received in a recess in the proximal end of the tubular sleeve housing, wherein the knob portion extends through the slot and radially away from the longitudinal axis of the stem, wherein the knob is attached to the tubular sleeve housing such that when the handle portion and the stem is rotated about the longitudinal axis of the stem with respect to the tubular sleeve housing, the knob's position within the slot changes.

5. The holder apparatus of claim 4, wherein when the holder apparatus is in its first configuration, the knob portion is at one end of the slot, and when the holder apparatus is in its second configuration, the knob portion is at the other end of the slot.

6. The holder apparatus of claim 4, wherein the slot comprises a main slot portion that extends circumferentially between the two ends, and a distally extending portion defining one of the two ends of the main slot portion, wherein the distally extending portion extends parallel to the longitudinal axis of the stem and enables a locking function that locks the holder apparatus in the second configuration.

7. The holder apparatus of claim 6, wherein the knob is attached to the tubular sleeve housing via an expanding element provided in the recess in the proximal end of the tubular sleeve housing, wherein the expanding element urges the knob radially outward away from the longitudinal axis of the stem and the knob comprises a detent portion that is wider than that main slot portion such that the detent portion is urged against the main slot portion and keeps the knob in the recess when the holder apparatus is between the first configuration and the second configuration, wherein the distally extending portion of the slot is wider than the main slot portion such that when the holder apparatus is in the second configuration, the knob is aligned with the distally extending portion of the slot whereby the detent portion of the knob gets pushed into the distally extending portion by the urging of the expanding element and lock the holder apparatus in the second configuration.

8. The holder apparatus of claim 7, wherein the expanding element is a coil spring.

9. The holder apparatus of claim 7, wherein the slot comprises a second distally extending portion provided at the other of the two ends of the main slot portion, wherein the second distally extending portion extends parallel to the longitudinal axis of the stem and is wider than the main slot portion such that when the holder apparatus is in the first configuration, the knob is aligned with the second distally extending portion, whereby the detent portion of the knob gets pushed into the distally extending portion by the urging of the expanding element and lock the holder apparatus in the first configuration.

10. The holder apparatus of claim 9, wherein the expanding element is a coil spring.

\* \* \* \* \*